(12) United States Patent
Wang

(10) Patent No.: US 7,348,142 B2
(45) Date of Patent: Mar. 25, 2008

(54) CANCER DIAGNOSTIC PANEL

(75) Inventor: Yixin Wang, San Diego, CA (US)

(73) Assignee: Veridex, LCC, Raritan, NJ (US)

( * ) Notice: Subject to any disclaimer, the term of this patent is extended or adjusted under 35 U.S.C. 154(b) by 496 days.

(21) Appl. No.: 10/393,567

(22) Filed: Mar. 21, 2003

(65) Prior Publication Data

US 2003/0194733 A1  Oct. 16, 2003

Related U.S. Application Data

(60) Provisional application No. 60/368,667, filed on Mar. 29, 2002.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search ............. None
See application file for complete search history.

(56) References Cited

U.S. PATENT DOCUMENTS

| | | | |
|---|---|---|---|
| 6,003,018 A | 12/1999 | Michaud et al. | |
| 6,175,824 B1 | 1/2001 | Breizman et al. | |
| 6,275,814 B1 | 8/2001 | Giansante et al. | |
| 6,350,576 B1 | 2/2002 | Wigler et al. | |
| 6,353,152 B1 | 3/2002 | Lee et al. | |
| 2003/0138793 A1* | 7/2003 | Su et al. ................ | 435/6 |

FOREIGN PATENT DOCUMENTS

WO   WO 00/55633 A3   9/2000

OTHER PUBLICATIONS

Su et al., "Molecular Clasification of Human Carcinomas by Use of Gene Expression Signatures," ☐☐Cancer Research 61: 7388-7393 (Oct. 2001).*

Bo, T.H. et al., "New feature subset selection procedures for classification of expression profiles", Genome Biology, Online!, vol. 3, No. 4, pp. 1-11, Mar. 2002, <URL:http://genomebiology.com/2002/3/4/research/0017.1>.
Golub, T.R. et al., "Molecular classification of cancer: Class discovery and class prediction by gene expression monitoring", American Association for the Advancement of Science, vol. 286, No. 5439, pp. 531-537, Oct. 1999.
Perou, C.M. et al., "Molecular portraits of human breast tumours", Nature, MacMillan Journals Ltd., London, GB, vol. 406, No. 6797, pp. 747-752, Aug. 2000.
Ramaswamy, Sridhar et al., "Multiclass cancer diagnosis using tumor gene expression signatures", Proceedings fo the National Academy of Sciences of the United States, vol. 98, No. 26, pp. 15149-15154, Dec. 2001.
Su, A.I. et al., "Molecular classification of human carcinomas by use of gene expression signatures", Cancer Research, American Association for Cancer Research, Baltimore, MD, USA, vol. 61, pp. 7388-7393, Oct. 2001.
Zhang, L. et al., "Gene expression profiles in normal and cancer cells", American Association for the Advancement of Science, vol. 276, pp. 1268-1272, May 1997.
Paul D. Kaplan,PhD, CFA, Vice-President and Economist, 225 North Michigan Avenue, SUite 700, Chicago, Il 60601-7676;"Asset Allocation Models Using the Markowitz Approach"; http://www.ibbotson.com/Research/papers/Markowitz_Approach/ Markowitz_Approach.pdf http://www.ibbotson.com/Research/papers/Markowitz_Approach/Markowitz_Approach.pdf http://www.elseware.fr/en/LINKS/TECHLNK.HTM.
Laura J. Vantveer et al; "Gene expression profiling predicts clinical outcome of breast cancer"; Nature/vol. 415/Jan. 13, 2002/www.nature.com; 2002 Macmillan Magazines Ltd.,pp. 530-536.
Partial European Search Report, dated Jan. 15, 2004, for European Appln. No. 03-25-2023.

* cited by examiner

*Primary Examiner*—Ethan Whisenant
(74) *Attorney, Agent, or Firm*—Todd F. Volyn

(57) ABSTRACT

A method of diagnosing cancer by identifying differential modulation of each gene (relative to the expression of the same genes in a normal population) in a combination of genes selected from two groups of genes.

Gene expression portfolios and kits for employing the method are further aspects of the invention.

3 Claims, No Drawings

CANCER DIAGNOSTIC PANEL

This application claims the benefit of U.S. Provisional Application No. 60/368,667 filed on Mar. 29, 2002.

BACKGROUND

The invention relates to the selection of portfolios of diagnostic markers.

A few single gene diagnostic markers such as her-2-neu are currently in use. Usually, however, diseases are not easily diagnosed with molecular diagnostics for one particular gene. Multiple markers are often required and the number of such markers that may be included in a assay based on differential gene modulation can be large, even in the hundreds of genes. It is desirable to group markers into portfolios so that the most reliable results are obtained using the smallest number of markers necessary to obtain such a result. This is particularly true in assays that contain multiple steps such as nucleic acid amplification steps.

SUMMARY OF THE INVENTION

The invention is a method of cancer by identifying differential modulation of each gene (relative to the expression of the same genes in a normal population) in a combination of genes selected from the group consisting of Seq. ID. No. 1-30, Seq. ID No. 32, Seq. ID No. 34 and Seq. ID No. 98. In another embodiment the combination is selected from the group consisting of Seq. ID No. 32-67, Seq. ID No. 69, and Seq ID. No. 98-100.

Gene expression portfolios and kits for employing the method are further aspects of the invention.

DETAILED DESCRIPTION

The methods of this invention can be used in conjunction with any method for determining the gene expression patterns of relevant cells as well as protein based methods of determining gene expression. Preferred methods for establishing gene expression profiles include determining the amount of RNA that is produced by a gene that can code for a protein or peptide. This is accomplished by reverse transcriptase PCR (RT-PCR), competitive RT-PCR, real time RT-PCR, differential display RT-PCR, Northern Blot analysis and other related tests. While it is possible to conduct these techniques using individual PCR reactions, it is best to amplify copy DNA (cDNA) or copy RNA (cRNA) produced from mRNA and analyze it via microarray. A number of different array configurations and methods for their production are known to those of skill in the art and are described in U.S. Patents such as: U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637; the disclosures of which are incorporated herein by reference.

Microarray technology allows for the measurement of the steady-state mRNA level of thousands of genes simultaneously thereby presenting a powerful tool for identifying effects such as the onset, arrest, or modulation of uncontrolled cell proliferation. Two microarray technologies are currently in wide use. The first are cDNA arrays and the second are oligonucleotide arrays. Although differences exist in the construction of these chips, essentially all downstream data analysis and output are the same. The product of these analyses are typically measurements of the intensity of the signal received from a labeled probe used to detect a cDNA sequence from the sample that hybridizes to a nucleic acid sequence at a known location on the microarray. Typically, the intensity of the signal is proportional to the quantity of cDNA, and thus mRNA, expressed in the sample cells. A large number of such techniques are available and useful. Preferred methods for determining gene expression can be found in U.S. Pat. Nos. 6,271,002 to Linsley, et al.; 6,218,122 to Friend, et al.; 6,218,114,to Peck, et al.; and 6,004,755 to Wang, et al., the disclosure of each of which is incorporated herein by reference.

Analysis of the expression levels is conducted by comparing such intensities. This is best done by generating a ratio matrix of the expression intensities of genes in a test sample versus those in a control sample. For instance, the gene expression intensities from a diseased tissue can be compared with the expression intensities generated from normal tissue of the same type (e.g., diseased colon tissue sample vs. normal colon tissue sample). A ratio of these expression intensities indicates the fold-change in gene expression between the test and control samples.

Modulated genes are those that are differentially expressed as up regulated or down regulated in non-normal cells. Up regulation and down regulation are relative terms meaning that a detectable difference (beyond the contribution of noise in the system used to measure it) is found in the amount of expression of the genes relative to some baseline. In this case, the baseline is the measured gene expression of a normal cell. The genes of interest in the non-normal cells are then either up regulated or down regulated relative to the baseline level using the same measurement method.

Preferably, levels of up and down regulation are distinguished based on fold changes of the intensity measurements of hybridized microarray probes. For example, in the case in which a 1.5 fold or more difference is used to make such distinctions, the diseased cell is found to yield at least 1.5 times more, or 1.5 times less intensity than the normal cells.

Other methods of making distinctions are available. For example, statistical tests can be used to find the genes most significantly different between diverse groups of samples. The Student's t-test is an example of a robust statistical test that can be used to find significant differences between two groups. The lower the p-value, the more compelling the evidence that the gene is showing a difference between the different groups. Nevertheless, since microarrays measure more than one gene at a time, tens of thousands of statistical tests may be asked at one time. Because of this, there is likelihood to see small p-values just by chance and adjustments for this using a Sidak correction as well as a randomization/permutation experiment can be made.

A p-value less than 0.05 by the t-test is evidence that the gene is significantly different. More compelling evidence is a p-value less then 0.05 after the Sidak correct is factored in. For a large number of samples in each group, a p-value less than 0.05 after the randomization/permutation test is the most compelling evidence of a significant difference.

Genes can be grouped so that information obtained about the set of genes in the group provides a sound basis for making clinically relevant judgments such as a diagnosis, prognosis, or treatment choice. These sets of genes make up the portfolios of the invention. As with most diagnostic markers, it is often desirable to use the fewest number of markers sufficient to make a correct medical judgment. This prevents a delay in treatment pending further analysis as well as inappropriate use of time and resources. Preferred optimal portfolio is one that employs the fewest number of markers for making such judgments while meeting conditions that maximize the probability that such judgments are indeed correct. These conditions will generally include sensitivity and specificity requirements. In the context of microarray based detection methods, the sensitivity of the portfolio can be reflected in the fold differences exhibited by a gene's expression in the diseased or aberrant state relative to the normal state. The detection of the differential expression of a gene is sensitive if it exhibits a large fold change relative to the expression of the gene in another state. Another aspect of sensitivity is the ability to distinguish signal from noise. For example, while the expression of a set of genes may show adequate sensitivity for defining a given disease state, if the signal that is generated by one (e.g., intensity measurements in microarrays) is below a level that easily distinguished from noise in a given setting (e.g., a clinical laboratory) then that gene should be excluded from the optimal portfolio. A procedure for setting conditions such as these that define the optimal portfolio can be incorporated into the inventive methods.

Specificity can be reflected in statistical measurements of the correlation of the signaling of gene expression with the condition of interest. If the differential expression of a set of genes is observed to produce a large fold change but they do so for a number of conditions other than the condition of interest (e.g. multiple disease states) then the gene expression profile for that set of genes is non-specific. Statistical measurements of correlation of data or the degree of consistency of data such as standard deviation, correlation coefficients, and the like can be a used as such measurements. In considering a group of genes for inclusion in a portfolio, a small standard deviation in expression measurements correlates with greater specificity. Genes that display similar expression patterns may be co-regulated by an identical factor that pushes the genes in the same direction. If this factor is sufficient but not necessary for classifying a sample, then these genes will fail to correctly identify a sample if the markers are all related to this single factor. Diversification then results in selecting as few markers as possible, yet covers as many different optimal expression patterns that are contained in the data set In the method of the invention, a group of genetic markers is selected for use in diagnostic applications. These groups of markers are "portfolios". Diagnostic applications include the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, the method can be used to establish portfolios for detecting the presence or likelihood of a subject contracting colon cancer or the likelihood that such a subject will respond favorably to cytotoxic drugs.

The portfolios selected by the method of the invention contain a number and type of markers that assure accurate and precise results and are economized in terms of the number of genes that comprise the portfolio. The method of the invention can be used to establish optimal gene expression portfolios for any disease, condition, or state that is concomitant with the expression of multiple genes. An optimal portfolio in the context of the instant invention refers to a gene expression profile that provides an assessment of the condition of a subject (based upon the condition for which the analysis was undertaken) according to predetermined standards of at least two of the following parameters: accuracy, precision, and number of genes comprising the portfolio.

Most preferably, the markers employed in the portfolio are nucleic acid sequences that express mRNA ("genes"). Expression of the markers may occur ordinarily in a healthy subject and be more highly expressed or less highly expressed when an event that is the object of the diagnostic application occurs. Alternatively, expression may not occur except when the event that is the object of the diagnostic application occurs.

Marker attributes, features, indicia, or measurements that can be compared to make diagnostic judgments are diagnostic parameters used in the method. Indicators of gene expression levels are the most preferred diagnostic parameters. Such indicators include intensity measurements read from microarrays, as described above. Other diagnostic parameters are also possible such as indicators of the relative degree of methylation of the markers.

Distinctions are made among the diagnostic parameters through the use of mathematical/statistical values that are related to each other. The preferred distinctions are mean signal readings indicative of gene expression and measurements of the variance of such readings. The most preferred distinctions are made by use of the mean of signal ratios between different group readings (e.g., microarray intensity measurements) and the standard deviations of the signal ratio measurements. A great number of such mathematical/statistical values can be used in their place such as return at a given percentile.

A relationship among diagnostic parameter distinctions is used to optimize the selection of markers useful for the diagnostic application. Typically, this is done through the use of linear or quadratic programming algorithms. However, heuristic approaches can also be applied or can be used to supplement input data selection or data output. The most preferred relationship is a mean-variance relationship such as that described in *Mean-Variance Analysis in Portfolio Choice and Capital Markets* by Harry M. Markowitz (Frank J. Fabozzi Associates, New Hope, Pa.: 2000, ISBN: 1-883249-75-9) which is incorporated herein by reference. The relationship is best understood in the context of the selection of stocks for a financial investment portfolio. This is the context for which the relationship was developed and elucidated.

The investor looking to optimize a portfolio of stocks can select from a large number of possible stocks, each having a historical rate of return and a risk factor. The mean variance method uses a critical line algorithm of linear programming or quadratic programming to identify all feasible portfolios that minimize risk (as measured by variance or standard deviation) for a given level of expected return and maximize expected return for a given level of risk. When standard deviation is plotted against expected return an efficient frontier is generated. Selection of stocks along the efficient frontier results in a diversified stock portfolio optimized in terms of return and risk.

When the mean variance relationship is used in the method of the instant invention, diagnostic parameters such as microarray signal intensity and standard deviation replace the return and risk factor values used in the selection of financial portfolios. Most preferably, when the mean variance relationship is applied, a commercial computer software application such as the "Wagner Associates Mean-Variance Optimization Application", referred to as "Wagner Software" throughout this specification. This software uses functions from the "Wagner Associates Mean-Variance Optimization Library" to determine an efficient frontier and optimal portfolios in the Markowitz sense. Since such applications are made for financial applications, it may be necessary to preprocess input data so that it can conform to conventions required by the software. For example, when Wagner Software is employed in conjunction with microarray intensity measurements the following data transformation method is employed.

A relationship between each genes baseline and experimental value must first be established. The preferred process is conducted as follows. A baseline class is selected. Typically, this will comprise genes from a population that does not have the condition of interest. For example, if one were interested in selecting a portfolio of genes that are diagnostic for breast cancer, samples from patients without breast cancer can be used to make the baseline class. Once the baseline class is selected, the arithmetic mean and standard deviation is calculated for the indicator of gene expression of each gene for baseline class samples. This indicator is typically the fluorescent intensity of a microarray reading. The statistical data computed is then used to calculate a baseline value of (X*Standard Deviation+Mean) for each gene. This is the baseline reading for the gene from which all other samples will be compared. X is a stringency variable selected by the person formulating the portfolio. Higher values of X are more stringent than lower. Preferably, X is in the range of 0.5 to 3 with 2 to 3 being more preferred and 3 being most preferred.

Ratios between each experimental sample (those displaying the condition of interest) versus baseline readings are then calculated. The ratios are then transformed to base 10 logarithmic values for ease of data handling by the software. This enables down regulated genes to display negative values necessary for optimization according to the Markman mean-variance algorithm using the Wagner Software.

The preprocessed data comprising these transformed ratios are used as inputs in place of the asset return values that are normally used in the Wagner Software when it is used for financial analysis purposes.

Once an efficient frontier is formulated, an optimized portfolio is selected for a given input level (return) or variance that corresponds to a point on the frontier. These inputs or variances are the predetermined standards set by the person formulating the portfolio. Stated differently, one seeking the optimum portfolio determines an acceptable input level (indicative of sensitivity) or a given level of variance (indicative of specificity) and selects the genes that lie along the efficient frontier that correspond to that input level or variance. The Wagner Software can select such genes when an input level or variance is selected. It can also assign a weight to each gene in the portfolio as it would for a stock in a stock portfolio.

Determining whether a sample has the condition for which the portfolio is diagnostic can be conducted by comparing the expression of the genes in the portfolio for the patient sample with calculated values of differentially expressed genes used to establish the portfolio. Preferably, a portfolio value is first generated by summing the multiples of the intensity value of each gene in the portfolio by the weight assigned to that gene in the portfolio selection process. A boundary value is then calculated by (Y*standard deviation+mean of the portfolio value for baseline groups) where Y is a stringency value having the same meaning as X described above. A sample having a portfolio value greater than the boundary value of the baseline class is then classified as having the condition. If desired, this process can be conducted iteratively in accordance with well known statistical methods for improving confidence levels. Optionally one can reiterate this process until best prediction accuracy is obtained.

The process of portfolio selection and characterization of an unknown is summarized as follows:
1. Choose baseline class
2. Calculate mean, and standard deviation of each gene for baseline class samples
3. Calculate (X*Standard Deviation+Mean) for each gene. This is the baseline reading from which all other samples will be compared. X is a stringency variable with higher values of X being more stringent than lower.
4. Calculate ratio between each Experimental sample versus baseline reading calculated in step 3.
5. Transform ratios such that ratios less than 1 are negative (eg. using Log base 10). (Down regulated genes now correctly have negative values necessary for MV optimization).
6. These transformed ratios are used as inputs in place of the asset returns that are normally used in the software application.
7. The software will plot the efficient frontier and return an optimized portfolio at any point along the efficient frontier.
8. Choose a desired return or variance on the efficient frontier.
9. Calculate the Portfolio's Value for each sample by summing the multiples of each gene's intensity value by the weight generated by the portfolio selection algorithm.
10. Calculate a boundary value by adding the mean Portfolio Value for Baseline groups to the multiple of Y and the Standard Deviation of the Baseline's Portfolio Values. Values greater than this boundary value shall be classified as the Experimental Class.
11. Optionally one can reiterate this process until best prediction accuracy is obtained.

A second portfolio can optionally be created by reversing the baseline and experimental calculation. This creates a new portfolio of genes which are up-regulated in the original baseline class. This second portfolio's value can be subtracted from the first to create a new classification value based on multiple portfolios.

Another useful method of pre-selecting genes from gene expression data so that it can be used as input for a process for selecting a portfolio is based on a threshold given by $$1 \leq \left| \frac{(\mu_t - \mu_n)}{(\sigma_t + \sigma_n)} \right|,$$

where $\mu_t$ is the mean of the subset known to possess the disease or condition, $\mu_n$ is the mean of the subset of normal samples, and $\sigma_t + \sigma_n$ represent the combined standard deviations. A signal to noise cutoff can also be used by pre-selecting the data according to a relationship such as $$0.5 \leq \left| \frac{(\mu_t - \text{MAX}_n)}{(\sigma_t + \sigma_n)} \right|.$$

This ensures that genes that are pre-selected based on their differential modulation are differentiated in a clinically significant way. That is, above the noise level of instrumentation appropriate to the task of measuring the diagnostic parameters. For each marker pre-selected according to these criteria, a matrix is established in which columns represents samples, rows represent markers and each element is a normalized intensity measurement for the expression of that marker according to the relationship $$\left|\frac{(\mu_t - I)}{(\mu_t)}\right|$$

where I is the intensity measurement.

Using this process of creating input for financial portfolio software make also allows one to set additional boundary conditions to define the optimal portfolios. For example, portfolio size can be limited to a fixed range or number of markers. This can be done either by making data pre-selection criteria more stringent $$\left(e.g., .8 \leq \left|\frac{(\mu_t - MAX_n)}{(\sigma_t + \sigma_n)}\right|\right)$$

instead of $$0.5 \leq \left|\frac{(\mu_t - MAX_n)}{(\sigma_t + \sigma_n)}\right|$$

or by using programming features such as restricting portfolio size. One could, for example, set the boundary condition that the efficient frontier is to be selected from among only the optimal 10 genes. One could also use all of the genes pre-selected for determining the efficient frontier and then limit the number of genes selected (e.g., no more than 10).

The process of selecting a portfolio can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with breast cancer. Output from the method would be an optimized set of genes that could include some genes that are expressed in peripheral blood as well as in diseased breast tissue. If sample used in the testing method are obtained from peripheral blood and certain genes differentially expressed in instances of breast cancer could also be differentially expressed in peripheral blood, then a heuristic rule can be applied in which a portfolio is selected from the efficient frontier excluding those that are differentially expressed in peripheral blood. Of course, the rule can be applied prior to the formation of the efficient frontier by, for example, applying the rule during data pre-selection.

Other heuristic rules can be applied that are not necessarily related to the biology in question. For example, one can apply the rule that only a given percentage of the portfolio can be represented by a particular gene or genes. Commercially available software such as the Wagner Software readily accommodates these types of heuristics. This can be useful, for example, when factors other than accuracy and precision (e.g., anticipated licensing fees) have an impact on the desirability of including one or more genes.

Other relationships aside from the mean-variance relationship can be used in the method of the invention provided that they optimize the portfolio according to predetermined attributes such as assay accuracy and precision. Two examples are the Martin simultaneous equation approach (Elton, Edwin J. and Martin J. Gruber (1987), *Modern Portfolio Theory Investment Analysis*, Third Edition, John Wiley, New York, 1987) and Genetic Algorithms (Davis, L., (1989), *Adapting Operator Probabilities in Genetic Algorithms*, in *Proceedings of the Third International Conference on Genetic Algorithms*, Morgan Kaufmann: San Mateo, pp. 61-69). There are also many ways to adapt the mean-variance relationship to handle skewed data such as where a marker detection technology exhibits a known bias. These include, for example, the Semi-Deviation method in which the square root of the average squared (negative) deviation from a reference signal and includes only those signal values that fall below the reference signal.

Articles of this invention include representations of the gene expression profiles that make up the portfolios useful for treating, diagnosing, prognosticating, and otherwise assessing diseases. These representations are reduced to a medium that can be automatically read by a machine such as computer readable media (magnetic, optical, and the like). The articles can also include instructions for assessing the gene expression profiles in such media. For example, the articles may comprise a CD ROM having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format.

Different types of articles of manufacture according to the invention are media or formatted assays used to reveal gene expression profiles. These can comprise, for example, microarrays in which sequence complements or probes are affixed to a matrix to which the sequences indicative of the genes of interest combine creating a readable determinant of their presence. When such a microarray contains an optimized portfolio great savings in time, process steps, and resources are attained by minimizing the number of cDNA or oligonucleotides that must be applied to the substrate, reacted with the sample, read by an analyzer, processed for results, and (sometimes) verified.

Other articles according to the invention can be fashioned into reagent kits for conducting hybridization, amplification, and signal generation indicative of the level of expression of the genes in the portfolios established through the method of the invention. Kits made according to the invention include formatted assays for determining the gene expression profiles. These can include all or some of the materials needed to conduct the assays such as reagents and instructions.

EXAMPLES

Example 1

Producing 2 an Optimized Portfolio

Gene expression data was recently produced from tissue samples representative of eleven different types of cancers. The data was published in Cancer Research 61:7388-7393, 2001 and are available online as referenced in the publication See, Andrew I. Su et al., "Molecular Classification of Human Carcinomas by Use of Gene Expression Signatures." The data included intensity measurements obtained with the use of "U95" oligonucleotide microarray (commercially available from Affymetrix, Inc.).

Measurements of the expression of genes from the published data (fluorescent intensity measurements) was used to select optimum gene expression portfolios for a panel of markers to determine whether a circulating cell is indicative of the presence of breast cancer, prostate cancer, ovarian cancer, colorectal cancer, or lung cancer. Such circulating cells would preferably be epithelial cells.

The data in the study was collected from the following samples: 24 adenocarcinomas, 12 infiltrating ductal breast adenocarcenomas, 21 colorectal adenocarcinomas, 23 ovarian adenocarcinomas, 25 lung carcinomas, and data from the following additional samples: 19 prostate adenocarcinomas, 12 breast carinomas, 13 colon carcinomas, 13 ovarian carcinomas, 13 ovarian carcinomas, and 89 lung carcenomas.

Using intensity readings from a collection of normal samples as the baseline class, the arithmetic mean, and standard deviation of each gene were calculated followed by a calculation of the value (X*Standard Deviation+Mean) for each gene. The stringency variable, X, was assigned a value of 3 in this case. Ratios were then calculated between each Experimental sample described in the study versus the baseline value calculations. The ratios were transformed into common logarithms. These values were then used as the input values for the Wagner Software.

This procedure selected an efficient frontier along which a minimum set of markers for each tumor type that have the lowest amount of variation for a selected level of differential (chosen at the best signal to noise ratio point). Optimization by the software resulted in the selection of a portfolio of 24 genes including 2 for prostate cancer, 5 for breast cancer, 6 for colon cancer, 2 for ovarian cancer, and 9 for lung cancer markers (Table 1).

TABLE 1

| Cancer Type | Accession | Name | Description | Seq, ID No. |
|---|---|---|---|---|
| PR | NM_001648 | KLK3 | kallikrein 3, (prostate specific antigen) | Seq. ID No. 1 |
| PR | NM_005551 | KLK2 | kallikrein 2, prostatic | Seq. ID No. 2 |
| BR | NM_004064 | CDKN1B | cyclin-dependent kinase inhibitor 1B (p27, Kip1) | Seq. ID No. 31 |
| BR | NM_002411 | MGB1 | mammaglobin 1 | Seq. ID No. 3 |
| BR | NM_005264 | GFRA1 | GDNF family receptor alpha 1 | Seq. ID No. 4 |
| BR | none | C18ORF1 | chromosome 18 open reading frame 1 | Seq. ID No. 98 |
| BR | NM_000095 | COMP | cartilage oligomeric matrix protein | Seq. ID No. 6 |
| CO | NM_001804 | CDX1 | caudal type homeo box transcription factor 1 | Seq. ID No. 8 |
| CO | NM_001046 | SLC12A2 | solute carrier family 12 (sodium/potassium/chloride transporters), member 2 | Seq. ID No. 9 |
| CO | NM_001285 | CLCA1 | chloride channel, calcium activated, family member 1 | Seq. ID No. 11 |
| CO | NM_007052 | NOX1 | NADPH oxidase 1 | Seq. ID No. 13 |

TABLE 1-continued

| Cancer Type | Accession | Name | Description | Seq, ID No. |
|---|---|---|---|---|
| CO | NM_002457 | MUC2 | mucin 2, intestinal/tracheal | Seq. ID No. 14 |
| CO | NM_004063 | CDH17 | cadherin 17, LI cadherin | Seq. ID No. 15 |
| LU_A | NM_021950 | MS4A2 | membrane-spanning 4-domains, subfamily A, member 2 | Seq. ID No. 17 |
| LU_A | NM_000964 | ASAHL | N-acylsphingosine amidohydrolase (acid ceramidase)-like | Seq. ID No. 18 |
| LU_A | NM_006495 | EVI2B | ecotropic viral integration site 2B | Seq. ID No. 20 |
| LU_A | NM_006864 | LILRB3 | leukocyte immunoglobulin-like receptor, subfamily B | Seq. ID No. 21 |
| LU_A | X67301 | None | H. sapiens mRNA for IgM heavy chain constant region (Ab63) | Seq. ID No. 22 |
| LU_A | NM_002123 | HLA-DQB1 | major histocompatibility complex, class II, DQ beta 1 | Seq. ID No. 23 |
| LU_S | NM_000673 | ADH7 | alcohol dehydrogenase 7 (class IV), mu or sigma polypeptide | Seq. ID No. 24 |
| LU_S | NM_003722 | TP63 | tumor protein 63 kDa with strong homology to p53 | Seq. ID No. 26 |
| LU_S | none | SOX2 | SRY (sex determining region Y)-box 2 | Seq. ID No. 32 |
| OV | NM_000906 | NPR1 | natriuretic peptide receptor A/guanylate cyclase A | Seq. ID No. 28, 29 |
| OV | NM_000378 | WT1 | Wilms tumor 1 | Seq. ID No. 30 |

Example 2

Heuristic Step

A heuristic rule was further applied to the portfolio obtained in Example 1. That is, the rule stated that if the gene/marker identified would likely be expressed in peripheral blood or were well-characterized tissue markers (e.g. PSA, mammaglobin, etc.), then such genes/marker would be removed from the portfolio. Application of the rule enabled the establishment of a portfolio of genes/markers that are optimized for use in a screening application in which the patient sample is obtained by assaying components found in the peripheral blood such as epithelial cells. The result of the selected portfolio contains 31 genes as shown in Table 2.

TABLE 2

| Cancer Type | Accession | Name | Description | Seq. ID No. |
|---|---|---|---|---|
| PR | Hs.12784 | KIAA0293 | KIAA0293 protein | Seq. ID No. 67 |
| PR | NM_006562 | LBX1 | transcription factor similar to D. melanogaster homeodomain | Seq. ID No. 33 |

TABLE 2-continued

| Cancer Type | Accession | Name | Description | Seq. ID No. |
|---|---|---|---|---|
| PR | NM_016026 | LOC51109 | protein lady bird late CGI-82 protein | Seq. ID No. 34 |
| PR | HG2261-HT2352 | None | Antigen | Seq. ID No. 99 |
| PR | NM_012449 | STEAP | six transmembrane epithelial antigen of the prostate | Seq. ID No. 35 |
| PR | NM_001634 | AMD1 | S-adenosyl-methionine decarboxylase 1 | Seq. ID No. 36 |
| PR | HG2261-HT2351 | None | Antigen I | Seq. ID No. 100 |
| PR | NM_006457 | LIM | LIM protein (similar to rat protein kinase C-binding enigma) | Seq. ID No. 37 |
| BR | NM_005853 | IRX5 | iroquois homeobox protein 5 | Seq. ID No. 38 |
| BR | NM_005264 | GFRA1 | GDNF family receptor alpha 1 | Seq. ID No. 39, 40 |
| BR | none | C18ORF1 | chromosome 18 open reading frame 1 | Seq. ID No. 98 |
| BR | NM_000095 | COMP | cartilage oligomeric matrix protein (pseudoachondroplasia, epiphyseal dysplasia 1, multiple) | Seq. ID No. 41, 42 |
| CO | NM_001265 | CDX2 | caudal type homeo box transcription factor 2 | Seq. ID No. 43 |
| CO | NM_001046 | SLC12A2 | solute carrier family 12 (sodium/potassium/chloride transporters), member 2 | Seq. ID No. 44, 45 |
| CO | NM_001285 | CLCA1 | chloride channel, calcium activated, family member 1 | Seq. ID No. 46, 47 |
| CO | NM_004063 | CDH17 | cadherin 17, LI cadherin (liver-intestine) | Seq. ID No. 48, 49 |
| OV | NM_000906 | NPR1 | natriuretic peptide receptor A/guanylate cyclase A (atrionatriuretic peptide receptor A) | Seq. ID No. 50, 51 |
| OV | NM_005504 | BCAT1 | branched chain aminotransferase 1, cytosolic | Seq. ID No. 52 |
| OV | NM_002398 | MEIS1 | Meis1 (mouse) homolog | Seq. ID No. 53 |
| OV | none | SPON1 | spondin 1, (f-spondin) extracellular matrix protein | Seq. ID No. 69 |
| OV | NM_001692 | None | M25809:Human endomembrane proton pump subunit mRNA I GenBank == M25809 | Seq. ID No. 54 |
| OV | NM_002774 | KLK6 | kallikrein 6 (neurosin, zyme) | Seq. ID No. 55 |
| LU_A | NM_000964 | ASAHL | N-acylsphingosine amidohydrolase (acid ceramidase)-like | Seq. ID No. 56, 57 |
| LU_A | NM_002838 | PTPRC | protein tyrosine phosphatase, receptor type, C | Seq. ID No. 58 |
| LU_A | NM_015364 | MD-2 | MD-2 protein | Seq. ID No. 59 |
| LU_A | NM_006875 | PIM2 | pim-2 oncogene | Seq. ID No. 60 |
| LU_S | NM_005554 | KRT6A | keratin 6A | Seq. ID No. 61 |
| LU_S | NM_000673 | ADH7 | alcohol dehydrogenase 7 (class IV), mu or sigma polypeptide | Seq. ID No. 62, 63 |
| LU_S | NM_003722 | TP63 | tumor protein 63 kDa with strong homology to p53 | Seq. ID No. 64, 65 |
| LU_S | none | SOX2 | SRY (sex determining region Y)-box 2 | Seq. ID No. 32 |
| LU_S | NM_005688 | ABCC5 | ATP-binding cassette, sub-family C (CFTR/MRP), member 5 | Seq. ID No. 66 |

Example 3

Prognostic Portfolios

A patient sample set with known clinical outcomes was used to test the portfolio selection method of the invention. The sample set is described in van't Veer, L. J et al. Gene Expression Profiling Predicts Clinical Outcome of Breast Cancer, Nature, 415, 530-536, (2002), incorporated herein by reference. In that study, breast tissue samples were obtained from 78 patients exhibiting sporadic breast tumors. The patients were all less than 55 years of age and presented with a tumor less than 5 cm. All were lymph node negative. Thirty four of the patients presented with distant metastases in less than 5 years while 44 showed no distant metastases in the same period.

Sample preparation and expression profiling are described in the reference. A prognostic marker portfolio of 70 genes was selected from consideration of about 5,000 genes differentially expressed in patients with different prognoses (metastasis v. no metastasis). The selection was made based on unsupervised clustering followed by a correlation coefficient analysis. This was done by calculating the correlation coefficient of the expression of each gene with disease outcome. Those significantly associated with disease by this analysis were then rank ordered with successive groups of five compared using the "leave-one-out" method until an "optimized" panel of 70 genes was selected.

The data from the study were then processed according to the method of the invention. Sample number 54 was removed from further analysis due to a high percentage of missing values. The mean and standard deviation of the intensity measurements for each gene were calculated using the non-metastatic samples as the baseline. A discriminating value of X*(Standard Deviation+Mean) was then calculated for each baseline gene (X was assigned a value of 3). This value was used to ensure the resulting portfolio would be stringent. A ratio of the discriminating value to the baseline value was then calculated for each metastatic sample. This ratio was then converted to a common logarithm. This data was then imported into Wagner Software which produced an efficient frontier from which a portfolio of 16 genes was selected. The baseline and experimental values were then reversed and a second portfolio of 12 markers representing genes up-regulated in the non-metastatic cases was produced. The second portfolio's value is subtracted from the first portfolios value to create a combined portfolio value from all 28 genes. This final portfolio is comprised of genes from Seq. ID No. 70-97. 17 of the genes of this portfolio were also present in the 70 gene portfolio described in the reference. The genes of the portfolio are identified below. (Seq. ID No. 70, Seq. ID No. 72, Seq. ID No. 73-77, Seq. ID No. 79, Seq. ID No. 80, Seq. ID No. 85, Seq. ID No. 87, Seq. ID No. 91-93, Seq. ID No. 95 and Seq. ID. No. 97.)

| 28 Gene list (2 Portfolios) Up in Metastatic Patients (Portfolio 1) | |
|---|---|
| Contig53226_RC | Seq. ID No. 89 |
| NM_012214 | Seq. ID No. 82 |
| NM_020386 | Seq. ID No. 86 |
| NM_004504 | Seq. ID No. 81 |
| AA555029_RC | Seq. ID No. 70 |
| AL080059 | Seq. ID No. 74 |
| AF055033 | Seq. ID No. 73 |
| NM_016448 | Seq. ID No. 85 |
| Contig40831_RC | Seq. ID No. 95 |
| Contig63649_RC | Seq. ID No. 91 |
| Contig24252_RC | Seq. ID No. 93 |
| NM_000436 | Seq. ID No. 75 |
| NM_002019 | Seq. ID No. 77 |
| Contig55313_RC | Seq. ID No. 90 |
| Contig25991 | Seq. ID No. 97 |
| NM_000788 | Seq. ID No. 76 |
| Up in Non-Metastatic Patients (Portfolio 2) AB033007 | Seq. ID No. 71 |
| Contig42421_RC | Seq. ID No. 96 |
| NM_003748 | Seq. ID No. 78 |
| NM_013262 | Seq. ID No. 83 |
| NM_003862 | Seq. ID No. 79 |
| NM_003882 | Seq. ID No. 80 |
| Contig48328_RC | Seq. ID No. 87 |
| NM_015416 | Seq. ID No. 84 |
| AB037863 | Seq. ID No. 72 |
| Contig27312_RC | Seq. ID No. 88 |
| Contig32125_RC | Seq. ID No. 92 |
| Contig49670_RC | Seq. ID No. 94 |
| 17 Overlap | |
| Systematic name | |
| NM_003862 | Seq. ID No. 79 |
| NM_003882 | Seq. ID No. 80 |
| Contig48328_RC | Seq. ID No. 87 |
| AA555029_RC | Seq. ID No. 70 |
| AL080059 | Seq. ID No. 74 |
| AF055033 | Seq. ID No. 73 |
| AF055033 | Seq. ID No. 73 |
| NM_016448 | Seq. ID No. 85 |
| AB037863 | Seq. ID No. 72 |
| Contig40831_RC | Seq. ID No. 95 |
| Contig63649_RC | Seq. ID No. 91 |
| Contig24252_RC | Seq. ID No. 93 |
| NM_000436 | Seq. ID No. 75 |
| NM_002019 | Seq. ID No. 77 |
| Contig32125_RC | Seq. ID No. 92 |
| Contig25991 | Seq. ID No. 97 |
| NM_000788 | Seq. ID No. 76 |

The two portfolios were then used to determine the prognosis of the 78 original samples by-comparing gene expression signatures from the microarray data according to the method for testing the classification accuracy described in the reference. In the case of the 70 gene portfolio, 81% of the samples were properly characterized according to an optimized threshold biased to include ambiguous signatures as indicative of poor prognosis (85% for an absolute threshold). This portfolio misclassified 3 patients with a poor prognosis as having a good prognosis using the optimized threshold (5 for the absolute threshold). Twelve patients with a good prognosis were misclassified as having a good prognosis when they had a bad prognosis using the optimized threshold (8 for absolute).

In the case of the 28 gene portfolio, 94% of the samples were properly characterized according to an optimized threshold biased to include ambiguous signatures as indicative of poor prognosis (93% for an absolute threshold). This portfolio misclassified 3 patients with a poor prognosis as having a good prognosis using the optimized threshold (5 for the absolute threshold). Three patients with a good prognosis were misclassified as having a good prognosis when they had a bad prognosis using the optimized threshold (2 for absolute).

Comparing the two profiles, it is apparent that the profiles selected according to the method of the invention are much more economical and produce results that are more accurate and reliable than those of the comparative portfolio.

I claim:

1. A method of diagnosing prostate, breast, colon, lung or ovarian cancer comprising identifying from a cell from a human patient, the differential modulation of each gene (relative to the expression of the same genes in a normal population) in a gene expression portfolio selected for use with peripheral blood samples and wherein the genes of said portfolio consist of those having Seq. ID. No. 32-37, 69, and 98-100 or which express products having such sequences, and comparing such modulation with that of the same genes found in cells associated with human prostate, breast, colon, lung, or ovarian cancers; and diagnosing the patient as having prostate, breast, colon, lung or ovarian cancer if the modulation of the gene expression portfolio of the patient is the same as that of the genes found in cells associated with prostate, breast, colon, lung or ovarian cancer and diagnosing the patient as not having prostate, breast, colon, lung or ovarian cancer if the modulation of the gene expression portfolio of the patient is not the same as that of the genes found in cells associated with prostate, breast, colon, lung or ovarian cancer.

2. The method of claim 1 wherein there is at least a 2 fold difference in the expression of the modulated genes.

3. The method of claim 1 wherein the p-value indicating differential modulation is less than 0.05.

* * * * *

SEQUENCE LISTING

```
<160> NUMBER OF SEQ ID NOS: 100

<210> SEQ ID NO 1
<211> LENGTH: 1466
<212> TYPE: DNA
<213> ORGANISM: human

<400> SEQUENCE: 1
agccccaagc ttaccacctg cacccggaga gctgtgtgtc accatgtggg tcccggttgt      60
cttcctcacc ctgtccgtga cgtggattgg tgctgcaccc ctcatcctgt ctcggattgt     120
gggaggctgg gagtgcgaga agcattccca acccotggcag gtgcttgtgg cctctcgtgg    180
cagggcagtc tgcggcggtg ttctggtgca ccccagtgg gtcctcacag ctgcccactg     240
```

-continued

```
catcaggaac aaaagcgtga tcttgctggg tcggcacagc ctgtttcatc ctgaagacac    300
aggccaggta tttcaggtca gccacagctt cccacacccg ctctacgata tgagcctcct    360
gaagaatcga ttcctcaggc caggtgatga ctccagccac gacctcatgc tgctccgcct    420
gtcagagcct gccgagctca cggatgctgt gaaggtcatg gacctgccca cccaggagcc    480
agcactgggg accacctgct acgcctcagg ctggggcagc attgaaccag aggagttctt    540
gaccccaaag aaacttcagt gtgtggacct ccatgttatt ccaatgacg tgtgtgcgca    600
agttcaccct cagaaggtga ccaagttcat gctgtgtgct ggacgctgga caggggggcaa    660
aagcacctgc tcgggtgatt ctgggggccc acttgtctgt aatggtgtgc ttcaaggtat    720
cacgtcatgg ggcagtgaac catgtgccct gcccgaaagg ccttccctgt acaccaaggt    780
ggtgcattac cggaagtgga tcaaggacac catcgtggcc aaccctgag cacccctatc    840
aacccctat tgtagtaaac ttggaaccttt ggaaatgacc aggccaagac tcaagcctcc    900
ccagttctac tgacctttgt ccttaggtgt gaggtccagg gttgctagga aagaaatca    960
gcagacacag gtgtagacca gagtgtttct taaatggtgt aattttgtcc tctctgtgtc   1020
ctggggaata ctggccatgc ctggagacat atcactcaat ttctctgagg acacagatag   1080
gatgggtgt ctgtgttatt tgtggggtac agagatgaaa gaggggtggg atccacactg   1140
agagagtgga gagtgacatg tgctggacac tgtccatgaa gcactgagca aagctggag   1200
gcacaacgca ccagacactc acagcaagga tggagctgaa aacataaccc actctgtcct   1260
ggaggcactg ggaagcctag agaaggctgt gagccaagga gggagggtct tcctttggca   1320
tgggatgggg atgaagtaag gagagggact ggaccccctg gaagctgatt cactatgggg   1380
ggaggtgtat tgaagtcctc cagacaaccc tcagatttga tgatttccta gtagaactca   1440
cagaaataaa gagctgttat actgtg                                         1466
```

<210> SEQ ID NO 2
<211> LENGTH: 786
<212> TYPE: DNA
<213> ORGANISM: human

<400> SEQUENCE: 2

```
atgtgggacc tggttctctc catcgccttg tctgtggggt gcactggtgc cgtgcccctc     60
atccagtctc ggattgtggg aggctgggag tgtgagaagc attcccaacc ctggcaggtg    120
gctgtgtaca gtcatggatg ggcacactgt gggggtgtcc tggtgcaccc ccagtgggtg    180
ctcacagctg cccattgcct aaagaagaat agccaggtct ggctgggtcg gcacaacctg    240
tttgagcctg aagacacagg ccagagggtc cctgtcagcc acagcttccc acaccgctc    300
tacaatatga gccttctgaa gcatcaaagc cttagaccag atgaagactc cagccatgac    360
ctcatgctgc tccgcctgtc agagcctgcc aagatcacag atgttgtgaa ggtcctgggc    420
ctgcccaccc aggagccagc actggggacc acctgctacg cctcaggctg gggcagcatc    480
gaaccagagg agttcttgcg ccccaggagt cttcagtgtg tgagcctcca tctcctgtcc    540
aatgacatgt gtgctagagc ttactctgag aaggtgacaga agttcatgtt gtgtgctggg    600
ctctggacag gtggtaaaga cacttgtggg ggtgattctg ggggtccact tgtctgtaat    660
ggggtgcttc aaggtatcac atcatggggc cctgagccat gtgccctgcc tgaaaagcct    720
gctgtgtaca ccaaggtggt gcattaccgg aagtggatca aggacaccat cgcagccaac    780
ccctga                                                                786
```

<210> SEQ ID NO 3
<211> LENGTH: 503
<212> TYPE: DNA
<213> ORGANISM: human

<400> SEQUENCE: 3

| | | | | | | |
|---|---|---|---|---|---|---|
| gacagcggct | tccttgatcc | ttgccacccg | cgactgaaca | ccgacagcag | cagcctcacc | 60 |
| atgaagttgc | tgatggtcct | catgctggcg | ccctctccc | agcactgcta | cgcaggctct | 120 |
| ggctgcccct | tattggagaa | tgtgatttcc | aagacaatca | atccacaagt | gtctaagact | 180 |
| gaatacaaag | aacttcttca | agagttcata | gacgacaatg | ccactacaaa | tgccatagat | 240 |
| gaattgaagg | aatgttttct | taaccaaacg | gatgaaactc | tgagcaatgt | tgaggtgttt | 300 |
| atgcaattaa | tatatgacag | cagtctttgt | gatttatttt | aactttctgc | aagacctttg | 360 |
| gctcacagaa | ctgcagggta | tggtgagaaa | ccaactacgg | attgctgcaa | accacacctt | 420 |
| ctctttctta | tgtcttttta | ctacaaaacta | caagacaatt | gttgaaacct | gctatacatg | 480 |
| tttatttttaa | taaattgatg | gca | | | | 503 |

<210> SEQ ID NO 4
<211> LENGTH: 2560
<212> TYPE: DNA
<213> ORGANISM: human

<400> SEQUENCE: 4

| | | | | | | |
|---|---|---|---|---|---|---|
| gaattccggc | cagaagaaat | ctggcctcgg | aacacgccat | tctccgcgcc | gcttccaata | 60 |
| accactaaca | tccctaacga | gcatccgagc | cgagggctct | gctcggaaat | cgtcctggcc | 120 |
| caactcggcc | cttcgagctc | tcgaagatta | ccgcatctat | tttttttttc | tttttttttct | 180 |
| tttcctagcg | cagataaagt | gagcccggaa | agggaaggag | ggggcgggga | caccattgcc | 240 |
| ctgaaagaat | aaataagtaa | ataaacaaac | tggctcctcg | ccgcagctgg | acgcggtcgg | 300 |
| ttgagtccag | gttgggtcgg | acctgaaccc | ctaaaagcgg | aaccgcctcc | cgccctcgcc | 360 |
| atcccggagc | tgagtcgccg | gcggcggtgg | ctgctgccag | acccggagtt | cctctttca | 420 |
| ctggatggag | ctgaactttg | gcggccaga | gcagcacagc | tgtccgggga | tcgctgcacg | 480 |
| ctgagctccc | tcggcaagac | ccagcggcgg | ctcgggattt | ttttgggggg | gcggggacca | 540 |
| gccccgcgcc | ggcaccatgt | tcctggcgac | cctgtacttc | gcgctgccgc | tcttggactt | 600 |
| gctcctgtcg | gccgaagtga | gcggcggaga | ccgcctggat | tgcgtgaaag | ccagtgatca | 660 |
| gtgcctgaag | gagcagagct | gcagcaccaa | gtaccgcacg | ctaaggcagt | gcgtggcggg | 720 |
| caaggagacc | aacttcagcc | tggcatccgg | cctggaggcc | aaggatgagt | gccgcagcgc | 780 |
| catggaggcc | ctgaagcaga | agtcgctcta | caactgccgc | tgcaagcggg | gtatgaagaa | 840 |
| ggagaagaac | tgcctgcgca | tttactggag | catgtaccag | agcctgcagg | gaaatgatct | 900 |
| gctggaggat | tccccatatg | aaccagttaa | cagcagattg | tcagatatat | tccgggtggt | 960 |
| cccattcata | tcagatgttt | ttcagcaagt | ggagcacatt | cccaaaggga | caactgcct | 1020 |
| ggatgcagcg | aaggcctgca | acctcgacga | catttgcaag | aagtacaggt | cggcgtacat | 1080 |
| caccccgtgc | accaccagcg | tgtccaacga | tgtctgcaac | cgccgcaagt | gccacaaggc | 1140 |
| cctccggcag | ttcttgaca | aggtcccggc | caagcacagc | tacggaatgc | tcttctgctc | 1200 |
| ctgccgggac | atcgcctgca | cagagcggag | gcgacagacc | atcgtgcctg | tgtgctccta | 1260 |
| tgaagagagg | gagaagccca | actgtttgaa | tttgcaggac | tcctgcaaga | cgaattacat | 1320 |
| ctgcagatct | cgccttgcgg | attttttttac | caactgccag | ccagagtcaa | ggtctgtcag | 1380 |

```
cagctgtcta aaggaaaact acgctgactg cctcctcgcc tactcggggc ttattggcac      1440
agtcatgacc cccaactaca tagactccag tagcctcagt gtggcccat ggtgtgactg       1500 cagcaacagt gggaacgacc tagaagagtg cttgaaattt ttgaatttct tcaaggacaa      1560
tacatgtctt aaaaatgcaa ttcaagcctt tggcaatggc tccgatgtga ccgtgtggca     1620
gccagccttc ccagtacaga ccaccactgc cactaccacc actgccctcc gggttaagaa      1680
caagcccctg gggccagcag ggtctgagaa tgaaattccc actcatgttt tgccaccgtg     1740
tgcaaattta caggcacaga agctgaaatc caatgtgtcg ggcaatacac acctctgtat     1800
ttccaatggt aattatgaaa agaaggtct cggtgcttcc agccacataa ccacaaaatc      1860
aatggctgct cctccaagct gtggtctgag cccactgctg gtcctggtgg taaccgctct     1920
gtccacccta ttatctttaa cagaaacatc atagctgcat taaaaaaata caatatggac     1980
atgtaaaaag acaaaaacca agttatctgt ttcctgttct cttgtatagc tgaaattcca    2040
gtttaggagc tcagttgaga aacagttcca ttcaactgga acattttttt ttttcctttt    2100
aagaaagctt cttgtgatcc ttcggggctt ctgtgaaaaa cctgatgcag tgctccatcc    2160
aaactcagaa ggctttggga tatgctgtat tttaaaggga cagtttgtaa cttgggctgt    2220
aaagcaaact ggggctgtgt tttcgatgat gatgatcatc atgatcatga tgattttaac    2280
agttttactt ctggcctttc ctagctagag aaggagttaa tatttctaag gtaactccca    2340
tatctccttt aatgacattg atttctaatg atataaattt cagcctacat tgatgccaag    2400
cttttttgcc acaaagaaga ttcttaccaa gagtgggctt tgtggaaaca gctggtactg    2460
atgttcacct ttatatatgt actagcattt tccacgctga tgtttatgta ctgtaaacag    2520
ttctgcactc ttgtacaaaa gaaaaaacca cccggaattc                          2560
```

<210> SEQ ID NO 5
<211> LENGTH: 2560
<212> TYPE: DNA
<213> ORGANISM: human

<400> SEQUENCE: 5

```
gaattccggc cagaagaaat ctggcctcgg aacacgccat tctccgcgcc gcttccaata      60
accactaaca tccctaacga gcatccgagc cgagggctct gctcggaaat cgtcctggcc     120
caactcggcc cttcgagctc tcgaagatta ccgcatctat ttttttttc ttttttttct     180 tttcctagcg cagataaagt gagcccggaa agggaaggag ggggcgggga caccattgcc     240
ctgaaagaat aaataagtaa ataaacaaac tggctcctcg ccgcagctgg acgcggtcgg    300
ttgagtccag gttgggtcgg acctgaaccc ctaaaagcgg aaccgcctcc cgccctcgcc    360
atcccggagc tgagtcgccg gcggcggtgg ctgctgccag accggagtt cctctttca     420 ctggatggag ctgaactttg gcggccaga gcagcacagc tgtccgggga tcgctgcacg    480
ctgagctccc tcggcaagac ccagcggcgg ctcgggattt ttttgggggg gcggggacca   540
gccccgcgcc ggcaccatgt tcctggcgac cctgtacttc gcgctgccgc tcttggactt    600
gctcctgtcg gccgaagtga gcggcggaga ccgcctggat tgcgtgaaag ccagtgatca    660
gtgcctgaag gagcagagct gcagcaccaa gtaccgcacg ctaaggcagt gcgtggcggg    720
caaggagacc aacttcagcc tggcatccgg cctggaggcc aaggatgagt gccgcagcgc    780
catggaggcc ctgaagcaga agtcgctcta caactgccgc tgcaagcggg gtatgaagaa    840
ggagaagaac tgcctgcgca tttactggag catgtaccag agcctgcagg gaatgatct    900 gctggaggat tccccatatg aaccagttaa cagcagattg tcagatatat tccgggtggt    960
```

-continued

```
cccattcata tcagatgttt ttcagcaagt ggagcacatt cccaaaggga acaactgcct    1020
ggatgcagcg aaggcctgca acctcgacga catttgcaag aagtacaggt cggcgtacat    1080
caccccgtgc accaccagcg tgtccaacga tgtctgcaac cgccgcaagt gccacaaggc    1140
cctccggcag ttctttgaca aggtcccggc caagcacagc tacggaatgc tcttctgctc    1200
ctgccgggac atcgcctgca cagagcggag gcgacagacc atcgtgcctg tgtgctccta    1260
tgaagagagg gagaagccca actgtttgaa tttgcaggac tcctgcaaga cgaattacat    1320
ctgcagatct cgccttgcgg attttttttac caactgccag ccagagtcaa ggtctgtcag    1380
cagctgtcta aaggaaaact acgctgactg cctcctcgcc tactcggggc ttattggcac    1440
agtcatgacc cccaactaca tagactccag tagcctcagt gtggcccat ggtgtgactg    1500 cagcaacagt gggaacgacc tagaagagtg cttgaaattt ttgaatttct tcaaggacaa    1560
tacatgtctt aaaaatgcaa ttcaagcctt tggcaatggc tccgatgtga ccgtgtggca    1620
gccagccttc ccagtacaga ccaccactgc cactaccacc actgccctcc gggttaagaa    1680
caagcccctg gggccagcag ggtctgagaa tgaaattccc actcatgttt tgccaccgtg    1740
tgcaaattta caggcacaga agctgaaatc caatgtgtcg ggcaatacac acctctgtat    1800
ttccaatggt aattatgaaa agaaggtct cggtgcttcc agccacataa ccacaaaatc    1860
aatggctgct cctccaagct gtggtctgag cccactgctg gtcctggtgg taaccgctct    1920
gtccacccta ttatctttaa cagaaacatc atagctgcat taaaaaaata caatatggac    1980
atgtaaaaag acaaaaacca agttatctgt ttcctgttct cttgtatagc tgaaattcca    2040
gtttaggagc tcagttgaga aacagttcca ttcaactgga acatttttt ttttccttt     2100 aagaaagctt cttgtgatcc ttcggggctt ctgtgaaaaa cctgatgcag tgctccatcc    2160
aaactcagaa ggctttggga tatgctgtat tttaaaggga cagtttgtaa cttgggctgt    2220
aaagcaaact ggggctgtgt tttcgatgat gatgatcatc atgatcatga tgattttaac    2280
agttttactt ctggcctttc ctagctagag aaggagttaa tatttctaag gtaactccca    2340
tatctccttt aatgacattg atttctaatg atataaattt cagcctacat tgatgccaag    2400 ctttttttgcc acaaagaaga ttcttaccaa gagtgggctt tgtggaaaca gctggtactg    2460
atgttcacct ttatatatgt actagcattt tccacgctga tgtttatgta ctgtaaacag    2520
ttctgcactc ttgtacaaaa gaaaaaacca cccggaattc                          2560
```

<210> SEQ ID NO 6
<211> LENGTH: 2439
<212> TYPE: DNA
<213> ORGANISM: human

<400> SEQUENCE: 6

```
cagcacccag ctccccgcca ccgccatggt ccccgacacc gcctgcgttc ttctgctcac      60
cctggctgcc ctcggcgcgt ccggacaggg ccagagcccg ttgggctcag acctgggccc     120
gcagatgctt cgggaactgc aggaaaccaa cgcggcgctg caggacgtgc gggactggct     180
gcggcagcag gtcagggaga tcacgttcct gaaaaacacg gtgatggagt gtgacgcgtg     240
cgggatgcag cagtcagtac gcaccggcct acccagcgtg cggcccctgc tccactgcgc     300
gcccggcttc tgcttccccg gcgtggcctg catccagacg gagagcggcg gccgctgcgg     360
cccctgcccc gcgggcttca cgggcaacgc ctcgcactgc accgacgtca acgagtgcaa     420
cgcccacccc tgcttccccc gagtccgctg tatcaacacc agcccggggt tccgctgcga     480
```

```
ggcttgcccg ccggggtaca gcggccccac ccaccagggc gtggggctgg ctttcgccaa        540
ggccaacaag caggtttgca cggacatcaa cgagtgtgag accgggcaac ataactgcgt        600
ccccaactcc gtgtgcatca acacccgggg ctccttccag tgcggcccgt gccagcccgg        660
cttcgtgggc gaccaggcgt ccggctgcca gcgcggcgca cagcgcttct gccccgacgg        720
ctcgcccagc gagtgccacg agcatgcaga ctgcgtccta gagcgcgatg gctcgcggtc        780
gtgcgtgtgt cgcgttggct gggccggcaa cgggatcctc tgtggtcgcg acactgacct        840
agacggcttc ccggacgaga agctgcgctg cccggagccg cagtgccgta aggacaactg        900
cgtgactgtg cccaactcag gcaggagga tgtggaccgc gatggcatcg agacgcctg         960 cgatccggat gccgacgggg acgggtccc caatgaaaag gacaactgcc cgctggtgcg        1020
gaacccagac cagcgcaaca cggacgagga caagtggggc gatgcgtgcg caactgccg        1080 gtcccagaag aacgacgacc aaaaggacac agaccaggac ggccggggcg atgcgtgcga      1140
cgacgacatc gacggcgacc ggatccgcaa ccaggccgac aactgcccta gggtacccaa        1200
ctcagaccag aaggacagtg atggcgatgg tatagggat gcctgtgaca actgtcccca         1260
gaagagcaac ccggatcagg cggatgtgga ccacgacttt gtgggagatg cttgtgacag        1320
cgatcaagac caggatggag acggacatca ggactctcgg gacaactgtc ccacggtgcc        1380
taacagtgcc caggaggact cagaccacga tggccaggt gatgcctgcg acgacgacga         1440
cgacaatgac ggagtccctg acagtcggga caactgccgc tggtgcctaa ccccggcca         1500 ggaggacgcg gacagggacg cgtgggcga cgtgtgccag gacgactttg atgcagacaa        1560
ggtggtagac aagatcgacg tgtgtccgga gaacgctgaa gtcacgctca ccgacttcag        1620
ggccttccag acagtcgtgc tggacccgga gggtgacgcg cagattgacc ccaactgggt        1680
ggtgctcaac cagggaaggg agatcgtgca gacaatgaac agcgacccag gcctggctgt        1740
gggttacact gccttcaatg gcgtggactt cgagggcacg ttccatgtga acacggtcac        1800
ggatgacgac tatgcgggct tcatctttgg ctaccaggac agctccagct tctacgtggt        1860
catgtggaag cagatggagc aaacgtattg gcaggcgaac cccttccgtg ctgtggccga        1920
gcctggcatc caactcaagg ctgtgaagtc ttccacaggc cccggggaac agctgcggaa        1980
cgctctgtgg catacaggag acacagagtc ccaggtgcgg ctgctgtgga aggacccgcg        2040
aaacgtgggt tggaaggaca agaagtccta tcgttggttc ctgcagcacc ggccccaagt        2100
gggctacatc agggtgcgat tctatgaggg ccctgagctg gtggccgaca gcaacgtggt        2160
cttggacaca accatgcggg gtggccgcct ggggtcttc tgcttctccc aggagaacat         2220
catctgggcc aacctgcgtt accgctgcaa tgacaccatc ccagaggact atgagccca         2280 tcagctgcgg caagcctagg gaccaggtg aggacccgcc ggatgacagc caccctcacc         2340
gcggctggat gggggctctg cacccagccc aagggtggc cgtcctgagg ggaagtgag         2400 aagggctcag agaggacaaa ataaagtgtg tgtgcaggg                               2439

<210> SEQ ID NO 7
<211> LENGTH: 2439
<212> TYPE: DNA
<213> ORGANISM: human

<400> SEQUENCE: 7
cagcacccag ctccccgcca ccgccatggt ccccgacacc gcctgcgttc ttctgctcac         60
cctggctgcc ctcggcgcgt ccggacaggg ccagagcccg ttgggctcag acctgggccc        120
gcagatgctt cggaactgc aggaaaccaa cgcggcgctg caggacgtgc gggactggct        180
```

| | | | | | |
|---|---|---|---|---|---|
| gcggcagcag | gtcagggaga | tcacgttcct | gaaaaacacg | gtgatggagt | gtgacgcgtg | 240 |
| cgggatgcag | cagtcagtac | gcaccggcct | acccagcgtg | cggcccctgc | tccactgcgc | 300 |
| gcccggcttc | tgcttccccg | gcgtggcctg | catccagacg | gagagcggcg | gccgctgcgg | 360 |
| ccccctgcccc | gcgggcttca | cgggcaacgg | ctcgcactgc | accgacgtca | acgagtgcaa | 420 |
| cgcccacccc | tgcttccccc | gagtccgctg | tatcaacacc | agcccggggt | tccgctgcga | 480 |
| ggcttgcccg | ccggggtaca | gcggccccac | ccaccagggc | gtggggctgg | ctttcgccaa | 540 |
| ggccaacaag | caggtttgca | cggacatcaa | cgagtgtgag | accgggcaac | ataactgcgt | 600 |
| ccccaactcc | gtgtgcatca | cacccgggg | ctccttccag | tgcggcccgt | gccagcccgg | 660 |
| cttcgtgggc | gaccaggcgt | ccggctgcca | gcgcggcgca | cagcgcttct | gccccgacgg | 720 |
| ctcgcccagc | gagtgccacg | agcatgcaga | ctgcgtccta | gagcgcgatg | gctcgcggtc | 780 |
| gtgcgtgtgt | cgcgttggct | gggccggcaa | cgggatcctc | tgtggtcgcg | acactgacct | 840 |
| agacggcttc | ccggacgaga | agctgcgctg | cccggagccg | cagtgccgta | aggacaactg | 900 |
| cgtgactgtg | cccaactcag | ggcaggagga | tgtggaccgc | gatggcatcg | gagacgcctg | 960 |
| cgatccggat | gccgacgggg | acggggtccc | caatgaaaag | gacaactgcc | cgctggtgcg | 1020 |
| gaacccagac | cagcgcaaca | cggacgagga | caagtggggc | gatgcgtgcg | acaactgccg | 1080 |
| gtcccagaag | aacgacgacc | aaaaggacac | agaccaggac | ggccggggcg | atgcgtgcga | 1140 |
| cgacgacatc | gacggcgacc | ggatccgcaa | ccaggccgac | aactgcccta | gggtacccaa | 1200 |
| ctcagaccga | aaggacagtg | atggcgatgg | tatagggga | tgcctgtgaca | actgtccccca | 1260 |
| gaagagcaac | ccggatcagg | cggatgtgga | ccacgacttt | gtgggagatg | cttgtgacag | 1320 |
| cgatcaagac | caggatggag | acggacatca | ggactctcgg | gacaactgtc | ccacggtgcc | 1380 |
| taacagtgcc | caggaggact | cagaccacga | tggccagggt | gatgcctgcg | acgacgacga | 1440 |
| cgacaatgac | ggagtccctg | acagtcggga | caactgccgc | tggtgcctaa | ccccggcca | 1500 |
| ggaggacgcg | gacagggacg | gcgtgggcga | cgtgtgccag | gacgactttg | atgcagacaa | 1560 |
| ggtggtagac | aagatcgacg | tgtgtccgga | gaacgctgaa | gtcacgctca | ccgacttcag | 1620 |
| ggccttccag | acagtcgtgc | tggacccgga | gggtgacgcg | cagattgacc | ccaactgggt | 1680 |
| ggtgctcaac | cagggaaggg | agatcgtgca | gacaatgaac | agcgacccag | gcctggctgt | 1740 |
| gggttacact | gccttcaatg | gcgtggactt | cgagggcacg | ttccatgtga | acacggtcac | 1800 |
| ggatgacgac | tatgcgggct | tcatctttgg | ctaccaggac | agctccagct | tctacgtggt | 1860 |
| catgtggaag | cagatggagc | aaacgtattg | gcaggcgaac | cccttccgtg | ctgtggccga | 1920 |
| gcctggcatc | caactcaagg | ctgtgaagtc | ttccacaggc | cccggggaac | agctgcggaa | 1980 |
| cgctctgtgg | catacaggag | acacagagtc | ccaggtgcgg | ctgctgtgga | aggacccgcg | 2040 |
| aaacgtgggt | tggaaggaca | agaagtccta | tcgttggttc | ctgcagcacc | ggccccaagt | 2100 |
| gggctacatc | agggtgcgat | tctatgaggg | ccctgagctg | gtggccgaca | gcaacgtggt | 2160 |
| cttggacaca | accatgcggg | gtggccgcct | ggggggtcttc | tgcttctccc | aggagaacat | 2220 |
| catctgggcc | aacctgcgtt | accgctgcaa | tgacaccatc | ccagaggact | atgagaccca | 2280 |
| tcagctgcgg | caagcctagg | gaccagggtg | aggacccgcc | ggatgacagc | caccctcacc | 2340 |
| gcggctggat | gggggctctg | cacccagccc | aagggggtggc | cgtcctgagg | gggaagtgag | 2400 |
| aagggctcag | agaggacaaa | ataaagtgtg | tgtgcaggg | | | 2439 |

<210> SEQ ID NO 8

<211> LENGTH: 1700
<212> TYPE: DNA
<213> ORGANISM: human

<400> SEQUENCE: 8

| | | | | | |
|---|---|---|---|---|---|
| haggtgagcg | gttgctcgtc | gtcggggcgg | ccggcagcgg | cggctccagg | gcccagcatg | 60 |
| cgcggggac | cccgcggcca | ccatgtatgt | gggctatgtg | ctggacaagg | attcgcccgt | 120 |
| gtaccccggc | ccagccaggc | cagccagcct | cggcctgggc | ccggcaaact | acggcccccc | 180 |
| ggccccgccc | ccggcgcccc | cgcagtaccc | cgacttctcc | agctactctc | acgtggagcc | 240 |
| ggccccgcg | ccccgacgg | cctgggggc | gcccttccct | gcgcccaagg | acgactgggc | 300 |
| cgccgcctac | ggcccgggcc | ccgcggcccc | tgccgccagc | ccagcttcgc | tggcattcgg | 360 |
| gccccctcca | gactttagcc | cggtgccggc | gccccctggg | cccggcccgg | gcctcctggc | 420 |
| gcagcccctc | gggggccggg | gcacaccgtc | tcgcccgga | gcgcagaggc | cgacgcccta | 480 |
| cgagtggatg | cggcgcagcg | tggcggccgg | aggcggcggt | ggcagcggta | agactcggac | 540 |
| caaggacaag | taccgcgtgg | tctacaccga | ccaccaacgc | ctggagctgg | agaaggagtt | 600 |
| tcattacagc | cgttacatca | caatccggcg | gaaatcagag | ctggctgcca | atctggggct | 660 |
| cactgaacgg | caggtgaaga | tctggttcca | aaaccggcgg | gcaaaggagc | gcaaagtgaa | 720 |
| caagaagaaa | cagcagcagc | aacagccccc | acagccgccg | atgggcccacg | acatcacggc | 780 |
| caccccagcc | gggccatccc | tgggggggcct | gtgtcccagc | aacaccagcc | tcctggccac | 840 |
| ctcctctcca | atgcctgtga | agaggagtt | tctgccatag | ccccatgccc | agcctgtgcg | 900 |
| ccgggggacc | tggggactcg | ggtgctggga | gtgtggctcc | tgtgggccca | ggaggtctgg | 960 |
| tccgagtctc | agccctgacc | ttctgggaca | tggtggacag | tcacctatcc | accctctgca | 1020 |
| tccccttggc | ccattgtgtg | cagtaagcct | gttggataaa | gaccttccag | ctcctgtgtt | 1080 |
| ctagacctct | gggggataag | ggagtccagg | gtggatgatc | tcaatctccc | gtgggcatct | 1140 |
| caagccccaa | atggttgggg | gagggggccta | gacaaggctc | caggcccca | ctcctcctcc | 1200 |
| atacgttcag | aggtgcagct | ggaggcctgt | gtgggaccca | cactgatcct | ggagaaaagg | 1260 |
| gatggagctg | aaaaagatgg | aatgcttgca | gagcatgacc | tgaggaggga | ggaacgtggt | 1320 |
| caactcacac | ctgcctcttc | tgcagcctca | cctctacctg | ccccatcat | aagggcactg | 1380 |
| agcccttccc | aggctggata | ctaagcacaa | agcccatagc | actgggctct | gatggctgct | 1440 |
| ccactgggtt | acagaatcac | agccctcatg | atcattctca | gtgagggctc | tggattgaga | 1500 |
| gggaggccct | gggaggagag | aaggggggcag | agtcttccct | accaggtttc | tacaccccg | 1560 |
| ccaggctgcc | catcagggcc | caggagccc | ccagaggact | ttattcggac | caagcagagc | 1620 |
| tcacagctgg | acaggtgttg | tatatagagt | ggaatctctt | ggatgcagct | tcaagaataa | 1680 |
| attttcttc | tcttttcaaa | | | | | 1700 |

<210> SEQ ID NO 9
<211> LENGTH: 4098
<212> TYPE: DNA
<213> ORGANISM: human

<400> SEQUENCE: 9

| | | | | | |
|---|---|---|---|---|---|
| ggtggcctct | gtggccgtcc | aggctagcgg | cggcccgcag | gcggcgggga | gaaagactct | 60 |
| ctcacctggt | cttgcggctg | tggccaccgc | cggccagggg | tgtggagggc | gtgctgccgg | 120 |
| agacgtccgc | cggggctctgc | agttccgccg | ggggtcgggc | agctatggag | ccgcggccca | 180 |
| cggcgccctc | ctccggcgcc | ccgggactgg | ccggggtcgg | ggagacgccg | tcagccgctg | 240 |

```
cgctggccgc agccagggtg gaactgcccg gcacggctgt gccctcggtg ccggaggatg      300
ctgcgcccgc gagccgggac ggcggcgggg tccgcgatga gggccccgcg gcggccgggg      360
acgggctggg cagacccttg ggcccaccc cgagccagag ccgtttccag gtggacctgg       420
tttccgagaa cgccgggcgg gccgctgctg cggcggcggc ggcggcggcg gcagcggcgg      480
cggctggtgc tggggcgggg gccaagcaga ccccgcgga cggggaagcc agcggcgaga       540
gcgagccagc taaaggcagc gaggaagcca agggccgctt ccgcgtgaac ttcgtggacc      600
cagctgcctc ctcgtcggct gaagacagcc tgtcagatgc tgccggggtc ggagtcgacg      660
ggcccaacgt gagcttccag aacggcgggg acacggtgct gagcgagggc agcagcctgc      720
actccggcgg cggcggcggc agtgggcacc accagcacta ctattatgat acccacacca      780
acacctacta cctgcgcacc ttcggccaca acaccatgga cgctgtgccc aggatcgatc      840
actaccggca cacagccgcg cagctgggcg agaagctgct ccggcctagc ctggcggagc      900
tccacgacga gctggaaaag gaaccttttg aggatggctt tgcaaatggg gaagaaagta      960
ctccaaccag agatgctgtg gtcacgtata ctgcagaaag taaggagtc gtgaagtttg       1020 gctggatcaa gggtgtatta gtacgttgta tgttaaacat ttggggtgtg atgcttttca      1080
ttagattgtc atggattgtg ggtcaagctg aataggtct atcagtcctt gtaataatga      1140
tggccactgt tgtgacaact atcacaggat tgtctacttc agcaatagca actaatggat      1200
ttgtaagagg aggaggagca tattatttaa tatctagaag tctagggcca gaatttggtg      1260
gtgcaattgg tctaatcttc gcctttgcca acgctgttgc agttgctatg tatgtggttg      1320
gatttgcaga aaccgtggtg gagttgctta aggaacattc catacttatg atagatgaaa      1380
tcaatgatat ccgaattatt ggagccatta cagtcgtgat tcttttaggt atctcagtag      1440
ctggaatgga gtgggaagca aaagctcaga ttgttctttt ggtgatccta cttcttgcta      1500
ttggtgattt cgtcataggaa acatttatcc cactggagca caagaagcca aaagggtttt      1560
ttggttataa atctgaaata tttaatgaga ctttgggcc cgattttcga gaggaagaga      1620
cttctttttc tgtatttgcc atctttttc ctgctgcaac tggtattctg gctggagcaa       1680
atatctcagg tgatcttgca gatcctcagt cagccatacc caaggaaca ctcctagcca       1740 ttttaattac tacattggtt tacgtaggaa ttgcagtatc tgtaggttct tgtgttgttc      1800
gagatgccac tggaaacgtt aatgacacta tcgtaacaga gctaacaaac tgtacttctg      1860
cagcctgcaa attaaacttt gatttttcat cttgtgaaag cagtccttgt tcctatggcc      1920
taatgaacaa cttccaggta atgagtatgg tgtcaggatt tacaccacta atttctgcag      1980
gtatattttc agccactctt tcttcagcat tagcatccct agtgagtgct cccaaaatat      2040
ttcaggctct atgtaaggac aacatctacc cagctttcca gatgtttgct aaaggttatg      2100
ggaaaaataa tgaacctctt cgtggctaca tcttaacatt cttaattgca cttggattca      2160
tcttaattgc tgaactgaat gttattgcac caattatctc aaacttcttc cttgcatcat      2220
atgcattgat caatttttca gtattccatg catcacttgc aaaatctcca ggatggcgtc      2280
ctgcattcaa atactacaac atgtggatat cacttcttgg agcaattctt tgttgcatag      2340
taatgttcgt cattaactgg tgggctgcat tgctaacata tgtgatagtc cttgggctgt      2400
atatttatgt tacctacaaa aaaccagatg tgaattgggg atcctctaca caagccctga      2460
cttacctgaa tgcactgcag cattcaattc gtctttctgg agtggaagac cacgtgaaaa      2520
actttaggcc acagtgtctt gttatgacag gtgctccaaa ctcacgtcca gctttacttc      2580
```

-continued

| | |
|---|---|
| atcttgttca tgatttcaca aaaaatgttg gtttgatgat ctgtggccat gtacatatgg | 2640 |
| gtcctcgaag acaagccatg aaagagatgt ccatcgatca agccaaatat cagcgatggc | 2700 |
| ttattaagaa caaatgaag gcattttatg ctccagtaca tgcagatgac ttgagagaag | 2760 |
| gtgcacagta tttgatgcag gctgctggtc ttggtcgtat gaagccaaac acacttgtcc | 2820 |
| ttggatttaa gaaagattgg ttgcaagcag atatgaggga tgtggatatg tatataaact | 2880 |
| tatttcatga tgcttttgac atacaatatg gagtagtggt tattcgccta aaagaaggtc | 2940 |
| tggatatatc tcatcttcaa ggacaagaag aattattgtc atcacaagag aaatctcctg | 3000 |
| gcaccaagga tgtggtagta agtgtggaat atagtaaaaa gtccgattta gatacttcca | 3060 |
| aaccactcag tgaaaaacca attacacaca aagttgagga agaggatggc aagactgcaa | 3120 |
| ctcaaccact gttgaaaaaa gaatccaaag gccctattgt gcctttaaat gtagctgacc | 3180 |
| aaaagcttct tgaagctagt acacagtttc agaaaaaaca aggaaagaat actattgatg | 3240 |
| tctggtggct ttttgatgat ggaggtttga ccttattgat accttacctt ctgacgacca | 3300 |
| agaaaaaatg gaaagactgt aagatcagag tattcattgg tggaaagata aacagaatag | 3360 |
| accatgaccg gagagcgatg gctactttgc ttagcaagtt ccggatagac ttttctgata | 3420 |
| tcatggttct aggagatatc aataccaaac caaagaaaga aaatattata gcttttgagg | 3480 |
| aaatcattga gccatacaga cttcatgaag atgataaaga gcaagatatt gcagataaaa | 3540 |
| tgaaagaaga tgaaccatgg cgaataacag ataatgagct tgaactttat aagaccaaga | 3600 |
| cataccggca gatcaggtta aatgagttat taaggaaca ttcaagcaca gctaatatta | 3660 |
| ttgtcatgag tctcccagtt gcacgaaaag gtgctgtgtc tagtgctctc tacatggcat | 3720 |
| ggttagaagc tctatctaag gacctaccac caatcctcct agttcgtggg aatcatcaga | 3780 |
| gtgtccttac cttctattca taaatgttct atacagtgga cagccctcca gaatggtact | 3840 |
| tcagtgccta gtgtagtaac ctgaaatctt caatgacaca ttaacatcac aatggcgaat | 3900 |
| ggtgactttt cttcacgat ttcattaatt tgaaagcaca caggaaagct tgctccattg | 3960 |
| ataacgtgta tggagacttc ggttttagtc aattccatat ctcaatctta atggtgattc | 4020 |
| ttctctgttg aactgaagtt tgtgagagta gttttccttt gctacttgaa tagcaataaa | 4080 |
| agcgtgttaa cttttttgg | 4098 |

<210> SEQ ID NO 10
<211> LENGTH: 4098
<212> TYPE: DNA
<213> ORGANISM: human

<400> SEQUENCE: 10

| | |
|---|---|
| ggtggcctct gtggccgtcc aggctagcgg cggcccgcag gcggcgggga gaaagactct | 60 |
| ctcacctggt cttgcggctg tggccaccgc cggccagggg tgtggagggc gtgctgccgg | 120 |
| agacgtccgc cggggctctgc agttccgccg ggggtcgggc agctatggag ccgcggccca | 180 |
| cggcgccctc ctccggcgcc ccgggactgg ccggggtcgg ggagacgccg tcagccgctg | 240 |
| cgctggccga agccagggtg gaactgcccg gcacggctgt gccctcggtg ccggaggatg | 300 |
| ctgcgcccgc gagccgggac ggcggcgggg tccgcgatga gggccccgcg gcggccgggg | 360 |
| acgggctggg cagaccccttg gggcccaccc cgagccagag ccgtttccag gtggacctgg | 420 |
| tttccgagaa cgccgggcgg gccgctgctg cggcggcgg ggcggcggcg gcagcggcgg | 480 |
| cggctggtgc tggggcgggg gccaagcaga ccccgcgga cggggaagcc agcggcgaga | 540 |
| gcgagccagc taaaggcagc gaggaagcca agggccgctt ccgcgtgaac ttcgtggacc | 600 |

-continued

```
cagctgcctc ctcgtcggct gaagacagcc tgtcagatgc tgccggggtc ggagtcgacg      660
ggcccaacgt gagcttccag aacggcgggg acacggtgct gagcgagggc agcagcctgc      720
actccggcgg cggcggcggc agtgggcacc accagcacta ctattatgat acccacacca      780
acacctacta cctgcgcacc ttcggccaca acaccatgga cgctgtgccc aggatcgatc      840
actaccggca cacagccgcg cagctgggcg agaagctgct ccggcctagc ctggcggagc      900
tccacgacga gctggaaaag gaaccttttg aggatggctt tgcaaatggg gaagaaagta      960
ctccaaccag agatgctgtg gtcacgtata ctgcagaaag taaaggagtc gtgaagtttg     1020
gctggatcaa gggtgtatta gtacgttgta tgttaaacat ttggggtgtg atgcttttca     1080
ttagattgtc atggattgtg ggtcaagctg aataggtct atcagtcctt gtaataatga      1140
tggccactgt tgtgacaact atcacaggat tgtctacttc agcaatagca actaatggat     1200
ttgtaagagg aggaggagca tattatttaa tatctagaag tctagggcca gaatttggtg     1260
gtgcaattgg tctaatcttc gcctttgcca acgctgttgc agttgctatg tatgtggttg     1320
gatttgcaga aaccgtggtg gagttgctta aggaacattc catacttatg atagatgaaa     1380
tcaatgatat ccgaattatt ggagccatta cagtcgtgat tcttttaggt atctcagtag     1440
ctggaatgga gtgggaagca aaagctcaga ttgttctttt ggtgatccta cttcttgcta     1500
ttggtgattt cgtcatagga acatttatcc cactggagag caagaagcca aaagggtttt     1560
ttggttataa atctgaaata tttaatgaga actttgggcc cgattttcga gaggaagaga     1620
ctttcttttc tgtatttgcc atctttttc ctgctgcaac tggtattctg gctggagcaa     1680
atatctcagg tgatcttgca gatcctcagt cagccatacc caaaggaaca ctcctagcca     1740
ttttaattac tacattggtt tacgtaggaa ttgcagtatc tgtaggttct tgtgttgttc     1800
gagatgccac tggaaacgtt aatgacacta tcgtaacaga gctaacaaac tgtacttctg     1860
cagcctgcaa attaaacttt gattttcat cttgtgaaag cagtccttgt tcctatggcc      1920
taatgaacaa cttccaggta atgagtatgg tgtcaggatt tacaccacta atttctgcag     1980
gtatattttc agccactctt tcttcagcat tagcatccct agtgagtgct cccaaaatat     2040
ttcaggctct atgtaaggac aacatctacc cagctttcca gatgtttgct aaaggttatg     2100
ggaaaaataa tgaacctctt cgtggctaca tcttaacatt cttaattgca cttggattca     2160
tcttaattgc tgaactgaat gttattgcac caattatctc aaacttcttc cttgcatcat     2220
atgcattgat caattttca gtattccatg catcacttgc aaaatctcca ggatggcgtc      2280
ctgcattcaa atactacaac atgtggatat cacttcttgg agcaattctt tgttgcatag     2340
taatgttcgt cattaactgg tgggctgcat tgctaacata tgtgatagtc cttggctgt      2400 atatttatgt tacctacaaa aaaccagatg tgaattgggg atcctctaca caagccctga     2460
cttacctgaa tgcactgcag cattcaattc gtctttctgg agtggaagac cacgtgaaaa     2520
actttaggcc acagtgtctt gttatgacag gtgctccaaa ctcacgtcca gctttacttc     2580
atcttgttca tgatttcaca aaaaatgttg gtttgatgat ctgtggccat gtacatatgg     2640
gtcctcgaag acaagccatg aaagagatgt ccatcgatca agccaaatat cagcgatggc     2700
ttattaagaa caaatgaag gcatttatg ctccagtaca tgcagatgac ttgagagaag       2760
gtgcacagta tttgatgcag gctgctggtc ttggtcgtat gaagccaaac acacttgtcc     2820
ttggatttaa gaaagattgg ttgcaagcag atatgaggga tgtggatatg tatataaact     2880
tatttcatga tgctttgac atacaatatg gagtagtggt tattcgccta aagaaggtc       2940
```

-continued

```
tggatatatc tcatcttcaa ggacaagaag aattattgtc atcacaagag aaatctcctg    3000
gcaccaagga tgtggtagta agtgtggaat atagtaaaaa gtccgattta gatacttcca    3060
aaccactcag tgaaaaacca attacacaca aagttgagga agaggatggc aagactgcaa    3120
ctcaaccact gttgaaaaaa gaatccaaag gccctattgt gcctttaaat gtagctgacc    3180
aaaagcttct tgaagctagt acacagtttc agaaaaaaca aggaaagaat actattgatg    3240
tctggtggct ttttgatgat ggaggtttga ccttattgat accttacctt ctgacgacca    3300
agaaaaaatg gaaagactgt aagatcagag tattcattgg tggaaagata aacagaatag    3360
accatgaccg gagagcgatg gctactttgc ttagcaagtt ccggatagac ttttctgata    3420
tcatggttct aggagatatc aataccaaac caaagaaaga aaatattata gcttttgagg    3480
aaatcattga gccatacaga cttcatgaag atgataaaga gcaagatatt gcagataaaa    3540
tgaaagaaga tgaaccatgg cgaataacag ataatgagct tgaactttat aagaccaaga    3600
cataccggca gatcaggtta aatgagttat taaaggaaca ttcaagcaca gctaatatta    3660
ttgtcatgag tctcccagtt gcacgaaaag gtgctgtgtc tagtgctctc tacatggcat    3720
ggttagaagc tctatctaag gacctaccac caatcctcct agttcgtggg aatcatcaga    3780
gtgtccttac cttctattca taaatgttct atacagtgga cagccctcca gaatggtact    3840
tcagtgccta gtagtaac ctgaaatctt caatgacaca ttaacatcac aatggcgaat    3900
ggtgactttt ctttcacgat ttcattaatt tgaaagcaca caggaaagct tgctccattg    3960
ataacgtgta tggagacttc ggttttagtc aattccatat ctcaatctta atggtgattc    4020
ttctctgttg aactgaagtt tgtgagagta gttttccttt gctacttgaa tagcaataaa    4080
agcgtgttaa cttttttgg                                                 4098
```

<210> SEQ ID NO 11
<211> LENGTH: 3311
<212> TYPE: DNA
<213> ORGANISM: human

<400> SEQUENCE: 11

```
tgctaatgct tttggtacaa atggatgtgg aatataattg aatattttct tgtttaaggg      60
gagcatgaag aggtgttgag gttatgtcaa gcatctggca cagctgaagg cagatggaaa     120
tatttacaag tacgcaattt gagactaaga tattgttatc attctcctat tgaagacaag     180
agcaatagta aaacacatca ggtcagggg ttaaagacct gtgataaacc acttccgata     240
agttggaaac gtgtgtctat attttcatat ctgtatatat ataatggtaa agaaagacac     300
cttcgtaacc cgcatttcc aaagagagga atcacaggga gatgtacagc aatggggcca     360
tttaagagtt ctgtgttcat cttgattctt caccttctag aaggggccct gagtaattca     420
ctcattcagc tgaacaacaa tggctatgaa ggcattgtcg ttgcaatcga ccccaatgtg     480
ccagaagatg aaacactcat tcaacaaata aaggacatgt gacccaggc atctctgtat     540 ctgtttgaag ctacaggaaa gcgattttat ttcaaaaatg ttgccatttt gattcctgaa     600
acatggaaga caaaggctga ctatgtgaga ccaaaacttg agacctacaa aaatgctgat     660
gttctggttg ctgagtctac tcctccaggt aatgatgaac cctacactga gcagatgggc     720
aactgtggag agaagggtga aggatccac ctcactcctg atttcattgc aggaaaaaag     780
ttagctgaat atggaccaca aggtaaggca tttgtccatg agtgggctca tctacgatgg     840
ggagtatttg acgagtacaa taatgatgag aaattctact tatccaatgg aagaatacaa     900
gcagtaagat gttcagcagg tattactggt acaaatgtag taaagaagtg tcagggaggc     960
```

```
agctgttaca ccaaaagatg cacattcaat aaagttacag gactctatga aaaaggatgt   1020
gagtttgttc tccaatcccg ccagacggag aaggcttcta taatgtttgc acaacatgtt   1080
gattctatag ttgaattctg tacagaacaa accacaaca aagaagctcc aaacaagcaa    1140
aatcaaaaat gcaatctccg aagcacatgg gaagtgatcc gtgattctga ggactttaag   1200 aaaccactc ctatgacaac acagccacca aatcccacct tctcattgct gcagattgga    1260
caaagaattg tgtgtttagt ccttgacaaa tctggaagca tggcgactgg taaccgcctc   1320
aatcgactga atcaagcagg ccagcttttc ctgctgcaga cagttgagct ggggtcctgg   1380
gttgggatgg tgacatttga cagtgctgcc catgtacaaa gtgaactcat acagataaac   1440
agtggcagtg cagggacac actcgccaaa agattacctg cagcagcttc aggagggacg    1500
tccatctgca gcgggcttcg atcggcattt actgtgatta ggaagaaata tccaactgat   1560
ggatctgaaa ttgtgctgct gacggatggg gaagacaaca ctataagtgg gtgctttaac   1620
gaggtcaaac aaagtggtgc catcatccac acagtcgctt tggggccctc tgcagctcaa   1680
gaactagagg agctgtccaa aatgacagga ggtttacaga catatgcttc agatcaagtt   1740
cagaacaatg gcctcattga tgcttttggg gcccttcat caggaaatgg agctgtctct    1800
cagcgctcca tccagcttga gagtaaggga ttaaccctcc agaacagcca gtggatgaat   1860
ggcacagtga tcgtggacag caccgtggga aaggacactt tgtttcttat cacctggaca   1920
acgcagcctc cccaaatcct tctctgggat cccagtggac agaagcaagg tggctttgta   1980
gtggacaaaa acaccaaaat ggcctacctc caaatcccag gcattgctaa ggttggcact   2040
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagcccctgat tgaatcagtg aatggaaaaa cagttacctt ggaactactg   2280
gataatggag caggtgctga tgctactaag gatgacggtg tctactcaag gtatttcaca   2340
acttatgaca cgaatggtag atacagtgta aaagtgcggg ctctgggagg agttaacgca   2400
gccagacgga gagtgatacc ccagcagagt ggagcactgt acatacctgg ctggattgag   2460
aatgatgaaa tacaatggaa tccaccaaga cctgaaatta ataaggatga tgttcaacac   2520
aagcaagtgt gtttcagcag aacatcctcg ggaggctcat tgtggcttc tgatgtccca    2580 aatgctccca tacctgatct cttcccacct ggccaaatca ccgacctgaa ggcggaaatt   2640
cacgggggca gtctcattaa tctgacttgg acagctcctg gggatgatta tgaccatgga   2700
acagctcaca agtatatcat tcgaataagt acaagtattc ttgatctcag agacaagttc   2760
aatgaatctc ttcaagtgaa tactactgct ctcatcccaa aggaagccaa ctctgaggaa   2820
gtctttttgt ttaaaccaga aaacattact tttgaaaatg gcacagatct tttcattgct   2880
attcaggctg ttgataaggt cgatctgaaa tcagaaatat ccaacattgc acgagtatct   2940
ttgtttattc ctccacagac tccgccagag acacctagtc ctgatgaaac gtctgctcct   3000
tgtcctaata ttcatatcaa cagcaccatt cctggcattc acattttaaa aattatgtgg   3060
aagtggatag agaactgca gctgtcaata gcctagggct gaattttgt cagataaata    3120 aaataaatca ttcatccttt ttttgattat aaaattttct aaaatgtatt ttagacttcc   3180 tgtaggggc gatatactaa atgtatatag tacatttata ctaaatgtat tcctgtaggg    3240
ggcgatatac taaatgtatt ttagacttcc tgtaggggc gataaaataa aatgctaaac    3300
```

```
                                           -continued
aactgggtaa a                                                   3311

<210> SEQ ID NO 12
<211> LENGTH: 3311
<212> TYPE: DNA
<213> ORGANISM: human

<400> SEQUENCE: 12
tgctaatgct tttggtacaa atggatgtgg aatataattg aatattttct tgtttaaggg     60
gagcatgaag aggtgttgag gttatgtcaa gcatctggca cagctgaagg cagatggaaa    120
tatttacaag tacgcaattt gagactaaga tattgttatc attctcctat tgaagacaag    180
agcaatagta aaacacatca ggtcaggggg ttaaagacct gtgataaacc acttccgata    240
agttggaaac gtgtgtctat attttcatat ctgtatatat ataatggtaa agaaagacac    300
cttcgtaacc cgcatttttcc aaagagagga atcacaggga gatgtacagc aatggggcca   360
tttaagagtt ctgtgttcat cttgattctt caccttctag aagggccct gagtaattca     420 ctcattcagc tgaacaacaa tggctatgaa ggcattgtcg ttgcaatcga ccccaatgtg    480
ccagaagatg aaacactcat tcaacaaata aggacatgg tgacccaggc atctctgtat     540
ctgtttgaag ctacaggaaa gcgattttat ttcaaaaatg ttgccatttt gattcctgaa    600
acatggaaga caaaggctga ctatgtgaga ccaaaacttg agacctacaa aaatgctgat    660
gttctggttg ctgagtctac tcctccaggt aatgatgaac cctacactga gcagatgggc    720
aactgtggag agaagggtga aaggatccac ctcactcctg atttcattgc aggaaaaaag    780
ttagctgaat atggaccaca aggtaaggca tttgtccatg agtgggctca tctacgatgg    840
ggagtatttg acgagtacaa taatgatgag aaattctact tatccaatgg aagaatacaa    900
gcagtaagat gttcagcagg tattactggt acaaatgtag taaagaagtg tcagggaggc    960
agctgttaca ccaaaagatg cacattcaat aaagttacag gactctatga aaaggatgt    1020 gagtttgttc tccaatcccg ccagacggag aaggcttcta taatgtttgc acaacatgtt    1080
gattctatag ttgaattctg tacagaacaa accacaacaa agaagctcc aaacaagcaa    1140 aatcaaaaat gcaatctccg aagcacatgg gaagtgatcc gtgattctga ggactttaag    1200
aaaaccactc ctatgacaac acagccacca aatcccacct tctcattgct gcagattgga    1260
caaagaattg tgtgtttagt ccttgacaaa tctggaagca tggcgactgg taaccgcctc    1320
aatcgactga atcaagcagg ccagcttttc ctgctgcaga cagttgagct ggggtcctgg    1380
gttgggatgg tgacatttga cagtgctgcc catgtacaaa gtgaactcat acagataaac    1440
agtggcagtg acagggacac actcgccaaa agattacctg cagcagcttc aggagggacg    1500
tccatctgca gcgggcttcg atcggcattt actgtgatta ggaagaaata tccaactgat    1560
ggatctgaaa ttgtgctgct gacggatggg gaagacaaca ctataagtgg gtgctttaac    1620
gaggtcaaac aaagtggtgc catcatccac acagtcgctt tggggccctc tgcagctcaa    1680
gaactagagg agctgtccaa aatgacagga ggtttacaga catatgcttc agatcaagtt    1740
cagaacaatg gcctcattga tgcttttggg gccctttcat caggaaatgg agctgtctct    1800
cagcgctcca tccagcttga gagtaaggga ttaaccctcc agaacagcca gtggatgaat    1860
ggcacagtga tcgtggacag caccgtggga aaggacactt tgtttcttat cacctggaca    1920
acgcagcctc cccaaatcct tctctgggat cccagtggac agaagcaagg tggctttgta    1980
gtggacaaaa acaccaaaat ggcctacctc caaatcccag cattgctaa ggttggcact    2040 tggaaataca gtctgcaagc aagctcacaa accttgaccc tgactgtcac gtcccgtgcg    2100
```

| | |
|---|---|
| tccaatgcta ccctgcctcc aattacagtg acttccaaaa cgaacaagga caccagcaaa | 2160 |
| ttccccagcc ctctggtagt ttatgcaaat attcgccaag gagcctcccc aattctcagg | 2220 |
| gccagtgtca cagccctgat tgaatcagtg aatggaaaaa cagttacctt ggaactactg | 2280 |
| gataatggag caggtgctga tgctactaag gatgacggtg tctactcaag gtatttcaca | 2340 |
| acttatgaca cgaatggtag atacagtgta aaagtgcggg ctctgggagg agttaacgca | 2400 |
| gccagacgga gagtgatacc ccagcagagt ggagcactgt acatacctgg ctggattgag | 2460 |
| aatgatgaaa tacaatggaa tccaccaaga cctgaaatta taaggatga tgttcaacac | 2520 |
| aagcaagtgt gtttcagcag aacatcctcg ggaggctcat tgtggcttc tgatgtccca | 2580 |
| aatgctccca tacctgatct cttcccacct ggccaaatca ccgacctgaa ggcggaaatt | 2640 |
| cacgggggca gtctcattaa tctgacttgg acagctcctg gggatgatta tgaccatgga | 2700 |
| acagctcaca gtatatcat tcgaataagt acaagtattc ttgatctcag agacaagttc | 2760 |
| aatgaatctc ttcaagtgaa tactactgct ctcatcccaa aggaagccaa ctctgaggaa | 2820 |
| gtcttttgt ttaaaccaga aaacattact tttgaaaatg gcacagatct tttcattgct | 2880 |
| attcaggctg ttgataaggt cgatctgaaa tcagaaatat ccaacattgc acgagtatct | 2940 |
| ttgtttattc ctcccacagac tccgccagag cacctagtc ctgatgaaac gtctgctcct | 3000 |
| tgtcctaata ttcatatcaa cagcaccatt cctggcattc acattttaaa aattatgtgg | 3060 |
| aagtggatag agaactgca gctgtcaata gcctagggct gaattttgt cagataaata | 3120 |
| aaataaatca ttcatccttt ttttgattat aaaatttct aaaatgtatt ttagacttcc | 3180 |
| tgtaggggc gatatactaa atgtatatag tacatttata ctaaatgtat tcctgtaggg | 3240 |
| ggcgatatac taaatgtatt ttagacttcc tgtaggggc gataaaataa aatgctaaac | 3300 |
| aactgggtaa a | 3311 |

```
<210> SEQ ID NO 13
<211> LENGTH: 2609
<212> TYPE: DNA
<213> ORGANISM: human
<220> FEATURE:
<221> NAME/KEY: misc_feature
<222> LOCATION: (2025)..(2025)
<223> OTHER INFORMATION: any kind of base
<220> FEATURE:
<221> NAME/KEY: misc_feature
<222> LOCATION: (2036)..(2036)
<223> OTHER INFORMATION: any kind of base
<220> FEATURE:
<221> NAME/KEY: misc_feature
<222> LOCATION: (2164)..(2164)
<223> OTHER INFORMATION: any kind of base
<220> FEATURE:
<221> NAME/KEY: misc_feature
<222> LOCATION: (2264)..(2264)
<223> OTHER INFORMATION: any kind of base

<400> SEQUENCE: 13
```

| | |
|---|---|
| gctgatagca cagttctgtc cagagaagga aggcggaata aacttattca ttcccaggaa | 60 |
| ctcttggggt aggtgtgtgt ttttcacatc ttaaaggctc acagaccctg cgctggacaa | 120 |
| atgttccatt cctgaaggac ctctccagaa tccggattgc tgaatcttcc ctgttgccta | 180 |
| gaagggctcc aaaccacctc ttgacaatgg gaaactgggt ggttaaccac tggttttcag | 240 |
| ttttgtttct ggttgtttgg ttagggctga atgttttcct gtttgtggat gccttcctga | 300 |
| aatatgagaa ggccgacaaa tactactaca caagaaaaat ccttgggtca acattggcct | 360 |

```
gtgcccgagc gtctgctctc tgcttgaatt ttaacagcac gctgatcctg cttcctgtgt    420
gtcgcaatct gctgtccttc ctgaggggca cctgctcatt ttgcagccgc acactgagaa    480
agcaattgga tcacaacctc accttccaca agctggtggc ctatatgatc tgcctacata    540
cagctattca catcattgca cacctgttta actttgactg ctatagcaga agccgacagg    600
ccacagatgg ctcccttgcc tccattctct ccagcctatc tcatgatgag aaaaaggggg    660
gttcttggct aaatcccatc cagtcccgaa acacgacagt ggagtatgtg acattcacca    720
gcgttgctgg tctcactgga gtgatcatga caatagcctt gattctcatg gtaacttcag    780
ctactgagtt catccggagg agttattttg aagtcttctg gtatactcac caccttttta    840
tcttctatat ccttggctta gggattcacg gcattggtgg aattgtccgg ggtcaaacag    900
aggagagcat gaatgagagt catcctcgca agtgtgcaga gtcttttgag atgtgggatg    960
atcgtgactc ccactgtagg cgccctaagt ttgaagggca tcccctgag tcttggaagt   1020 ggatccttgc accggtcatt ctttatatct gtgaaaggat cctccggttt taccgctccc   1080
agcagaaggt tgtgattacc aaggttgtta tgcacccatc caaagttttg gaattgcaga   1140
tgaacaagcg tggcttcagc atggaagtgg ggcagtatat ctttgttaat tgcccctcaa   1200
tctctctcct ggaatggcat cctttactt tgacctctgc tccagaggaa gatttcttct   1260
ccattcatat ccgagcagca ggggactgga cagaaaatct cataagggct ttcgaacaac   1320
aatattcacc aattcccagg attgaagtgg atggtcsctt tggcacagcc agtgaggatg   1380
ttttccagta tgaagtggct gtgctggttg gagcaggaat tggggtcacc ccctttgctt   1440
ctatcttgaa atccatctgg tacaaattcc agtgtgcaga ccacaacctc aaaacaaaaa   1500
agatctattt ctactggatc tgcagggaga caggtgcctt ttcctggttc aacaacctgt   1560
tgacttccct ggaacaggag atggaggaat taggcaaagt gggttttcta aactaccgtc   1620
tcttcctcac cggatgggac agcaatattg ttggtcatgc agcattaaac tttgacaagg   1680
ccactgacat cgtgacaggt ctgaaacaga aaacctcctt tgggagacca atgtgggaca   1740
atgagttttc tacaatagct acctcccacc ccaagtctgt agtgggagtt ttcttatgtg   1800
gccctcggac tttggcaaag agcctgcgca atgctgtca ccgatattcc agtctggatc   1860
ctagaaaggt tcaattctac ttcaacaaag aaaattttg agttatagga ataaggacgg   1920
taatctgcat tttgtctctt tgtatcttca gtaattgagt tataggaata aggacggtaa   1980
tctgcatttt gtctctttgt atcttcagta atttacttgg tctcntcagg tttgancagt   2040
cactttagga taagaatgtg cctctcaagc cttgactccc tggtattctt tttttgattg   2100
cattcaactt cgttacttga gcttcagcaa cttaagaact tctgaagttc ttaaagttct   2160
gaanttctta aagcccatgg atcctttctc agaaaaataa ctgtaaatct ttctggacag   2220
ccatgactgt agcaaggctt gatagcagaa gtttggtggt tcanaattat acaactaatc   2280
ccaggtgatt ttatcaattc cagtgttacc atctcctgag ttttggtttg taatcttttg   2340
tccctcccac ccccacagaa gattttaagt agggtgactt tttaaataaa aatttattga   2400
ataattaatg ataaaacata ataataaaca taaataataa acaaaattac cgagaacccc   2460
atccccatat aacaccaaca gtgtacatgt ttactgtcac ttttgatatg gtttatccag   2520
tgtgaacagc aatttattat ttttgctcat caaaaaataa aggattttt ttcacttgaa   2580 aaaaaaaaa aaaaaaaaaa aaaaaaaaa                                     2609
```

<210> SEQ ID NO 14
<211> LENGTH: 15720

<212> TYPE: DNA
<213> ORGANISM: human

<400> SEQUENCE: 14

| | | | | | |
|---|---|---|---|---|---|
| caacccacac | cgcccctgcc | agccaccatg | gggctgccac | tagcccgcct | ggcggctgtg | 60 |
| tgcctggccc | tgtctttggc | aggggctccg | gagctccaga | cagagggcag | aacccgatac | 120 |
| cacggccgca | acgtctgcag | cacctggggc | aacttccact | acaagacctt | cgacggggac | 180 |
| gtcttccgct | tccccggcct | ctgcgactac | aacttcgcct | ccgactgccg | aggctcctac | 240 |
| aaggaatttg | ctgtgcacct | gaagcggggt | ccgggccagg | ctgaggcccc | cgccggggtg | 300 |
| gagtccatcc | tgctgaccat | caaggatgac | accatctacc | tcacccgcca | cctggctgtg | 360 |
| cttaacgggg | ccgtggtcag | caccccgcac | tacagcccccg | ggctgctcat | tgagaagagc | 420 |
| gatgcctaca | ccaaagtcta | ctcccgcgcc | ggcctcaccc | tcatgtggaa | ccgggaggat | 480 |
| gcactcatgc | tggagctgga | cactaagttc | cggaaccaca | cctgtggcct | ctgcggggac | 540 |
| tacaacggcc | tgcagagcta | ttcagaattc | ctctctgacg | gcgtgctctt | cagtcccctg | 600 |
| gagtttggga | acatgcagaa | gatcaaccag | cccgatgtgg | tgtgtgagga | tcccgaggag | 660 |
| gaggtggccc | ccgcatcctg | ctccgagcac | cgcgccgagt | gtgagaggct | gctgaccgcc | 720 |
| gaggcctccg | cggactgtca | ggacctggtg | ccgctggagc | cgtatctgcg | cgcctgccag | 780 |
| caggaccgct | gccggtgccc | gggcggtgac | acctgcgtct | gcagcaccgt | ggccgagttc | 840 |
| tcccgccagt | gctcccacgc | cggcggccgg | cccgggaact | ggaggaccgc | cacgctctgc | 900 |
| cccaagacct | gccccgggaa | cctggtgtac | ctggagagcg | gctcgccctg | catggacacc | 960 |
| tgctcacacc | tggaggtgag | cagcctgtgc | gaggagcacc | gcatggacgg | ctgtttctgc | 1020 |
| ccagaaggca | ccgtatatga | cgacatcggg | gacagtggcg | cgttcctgt | gagccagtgc | 1080 |
| cactgcaggc | tgcacggaca | cctgtacaca | ccgggccagg | agatcaccaa | tgactgcgag | 1140 |
| cagtgtgtct | gtaacgctgg | ccgctgggtg | tgcaaagacc | tgccctgccc | cggcacctgt | 1200 |
| gccctggaag | gcggctccca | catcaccacc | ttcgatggga | agacgtacac | cttccacggg | 1260 |
| gactgctact | atgtcctggc | caagggtgac | cacaacgatt | cctacgctct | cctgggcgag | 1320 |
| ctggccccct | gtggctccac | agacaagcag | acctgcctga | gacggtggt | gctgctggct | 1380 |
| gacaagaaga | agaatgcggt | ggtcttcaag | tccgatggca | gtgtactgct | caaccagctg | 1440 |
| caggtgaacc | tgccccacgt | gaccgcgagc | ttctctgtct | tccgcccgtc | ttcctaccac | 1500 |
| atcatggtga | gcatgccat | ggcgtccgg | ctgcaggtgc | agctggcccc | agtcatgcaa | 1560 |
| ctctttgtga | cactggacca | ggcctcccag | gggcaggtgc | agggcctctg | cgggaacttc | 1620 |
| aacggcctgg | aaggtgacga | cttcaagacg | gccagcgggc | tggtgaggc | cacggggcc | 1680 |
| ggctttgcca | acacctggaa | ggcacagtca | acctgccatg | acaagctgga | ctggttggac | 1740 |
| gatccctgct | ccctgaacat | cgagagcgcc | aactacgccg | agcactggtg | ctccctcctg | 1800 |
| aagaagacag | agacccccctt | tggcaggtgc | cactcggctg | tggaccctgc | tgagtattac | 1860 |
| aagaggtgca | aatatgacac | gtgtaactgt | cagaacaatg | aggactgcct | gtgcgccgcc | 1920 |
| ctgtcctcct | acgcgcgcgc | ctgcaccgcc | aagggcgtca | tgctgtgggg | ctggcgggag | 1980 |
| catgtctgca | acaaggatgt | gggctcctgc | cccaactcgc | aggtcttcct | gtacaacctg | 2040 |
| accacctgcc | agcagacctg | ccgctccctc | tccgaggccg | cacagcactg | tctcgagggc | 2100 |
| tttgcgcctg | tggacggctg | cggctgccct | gaccacacct | tcctggacga | aagggccgc | 2160 |
| tgcgtacccc | tggccaagtg | ctcctgttac | caccgcggtc | tctacctgga | ggcgggggat | 2220 |

-continued

```
gtggtcgtca ggcaggaaga acgatgtgtg tgccgggatg ggcggctgca ctgtaggcag    2280
atccggctga tcggccagag ctgcacggcc ccaaagatcc acatggactg cagcaacctg    2340
actgcactgg ccacctcgaa gccccgagcc ctcagctgcc agacgctggc cgccggctat    2400
taccacacag agtgtgtcag tggctgtgtg tgccccgacg ggctgatgga tgacggccgg    2460
ggtggctgcg tggtggagaa ggaatgccct tgcgtccata caacgacct gtattcttcc     2520 ggcgccaaga tcaaggtgga ctgcaatacc tgcacctgca agagaggacg ctgggtgtgc    2580
acccaggctg tgtgccatgg cacctgctcc atttacggga gtggccacta catcaccttt    2640
gatgggaagt actacgactt tgacggacac tgctcctacg tggctgttca ggactactgc    2700
ggccagaact cctcactggg ctcattcagc atcatcaccg agaacgtccc ctgtggcact    2760
acgggcgtca cctgctccaa ggccatcaag atcttcatgg ggaggacgga gctgaagttg    2820
gaagacaagc accgtgtggt gatccagcgt gatgagggtc accacgtggc ctacaccacg    2880
cgggaggtgg gccagtacct ggtggtggag tccagcacgg gcatcatcgt catctgggac    2940
aagaggacca ccgtgttcat caagctggct ccctcctaca agggcaccgt gtgtggcctg    3000
tgtgggaact tgaccaccg ctccaacaac gacttcacca cgcgggacca catggtggtg     3060
agcagcgagc tggacttcgg gaacagctgg aaggaggccc ccacctgccc agatgtgagc    3120
accaaccccg agccctgcag cctgaacccg caccgccgct cctgggccga agcagtgc      3180 agcatcctca aaagcagcgt gttcagcatc tgccacagca aggtggaccc caagcccttc    3240
tacgaggcct gtgtgcacga ctcgtgctcc tgtgacacgg gtggggactg tgagtgcttc    3300
tgctctgccg tggcctccta cgcccaggag tgtaccaaag agggggcctg cgtgttctgg    3360
aggacgccgg acctgtgccc catattctgc gactactaca accctccgca tgagtgtgag    3420
tggcactatg agccatgtgg gaaccggagc ttcgagacct gcaggaccat caacggcatc    3480
cactccaaca tctccgtgtc ctacctggag ggctgctacc cccggtgccc caaggacagg    3540
cccatctatg aggaggatct gaagaagtgt gtcactgcag acaagtgtgg ctgctatgtc    3600
gaggacaccc actacccacc tggagcatcg gttcccaccg aggagacctg caagtcctgc    3660
gtgtgtacca actcctccca agtcgtctgc aggccggagg aaggaaagat tcttaaccag    3720
acccaggatg cgccttctg ctactgggag atctgtggcc ccaacgggac ggtgagaag     3780 cacttcaaca tctgttccat tacgacacgc ccgtccaccc tgaccacctt caccaccatc    3840
accctcccca ccaccccac ctccttcacc actaccacca ccaccaccac cccgacctcc     3900
agcacagttt tatcaacaac tccgaagctg tgctgcctct ggtctgactg gatcaatgag    3960
gaccacccca gcagtggcag cgacgacggt gaccgagaac catttgatgg ggtctgcggg    4020
gcccctgagg acatcgagtg caggtcggtc aaggatcccc acctcagctt ggagcagcat    4080
ggccagaagg tgcagtgtga tgtctctgtt gggttcattt gcaagaatga agaccagttt    4140
ggaaatggac catttggact tgttacgac tacaagatac gtgtcaattg ttgctggccc     4200
atggataagt gtatcaccac tcccagccct ccaactacca ctcccagccc tccaccaacc    4260
acgacgacca cccttccacc aaccaccacc cccagccctc caaccaccac cacaaccacc    4320
cctccaccaa ccaccacccc cagccctcca ataaccacca cgaccacccc tctaccaacc    4380
accactccca gccctccaat aagcaccaca accacccctc caccaaccac cactcccagc    4440
cctccaacca ccactcccag ccctccaacc accactccca gccctccaac aaccaccaca    4500 accaccctc caccaaccac cactcccagc cctccaatga ctacgccat cactccacca      4560 gccagcacta ccacccttcc accaaccacc actcccagcc ctccaacaac caccacaacc    4620
```

```
acccctccac caaccaccac tcccagtcct ccaacgacta cgcccatcac tccaccaacc    4680
agcactacta cccttccacc aaccaccact cccagccctc caccaaccac cacaaccacc    4740
cctccaccaa ccaccactcc cagccctcca acaaccacca ctcccagtcc tcaacaatc    4800
accacaacca cccctccacc aaccaccact cccagccctc caacaacgac cacaaccacc    4860
cctccaccaa ccaccactcc cagccctcca acgactacac ccatcactcc accaaccagc    4920
actaccaccc ttccaccaac caccactccc agccctccac caaccaccac aaccacccct    4980
ccaccaacca ccactcccag ccctccaaca accaccactc ccagccctcc aataaccacc    5040
acaaccaccc ctccaccaac caccactccc agctctccaa taaccaccac tcccagccct    5100
ccaacaacca ccatgaccac cccttcacca accaccaccc cagctctccc aataaccacc    5160
acaaccaccc cttcctcaac taccactccc agccctccac caaccaccat gaccacccct    5220
tcaccaacca ccactcccag ccctccaaca accaccatga ccacccttcc accaaccacc    5280
acttccagcc ctctaacaac tactcctcta cctccatcaa taactcctcc tacattttca    5340
ccattctcaa cgacaacccc tactacccca tgcgtgcctc tctgcaattg gactggctgg    5400
ctggattctg gaaacccaa cttttcacaaa ccaggtggag acacagaatt gattggagac    5460
gtctgtggac caggctgggc agctaacatc tcttgcagag ccaccatgta tcctgatgtt    5520
cccattggac agcttggaca aacagtggtg tgtgatgtct ctgtggggct gatatgcaaa    5580
aatgaagacc aaaagccagg tggggtcatc cctatggcct tctgcctcaa ctacgagatc    5640
aacgttcagt gctgtgagtg tgtcacccaa cccaccacca tgacaaccac caccacagag    5700
aacccaactc cgccaaccac gacacccatc accaccacca ctacggtgac cccaacccca    5760
acacccaccg gcacacagac cccaaccacg acacccatca ccaccaccac tacggtgacc    5820
ccaaccccaa cacccaccgg cacacagacc caaccacga cacccatcac caccaccact    5880
acggtgaccc caaccccaac acccaccggc acacagaccc caaccacgac acccatcacc    5940
accaccacta cggtgacccc aaccccaaca cccaccggca cacagacccc aaccacgaca    6000
cccatcacca ccaccactac ggtgacccca accccaacac ccaccggcac acagacccca    6060
accacgacac ccatcaccac caccactacg gtgacccccaa ccccaacacc caccggcaca    6120
cagaccccaa ccacgacacc catcaccacc accactacgg tgaccccaac ccaacaccc    6180
accggcacac agacccaac cacgacaccc atcaccacca ccactacggt gaccccaacc    6240
ccaacaccca ccggcacaca gacccccaacc acgacaccca tcaccaccac cactacggtg    6300
accccaaccc caacacccac cggcacacag accccaacca cgacacccat caccaccacc    6360
actacggtga ccccaacccc aacacccacc ggcacacaga ccccaaccac gacacccatc    6420
accaccacca ctacggtgac cccaaccccca acacccaccg gcacacagac cccaaccacg    6480
acacccatca ccaccaccac tacggtgacc ccaaccccaa cacccaccgg cacacagacc    6540
ccaaccacga cacccatcac caccaccact acggtgaccc caaccccaac acccaccggc    6600
acacagaccc caaccacgac acccatcacc accaccacta cggtgacccc aaccccaaca    6660
cccaccggca cacagacccc aaccacgaca cccatcacca ccaccactac ggtgacccca    6720
accccaacac caccggcac acagacccca accacgacac ccatcaccac caccactacg    6780
gtgaccccaa ccccaacacc caccggcaca cagaccccaa ccacgacacc catcaccacc    6840
accactacgg tgaccccaac cccaacaccc accggcacac agaccccaac cacgacaccc    6900
atcaccacca ccactacggt gaccccaacc ccaacaccca ccggcacaca gaccccaacc    6960
```

-continued

```
acgacaccca tcaccaccac cactacggtg accccaaccc caacacccac cggcacacag   7020
accccaacca cgacacccat caccaccacc actacggtga ccccaacccc aacacccacc   7080
ggcacacaga ccccaaccac gacacccatc accaccacca ctacggtgac ccccaacccca  7140 acacccaccg gcacacagac cccaaccacg acacccatca ccaccaccac tacggtgacc   7200
ccaaccccaa cacccaccgg cacacagacc caaccacga cacccatcac caccaccact   7260
acggtgaccc caaccccaac acccaccggc acacagaccc caaccacgac acccatcacc   7320
accaccacta cggtgacccc aaccccaaca cccaccggca cacagacccc aaccacgaca   7380
cccatcacca ccaccactac ggtgacccca accccaacc ccaccggcac acagacccca   7440
accacgacac ccatcaccac caccactacg gtgacccccaa ccccaacacc caccggcaca   7500 cagacccca ccacgacacc catcaccacc accactacgg tgaccccaac cccaacaccc   7560
accggcacac agaccccaac cacgacaccc atcaccacca ccactacggt gaccccaacc   7620
ccaacaccca ccggcacaca gaccccaacc acgacaccca tcaccaccac cactacggtg   7680
accccaaccc caacacccac cggcacacag accccaacca cgacacccat caccaccacc   7740
actacggtga ccccaacccc aacacccacc ggcacacaga ccccaaccac gacacccatc   7800
accaccacca ctacggtgac ccccaacccca acacccaccg gcacacagac cccaaccacg   7860
acacccatca ccaccaccac tacggtgacc ccaaccccaa cacccaccgg cacacagacc   7920 caaccacga cacccatcac caccaccact acggtgaccc caaccccaac acccaccggc   7980
acacagaccc caaccacgac acccatcacc accaccacta cggtgacccc aaccccaaca   8040
cccaccggca cacagacccc aaccacgaca cccatcacca ccaccactac ggtgacccca   8100
accccaacac ccaccggcac acagacccca ccacgacac catcaccac caccactacg   8160 gtgaccccaa ccccaacacc caccggcaca cagacccca ccacgacacc catcaccacc   8220
accactacgg tgaccccaac cccaacaccc accggcacac agaccccaac cacgacaccc   8280
atcaccacca ccactacggt gaccccaacc ccaacaccca ccggcacaca gaccccaacc   8340
acgacaccca tcaccaccac cactacggtg accccaaccc caacacccac cggcacacag   8400
accccaacca cgacacccat caccaccacc actacggtga ccccaacccc aacacccacc   8460
ggcacacaga ccccaaccac gacacccatc accaccacca ctacggtgac ccccaacccca  8520 acacccaccg gcacacagac cccaaccacg acacccatca ccaccaccac tacggtgacc   8580
ccaaccccaa cacccaccgg cacacagacc caaccacga cacccatcac caccaccact   8640
acggtgaccc caaccccaac acccaccggc acacagaccc caaccacgac acccatcacc   8700
accaccacta cggtgacccc aaccccaaca cccaccggca cacagacccc aaccacgaca   8760
cccatcacca ccaccactac ggtgacccca accccaacac caccggcac acagacccca   8820 accacgacac ccatcaccac caccactacg gtgacccccaa ccccaacacc caccggcaca   8880 cagacccca ccacgacacc catcaccacc accactacgg tgaccccaac cccaacaccc   8940
accggcacac agaccccaac cacgacaccc atcaccacca ccactacggt gaccccaacc   9000
ccaacaccca ccggcacaca gaccccaacc acgacaccca tcaccaccac cactacggtg   9060
accccaaccc caacacccac cggcacacag accccaacca cgacacccat caccaccacc   9120
actacggtga ccccaacccc aacacccacc ggcacacaga ccccaaccac gacacccatc   9180
accaccacca ctacggtgac ccccaacccca acacccaccg gcacacagac cccaaccacg   9240
acacccatca ccaccaccac tacggtgacc ccaaccccaa cacccaccgg cacacagacc   9300 caaccacga cacccatcac caccaccact acggtgaccc caaccccaac acccaccggc   9360
```

```
acacagaccc caaccacgac acccatcacc accaccacta cggtgacccc aaccccaaca    9420
cccaccggca cacagacccc aaccacgaca cccatcacca ccaccactac ggtgacccca    9480
accccaacac ccaccggcac acagacccca accacgacac ccatcaccac caccactacg    9540
gtgaccccaa ccccaacacc caccggcaca cagacccca ccacgacacc catcaccacc    9600
accactacgg tgaccccaac cccaacaccc accggcacac agaccccaac cacgacaccc    9660
atcaccacca ccactacggt gaccccaacc ccaacaccca ccggcacaca gaccccaacc    9720
acgacaccca tcaccaccac cactacggtg accccaaccc caacacccac cggcacacag    9780
accccaacca cgacacccat caccaccacc actacggtga ccccaacccc aacacccacc    9840
ggcacacaga ccccaaccac gacacccatc accaccacca ctacggtgac ccaaccccca    9900
acacccaccg gcacacagac cccaaccacg acacccatca ccaccaccac tacggtgacc    9960
ccaaccccaa cacccaccgg cacagaccc caaccacga cacccatcac caccaccact   10020
acggtgaccc caaccccaac acccaccggc acagaccc caaccacgac acccatcacc   10080
accaccacta cggtgacccc aaccccaaca cccaccggca cacagacccc aaccacgaca   10140
cccatcacca ccaccactac ggtgacccca ccccaacac ccaccggcac acagacccca   10200
accacgacac ccatcaccac caccactacg gtgaccccaa ccccaacacc caccggcaca   10260
cagacccca ccacgacacc catcaccacc accactacgg tgaccccaac cccaacaccc   10320
accggcacac agaccccaac cacgacaccc atcaccacca ccactacggt gaccccaacc   10380
ccaacaccca ccggcacaca gaccccaacc acgacaccca tcaccaccac cactacggtg   10440
accccaaccc caacacccac cggcacacag accccaacca cgacacccat caccaccacc   10500
actacggtga ccccaacccc aacacccacc ggcacacaga ccccaaccac gacacccatc   10560
accaccacca ctacggtgac ccaaccccca acacccaccg gcacacagac cccaaccacg   10620
acacccatca ccaccaccac tacggtgacc caaccccaa cacccaccgg cacagaccc   10680
ccaaccacga cacccatcac caccaccact acggtgaccc caaccccaac acccaccggc   10740
acagaccc caaccacgac acccatcacc accaccacta cggtgacccc aaccccaaca   10800
cccaccggca cacagacccc aaccacgaca cccatcacca ccaccactac ggtgacccca   10860
accccaacac ccaccggcac acagacccca ccacgacacc catcaccac caccactacg   10920
gtgaccccaa ccccaacacc caccggcaca cagacccca ccacgacacc catcaccacc   10980
accactacgg tgaccccaac cccaacaccc accggcacac agaccccaac cacgacaccc   11040
atcaccacca ccactacggt gaccccaacc ccaacaccca ccggcacaca gaccccaacc   11100
acgacaccca tcaccaccac cactacggtg accccaaccc caacacccac cggcacacag   11160
accccaacca cgacacccat caccaccacc actacggtga ccccaacccc aacacccacc   11220
ggcacacaga ccccaaccac gacacccatc accaccacca ctacggtgac ccaaccccca   11280
acacccaccg gcacacagac cccaaccacg acacccatca ccaccaccac tacggtgacc   11340
ccaaccccaa cacccaccgg cacagaccc caaccacga cacccatcac caccaccact   11400
acggtgaccc caaccccaac acccaccggc acagaccc caaccacgac acccatcacc   11460
accaccacta cggtgacccc aaccccaaca cccaccggca cacagacccc aaccacgaca   11520
cccatcacca ccaccactac ggtgacccca ccccaacac ccaccggcac acagacccca   11580
accacgacac ccatcaccac caccactacg gtgaccccaa ccccaacacc caccggcaca   11640
cagacccca ccacgacacc catcaccacc accactacgg tgaccccaac cccaacaccc   11700
```

```
accggcacac agaccccaac cacgacaccc atcaccacca ccactacggt gacccccaacc   11760
ccaacacccca ccggcacaca gaccccaacc acgacaccca tcaccaccac cactacggtg   11820
accccaaccc caacacccac cggcacacag accccaacca cgacacccat caccaccacc   11880
actacggtga ccccaacccc aacacccacc ggcacacaga ccccaaccac gacacccatc   11940
accaccacca ctacggtgac cccaacccca cacccaccg gcacacagac cccaaccacg   12000
acacccatca ccaccaccac tacggtgacc ccaacccccaa cacccaccgg cacacagacc   12060
ccaaccacga cacccatcac caccaccact acggtgaccc caaccccaac acccaccggc   12120
acacagaccc caaccacgac acccatcacc accaccacta cggtgacccc aaccccaaca   12180
cccaccggca cacagacccc aaccacgaca cccatcacca ccaccactac ggtgacccca   12240
accccaacac ccaccggcac acagacccca accacgaca ccatcaccac caccactacg   12300
gtgaccccaa ccccaacacc caccggcaca cagacccccaa ccacgacacc catcaccacc   12360
accactacgg tgaccccaac cccaacaccc accggcacac agaccccaac cacgacaccc   12420
atcaccacca ccactacggt gaccccaacc ccaacaccca ccggcacaca gaccccaacc   12480
acgacaccca tcaccaccac cactacggtg accccaaccc caacacccac cggcacacag   12540
accccaacca cgacacccat caccaccacc actacggtga ccccaaccccc aacacccacc   12600
ggcacacaga ccgggccccc cacccacaca agcacagcac cgattgctga gttgaccaca   12660
tccaatcctc cgcctgagtc ctcaacccct cagacctctc ggtccacctc ttcccctctc   12720
acggagtcaa ccaccccttct gagtacccta ccacctgcca ttgagatgac cagcacggcc   12780
ccaccctcca cacccacggc acccacgacc acgagcggag gccacacact gtctccaccg   12840
cccagcacca ccacgtcccc tccaggcacc cccactcgcg gtaccacgac cgggtcatct   12900
tcagccccca ccccccagcac tgtgcagacg accaccacca gtgcctggac cccaacgccg   12960
accccactct ccacacccag catcatcagg accacaggcc tgaggcccta cccttcctct   13020
gtgcttatct gctgtgtcct gaacgacacc tactacgcac caggtgagga ggtgtacaac   13080
ggcacatacg gagacacctg ttatttcgtc aactgctcac tgagctgtac gttggagttc   13140
tataactggt cctgcccatc cacgccctcc ccaacaccca cgccctccaa gtcgacgccc   13200
acgccttcca agccatcgtc cacgccctcc aagccgacgc ccggcaccaa gccccccgag   13260
tgcccagact ttgatcctcc cagacaggag aacgagactt ggtggctgtg cgactgcttc   13320
atggccacgt gcaagtacaa caacacggtg gagatcgtga aggtggagtg tgagccgccg   13380
cccatgccca cctgctccaa cggcctccaa cccgtgcgcg tcgaggaccc cgacggctgc   13440
tgctggcact gggagtgcga ctgctactgc acgggctggg gcgacccgca ctatgtcacc   13500
ttcgacggac tctactacag ctaccagggc aactgcacct acgtgctggt ggaggagatc   13560
agcccctccg tggacaactt cggagtttac atcgacaact accactgcga tcccaacgac   13620
aaggtgtcct gtccccgcac cctcatcgtg cgccacgaga cccaggaggt gctgatcaag   13680
accgtgcata tgatgcccat gcaggtgcag gtgcaggtga acaggcaggc ggtggcactg   13740
ccctacaaga agtacgggct ggaggtgtac cagtctggca tcaactacgt ggtggacatc   13800
cccgagctgg gtgtcctcgt ctcctacaat ggcctgtcct tctccgtcag gctgccctac   13860
caccggtttg gcaacaacac caagggccag tgtggcacct gcaccaacac cacctccgac   13920
gactgcattc tgcccagcgg ggagatcgtc tccaactgtg aggctgcggc tgaccagtgg   13980
ctggtgaacg acccctccaa gccacactgc cccacagca gctccacgac caagcgcccc   14040
gccgtcactg tgcccgggg cggtaaaacg accccacaca aggactgcac cccatctccc   14100
```

-continued

```
ctctgccagc tcatcaagga cagcctgttt gcccagtgcc acgcactggt gcccccgcag    14160
cactactacg atgcctgcgt gttcgacagc tgcttcatgc cgggctcgag cctggagtgc    14220
gccagtctgc aggcctacgc agccctctgt gcccagcaga acatctgcct cgactggcgg    14280
aaccacacgc atggggcctg cttggtggag tgcccatctc acagggagta ccaggcctgt    14340
ggccctgcag aagagcccac gtgcaaatcc agctcctccc agcagaacaa cacagtcctg    14400
gtggaaggct gcttctgtcc tgagggcacc atgaactacg ctcctggctt tgatgtctgc    14460
gtgaagacct gcggctgtgt gggacctgac aatgtgccca gagagtttgg ggagcacttc    14520
gagttcgact gcaagaactg tgtctgcctg gagggtggaa gtggcatcat ctgccaaccc    14580
aagaggtgca gccagaagcc cgttacccac tgcgtggaag acggcaccta cctcgccacg    14640
gaggtcaacc ctgccgacac ctgctgcaac attaccgtct gcaagtgcaa caccagcctg    14700
tgcaaagaga gccctccgt gtgcccgctg ggattcgaag tgaagagcaa gatggtgcct    14760
ggaaggtgct gtcccttcta ctggtgtgag tccaaggggg tgtgtgttca cgggaatgct    14820
gagtaccagc ccggttctcc agtttattcc tccaagtgcc aggactgcgt gtgcacggac    14880
aaggtggaca acaacaccct gctcaacgtc atcgcctgca cccacgtgcc ctgcaacacc    14940
tcctgcagcc ctggcttcga actcatggag gcccccgggg agtgctgtaa gaagtgtgaa    15000
cagacgcact gtatcatcaa acggcccgac aaccagcacg tcatcctgaa gcccggggac    15060
ttcaagagcg acccgaagaa caactgcaca ttcttcagct gcgtgaagat ccacaaccag    15120
ctcatctcgt ccgtctccaa catcacctgc cccaactttg atgccagcat ttgcatcccg    15180
ggctccatca cattcatgcc caatggatgc tgcaagacct gcaccctcg caatgagacc    15240 agggtgccct gctccaccgt ccccgtcacc acggaggttt cgtacgccgg ctgcaccaag    15300
accgtcctca tgaatcattg ctccgggtcc tgcgggacat tgtcatgta ctcggccaag    15360 gcccaggccc tggaccacag ctgctcctgc tgcaaagagg agaaaaccag ccagcgtgag    15420
gtggtcctga gctgccccaa tggcggctcg ctgacacaca cctacaccca catcgagagc    15480
tgccagtgcc aggacaccgt ctgcgggctc ccaccggca cctcccgccg ggcccggcgc    15540
tcccctaggc atctggggag cgggtgagcg gggtgggcac agccccctc actgccctcg    15600 acagctttac ctcccccgga ccctctgagc ctcctaagct cggcttcctc tcttcagata    15660
tttattgtct gagtctttgt tcagtccttg cttttccaata ataaactcag ggggacatgc    15720
```

<210> SEQ ID NO 15
<211> LENGTH: 3697
<212> TYPE: DNA
<213> ORGANISM: human

<400> SEQUENCE: 15

```
agggagtgtt cccgggggag atactccagt cgtagcaaga gtctcgacca ctgaatggaa      60
gaaaaggact ttaaccacc attttgtgac ttacagaaag gaatttgaat aaagaaaact     120
atgatacttc aggcccatct tcactccctg tgtcttctta tgctttattt ggcaactgga     180
tatggccaag aggggaagtt tagtggaccc ctgaaaccca tgacattttc tatttatgaa     240
ggccaagaac cgagtcaaat tatattccag tttaaggcca atcctcctgc tgtgactttt     300
gaactaactg gggagacaga caacatattt gtgatagaac ggagggact tctgtattac     360 aacagagcct tggacaggga aacaagatct actcacaatc tccaggttgc agccctggac     420
gctaatggaa ttatagtgga gggtccagtc cctatcacca tagaagtgaa ggacatcaac     480
```

```
gacaatcgac ccacgtttct ccagtcaaag tacgaaggct cagtaaggca gaactctcgc      540
ccaggaaagc ccttcttgta tgtcaatgcc acagacctgg atgatccggc cactcccaat      600
ggccagcttt attaccagat tgtcatccag cttcccatga tcaacaatgt catgtacttt      660
cagatcaaca acaaaacggg agccatctct cttacccgag agggatctca ggaattgaat      720
cctgctaaga atccttccta taatctggtg atctcagtga aggacatggg aggccagagt      780
gagaattcct tcagtgatac cacatctgtg atatccatag tgacagagaa tatttggaaa      840
gcaccaaaac ctgtggagat ggtggaaaac tcaactgatc ctcaccccat caaaatcact      900
caggtgcggt ggaatgatcc cggtgcacaa tattccttag ttgacaaaga gaagctgcca      960
agattcccat tttcaattga ccaggaagga gatatttacg tgactcagcc cttggaccga     1020
gaagaaaagg atgcatatgt tttttatgca gttgcaaagg atgagtacgg aaaaccactt     1080
tcatatccgc tggaaattca tgtaaaagtt aaagatatta atgataatcc acctacatgt     1140
ccgtcaccag taaccgtatt tgaggtccag gagaatgaac gactgggtaa cagtatcggg     1200
acccttactg cacatgacag ggatgaagaa atactgccaa cagttttctt aaactacagg     1260
attgtggagc aaactcccaa acttcccatg gatggactct tcctaatcca aacctatgct     1320
ggaatgttac agttagctaa acagtccttg aagaagcaag atactcctca gtacaactta     1380
acgatagagg tgtctgacaa agatttcaag acccttgtt ttgtgcaaat caacgttatt     1440
gatatcaatg atcagatccc catctttgaa aaatcagatt atggaaacct gactcttgct     1500
gaagacacaa acattgggtc caccatctta accatccagg ccactgatgc tgatgagcca     1560
tttactggga gttctaaaat tctgtatcat atcataaagg gagacagtga gggacgcctg     1620
ggggttgaca cagatcccca taccaacacc ggatatgtca taattaaaaa gcctcttgat     1680
tttgaaacag cagctgtttc caacattgtg ttcaaagcag aaaatcctga gcctctagtg     1740
tttggtgtga agtacaatgc aagttctttt gccaagttca cgcttattgt gacagatgtg     1800
aatgaagcac ctcaattttc ccaacacgta ttccaagcga agtcagtga  ggatgtagct     1860 ataggcacta aagtgggcaa tgtgactgcc aaggatccag aaggtctgga cataagctat     1920
tcactgaggg gagacacaag aggttggctt aaaattgacc acgtgactgg tgagatcttt     1980
agtgtggctc cattggacag agaagccgga agtccatatc gggtacaagt ggtggccaca     2040
gaagtagggg ggtcttcctt gagctctgtg tcagagttcc acctgatcct tatggatgtg     2100
aatgacaacc ctcccaggct agccaaggac tacacgggct tgttcttctg ccatcccctc     2160
agtgcacctg gaagtctcat tttcgaggct actgatgatg atcagcactt atttcggggt     2220
ccccatttta catttccct cggcagtgga agcttacaaa acgactggga agtttccaaa     2280
atcaatggta ctcatgcccg actgtctacc aggcacacag agtttgagga gagggagtat     2340
gtcgtcttga tccgcatcaa tgatgggggt cggccaccct ggaaggcat  tgtttcttta     2400 ccagttacat tctgcagttg tgtggaagga agttgtttcc ggccagcagg tcaccagact     2460 gggatacca ctgtgggcat ggcagttggt atactgctga ccaccttct  ggtgattggt     2520 ataattttag cagttgtgtt tatccgcata aagaaggata aaggcaaaga taatgttgaa     2580
agtgctcaag catctgaagt caaacctctg agaagctgaa tttgaaaagg aatgtttgaa     2640
tttatatagc aagtgctatt tcagcaacaa ccatctcatc ctattacttt tcatctaacg     2700
tgcattataa ttttttaaac agatattccc tcttgtcctt taatatttgc taaatatttc     2760
ttttttgagg tggagtcttg ctctgtcgcc caggctggag tacagtggtg tgatcccagc     2820
tcactgcaac ctccgcctcc tgggttcaca tgattctcct gcctcagctt cctaagtagc     2880
```

```
tgggtttaca ggcacccacc accatgccca gctaattttt gtattttaa tagagacggg    2940 gtttcgccat ttggccaggc tggtcttgaa ctcctgacgt caagtgatct gcctgccttg    3000
gtctcccaat acaggcatga accactgcac ccacctactt agatatttca tgtgctatag    3060
acattagaga gatttttcat ttttccatga cattttcct ctctgcaaat ggcttagcta    3120
cttgtgtttt tcccttttgg ggcaagacag actcattaaa tattctgtac attttttctt    3180
tatcaaggag atatatcagt gttgtctcat agaactgcct ggattccatt tatgtttttt    3240
ctgattccat cctgtgtccc cttcatcctt gactcctttg gtatttcact gaatttcaaa    3300
catttgtcag agaagaaaaa cgtgaggact caggaaaaat aaataaataa agaacagcc    3360 ttttccctta gtattaacag aaatgtttct gtgtcattaa ccatctttaa tcaatgtgac    3420
atgttgctct ttggctgaaa ttcttcaact tggaaatgac acagacccac agaaggtgtt    3480
caaacacaac ctactctgca aaccttggta aaggaaccag tcagctggcc agatttcctc    3540
actacctgcc atgcatacat gctgcgcatg ttttcttcat tcgtatgtta gtaaagtttt    3600
ggttattata tatttaacat gtggaagaaa acaagacatg aaaagagtgg tgacaaatca    3660
agaataaaca ctggttgtag tcagttttgt ttgttaa                            3697

<210> SEQ ID NO 16
<211> LENGTH: 3697
<212> TYPE: DNA
<213> ORGANISM: human

<400> SEQUENCE: 16
agggagtgtt cccgggggag atactccagt cgtagcaaga gtctcgacca ctgaatggaa      60
gaaaaggact tttaaccacc attttgtgac ttacagaaag gaatttgaat aaagaaaact     120
atgatacttc aggcccatct tcactccctg tgtcttctta tgctttattt ggcaactgga     180
tatggccaag aggggaagtt tagtggaccc ctgaaaccca tgacattttc tatttatgaa     240
ggccaagaac cgagtcaaat tatattccag tttaaggcca atcctcctgc tgtgactttt     300
gaactaactg gggagacaga caacatattt gtgatagaac ggggggact tctgtattac     360 aacagagcct tggacaggga acaagatctc actcacaatc tccaggttgc agccctggac     420
gctaatggaa ttatagtgga gggtccagtc cctatcacca tagaagtgaa ggacatcaac     480
gacaatcgac ccacgtttct ccagtcaaag tacgaaggct cagtaaggca gaactctcgc     540
ccaggaaagc ccttcttgta tgtcaatgcc acagacctgg atgatccggc cactcccaat     600
ggccagcttt attaccagat tgtcatccag cttcccatga tcaacaatgt catgtacttt     660
cagatcaaca caaaacggga agccatctct cttacccgag agggatctca ggaattgaat     720
cctgctaaga atccttccta taatctggtg atctcagtga aggacatggg aggccagagt     780
gagaattcct tcagtgatac cacatctgtg gatatcatag tgacagagaa tatttggaaa     840
gcaccaaaac ctgtggagat ggtggaaaac tcaactgatc ctcaccccat caaaatcact     900
caggtgcggt ggaatgatcc cggtgcacaa tattccttag ttgacaaaga gaagctgcca     960
agattcccat tttcaattga ccaggaagga gatatttacg tgactcagcc cttggaccga    1020
gaagaaaagg atgcatatgt tttttatgca gttgcaaagg atgagtacgg aaaaccactt    1080
tcatatccgc tggaaattca tgtaaaagtt aaagatatta atgataatcc acctacatgt    1140
ccgtcaccag taaccgtatt tgaggtccag gagaatgaac gactgggtaa cagtatcggg    1200 accccttactg cacatgacag ggatgaagaa atactgccaa cagttttcct aaactacagg    1260
```

```
attgtggagc aaactcccaa acttcccatg gatggactct tcctaatcca aacctatgct    1320
ggaatgttac agttagctaa acagtccttg aagaagcaag atactcctca gtacaactta    1380
acgatagagg tgtctgacaa agatttcaag acccttgtt ttgtgcaaat caacgttatt    1440
gatatcaatg atcagatccc catctttgaa aaatcagatt atggaaacct gactcttgct    1500
gaagacacaa acattgggtc caccatctta accatccagg ccactgatgc tgatgagcca    1560
tttactggga gttctaaaat tctgtatcat atcataaagg gagacagtga gggacgcctg    1620
ggggttgaca cagatcccca taccaacacc ggatatgtca taattaaaaa gcctcttgat    1680
tttgaaacag cagctgtttc caacattgtg ttcaaagcag aaaatcctga gcctctagtg    1740
tttggtgtga agtacaatgc aagttctttt gccaagttca cgcttattgt gacagatgtg    1800
aatgaagcac ctcaatttc ccaacacgta ttccaagcga aagtcagtga ggatgtagct    1860
ataggcacta aagtgggcaa tgtgactgcc aaggatccag aaggtctgga cataagctat    1920
tcactgaggg gagacacaag aggttggctt aaaattgacc acgtgactgg tgagatcttt    1980
agtgtggctc cattggacag agaagccgga agtccatatc gggtacaagt ggtggccaca    2040
gaagtagggg ggtcttcctt gagctctgtg tcagagttcc acctgatcct tatggatgtg    2100
aatgacaacc ctcccaggct agccaaggac tacacgggct tgttcttctg ccatccctc    2160 agtgcacctg gaagtctcat tttcgaggct actgatgatg atcagcactt atttcggggt    2220
ccccatttta cattttccct cggcagtgga agcttacaaa acgactggga agtttccaaa    2280
atcaatggta ctcatgcccg actgtctacc aggcacacag agtttgagga gagggagtat    2340
gtcgtcttga tccgcatcaa tgatgggggt cggccaccct ggaaggcat tgtttctta    2400 ccagttacat tctgcagttg tgtggaagga agttgtttcc ggccagcagg tcaccagact    2460
gggataccca ctgtgggcat ggcagttggt atactgctga ccaccttct ggtgattggt    2520 ataattttag cagttgtgtt tatccgcata aagaaggata aaggcaaaga taatgttgaa    2580
agtgctcaag catctgaagt caaaccctctg agaagctgaa tttgaaaagg aatgtttgaa    2640
tttatatagc aagtgctatt tcagcaacaa ccatctcatc ctattacttt tcatctaacg    2700
tgcattataa tttttaaac agatattccc tcttgtcctt taatatttgc taaatatttc    2760
ttttttgagg tggagtcttg ctctgtcgcc caggctggag tacagtggtg tgatcccagc    2820
tcactgcaac ctccgcctcc tgggttcaca tgattctcct gcctcagctt cctaagtagc    2880
tgggtttaca ggcacccacc accatgccca gctaattttt gtattttaa tagagacggg    2940 gtttcgccat ttggccaggc tggtcttgaa ctcctgacgt caagtgatct gcctgccttg    3000
gtctcccaat acaggcatga accactgcac ccacctactt agatatttca tgtgctatag    3060
acattagaga gattttctcat ttttccatga cattttccct ctctgcaaat ggcttagcta    3120
cttgtgtttt tcccttttgg ggcaagacag actcattaaa tattctgtac atttttctt    3180 tatcaaggag atatatcagt gttgtctcat agaactgcct ggattccatt tatgtttttt    3240
ctgattccat cctgtgtccc cttcatcctt gactcctttg gtatttcact gaatttcaaa    3300
catttgtcag agaagaaaaa cgtgaggact caggaaaaat aaataaataa aagaacagcc    3360
tttcccctta gtattaacag aaatgtttct gtgtcattaa ccatctttaa tcaatgtgac    3420
atgttgctct ttggctgaaa ttcttcaact tggaaatgac acagacccac agaaggtgtt    3480
caaacacaac ctactctgca aaccttggta aaggaaccag tcagctggcc agatttcctc    3540
actacctgcc atgcatacat gctgcgcatg ttttcttcat tcgtatgtta gtaaagtttt    3600
ggttattata tatttaacat gtggaagaaa acaagacatg aaaagagtgg tgacaaatca    3660
```

```
agaataaaca ctggttgtag tcagttttgt ttgttaa                              3697

<210> SEQ ID NO 17
<211> LENGTH: 1597
<212> TYPE: DNA
<213> ORGANISM: human

<400> SEQUENCE: 17
aacaaactgc acccactgaa ctccgcagct agcatccaaa tcagcccttg agatttgagg      60
ccttggagac tcaggagttt tgagagcaaa atgacaacac ccagaaattc agtaaatggg     120
actttcctgg cagagccaat gaaaggccct attgctatgc aatctggtcc aaaaccactc     180
ttcaggagga tgtcttcact ggtgggcccc acgcaaagct tcttcatgag ggaatctaag     240
actttggggg ctgtccagat tatgaatggg ctcttccaca ttgccctggg gggtcttctg     300
atgatcccag cagggatcta tgcacccatc tgtgtgactg tgtggtaccc tctctgggga     360
ggcattatgt atattatttc cggatcactc ctggcagcaa cggagaaaaa ctccaggaag     420
tgtttggtca aaggaaaaat gataatgaat tcattgagcc tctttgctgc catttctgga     480
atgattcttt caatcatgga catacttaat attaaaattt cccatttttt aaaaatggag     540
agtctgaatt ttattagagc tcacacacca tatattaaca tatacaactg tgaaccagct     600
aatccctctg agaaaaactc cccatctacc caatactgtt acagcataca atctctgttc     660
ttgggcattt tgtcagtgat gctgatcttt gccttcttcc aggaacttgt aatagctggc     720
atcgttgaga atgaatggaa aagaacgtgc tccagaccca atctaacat agttctcctg      780 tcagcagaag aaaaaaaaga acagactatt gaaataaaag aagaagtggt tgggctaact     840
gaaacatctt cccaaccaaa gatgaagaa gacattgaaa ttattccaat ccaagaagag      900
gaagaagaag aaacagagac gaactttcca gaacctcccc aagatcagga atcctcacca     960
atagaaaatg acagctctcc ttaagtgatt tcttctgttt tctgtttcct tttttaaaca    1020
ttagtgttca tagcttccaa gagacatgct gactttcatt tcttgaggta ctctgcacat    1080
acgcaccaca tctctatctg gcctttgcat ggagtgacca tagctccttc tctcttacat    1140
tgaatgtaga gaatgtagcc attgtagcag cttgtgttgt cacgcttctt cttttgagca    1200
actttcttac actgaagaaa ggcagaatga gtgcttcaga atgtgatttc ctactaacct    1260
gttccttgga taggcttttt agtatagtat ttttttttgt cattttctcc atcagcaacc    1320
agggagactg cacctgatgg aaaagatata tgactgcttc atgacattcc taaactatct    1380
tttttttatt ccacatctac gttttggtg gagtcccttt tgcatcattg ttttaaggat      1440
gataaaaaaa aaataacaac tagggacaat acagaaccca ttccatttat ctttctacag    1500
ggctgacatt gtggcacatt cttagagtta ccacacccca tgagggaagc tctaaatagc    1560
caacacccat ctgttttttg taaaaacagc atagctt                              1597

<210> SEQ ID NO 18
<211> LENGTH: 2907
<212> TYPE: DNA
<213> ORGANISM: human

<400> SEQUENCE: 18
gccatctggg cccaggcccc atgccccgag gaggggtggt ctgaagccca ccagagcccc      60
ctgccagact gtctgcctcc cttctgactg tggccgcttg gcatggccag caacagcagc     120
tcctgcccga cacctggggg cgggcacctc aatgggtacc cggtgcctcc ctacgccttc     180
```

-continued

| | |
|---|---|
| ttcttccccc ctatgctggg tggactctcc ccgccaggcg ctctgaccac tctccagcac | 240 |
| cagcttccag ttagtggata tagcacacca tccccagccc ccattgagac ccagagcagc | 300 |
| agttctgaag agatagtgcc cagccctccc tcgccacccc ctctacccccg catctacaag | 360 |
| ccttgctttg tctgtcagga caagtcctca ggctaccact atggggtcag cgcctgtgag | 420 |
| ggctgcaagg gcttcttccg ccgcagcatc cagaagaaca tggtgtacac gtgtcaccgg | 480 |
| gacaagaact gcatcatcaa caaggtgacc cggaaccgct gccagtactg ccgactgcag | 540 |
| aagtgctttg aagtgggcat gtccaaggag tctgtgagaa cgaccgaaa caagaagaag | 600 |
| aaggaggtgc ccaagcccga gtgctctgag agctacacgc tgacgccgga ggtggggag | 660 |
| ctcattgaga aggtgcgcaa agcgcaccag gaaaccttcc ctgccctctg ccagctgggc | 720 |
| aaatacacta cgaacaacag ctcagaacaa cgtgtctctc tggacattga cctctgggac | 780 |
| aagttcagtg aactctccac caagtgcatc attaagactg tggagttcgc caagcagctg | 840 |
| cccggcttca ccaccctcac catcgccgac cagatcaccc tcctcaaggc tgcctgcctg | 900 |
| gacatcctga tcctgcggat ctgcacgcgg tacacgcccg agcaggacac catgaccttc | 960 |
| tcggacgggt gaccctgaa ccggacccag atgcacaacg ctggcttcgg cccccctcacc | 1020 |
| gacctggtct ttgccttcgc caaccagctg ctgcccctgg agatggatga tgcggagacg | 1080 |
| gggctgctca gcgccatctg cctcatctgc ggagaccgcc aggacctgga gcagccggac | 1140 |
| cgggtggaca tgctgcagga gccgctgctg gaggcgctaa aggtctacgt gcggaagcgg | 1200 |
| aggcccagcc gccccccacat gttccccaag atgctaatga agattactga cctgcgaagc | 1260 |
| atcagcgcca agggggctga gcgggtgatc acgctgaaga tggagatccc gggctccatg | 1320 |
| ccgcctctca tccaggaaat gttggagaac tcagagggcc tggacactct gagcggacag | 1380 |
| ccggggggtg ggggcggga cggggtggc ctggcccccc cgccaggcag ctgtagcccc | 1440 |
| agcctcagcc ccagctccaa cagaagcagc ccggccaccc actccccgtg accgccacg | 1500 |
| ccacatggac acagccctcg ccctccgccc cggctttct ctgcctttct accgaccatg | 1560 |
| tgaccccgca ccagccctgc ccccacctgc cctcccgggc agtactgggg accttccctg | 1620 |
| ggggacgggg agggaggagg cagcgactcc ttggacagag gcctgggccc tcagtggact | 1680 |
| gcctgctccc acagcctggg ctgacgtcag aggccgaggc caggaactga gtgaggcccc | 1740 |
| tggtcctggg tctcaggatg ggtcctgggg gcctcgtgtt catcaagaca cccctctgcc | 1800 |
| cagctcacca catcttcatc accagcaaac gccaggactt ggctccccca tcctcagaac | 1860 |
| tcacaagcca ttgctcccca gctggggaac ctcaacctcc ccctgcctc ggttggtgac | 1920 |
| agaggggtg ggacagggc gggggttcc ccctgtacat accctgccat accaaccccca | 1980 |
| ggtattaatt ctcgctggtt ttgtttttat tttaattttt ttgttttgat ttttttaata | 2040 |
| agaattttca ttttaagcac atttatactg aaggaatttg tgctgtgtat tgggggagc | 2100 |
| tggatccaga gctggagggg gtgggtccgg ggagggagt ggctcggaag ggccccccac | 2160 |
| tctcctttca tgtccctgtg ccccccagtt ctcctcctca gccttttcct cctcagtttt | 2220 |
| ctctttaaaa ctgtgaagta ctaactttcc aaggcctgcc ttcccctccc tcccactgga | 2280 |
| gaagccgcca gccccctttct ccctctgcct gaccactggg tgtggacggt gtgggcagc | 2340 |
| cctgaaagga caggctcctg gccttggcac ttgcctgcac ccaccatgag gcatggagca | 2400 |
| gggcagagca agggcccggg gacagagttt cccagacct ggctcctcgg cagagctgcc | 2460 |
| tcccgtcagg gccacatca tctaggctcc ccagccccca ctgtgaaggg gctgccagg | 2520 |
| ggcccgagct gccccccaccc ccggcctcag ccaccagcac ccccataggg ccccagaca | 2580 |

-continued

| | |
|---|---|
| ccacacacat gcgcgtgcgc acacacacaa acacacacac actggacagt agatgggccg | 2640 |
| acacacactt ggcccgagtt cctccatttc cctggcctgc cccccacccc caacctgtcc | 2700 |
| cacccccgtg cccctccttt accccgcagg acgggcctac aggggggtct cccctcaccc | 2760 |
| ctgcaccccc agctggggga gctggctctg ccccgacctc cttcaccagg ggttggggcc | 2820 |
| ccttcccctg gagcccgtgg gtgcacctgt tactgttggg cttccactg agatctactg | 2880 |
| gataaagaat aaagttctat ttattct | 2907 |

<210> SEQ ID NO 19
<211> LENGTH: 2907
<212> TYPE: DNA
<213> ORGANISM: human

<400> SEQUENCE: 19

| | |
|---|---|
| gccatctggg cccaggcccc atgccccgag gaggggtggt ctgaagccca ccagagcccc | 60 |
| ctgccagact gtctgcctcc cttctgactg tggccgcttg gcatggccag caacagcagc | 120 |
| tcctgcccga cacctggggg cgggcacctc aatgggtacc cggtgcctcc ctacgccttc | 180 |
| ttcttccccc ctatgctggg tggactctcc ccgccaggcg ctctgaccac tctccagcac | 240 |
| cagcttccag ttagtggata tagcacacca tccccagcca ccattgagac ccagagcagc | 300 |
| agttctgaag agatagtgcc cagccctccc tcgccacccc ctctacccg catctacaag | 360 |
| ccttgctttg tctgtcagga caagtcctca ggctaccact atggggtcag cgcctgtgag | 420 |
| ggctgcaagg gcttcttccg ccgcagcatc cagaagaaca tggtgtacac gtgtcaccgg | 480 |
| gacaagaact gcatcatcaa caaggtgacc cggaaccgct gccagtactg ccgactgcag | 540 |
| aagtgctttg aagtgggcat gtccaaggag tctgtgagaa cgaccgaaa caagaagaag | 600 |
| aaggaggtgc ccaagcccga gtgctctgag agctacacgc tgacgccgga ggtgggggag | 660 |
| ctcattgaga aggtgcgcaa agcgcaccag gaaaccttcc ctgccctctg ccagctgggc | 720 |
| aaatacacta cgaacaacag ctcagaacaa cgtgtctctc tggacattga cctctgggac | 780 |
| aagttcagtg aactctccac caagtgcatc attaagactg tggagttcgc caagcagctg | 840 |
| cccggcttca ccaccctcac catcgccgac cagatcaccc tcctcaaggc tgcctgcctg | 900 |
| gacatcctga tcctgcggat ctgcacgcgg tacacgcccg agcaggacac catgaccttc | 960 |
| tcggacgggc tgaccctgaa ccggacccag atgcacaacg ctggcttcgg cccccctcacc | 1020 |
| gacctggtct ttgccttcgc caaccagctg ctgcccctgg agatggatga tgcggagacg | 1080 |
| gggctgctca gcgccatctg cctcatctgc ggagaccgcc aggacctgga gcagccggac | 1140 |
| cgggtggaca tgctgcagga gccgctgctg gaggcgctaa aggtctacgt gcggaagcgg | 1200 |
| aggcccagcc gccccacat gttccccaag atgctaatga agattactga cctgcgaagc | 1260 |
| atcagcgcca aggggctga gcgggtgatc acgctgaaga tggagatccc gggctccatg | 1320 |
| ccgcctctca tccaggaaat gttggagaac tcagagggcc tggacactct gagcggacag | 1380 |
| ccgggggtg gggggcggga cggggtggc ctggccccc cgccaggcag ctgtagcccc | 1440 |
| agcctcagcc ccagctccaa cagaagcagc ccggccaccc actcccgtg accgccacg | 1500 |
| ccacatggac acagccctcg ccctccgccc cggcttttct ctgcctttct accgaccatg | 1560 |
| tgaccccgca ccagccctgc ccccacctgc cctccgggc agtactgggg accttccctg | 1620 |
| ggggacgggg aggaggagg cagcgactcc ttggacagag gcctgggccc tcagtggact | 1680 |
| gcctgctccc acagcctggg ctgacgtcag aggccgaggc caggaactga gtgaggcccc | 1740 |

```
tggtcctggg tctcaggatg ggtcctgggg gcctcgtgtt catcaagaca cccctctgcc    1800
cagctcacca catcttcatc accagcaaac gccaggactt ggctccccca tcctcagaac    1860
tcacaagcca ttgctcccca gctggggaac ctcaacctcc ccctgcctc ggttggtgac     1920 agaggggtg gacaggggc ggggggttcc ccctgtacat accctgccat accaacccca      1980
ggtattaatt ctcgctggtt ttgttttat tttaatttt ttgttttgat tttttaata       2040 agaattttca ttttaagcac atttatactg aaggaatttg tgctgtgtat tggggggagc    2100
tggatccaga gctggagggg gtgggtccgg gggagggagt ggctcggaag gggccccac     2160 tctcctttca tgtccctgtg cccccagtt ctcctcctca gccttttcct cctcagtttt     2220
ctctttaaaa ctgtgaagta ctaacttcc aaggcctgcc ttcccctccc tcccactgga     2280
gaagccgcca gccccttct ccctctgcct gaccactggg tgtggacggt gtggggcagc     2340
cctgaaagga caggctcctg gccttggcac ttgcctgcac ccaccatgag gcatggagca    2400
gggcagagca agggccccgg gacagagttt tcccagacct ggctcctcgg cagagctgcc    2460
tcccgtcagg gcccacatca tctaggctcc ccagccccca ctgtgaaggg gctggccagg    2520
ggcccgagct gccccaccc ccggcctcag ccaccagcac cccatagggg ccccagaca     2580 ccacacacat gcgcgtgcgc acacacacaa acacacacac actggacagt agatgggccg    2640
acacacactt ggcccgagtt cctccatttc cctggcctgc cccccacccc caacctgtcc    2700 caccccgtg cccccctctt acccgcagg acgggcctac aggggggtct cccctcaccc     2760 ctgcacccc agctggggga gctggctctg ccccgacctc cttcaccagg ggttggggcc    2820
ccttcccctg gagcccgtgg gtgcacctgt tactgttggg cttttccactg agatctactg   2880 gataaagaat aaagttctat ttattct                                        2907

<210> SEQ ID NO 20
<211> LENGTH: 1347
<212> TYPE: DNA
<213> ORGANISM: human

<400> SEQUENCE: 20
atggatccca atatttcat cttaattttg tttgtggac acctgaacaa tacattttt        60 tcaaagacag agacaattac aacagagaag cagtcacagc ctaccttata cacatcatca    120
atgtcacagg tattggctaa ttctcaaaac acaacaggga atcctttggg tcaaccaaca    180
caattcagcg acacttttc tggacaatca atatcacctg ccaaagtcac tgctggacaa     240
ccaacaccag ctgtctatac ctcttctgaa aaaccagaag cacatacttc tgctggacaa    300
ccacttgcct acaacaccaa acaaccaaca ccaatagcca cacctcctc ccagcaagcc     360 gtgttcacct ctgccagaca actaccatct gcccgtactt ctaccacaca accaccaaag    420
tcatttgtct atacttttac tcaacaatca tcatctgtcc agatcccttc tagaaaacaa    480
ataactgttc ataatccatc cacacaacca acatcaactg tcaaaattc acctaggagt     540 acaccaggat ttatcttaga tactaccagt aacaaacaaa ccccacaaaa aaacaattat    600
aattcaatag ctgccatact aattggtgta cttctgactt ctatgttggt agctataatc    660
atcattgtac tttggaaatg cttaaggaaa ccagttttaa atgatcaaaa ttgggcaggt    720
agatctccat ttgctgatgg agaaccccct gacatttgta tggataacat cagagaaaat    780
gaaatatcca caaaacgtac atcaatcatt tcacttacac cctggaaacc aagcaaaagc    840
acacttttag cagatgactt agaaattaag ttgtttgaat caagtgaaaa cattgaagac    900
tccaacaacc ccaaaacaga gaaataaaaa gatcaagtaa atggtacatc agaagatagt    960
```

```
gctgatggtt caacagttgg aactgctgtt tcttcttcag atgatgcaga tctgcctcca    1020
ccacctcccc ttctggattt ggaaggacag gaaagtaacc aatctgacaa acccacaatg    1080
acaattgtat ctcctcttcc aaatgattct actagtctcc ctccatctct ggactgtctc    1140
aatcaagact gtggagatca taaatctgag ataatacaat catttccacc gcttgactca    1200
cttaacttgc ccctgccacc agtagatttt atgaaaaacc aagaagattc caaccttgag    1260
atccagtgtc aggagttctc tattcctccc aactctgatc aagatcttaa tgaatccctg    1320
ccacctccac ctgcagaact gttataa                                        1347

<210> SEQ ID NO 21
<211> LENGTH: 2170
<212> TYPE: DNA
<213> ORGANISM: human

<400> SEQUENCE: 21
ctgagggctc atccctctgc agagcgcggg gtcaccggga ggagacgcca tgacgcccgc      60
cctcacagcc ctgctctgcc ttgggctgag tctgggcccc aggacccgcg tgcaggcagg     120 gccccttcccc aaacccaccc tctgggctga gccaggctct gtgatcagct gggggagccc    180
cgtgaccatc tggtgtcagg ggagcctgga ggcccaggag taccgactgg ataaagaggg     240
aagcccagag cccttggaca gaaataaccc actggaaccc aagaacaagg ccagattctc     300
catcccatcc atgacagagc accatgcggg gagataccgc tgccactatt acagctctgc     360
aggctggtca gagcccagcg accccctgga gctggtgatg acaggattct acaacaaacc     420
caccctctca gccctgccca gccctgtggt ggcctcaggg gggaatatga ccctccgatg     480
tggctcacag aagggatatc accatttgt tctgatgaag gaaggagaac accagctccc     540
ccggaccctg gactcacagc agctccacag tgggggggttc caggccctgt tccctgtggg     600
ccccgtgaac cccagccaca ggtggaggtt cacatgctat tactattata tgaacacccc     660
ccaggtgtgg tcccaccccca gtgaccccct ggagattctg ccctcaggcg tgtctaggaa     720
gccctccctc ctgaccctgc agggccctgt cctggcccct gggcagagcc tgaccctcca     780
gtgtggctct gatgtcggct acgacagatt tgttctgtat aaggaggggg aacgtgactt     840
cctccagcgc cctggccagc agccccaggc tgggctctcc caggccaact tcaccctggg     900
ccctgtgagc ccctcccacg ggggccagta caggtgctat ggtgcacaca acctctcctc     960
cgagtggtcg gcccccagcg acccccctgaa catcctgatg gcaggacaga tctatgacac    1020
cgtctccctg tcagcacagc cgggccccac agtggcctca ggagagaacg tgaccctgct    1080
gtgtcagtca tggtggcagt ttgacacttt ccttctgacc aaagaagggg cagcccatcc    1140
cccactgcgt ctgagatcaa tgtacggagc tcataagtac caggctgaat tccccatgag    1200
tcctgtgacc tcagcccacg cggggaccta caggtgctac ggctcataca gctccaaccc    1260
ccacctgctg tctttcccca gtgagcccct ggaactcatg gtctcaggac actctggagg    1320
ctccagcctc ccacccacag gccgccctc cacacctggt ctgggaagat acctggaggt    1380
tttgattggg gtctcggtgg ccttcgtcct gctgctcttc ctcctcctct tcctcctcct    1440
ccgacgtcag cgtcacagca aacacaggac atctgaccag agaaagactg atttccagcg    1500
tcctgcaggg gctgcggaga cagagcccaa ggacaggggc ctgctgagga ggtccagccc    1560
agctgctgac gtccaggaag aaaacctcta tgctgccgtg aaggacacac agtctgagga    1620
cagggtggag ctggacagtc agagcccaca cgatgaagac ccccaggcag tgacgtatgc    1680
```

-continued

| | |
|---|---|
| cccggtgaaa cactccagtc ctaggagaga aatggcctct cctccctcct cactgtctgg | 1740 |
| ggaattcctg gacacaaagg acagacaggt ggaagaggac aggcagatgg acactgaggc | 1800 |
| tgctgcatct gaagcctccc aggatgtgac ctacgcccag ctgcacagct tgacccttag | 1860 |
| acggaaggca actgagcctc ctccatccca ggaagggaa cctccagctg agcccagcat | 1920 |
| ctacgccact ctggccatcc actagcccgg ggggtacgca gaccccacac tcagcagaag | 1980 |
| gagactcagg actgctgaag gcacgggagc tgccccagt ggacaccagt gaaccccagt | 2040 |
| cagcctggac ccctaacaca gaccatgagg agacgctggg aacttgtggg actcacctga | 2100 |
| ctcaaagatg actaatatcg tcccattttg gaaataaagc aacagacttc tcaacaatca | 2160 |
| atgagttaat | 2170 |

<210> SEQ ID NO 22
<211> LENGTH: 1453
<212> TYPE: DNA
<213> ORGANISM: human
<400> SEQUENCE: 22

| | |
|---|---|
| gggagtgcat ccgccccaac ccttttcccc ctcgtctcct gtgagaattc cccgtcggat | 60 |
| acgagcagcg tggccgttgg ctgcctcgca caggacttcc ttcccgactc catcactttc | 120 |
| tcctggaaat acaagaacaa ctctgacatc agcagcaccc ggggcttccc atcagtcctg | 180 |
| agaggggca agtacgcagc cacctcacag gtgctgctgc cttccaagga cgtcatgcag | 240 |
| ggcacagacg aacacgtggt gtgcaaagtc cagcacccca acggcaacaa agaaaagaac | 300 |
| gtgcctcttc cagtgattgc cgagctgcct cccaaagtga gcgtcttcgt cccacccgc | 360 |
| gacggcttct tcggcaaccc ccgcaagtcc aagctcatct gccaggccac gggtttcagt | 420 |
| ccccggcaga ttcaggtgtc ctggctgcgc gaggggaagc aggtggggtc tggcgtcacc | 480 |
| acggaccagg tgcaggctga ggccaaagag tctgggccca cgacctacaa ggtgaccagc | 540 |
| acactgacca tcaaagagag cgactggctc agccagagca tgttcacctg ccgcgtggat | 600 |
| cacaggggcc tgaccttcca gcagaatgcg tcctccatgt gtgtccccga tcaagacaca | 660 |
| gccatccggg tcttcgccat ccccccatcc tttgccagca tcttcctcac caagtccacc | 720 |
| aagttgacct gcctggtcac agacctgacc acctatgaca gcgtgaccat ctcctggacc | 780 |
| cgccagaatg gcgaagctgt gaaaacccac accaacatct ccgagagcca ccccaatgcc | 840 |
| actttcagcg ccgtgggtga ggccagcatc tgcgaggatg actggaattc cggggagagg | 900 |
| ttcacgtgca ccgtgaccca cacagacctg ccctcgccac tgaagcagac catctcccgg | 960 |
| cccaagggg tggccctgca caggcccgat gtctacttgc tgccaccagc ccgggagcag | 1020 |
| ctgaacctgc gggagtcggc caccatcacg tgcctggtga cgggcttctc tccgcggac | 1080 |
| gtcttcgtgc agtggatgca gagggggcag cccttgtccc ggagaagta tgtgaccagc | 1140 |
| gccccaatgc ctgagcccca ggccccaggc cggtacttcg cccacagcat cctgaccgtg | 1200 |
| tccgaagagg aatggaacac gggggagacc tacacctgcg tggtggccca tgaggcctg | 1260 |
| cccaacaggt tcaccgagag gaccgtggac aagtccaccg gtaaacccac cctgtacaac | 1320 |
| gtgtccctgg tcatgtccga cacagctggc acctgctact gaccctgctg gcctgcccac | 1380 |
| aggctcgggg cggctggccg ctctgtgtgt gcatgcaaac taacccgtgt caacggggtg | 1440 |
| agatgttgca tct | 1453 |

<210> SEQ ID NO 23
<211> LENGTH: 1192

<212> TYPE: DNA
<213> ORGANISM: human

<400> SEQUENCE: 23

| | | | | | |
|---|---|---|---|---|---|
| cagatccatc | aggtccaagc | tgtgttgact | accactgctt | ttcccttcgt | ctcaattatg | 60 |
| tcttggaaga | aggctttgcg | gatccctgga | ggccttcggg | tagcaactgt | gaccttgatg | 120 |
| ctggcgatgc | tgagcacccc | ggtggctgag | ggcagagact | ctcccgagga | tttcgtgtac | 180 |
| cagtttaagg | gcatgtgcta | cttcaccaac | gggacggagc | gcgtgcgtct | tgtgaccaga | 240 |
| tacatcctata | accgagagga | gtacgcacgc | ttcgacagcg | acgtggggt | gtatcgggcg | 300 |
| gtgacgccgc | tggggccgcc | tgacgccgag | tactggaaca | gccagaagga | agtcctggag | 360 |
| aggacccggg | cggagttgga | cacggtgtgc | agacacaact | accagttgga | gctccgcacg | 420 |
| accttgcagc | ggcgagtgga | gcccacagtg | accatctccc | catccaggac | agaggccctc | 480 |
| aaccaccaca | acctgctggt | ctgctcagtg | acagatttct | atccagccca | gatcaaagtc | 540 |
| cggtggtttc | ggaatgacca | ggaggagaca | actggcgttg | tgtccacccc | ccttattagg | 600 |
| aacggtgact | ggaccttcca | gatcctggtg | atgctggaaa | tgactcccca | gcgtggagac | 660 |
| gtctacacct | gccacgtgga | gcaccccagc | ctccagaacc | ccatcatcgt | ggagtggcgg | 720 |
| gctcagtctg | aatctgccca | gagcaagatg | ctgagtggca | ttggaggctt | cgtgctgggg | 780 |
| ctgatcttcc | tcgggctggg | ccttattatc | catcacagga | gtcagaaagg | gctcctgcac | 840 |
| tgactcctga | gactatttta | actgggattg | gttatcactt | ttctgtaacg | cctgcttgtc | 900 |
| cctgcccaga | attcccagct | gcctgtgtca | gcctgtcccc | cgagatcaga | gtcctaccgt | 960 |
| ggctgtcacg | cagccaccag | gtcatctcct | ttcatcccca | cctcaaggct | gatggctgtg | 1020 |
| accctgcttc | ctgcactgac | ccagagcctc | tgcctgtgca | cggccagctg | cgtctactga | 1080 |
| ggccccaagg | ggtttctgtt | tctattctct | cctcagactg | ctcaagagaa | gcacatgaaa | 1140 |
| accattacct | gactttagag | cttttttaca | taattaaaca | tgatcctgag | tt | 1192 |

<210> SEQ ID NO 24
<211> LENGTH: 2048
<212> TYPE: DNA
<213> ORGANISM: human

<400> SEQUENCE: 24

| | | | | | |
|---|---|---|---|---|---|
| atgtgaaggc | acaagctgct | gttatataca | acagagtgaa | ctgagcatca | gtcagaaaaa | 60 |
| gtctatgttt | gcagaaatac | agatccaaga | caaagacagg | atgggcactg | ctggaaaagt | 120 |
| tattaaatgc | aaagcagctg | tgctttggga | gcagaagcaa | cccttctcca | ttgaggaaat | 180 |
| agaagttgcc | ccaccaaaga | ctaaagaagt | tcgcattaag | attttggcca | caggaatctg | 240 |
| tcgcacagat | gaccatgtga | taaaaggaac | aatggtgtcc | aagtttccag | tgattgtggg | 300 |
| acatgaggca | actgggattg | tagagagcat | tggagaagga | gtgactacag | tgaaaccagg | 360 |
| tgacaaagtc | atccctctct | ttctgccaca | atgtagagaa | tgcaatgctt | gtcgcaaccc | 420 |
| agatggcaac | ctttgcatta | ggagcgatat | tactggtcgt | ggagtactgg | ctgatggcac | 480 |
| caccagattt | acatgcaagg | gcaaaccagt | acaccacttc | atgaacacca | gtacatttac | 540 |
| cgagtacaca | gtggtggatg | aatcttctgt | tgctaagatt | gatgatgcag | ctcctcctga | 600 |
| gaaagtctgt | ttaattggct | gtgggttttc | cactggatat | ggcgctgctg | ttaaaactgg | 660 |
| caaggtcaaa | cctggttcca | cttgcgtcgt | ctttggcctg | ggaggagttg | gcctgtcagt | 720 |
| catcatgggc | tgtaagtcag | ctggtgcatc | taggatcatt | gggattgacc | tcaacaaaga | 780 |

-continued

```
caaatttgag aaggccatgg ctgtaggtgc cactgagtgt atcagtccca aggactctac    840
caaacccatc agtgaggtgc tgtcagaaat gacaggcaac aacgtgggat acacctttga    900
agttattggg catcttgaaa ccatgattga tgccctggca tcctgccaca tgaactatgg    960
gaccagcgtg gttgtaggag ttcctccatc agccaagatg ctcacctatg acccgatgtt   1020
gctcttcact ggacgcacat ggaagggatg tgtctttgga ggtttgaaaa gcagagatga   1080
tgtcccaaaa ctagtgactg agttcctggc aaagaaattt gacctggacc agttgataac   1140
tcatgtttta ccatttaaaa aaatcagtga aggatttgag ctgctcaatt caggacaaag   1200
cattcgaacg gtcctgacgt tttgagatcc aaagtggcag gaggtctgtg ttgtcatggt   1260
gaactggagt ttctcttgtg agagttccct catctgaaat catgtatctg tctcacaaat   1320
acaagcataa gtagaagatt tgttgaagac atagaaccct tataagaat tattaacctt    1380
tataaacatt taaagtcttg tgagcacctg ggaattagta taataacaat gttaatattt   1440
ttgatttaca ttttgtaagg ctataattgt atcttttaag aaaacataca cttggatttc   1500
tatgttgaaa tggagatttt taagagtttt aaccagctgc tgcagatata aactcaaaa    1560
cagatatagc gtataaagat atagtaaatg catctcccag agtaatattc acttaacaca   1620
ttgaaactat tattttttag atttgaatat aaatgtattt tttaaacact tgttatgagt   1680
taacttggat tacattttga aatcagttca ttccatgatg catattactg gattagatta   1740
agaaagacag aaaagattaa gggacgggca cattttcaa cgattaagaa tcatcattac    1800
ataacttggt gaaactgaaa aagtatatca tatgggtaca caaggctatt tgccagcata   1860
tattaatatt ttagaaaata ttccttttgt aatactgaat ataaacatag agctagagtc   1920
atattatcat acttatcata atgttcaatt tgatacagta gaattgcaag tccctaagtc   1980
cctattcact gtgcttagta gtgactccat ttaataaaaa gtgttttag ttttttaacaa   2040
ctaaaccg                                                            2048
```

<210> SEQ ID NO 25
<211> LENGTH: 2048
<212> TYPE: DNA
<213> ORGANISM: human

<400> SEQUENCE: 25

```
atgtgaaggc acaagctgct gttatataca acagagtgaa ctgagcatca gtcagaaaaa     60
gtctatgttt gcagaaatac agatccaaga caaagacagg atgggcactg ctggaaaagt    120
tattaaatgc aaagcagctg tgctttggga gcagaagcaa cccttctcca ttgaggaaat    180
agaagttgcc ccaccaaaga ctaaagaagt tcgcattaag attttggcca caggaatctg    240
tcgcacagat gaccatgtga taaaaggaac aatggtgtcc aagtttccag tgattgtggg    300
acatgaggca actgggattg tagagagcat tggagaagga gtgactacag tgaaaccagg    360
tgacaaagtc atccctctct ttctgccaca atgtagagaa tgcaatgctt gtcgcaaccc    420
agatggcaac ctttgcatta ggagcgatat tactggtcgt ggagtactgg ctgatggcac    480
caccagattt acatgcaagg gcaaaccagt acaccacttc atgaacacca gtacatttac    540
cgagtacaca gtggtggatg aatcttctgt tgctaagatt gatgatgcag ctcctcctga    600
gaaagtctgt ttaattggct gtgggttttc cactggatat ggcgctgctg ttaaaactgg    660
caaggtcaaa cctggttcca cttgcgtcgt ctttggcctg ggaggagttg gcctgtcagt    720
catcatgggc tgtaagtcag ctggtgcatc taggatcatt gggattgacc tcaacaaaga    780
caaatttgag aaggccatgg ctgtaggtgc cactgagtgt atcagtccca aggactctac    840
```

```
caaacccatc agtgaggtgc tgtcagaaat gacaggcaac aacgtgggat acacctttga    900
agttattggg catcttgaaa ccatgattga tgccctggca tcctgccaca tgaactatgg    960
gaccagcgtg gttgtaggag ttcctccatc agccaagatg ctcacctatg acccgatgtt   1020
gctcttcact ggacgcacat ggaagggatg tgtctttgga ggtttgaaaa gcagagatga   1080
tgtcccaaaa ctagtgactg agttcctggc aaagaaattt gacctggacc agttgataac   1140
tcatgtttta ccatttaaaa aaatcagtga aggatttgag ctgctcaatt caggacaaag   1200
cattcgaacg gtcctgacgt tttgagatcc aaagtggcag gaggtctgtg ttgtcatggt   1260
gaactggagt ttctcttgtg agagttccct catctgaaat catgtatctg tctcacaaat   1320
acaagcataa gtagaagatt tgttgaagac atagaaccct tataaagaat tattaacctt   1380
tataaacatt taaagtcttg tgagcacctg ggaattagta taataacaat gttaatattt   1440
ttgatttaca ttttgtaagg ctataattgt atcttttaag aaaacataca cttggatttc   1500
tatgttgaaa tggagatttt taagagtttt aaccagctgc tgcagatata aactcaaaa    1560 cagatatagc gtataaagat atagtaaatg catctcccag agtaatattc acttaacaca   1620
ttgaaactat tattttttag atttgaatat aaatgtattt tttaaacact tgttatgagt   1680
taacttggat tacattttga aatcagttca ttccatgatg catattactg gattagatta   1740
agaaagacag aaaagattaa gggacgggca catttttcaa cgattaagaa tcatcattac   1800
ataacttggt gaaactgaaa aagtatatca tatgggtaca caaggctatt tgccagcata   1860
tattaatatt ttagaaaata ttccttttgt aatactgaat ataaacatag agctagagtc   1920
atattatcat acttatcata atgttcaatt tgatacagta gaattgcaag tccctaagtc   1980
cctattcact gtgcttagta gtgactccat ttaataaaaa gtgttttag tttttaacaa    2040 ctaaaccg                                                             2048
```

```
<210> SEQ ID NO 26
<211> LENGTH: 2816
<212> TYPE: DNA
<213> ORGANISM: human

<400> SEQUENCE: 26
```

```
tcgttgatat caaagacagt tgaaggaaat gaatttgaa acttcacggt gtgccaccct      60
acagtactgc cctgacccct acatccagcg tttcgtagaa acccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg gccacagtac   360
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tcccctccaa caccgactac    540
ccaggcccgc acagtttcga cgtgtccttc cagcagtcga gcaccgccaa gtcggccacc    600
tggacgtatt ccactgaact gaagaaactc tactgccaaa ttgcaaagac atgcccccatc   660 cagatcaagg tgatgacccc acctcctcag ggagctgtta ccgcgccat gcctgtctac    720 aaaaaagctg agcacgtcac ggaggtggtg aagcggtgcc ccaaccatga gctgagccgt   780
gaattcaacg agggacagat tgcccctcct agtcatttga ttcgagtaga ggggaacagc    840
```

```
catgcccagt atgtagaaga tcccatcaca ggaagacaga gtgtgctggt accttatgag      900
ccaccccagg ttggcactga attcacgaca gtcttgtaca atttcatgtg taacagcagt      960
tgtgttggag ggatgaaccg ccgtccaatt ttaatcattg ttactctgga aaccagagat     1020
gggcaagtcc tgggccgacg ctgctttgag gcccggatct gtgcttgccc aggaagagac     1080
aggaaggcgg atgaagatag catcagaaag cagcaagttt cggacagtac aaagaacggt     1140
gatggtacga agcgcccgtt tcgtcagaac acacatggta tccagatgac atccatcaag     1200
aaacgaagat ccccagatga tgaactgtta tacttaccag tgaggggccg tgagacttat     1260
gaaatgctgt tgaagatcaa agagtccctg gaactcatgc agtaccttcc tcagcacaca     1320
attgaaacgt acaggcaaca gcaacagcag cagcaccagc acttacttca gaaacatctc     1380
ctttcagcct gcttcaggaa tgagcttgtg gagccccgga gagaaactcc aaaacaatct     1440
gacgtcttct ttagacattc caagccccca aaccgatcag tgtacccata gagccctatc     1500
tctatatttt aagtgtgtgt gttgtatttc catgtgtata tgtgagtgtg tgtgtgtgta     1560
tgtgtgtgcg tgtgtatcta gccctcataa acaggacttg aagcactttt ggctcagaga     1620
cccaactgct caaaggcaca aagccactag tgagagaatc ttttgaaggg actcaaacct     1680
ttacaagaaa ggatgttttc tgcagatttt gtatccttag accggccatt ggtgggtgag     1740
gaaccactgt gtttgtctgt gagctttctg ttgtttcctg ggagggaggg gtcaggtggg     1800
gaaaggggca ttaagatgtt tattggaacc cttttctgtc ttcttctgtt gttttttctaa     1860 aattcacagg gaagcttttg agcaggtctc aaacttaaga tgtctttttta agaaaaggag     1920 aaaaaagttg ttattgtctg tgcataagta agttgtaggt gactgagaga ctcagtcaga     1980 ccctttttaat gctggtcatg taataatatt gcaagtagta agaaacgaag gtgtcaagtg     2040
tactgctggg cagcgaggtg atcattacca aaagtaatca actttgtggg tggagagttc     2100
tttgtgagaa cttgcattat ttgtgtcctc ccctcatgtg taggtagaac atttcttaat     2160
gctgtgtacc tgcctctgcc actgtatgtt ggcatctgtt atgctaaagt ttttcttgta     2220
catgaaaccc tggaagacct actacaaaaa aactgttgtt tggcccccat agcaggtgaa     2280
ctcattttgt gcttttaata gaaagacaaa tccaccccag taatattgcc cttacgtagt     2340
tgtttaccat tattcaaagc tcaaaataga atttgaagcc ctctcacaaa atctgtgatt     2400
aatttgctta attagagctt ctatccctca agcctaccta ccataaaacc agccatatta     2460
ctgatactgt tcagtgcatt tagccaggag acttacgttt tgagtaagtg agatccaagc     2520
agacgtgtta aaatcagcac tcctggactg gaaattaaag attgaagggg tagactactg     2580
ttcttttttt tactcaaaag tttagagaat ctctgtttct ttccatttta aaaacatatt     2640
ttaagataat agcataaaga ctttaaaaat gttcctcccc tccatcttcc cacacccagt     2700
caccagcact gtattttctg tcaccaagac aatgatttct tgttattgag ctgttgctt     2760 ttgtggatgt gtgattttaa ttttcaataa acttttgcat cttggtttaa aagaaa          2816
```

<210> SEQ ID NO 27
<211> LENGTH: 2816
<212> TYPE: DNA
<213> ORGANISM: human

<400> SEQUENCE: 27

```
tcgttgatat caaagacagt tgaaggaaat gaattttgaa acttcacggt gtgccaccct       60
acagtactgc cctgacccct acatccagcg tttcgtagaa acccagctca tttctcttgg      120
aaagaaagtt attaccgatc caccatgtcc cagagcacac agacaaatga attcctcagt      180
```

-continued

```
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg ccacagtac     360
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tccccctccaa caccgactac   540
ccaggcccgc acagtttcga cgtgtccttc cagcagtcga gcaccgccaa gtcggccacc    600
tggacgtatt ccactgaact gaagaaactc tactgccaaa ttgcaaagac atgccccatc    660
cagatcaagg tgatgacccc acctcctcag ggagctgtta tccgcgccat gcctgtctac    720
aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtccttgtaca atttcatgtg taacagcagt   960
tgtgttggag ggatgaaccg ccgtccaatt ttaatcattg ttactctgga aaccagagat   1020
gggcaagtcc tgggccgacg ctgctttgag gcccggatct gtgcttgccc aggaagagac   1080
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgaggggccg tgagacttat   1260
gaaatgctgt tgaagatcaa agagtccctg gaactcatgc agtaccttcc tcagcacaca   1320
attgaaacgt acaggcaaca gcaacagcag cagcaccagc acttacttca gaaacatctc   1380
ctttcagcct gcttcaggaa tgagcttgtg gagccccgga gagaaactcc aaaacaatct   1440
gacgtcttct ttagacattc caagcccccca aaccgatcag tgtacccata gagccctatc   1500
tctatatttt aagtgtgtgt gttgtatttc catgtgtata tgtgagtgtg tgtgtgtgta   1560
tgtgtgtgcg tgtgtatcta gccctcataa acaggacttg aagacacttt ggctcagaga   1620
cccaactgct caaaggcaca aagccactag tgagagaatc ttttgaaggg actcaaacct   1680
ttacaagaaa ggatgttttc tgcagatttt gtatccttag accggccatt ggtgggtgag   1740
gaaccactgt gtttgtctgt gagctttctg ttgtttcctg ggagggaggg gtcaggtggg   1800
gaaaggggca ttaagatgtt tattggaacc cttttctgtc ttcttctgtt gttttttctaa   1860
aattcacagg gaagcttttg agcaggtctc aaacttaaga tgtcttttta agaaaaggag   1920
aaaaaagttg ttattgtctg tgcataagta agttgtaggt gactgagaga ctcagtcaga   1980
ccctttttaat gctggtcatg taataatatt gcaagtagta agaaacgaag gtgtcaagtg   2040
tactgctggg cagcgaggtg atcattacca aaagtaatca actttgtggg tggagagttc   2100
tttgtgagaa cttgcattat ttgtgtcctc ccctcatgtg taggtagaac atttcttaat   2160
gctgtgtacc tgcctctgcc actgtatgtt ggcatctgtt atgctaaagt ttttcttgta   2220
catgaaaccc tggaagacct actacaaaaa aactgttgtt tggccccat agcaggtgaa    2280
ctcattttgt gcttttaata gaaagacaaa tccaccccag taatattgcc cttacgtagt   2340
tgtttaccat tattcaaagc tcaaaataga atttgaagcc ctctcacaaa atctgtgatt   2400
aatttgctta attagagctt ctatccctca agcctaccta ccataaaacc agccatatta   2460
ctgatactgt tcagtgcatt tagccaggag acttacgttt tgagtaagtg agatccaagc   2520
```

| agacgtgtta | aaatcagcac | tcctggactg | gaaattaaag | attgaaaggg | tagactactt | 2580 |
| tcttttttt | tactcaaaag | tttagagaat | ctctgtttct | ttccatttta | aaaacatatt | 2640 |
| ttaagataat | agcataaaga | ctttaaaaat | gttcctcccc | tccatcttcc | cacacccagt | 2700 |
| caccagcact | gtattttctg | tcaccaagac | aatgattttct | tgttattgag | gctgttgctt | 2760 |
| ttgtggatgt | gtgattttaa | ttttcaataa | acttttgcat | cttggtttaa | aagaaa | 2816 |

<210> SEQ ID NO 28
<211> LENGTH: 3803
<212> TYPE: DNA
<213> ORGANISM: human

<400> SEQUENCE: 28

| ccatggtagg | agcgctcgcc | tcgctgcggt | gcccgctgag | gccatgccgg | ggccccggcg | 60 |
| ccccgctggc | tcccgcctgc | gcctgctcct | gctcctgctg | ctgccgccgc | tgctgctgct | 120 |
| gctccggggc | agccacgcgg | gcaacctgac | ggtagccgtg | gtactgccgc | tggccaatac | 180 |
| ctcgtacccc | tggtcgtggg | cgcgcgtggg | acccgccgtg | gagctggccc | tggcccaggt | 240 |
| gaaggcgcgc | cccgacttgc | tgccgggctg | gacggtccgc | acggtgctgg | gcagcagcga | 300 |
| aaacgcgctg | ggcgtctgct | ccgacaccgc | agcgcccctg | gccgcggtgg | acctcaagtg | 360 |
| ggagcacaac | cccgctgtgt | tcctgggccc | cggctgcgtg | tacgccgccg | ccccagtggg | 420 |
| gcgcttcacc | gcgcactggc | gggtcccgct | gctgaccgcc | ggcgccccgg | cgctgggctt | 480 |
| cggtgtcaag | gacgagtatg | cgctgaccac | ccgcgcgggg | cccagctacg | ccaagctggg | 540 |
| ggacttcgtg | gcggcgctgc | accgacggct | gggctgggag | cgccaagcgc | tcatgctcta | 600 |
| cgcctaccgg | ccgggtgacg | aagagcactg | cttcttcctc | gtggaggggc | tgttcatgcg | 660 |
| ggtccgcgac | cgcctcaata | ttacggtgga | ccacctggag | ttcgccgagg | acgacctcag | 720 |
| ccactacacc | aggctgctgc | ggaccatgcc | gcgcaaaggc | cgagttatct | acatctgcag | 780 |
| ctcccctgat | gccttcagaa | ccctcatgct | cctggccctg | gaagctggct | tgtgtgggga | 840 |
| ggactacgtt | tcttccacc | tggatatctt | tgggcaaagc | ctgcaaggtg | gacagggccc | 900 |
| tgctccccgc | aggccctggg | agagagggga | tgggcaggat | gtcagtgccc | gccaggcctt | 960 |
| tcaggctgcc | aaaatcatta | catataaaga | cccagataat | cccgagtact | ggaattcct | 1020 |
| gaagcagtta | aaacacctgg | cctatgagca | gttcaacttc | accatggagg | atggcctggt | 1080 |
| gaacaccatc | ccagcatcct | tccacgacgg | gctcctgctc | tatatccagg | cagtgacgga | 1140 |
| gactctggca | catgggggaa | ctgttactga | tgggagaaac | atcactcagc | ggatgtggaa | 1200 |
| ccgaagcttt | caaggtgtga | caggatacct | gaaaattgat | agcagtggcg | atcgggaaac | 1260 |
| agacttctcc | ctctgggata | tggatcccga | gaatggtgcc | ttcaggggttg | tactgaacta | 1320 |
| caatgggact | tcccaagagc | tggtggctgt | gtcggggcgc | aaactgaact | ggcccctggg | 1380 |
| gtaccctcct | cctgacatcc | ccaaatgtgg | ctttgacaac | gaagacccag | catgcaacca | 1440 |
| agatcaccctt | tccaccctgg | aggtgctggc | tttggtgggc | agcctctcct | tgctcggcat | 1500 |
| tctgattgtc | tccttcttca | tatacaggaa | gatgcagctg | gagaaggaac | tggcctcgga | 1560 |
| gctgtggcgg | gtgcgctggg | aggacgttga | gcccagtagc | cttgagaggc | acctgcggag | 1620 |
| tgcaggcagc | cggctgaccc | tgagcggag | aggctccaat | tacggctccc | tgctaaccac | 1680 |
| agagggccag | ttccaagtct | ttgccaagac | agcatattat | aagggcaacc | tcgtggctgt | 1740 |
| gaaacgtgtg | aaccgtaaac | gcattgagct | gacacgaaaa | gtcctgtttg | aactgaagca | 1800 |
| tatgcgggat | gtgcagaatg | aacacctgac | caggtttgtg | ggagcctgca | ccgaccccc | 1860 |

```
caatatctgc atcctcacag agtactgtcc ccgtgggagc ctgcaggaca ttctggagaa    1920
tgagagcatc accctggact ggatgttccg gtactcactc accaatgaca tcgtcaaggg    1980
catgctgttt ctacacaatg gggctatctg ttcccatggg aacctcaagt catccaactg    2040
cgtggtagat gggcgctttg tgctcaagat caccgactat gggctggaga gcttcaggga    2100
cctggaccca gagcaaggac acccgtttta tgccaaaaag ctgtggacgg cccctgagct    2160
cctgcgaatg gcttcacccc ctgtgcgggg ctcccaggct ggtgacgtat acagctttgg    2220
gatcatcctt caggagattg ccctgaggag tggggtcttc cacgtggaag gtttggacct    2280
gagccccaaa gagatcatcg agcgggtgac tcggggtgag cagcccccct tccggccctc    2340
cctggccctg cagagtcacc tggaggagtt ggggctgctc atgcagcggt gctgggctga    2400
ggacccacag gagaggccac cattccagca gatccgcctg acgttgcgca aatttaacag    2460
ggagaacagc agcaacatcc tggacaacct gctgtcccgc atggagcagt acgcgaacaa    2520
tctggaggaa ctggtggagg agcggaccca ggcatacctg aggagaaagc gcaaggctga    2580
ggccctgctc taccagatcc tgcctcactc agtggctgag cagctgaagc gtggggagac    2640
ggtgcaggcc gaagcctttg acagtgttac catctacttc agtgacattg tgggtttcac    2700
agcgctgtcg gcggagagca cacccatgca ggtggtgacc ctgctcaatg acctgtacac    2760
ttgctttgat gctgtcatag acaactttga tgtgtacaag gtggagacaa ttggcgatgc    2820
ctacatggtg gtgtcagggc tccctgtgcg gaacgggcgg ctacacgcct gcgaggtagc    2880
ccgcatggcc ctggcactgc tggatgctgt gcgctccttc gaatccgcc accggccccca    2940
ggagcagctg cgcttgcgca ttggcatcca cacaggacct gtgtgtgctg agtggtggg    3000
actgaagatg ccccgttact gtctctttgg ggatacagtc aacacagcct caagaatgga    3060
gtctaatggg gaagccctga agatccactt gtcttctgag accaaggctg tcctggagga    3120
gtttggtggt ttcgagctgg agcttcgagg ggatgtagaa atgaagggca aaggcaaggt    3180
tcggacctac tggctccttg gggagagggg gagtagcacc cgaggctgac ctgcctcctc    3240
tcctatccct ccacacctcc cctaccctgt gccagaagca acagaggtgc caggcctcag    3300
cctcacccac agcagcccca tcgccaaagg atggaagtaa tttgaatagc tcaggtgtgc    3360
tgaccccagt gaagacacca gataggacct ctgagagggg actggcatgg ggggatctca    3420
gagcttacag gctgagccaa gcccacggcc atgcacaggg acactcacac aggcacacgc    3480
acctgctctc cacctggact caggccgggc tgggctgtgg atccttgatc ccctccccctc    3540
cccatgctct cctccctcag ccttgctacc ctgtgactta ctgggaggag agtcacctga    3600
aggggaacat gaaaagagac taggtgaaga gagggcaggg gagcccacat ctggggctgg    3660
cccacaatac ctgctccccc gacccctcc acccagcagt agacacagtg cacaggggag    3720
aagaggggtg gcgcagaagg gttgggggcc tgtatgcctt gcttctacca tgagcagaga    3780
caattaaaat ctttattcca gtg                                            3803

<210> SEQ ID NO 29
<211> LENGTH: 3802
<212> TYPE: DNA
<213> ORGANISM: human

<400> SEQUENCE: 29
ccatggtagg agcgctcgcc tcgctgcggt gccgctgag gccatgccgg ggccccggcg       60
ccccgctggc tcccgcctgc gcctgctcct gtcctgctg ctgccgccgc tgctgctgct      120
```

| | |
|---|---|
| gctccggggc agccacgcgg gcaacctgac ggtagccgtg gtactgccgc tggccaatac | 180 |
| ctcgtacccc tggtcgtggg cgcgcgtggg acccgccgtg gagctggccc tggcccaggt | 240 |
| gaaggcgcgc cccgacttgc tgccgggctg acggtccgc acggtgctgg gcagcagcga | 300 |
| aaacgcgctg ggcgtctgct ccgacaccgc agcgcccctg gccgcggtgg acctcaagtg | 360 |
| ggagcacaac cccgctgtgt tcctgggccc cggctgcgtg tacgccgccg ccccagtggg | 420 |
| gcgcttcacc gcgcactggc gggtcccgct gctgaccgcc ggcgccccgg cgctgggctt | 480 |
| cggtgtcaag gacgagtatg cgctgaccac ccgcgcgggg cccagctacg ccaagctggg | 540 |
| ggacttcgtg gcggcgctgc accgacggct gggctgggag cgccaagcgc tcatgctcta | 600 |
| cgcctaccgg ccgggtgacg aagagcactg cttcttcctc gtggaggggc tgttcatgcg | 660 |
| ggtccgcgac cgcctcaata ttacggtgga ccacctggag ttcgccgagg acgacctcag | 720 |
| ccactacacc aggctgctgc ggaccatgcc gcgcaaaggc cgagttatct acatctgcag | 780 |
| ctcccctgat gccttcagaa ccctcatgct cctggccctg gaagctggct tgtgtgggga | 840 |
| ggactacgtt ttcttccacc tggatatctt tgggcaaagc ctgcaaggtg gacagggccc | 900 |
| tgctccccgc aggccctggg agagagggga tgggcaggat gtcagtgccc gccaggcctt | 960 |
| tcaggctgcc aaaatcatta catataaaga cccagataat cccgagtact ggaattcct | 1020 |
| gaagcagtta aaacacctgg cctatgagca gttcaacttc accatggagg atggcctggt | 1080 |
| gaacaccatc ccagcatcct tccacgacgg gctcctgctc tatatccagg cagtgacgga | 1140 |
| gactctggca catgggggaa ctgttactga tggggagaac atcactcagc ggatgtggaa | 1200 |
| ccgaagcttt caaggtgtga caggatacct gaaaattgat agcagtggcg atcgggaaac | 1260 |
| agacttctcc ctctgggata tggatcccga gaatggtgcc ttcagggttg tactgaacta | 1320 |
| caatgggact tcccaagagc tggtggctgt gtcggggcgc aaactgaact ggcccctggg | 1380 |
| gtaccctcct cctgacatcc ccaaatgtgg ctttgacaac gaagaccag catgcaacca | 1440 |
| agatcacctt tccacctgg aggtgctggc tttggtgggc agcctctcct tgctcggcat | 1500 |
| tctgattgtc tccttcttca tatacaggaa gatgcagctg gagaaggaac tggcctcgga | 1560 |
| gctgtggcgg gtgcgctggg aggacgttga gcccagtagc cttgagaggc acctgcggag | 1620 |
| tgcaggcagc cggctgaccc tgagcgggag aggctccaat tacggctccc tgctaaccac | 1680 |
| agagggccag ttccaagtct tgccaagac agcatattat aagggcaacc tcgtggctgt | 1740 |
| gaaacgtgtg aaccgtaaac gcattgagct gacacgaaaa gtcctgtttg aactgaagca | 1800 |
| tatgcgggat gtgcagaatg aacacctgac caggtttgtg ggagcctgca ccgaccccc | 1860 |
| caatatctgc atcctcacag agtactgtcc ccgtgggagc ctgcaggaca ttctggagaa | 1920 |
| tgagagcatc accctggact ggatgttccg gtactcactc accaatgaca tcgtcaaggg | 1980 |
| catgctgttt ctacacaatg gggctatctg ttcccatggg aacctcaagt catccaactg | 2040 |
| cgtggtagat gggcgctttg tgctcaagat caccgactat gggctggaga gcttcaggga | 2100 |
| cctggacccca gagcaaggac acaccgttta tgccaaaaag ctgtggacgg cccctgagct | 2160 |
| cctgcgaatg gcttcacccc ctgtgcgggg ctcccaggct ggtgacgtat acagctttgg | 2220 |
| gatcatcctt caggagattg ccctgaggag tgggtcttc cacgtggaag gtttggacct | 2280 |
| gagccccaaa gagatcatcg agcgggtgac tcggggtgag cagccccct tccggccctc | 2340 |
| cctggccctg cagagtcacc tggaggagtt ggggctgctc atgcagcggt gctgggctga | 2400 |
| ggacccacag gagaggccac cattccagca gatccgcctg acgttgcgca aatttaacag | 2460 |
| ggagaacagc agcaacatcc tggacaacct gctgtcccgc atggagcagt acgcgaacaa | 2520 |

```
tctggaggaa ctggtggagg agcggaccca ggcatacctg gaggagaagc gcaaggctga    2580
ggccctgctc taccagatcc tgcctcactc agtggctgag cagctgaagc gtggggagac    2640
ggtgcaggcc gaagcctttg acagtgttac catctacttc agtgacattg tgggtttcac    2700
agcgctgtcg gcggagagca cacccatcag gtggtgaccc tgctcaatga cctgtacact    2760
tgctttgatg ctgtcataga caactttgat gtgtacaagg tggagacaat ggcgatgcc     2820 tacatggtgg tgtcagggct ccctgtgcgg aacgggcggc tacacgcctg cgaggtagcc    2880
cgcatggccc tggcactgct ggatgctgtg cgctccttcc gaatccgcca ccggccccag    2940
gagcagctgc gcttgcgcat tggcatccac acaggacctg tgtgctgtgg agtggtggga    3000
ctgaagatgc cccgttactg tctctttggg gatacagtca acacagcctc aagaatggag    3060
tctaatgggg aagccctgaa gatccacttg tcttctgaga ccaaggctgt cctggaggag    3120
tttggtggtt tcgagctgga gcttcgaggg gatgtagaaa tgaagggcaa aggcaaggtt    3180 cggaccctact ggctccttgg ggagaggggg agtagcaccc gaggctgacc tgcctcctct   3240
cctatccctc cacacctccc ctaccctgtg ccagaagcaa cagaggtgcc aggcctcagc    3300
ctcacccaca gcagccccat cgccaaagga tggaagtaat ttgaatagct caggtgtgct    3360
gaccccagtg aagacaccag ataggacctc tgagagggga ctggcatggg gggatctcag    3420
agcttacagg ctgagccaag cccacggcca tgcacaggga cactcacaca ggcacacgca    3480
cctgctctcc acctggactc aggccgggct gggctgtgga tccttgatcc cctcccctcc    3540
ccatgctctc ctccctcagc cttgctaccc tgtgacttac tgggaggaga gtcacctgaa    3600
ggggaacatg aaaagagact aggtgaagag agggcagggg agcccacatc tggggctggc    3660
ccacaatacc tgctcccccg accccctcca cccagcagta gacacagtgc acaggggaga    3720
agaggggtgg cgcagaaggg ttgggggcct gtatgccttg cttctaccat gagcagagac    3780
aattaaaatc tttattccag tg                                             3802

<210> SEQ ID NO 30
<211> LENGTH: 2970
<212> TYPE: DNA
<213> ORGANISM: human

<400> SEQUENCE: 30
ggggtaagga gttcaaggca gcgcccacac ccgggggctc tccgcaaccc gaccgcctgt      60 ccgctcccc acttcccgcc ctccctccca cctactcatt cacccaccca cccacccaga     120
gccgggacgg cagcccaggc gcccgggccc cgccgtctcc tcgccgcgat cctggacttc    180
ctcttgctgc aggacccggc ttccacgtgt gtcccggagc cggcgtctca gcacacgctc    240
cgctccgggc ctgggtgcct acagcagcca gagcagcagg gagtccggga cccgggcggc    300
atctgggcca agttaggcgc cgccgaggcc agcgctgaac gtctccaggg ccggaggagc    360
cgcggggcgt ccgggtctga gcctcagcaa atgggctccg acgtgcggga cctgaacgcg    420
ctgctgcccg ccgtcccctc cctggtggc ggcggcggct gtgccctgcc tgtgagcggc     480
gcggcgcagt gggcgccggt gctggacttt gcgccccgg gcgcttcggc ttacgggtcg     540
ttgggcggcc ccgcgccgcc accggctccg ccgccacccc gccgccgcc gcctcactcc     600 ttcatcaaac aggagccgag ctggggcggc gcggagccgc acgaggagca gtgcctgagc    660
gccttcactg tccactttc cggccagttc actggcacag ccggagcctg tcgctacggg    720
cccttcggtc ctcctccgcc cagccaggcg tcatccggcc aggccaggat gtttcctaac    780
```

```
gcgccctacc tgcccagctg cctcgagagc cagcccgcta ttcgcaatca gggttacagc      840
acggtcacct tcgacgggac gcccagctac ggtcacacgc cctcgcacca tgcggcgcag      900
ttccccaacc actcattcaa gcatgaggat cccatgggcc agcagggctc gctgggtgag      960
cagcagtact cggtgccgcc cccggtctat ggctgccaca cccccaccga cagctgcacc     1020
ggcagccagg ctttgctgct gaggacgccc tacagcagtg acaatttata ccaaatgaca     1080
tcccagcttg aatgcatgac ctggaatcag atgaacttag gagccacctt aaagggccac     1140
agcacagggt acgagagcga taaccacaca acgcccatcc tctgcggagc caatacaga      1200 atacacacgc acggtgtctt cagaggcatt caggatgtgc gacgtgtgcc tggagtagcc     1260
ccgactcttg tacggtcggc atctgagacc agtgagaaac gcccttcat gtgtgcttac      1320 ccaggctgca ataagagata ttttaagctg tcccacttac agatgcacag caggaagcac     1380
actggtgaga accataccag tgtgacttc aaggactgtg aacgaaggtt ttctcgttca       1440
gaccagctca aaagacacca aaggagacat acaggtgtga accattcca gtgtaaagct      1500 tgtcagcgaa agttctcccg gtccgaccac ctgaagaccc acaccaggac tcatacaggt     1560
gaaaagccct tcagctgtcg gtggccaagt tgtcagaaaa agtttgcccg gtcagatgaa     1620
ttagtccgcc atcacaacat gcatcagaga acatgacca aactccagct ggcgctttga      1680
ggggtctccc tcggggaccg ttcagtgtcc caggcagcac agtgtgtgaa ctgctttcaa     1740
gtctgactct ccactcctcc tcactaaaaa ggaaacttca gttgatcttc ttcatccaac     1800
ttccaagaca agataccggt gcttctggaa actaccaggt gtgcctggaa gagttggtct     1860
ctgccctgcc tactttagt tgactcacag gccctggaga agcagctaac aatgtctggt       1920
tagttaaaag cccattgcca tttggtctgg atttctact gtaagaagag ccatagctga       1980
tcatgtcccc ctgacccttc ccttcttttt ttatgctcgt tttcgctggg gatggaatta     2040
ttgtaccatt ttctatcatg gaatatttat aggccagggc atgtgtatgt gtctgctaat     2100
gtaaactttg tcatggtttc catttactaa cagcaacagc aagaaataaa tcagagagca     2160
aggcatcggg ggtgaatctt gtctaacatt cccgaggtca gccaggctgc taacctggaa     2220
agcaggatgt agttctgcca ggcaactttt aaagctcatg catttcaagc agctgaagaa     2280
agaatcagaa ctaaccagta cctctgtata gaaatctaaa agaattttac cattcagtta     2340
attcaatgtg aacactggca cactgctctt aagaaactat gaagatctga gattttttg     2400 tgtatgtttt tgactctttt gagtggtaat catatgtgtc tttatagatg tacataccttc    2460 cttgcacaaa tggagggaa ttcattttca tcactggag tgtccttagt gtataaaaac       2520
catgctggta tatggcttca agttgtaaaa atgaaagtga cttttaaaga aaatagggga     2580
tggtccagga tctccactga taagactgtt tttaagtaac ttaaggacct ttgggtctac     2640
aagtatatgt gaaaaaaatg agacttactg ggtgaggaaa tccattgttt aaagatggtc     2700
gtgtgtgtgt gtgtgtgtgt gtgtgtgttg tgttgtgttt tgtttttaa gggagggaat     2760 ttattattta ccgttgcttg aaattactgt gtaaatatat gtctgataat gatttgctct     2820
ttgacaacta aaattaggac tgtataagta ctagatgcat cactgggtgt tgatcttaca     2880
agatattgat gataacactt aaaattgtaa cctgcatttt tcactttgct ctcaattaaa     2940
gtctattcaa aaggaaaaaa aaaaaaaaaa                                       2970

<210> SEQ ID NO 31
<211> LENGTH: 2422
<212> TYPE: DNA
<213> ORGANISM: human
```

-continued

<400> SEQUENCE: 31

```
gtcagcctcc cttccaccgc catattgggc cactaaaaaa agggggctcg tcttttcggg      60
gtgttttttct cccctcccc tgtcccgct tgctcacggc tctgcgactc cgacgccggc     120
aaggtttgga gagcggctgg gttcgcggga cccgcgggct tgcacccgcc cagactcgga    180
cgggctttgc caccctctcc gcttgcctgg tcccctctcc tctccgccct cccgctcgcc    240
agtccatttg atcagcggag actcggcggc cgggccgggg cttcccgca gcccctgcgc    300
gctcctagag ctcgggccgt ggctcgtcgg ggtctgtgtc ttttggctcc gagggcagtc    360
gctgggcttc cgagagggt tcgggccgcg taggggcgct ttgttttgtt cggttttgtt    420
tttttgagag tgcgagagag gcggtcgtgc agacccggga gaaagatgtc aaacgtgcga    480
gtgtctaacg ggagccctag cctggagcgg atggacgcca ggcaggcgga gcacccaag    540
ccctcggcct gcaggaacct cttcggcccg gtggaccacg aagagttaac ccgggacttg    600
gagaagcact gcagagacat ggaagaggcg agccagcgca agtggaattt cgattttcag    660
aatcacaaac ccctagaggg caagtacgag tggcaagagg tggagaaggg cagcttgccc    720
gagttctact acagacccc gcggcccccc aaaggtgcct gcaaggtgcc ggcgcaggag    780
agccaggatg tcagcgggag ccgcccggcg gcgcctttaa ttggggctcc ggctaactct    840
gaggacacgc atttggtgga cccaaagact gatccgtcgg acagccagac ggggttagcg    900
gagcaatgcg caggaataag gaagcgacct gcaaccgacg attcttctac tcaaaacaaa    960
agagccaaca gaacagaaga aaatgtttca gacggttccc caaatgccgg ttctgtggag   1020
cagacgccca agaagcctgg cctcagaaga cgtcaaacgt aaacagctcg aattaagaat   1080
atgtttcctt gtttatcaga tacatcactg cttgatgaag caaggaagat atacatgaaa   1140
atttttaaaaa tacatatcgc tgacttcatg gaatggacat cctgtataag cactgaaaaa   1200
caacaacaca ataacactaa aatttttaggc actcttaaat gatctgcctc taaaagcgtt   1260
ggatgtagca ttatgcaatt aggttttttcc ttatttgctt cattgtacta cctgtgtata   1320
tagttttttac ctttttatgta gcacataaac tttggggaag ggagggcagg gtggggctga   1380
ggaactgacg tggagcgggg tatgaagagc ttgctttgat ttacagcaag tagataaata   1440
tttgacttgc atgaagagaa gcaattttgg ggaagggttt gaattgtttt ctttaaagat   1500
gtaatgtccc tttcagagac agctgatact tcatttaaaa aaatcacaaa aatttgaaca   1560
ctggctaaag ataattgcta tttattttta caagaagttt attctcattt gggagatctg   1620
gtgatctccc aagctatcta agtttgtta gatagctgca tgtggctttt ttaaaaaagc   1680
aacagaaacc tatcctcact gccctcccca gtctctctta aagttggaat ttaccagtta   1740
attactcagc agaatggtga tcactccagg tagtttgggg caaaaatccg aggtgcttgg   1800
gagttttgaa tgttaagaat tgaccatctg ctttttattaa atttgttgac aaaattttct   1860
cattttcttt tcacttcggg ctgtgtaaac acagtcaaaa taattctaaa tccctcgata   1920
tttttaaaga tctgtaagta acttcacatt aaaaaatgaa atatttttta atttaaagct   1980
tactctgtcc atttatccac aggaaagtgt tatttttaaa ggaaggttca tgtagagaaa   2040
agcacacttg taggataagt gaatggata ctacatcttt aaacagtatt tcattgcctg   2100
tgtatggaaa aaccatttga agtgtacctg tgtacataac tctgtaaaaa cactgaaaaa   2160
ttatactaac ttatttatgt taaaagattt tttttaatct agacaatata caagccaaag   2220
tggcatgttt tgtgcatttg taaatgctgt gttgggtaga ataggttttc ccctcttttg   2280
```

```
ttaaataata tggctatgct taaaaggttg catactgagc caagtataat tttttgtaat    2340
gtgtgaaaaa gatgccaatt attgttacac attaagtaat caataaagaa aacttccata    2400
gctaaaaaaa aaaaaaaaaa aa                                             2422
```

<210> SEQ ID NO 32
<211> LENGTH: 1181
<212> TYPE: DNA
<213> ORGANISM: human

<400> SEQUENCE: 32

```
ggcacgaggc ccgggccccc caaagtcccg gccgggccga ggtcggcgg ccgccggcgg      60 gccgggcccg cgcacagcgc ccgcatgtac aacatgatgg agacggagct gaagccgccg    120
ggcccgcagc aaacttcggg gggcggcggc ggcaactcca ccgcggcggc ggccggcggc    180
aaccagaaaa acagcccgga ccgcgtcaag cggcccatga atgccttcat ggtgtggtcc    240
cgcgggcagc ggcgcaagat ggcccaggag aaccccaaga tgcacaactc ggagatcagc    300
aagcgcctgg gcgccgagtg gaaacttttg tcggagacgg agaagcggcc gttcatcgac    360
gaggctaagc ggctgcgagc gctgcacatg aaggagcacc cggattataa ataccggccc    420
cggcggaaaa ccaagacgct catgaagaag ataagtaca cgctgcccgg cgggctgctg     480
gcccccggcg gcaatagcat ggcgagcggg gtcggggtgg gcgccggcct gggcgcgggc    540
gtgaaccagc gcatggacag ttacgcgcac atgaacggct ggagcaacgg cagctacagc    600
atgatgcagg accagctggg ctacccgcag caccccgggcc tcaatgcgca cggcgcagcg    660
cagatgcagc ccatgcaccg ctacgacgtg agcgccctgc agtacaactc catgaccagc    720
tcgcagacct acatgaacgg ctcgcccacc tacagcatgt cctactcgca gggcgcacc    780 cctggcatgg ctcttggctc catgggttcg gtggtcaagt ccgaggccag ctccagcccc    840
cctgtggtta cctcttcctc ccactccagg gcgccctgcc aggccgggga cctccgggac    900
atgatcagca tgtatctccc cggcgccgag gtgccggaac ccgccgcccc cagcagactt    960
cacatgtccc agcactacca gagcggcccg gtgcccggca cggccattaa cggcacactg   1020
cccctctcac acatgtgagg gccggacagc gaactggagg ggggagaaat tttcaaagaa   1080
aaacgaggga aatgggaggg gtgcaaaaga ggagagtaag aaacagcatg gagaaacccc   1140
ggtacgctca aaaaaaaaaa aaaaaaaaa aaaaaaaaa a                         1181
```

<210> SEQ ID NO 33
<211> LENGTH: 1305
<212> TYPE: DNA
<213> ORGANISM: human

<400> SEQUENCE: 33

```
ggggcccccgc gccggcccgc gccctgccca gtgcggcctc cttccacccg ccgctgcctg    60
gcccgcgccg tccggccgag ctgcccggcg ggctggtccc cgcgcccgag ccgcccggcc   120
gggaccccga acaaggccga gatgacttcc aaggaggacg gcaaggcggc gccgggggag   180
gagcggcgcc gcagcccgct ggaccacctg cctccgcctg ccaactccaa caagccagac   240
gccgttcagc atcgaggaca tcctcaacaa gccgtctgtg cggagaagtt actcgctgcg   300
tggggcggca cacctgctgg ccgccgcgga caagcacgcg cagggcggct tgccctggcg   360
ggccgcgcgc tgctctcgaa gacctcgccg ctgtgcgcgc tggaggagct cgccagcaag   420
acgtttaagg ggctggaggt cagcgttctg caggcagccg aaggccgcga cggtatgacc   480
atctttgggc agcggcagac ccctaagaag cggcgaaagt cgcgcacggc cttcaccaac   540
```

```
caccagatct atgaattgga aaagcgcttt ctataccaga agtacctgtc ccccgccgat      600
cgcgaccaaa tcgcgcagca gctgggcctc accaacgcgc aagtcatcac ctggttccag      660
aatcggcgcg ctaagctcaa gcgggaactg gaggagatga aggccgacgt ggagtccccc      720
aagaaactgg cccccagcgg gcagatggac atcgtggcgc tggccgaact cgagcagaac      780
tcggaggcca cagccggcgg tggcggcggc tgcggcaggg ccaagtcgag gcccggctct      840
ccggtcctcc ccccaggcgc cccgaaggcc cccggcgct gcgccctgca gctctcgcct       900
gcctctccgc tcacggacca gccggccagc agcaggact gctcggagga cgaggaagac       960
gaagagatcg acgtggacga ttgagcggcg ccccgggtct tccgccgccc tgggctccta     1020
gcgctcgaaa gccaacgcc tcccggaccg gaccgccgag gggagctggg acctcctctg      1080
ccactcccgc tcctcccct gtccccggac tcggctcctg gcagccgcct cttccctctc      1140
gaagcaataa acccaggctg gccggccggg ccggccgcca ccagcggcct ccgccgcccc     1200
ggaagccctc gccgagcaat tctgtatggc ttctatataa atatttaaac ctatatagcg     1260
ggttctcccc aaaaaaaaaa aaaaaaaaaa aaaaaaaaaa aaaaa                     1305

<210> SEQ ID NO 34
<211> LENGTH: 1926
<212> TYPE: DNA
<213> ORGANISM: human

<400> SEQUENCE: 34
gctggagcat cccgctctgg tgccgctgca gccggcagag atggttgagc tcatgttccc       60
gctgttgctc ctccttctgc ccttccttct gtatatggct gcgccccaaa tcaggaaaat      120
gctgtccagt ggggtgtgta catcaactgt tcagcttcct gggaaagtag ttgtggtcac      180
aggagctaat acaggtatcg ggaaggagac agccaaagag ctggctcaga gaggagctcg      240
agtatattta gcttgccggg atgtggaaaa ggggaattg gtggcaaag agatccagac        300 cacgacaggg aaccagcagg tgttggtgcg gaaactggac ctgtctgata ctaagtctat      360
tcgagctttt gctaagggct tcttagctga ggaaaagcac ctccacgttt tgatcaacaa      420
tgcaggagtg atgatgtgtc cgtactcgaa gacagcagat ggctttgaga tgcacatagg      480
agtcaaccac ttgggtcact tcctcctaac ccatctgctg ctagagaaac taaaggaatc      540
agccccatca aggatagtaa atgtgtcttc cctcgcacat cacctgggaa ggatccactt      600
ccataacctg cagggcgaga aattctacaa tgcaggcctg gcctactgtc acagcaagct      660
agccaacatc ctcttcaccc aggaactggc ccggagacta aaaggctctg gcgttacgac      720
gtattctgta caccctggca cagtccaatc tgaactggtt cggcactcat cttccatgag      780
atggatgtgg tggcttttct cctttttcat caagactcct cagcagggag cccagaccag      840
cctgcactgt gccttaacag aaggtcttga gattctaagt gggaatcatt tcagtgactg      900
tcatgtggca tgggtctctg cccaagctcg taatgagact atagcaaggc ggctgtggga      960
cgtcagttgt gacctgctgg gcctcccaat agactaacag gcagtgcagt tggacccaag     1020
agaagactgc agcagactac acagtacttc ttgtcaaaat gattctcctt caaggttttc     1080 aaaacctta gcacaaagag agcaaaacct tccagccttg cctgcttggt gtccagttaa      1140
aactcagtgt actgccagat tcgtctaaat gtctgtcatg tccagattta ctttgcttct     1200
gttactgcca gagttactag agatatcata ataggataag aagaccctca tatgacctgc     1260
acagctcatt ttccttctga aagaaactac tacctaggag aatctaagct atagcaggga     1320
```

```
tgatttatgc aaatttgaac tagcttcttt gttcacaatt cagttcctcc caaccaacca    1380
gtcttcactt caagagggcc acactgcaac ctcagcttaa catgaataac aaagactggc    1440
tcaggagcag ggcttgccca ggcatggtgg atcaccggag tcagtagttc aagaccagcc    1500
tggccaacat ggtgaaaccc cacctctact aaaaattgtg tatatctttg tgtgtcttcc    1560
tgtttatgtg tgccaaggga gtattttcac aaagttcaaa acagccacaa taatcagaga    1620
tggagcaaac cagtgccatc cagtctttat gcaaatgaaa tgctgcaaag ggaagcagat    1680
tctgtatatg ttggtaacta cccaccaaga gcacatgggt agcagggaag aagtaaaaaa    1740
agagaaggag aatactggaa gataatgcac aaaatgaagg gactagttaa ggattaacta    1800
gccctttaag gattaactag ttaaggatta atagcaaaag acattaaata tgctaacata    1860
gctatggagg aattgagggc aagcacccag gactgatgag gtcttaacaa aaaccagtgt    1920
ggcaaa                                                              1926

<210> SEQ ID NO 35
<211> LENGTH: 1195
<212> TYPE: DNA
<213> ORGANISM: human

<400> SEQUENCE: 35
ccgagactca cggtcaagct aaggcgaaga gtgggtggct gaagccatac tattttatag     60
aattaatgga aagcagaaaa gacatcacaa accaagaaga actttggaaa atgaagccta    120
ggagaaattt agaagaagac gattatttgc ataaggacac gggagagacc agcatgctaa    180
aaagacctgt gcttttgcat ttgcaccaaa cagcccatgc tgatgaattt gactgccctt    240
cagaacttca gcacacacag gaactctttc cacagtggca cttgccaatt aaaatagctg    300
ctattatagc atctctgact tttctttaca ctcttctgag ggaagtaatt cacccttag    360 caacttccca tcaacaatat ttttataaaa ttccaatcct ggtcatcaac aaagtcttgc    420
caatggtttc catcactctc ttggcattgg tttacctgcc aggtgtgata gcagcaattg    480
tccaacttca taatggaacc aagtataaga agtttccaca ttggttggat aagtggatgt    540
taacaagaaa gcagtttggg cttctcagtt tctttttgc tgtactgcat gcaatttata    600
gtctgtctta cccaatgagg cgatcctaca gatacaagtt gctaaactgg gcatatcaac    660
aggtccaaca aaataaagaa gatgcctgga ttgagcatga tgtttggaga atggagattt    720
atgtgtctct gggaattgtg ggattggcaa tactggctct gttggctgtg acatctattc    780
catctgtgag tgactctttg acatggagag aatttcacta tattcagagc aagctaggaa    840
ttgtttccct tctactgggc acaatacacg cattgatttt tgcctggaat aagtggatag    900
atataaaaca atttgtatgg tatacacctc caactttat gatagctgtt ttccttccaa    960
ttgttgtcct gatatttaaa agcatactat tcctgccatg cttgaggaag aagatactga   1020
agattagaca tggttgggaa gacgtcacca aaattaacaa aactgagata tgttcccagt   1080
tgtagaatta ctgtttacac acattttgt tcaatattga tatattttat caccaacatt   1140
tcaagtttgt atttgttaat aaaatgatta ttcaaggaaa aaaaaaaaa aaaaa         1195

<210> SEQ ID NO 36
<211> LENGTH: 3414
<212> TYPE: DNA
<213> ORGANISM: human

<400> SEQUENCE: 36
gcttacacag tatggccggc gacattagct agcgctcgct ctactctctc taacgggaaa     60
```

```
gcagcggaat acaagagact gaactgtatc tgcctctatt tccaaaagac tcacgttcaa    120
cttccgctca cacaaagccg ggaaaatttt attagtcctt ttttaaaaa aagttaatat    180 aaaattatag caaaaaaaaa aaggaacctg aactttagta acacagctgg aacaatcgca    240
gcggcggcgg cagcggcggg agaagaggtt taatttagtt gattttctgt ggttgttggt    300
tgttcgctag tctcacggtg atggaagctg cacatttttt cgaagggacc gagaagctgc    360
tggaggtttg gttctcccgg cagcagcccg acgcaaacca aggatctggg gatcttcgca    420
ctatcccaag atctgagtgg gacatacttt tgaaggatgt gcaatgttca atcataagtg    480
tgacaaaaac tgacaagcag gaagcttatg tactcagtga gagtagcatg tttgtctcca    540
agagacgttt cattttgaag acatgtggta ccaccctctt gctgaaagca ctggttcccc    600
tgttgaagct tgctagggat tacagtgggt ttgactcaat tcaaagcttc ttttattctc    660
gtaagaattt catgaagcct tctcaccaag ggtacccaca ccggaatttc caggaagaaa    720
tagagtttct taatgcaatt ttcccaaatg gagcaggata ttgtatggga cgtatgaatt    780
ctgactgttg gtacttatat actctggatt cccagagag tcgggtaatc agtcagccag    840
atcaaacctt ggaaattctg atgagtgagc ttgacccagc agttatggac cagttctaca    900
tgaaagatgg tgttactgca aaggatgtca ctcgtgagag tggaattcgt gacctgatac    960
caggttctgt cattgatgcc acaatgttca atccttgtgg gtattcgatg aatggaatga   1020
aatcggatgg aacttattgg actattcaca tcactccaga accagaattt tcttatgtta   1080
gctttgaaac aaacttaagt cagacctcct atgatgacct gatcaggaaa gttgtagaag   1140
tcttcaagcc aggaaaattt gtgaccacct tgtttgttaa tcagagttct aaatgtcgca   1200
cagtgcttgc ttcgccccag aagattgaag gttttaagcg tcttgattgc cagagtgcta   1260
tgttcaatga ttacaatttt gttttttacca gttttgctaa gaagcagcaa caacagcaga   1320
gttgattaag aaaaatgaag aaaaaacgca aaaagagaac acatgtagaa ggtggtggat   1380 gcttctctaga tgtcgatgct gggggcagtg cttttccataa ccaccactgt gtagttgcag   1440
aaagccctag atgtaatgat agtgtaatca ttttgaattg tatgcattat tatatcaagg   1500
agttagatat cttgcatgaa tgctctcttc tgtgtttagg tattctctgc cactcttgct   1560
gtgaaattga agtggatgta gaaaaaacct tttactatat gaaactttac aacacttgtg   1620
aaagcaactc aatttggttt atgcacagtg taatatttct ccaagtatca tccaaaattc   1680
cccacagaca aggctttcgt cctcattagg tgttggcctc agcctaaccc tctaggactg   1740
ttctattaaa ttgctgccag aattttacat ccagttacct ccactttcta gaacatattc   1800
tttactaatg ttattgaaac caatttctac ttcatactga tgtttttgga aacagcaatt   1860 aaagttttc ttccatagtt gagtccttag aaaatgattc cagttactca ttttgcatat   1920
tgctatttaa cattattgga ccctgcattt atagtccttt gatttcttcc ctctccctgg   1980
tgtctccccc aagaccccaa ataaagcaat accctgttaa cactgtgggt ttatatacta   2040
attctatacc ccagatgggg aattagggg gagatggtcc ctgggcttaa tattcttta   2100 agggcatggg aatttagcct ctctttatt gtaatgtgct cttttggaaa atagttggtt   2160
agcagggaga ccagagttgt agattgagat tgggtgtact ggctgttctg tggaaaacat   2220
acattctgtg ttcctcgaat aagtgaaatt gagcttctaa tgagatgcac ccctttacta   2280
acttgatgat gatataaaat tcatttttat ttagttaatt accagagaga tttagcataa   2340
ttttgcttct ggattcagta aatcaagtca gcttggatca ttcaccttaa cttttccttt   2400
```

-continued

```
agcagccctt tccactagtt tcccattaag tagtgttcta taaactttga tccaaagcag     2460
aatcaatgtc ttttccatct cgtgacttaa agttctgtga ctgtgatgca tgtgagtgtt     2520
ccgacttcat ctgttcctct taactacggt gtttccctta ccgatcggca ttcataggat     2580
gaaatgaatg actgtcccag aatgagaatt tgtccagatt attcagataa acatcataaa     2640
gagaataaca ttataaataa gtagaatatg aataaataga ataataaaat tccaaaatac     2700
tcaatgggaa atgactagta ataggctt tcaagagttg gtacctttac gtatatttgc       2760
agattctctg ggattttaag gaactgagaa aacagaaaag ttgactaaat tttatatttc     2820
ttgtcctcta aatattttga taatttctgg attgatgcag tgatgttttt cgttccttgt     2880
atttataaat gaaacctttt ttttggtgtt tctaaaccta aaatctactt ggtttgaaat     2940
caagtggttg aacactgtt tgactttat ttgaagcatg ttgttgattg aaaatttcat       3000
tgaggaagtt ttcaatcagt gtgatcagtt tgattctgta atgagcacag cacctaatat     3060
tttgaggagc tctgttttga ggaccaatgc ttaaggtgga ccttgttgct aaacaatatc     3120
ccaatagatt tgttgacttg aggtctggtt tggttttgtt tttgttttgt tttggttttg     3180
ttttgtttcc caatagaatt aagaattcta atgttgaaaa actgtataaa tttttatggg     3240
acaaagccta gaaaagagaa atgtagtttg aatcataatc taaatcatcg tatgatagga     3300
aggaaaagtt ttggtgccat aatttctcct ttcactggtg ttggacttaa atcagttgaa     3360
atgtatttct gtaccacaat ttacgcttca ataaaagttt aattgtctag tgag           3414

<210> SEQ ID NO 37
<211> LENGTH: 3287
<212> TYPE: DNA
<213> ORGANISM: human

<400> SEQUENCE: 37
agactgaggc ggaggcagcc ccgcgccgcg ccggacccga gcatatttca ttttctgtca       60
ttggactttg agccattaga accatgagca actacagtgt gtcactggtt ggcccagctc      120
cttggggttt ccggctgcag ggcggtaagg atttcaacat gcctctgaca atctctagtc      180
taaaagatgg cggcaaggca gcccaggcaa atgtaagaat aggcgatgtg gttctcagca      240
ttgatggaat aaatgcacaa ggaatgactc atcttgaagc ccagaataag attaagggtt      300
gtacaggctc tttgaatatg actctgcaaa gagcatctgc tgcacccaag cctgagccgg      360
ttcctgttca aaagggagaa cctaaagaag tagttaaacc tgtgcccatt acatctcctg      420
ctgtgtccaa agtcacttcc acaaacaaca tggcctacaa taaggcacca cggccttttg      480
gttctgtgtc ttcaccaaaa gtcacatcca tcccatcacc atcgtctgcc ttcaccccag      540
cccatgcgac cacctcatca catgcttccc cttcacccgt ggctgccgtc actcctcccc      600
tgttcgctgc atctggactg catgctaatg ccaatcttag tgctgaccag tctccatctg      660
cactgagcgc tggtaaaact gcagttaatg tcccacggca gccacagtc accagcgtgt       720 gttccgagac ttctcaggag ctagcagagg gacagagaag aggatcccag ggtgacagta      780
aacagcaaaa tggcccacca agaaaacaca ttgtggagcg ctatacagag ttttatcatg      840
tacccactca cagtgatgcc agcaagaaga gactgattga ggatactgaa gactggcgtc      900
caagaactgg aacaactcag tctcgctctt tccgaatcct tgcccagatc actgggactg      960
aacatttgaa agaatctgaa gccgataata caaagaaggc aaataactct caggagcctt     1020
ctccgcagtt ggcttccttg gtagcttcca cacggagcat gcccgagagc ctggacagcc     1080
caacctctgg cagaccaggg gttaccagcc tcacaactgc agctgccttc aagcctgtag     1140
```

```
gatccactgg cgtcatcaag tcaccaagct ggcaacggcc aaaccaagga gtaccttcca    1200
ctggaagaat ctcaaacagc gctacttact caggatcagt ggcaccagcc aactcagctt    1260
tgggacaaac ccagccaagt gaccaggaca ctttagtgca aagagctgag cacattccag    1320
cagggaaacg aactccgatg tgcgcccatt gtaaccaggt catcagagga ccattcttag    1380
tggcactggg gaaatcttgg cacccagaag aattcaactg cgctcactgc aaaaatacaa    1440
tggcctacat tggatttgta gaggagaaag gagccctgta ttgtgagctg tgctatgaga    1500
aattctttgc ccctgaatgt ggtcgatgcc aaaggaagat ccttggagaa gtcatcaatg    1560
cgttgaaaca aacttggcat gtttcctgtt ttgtgtgtgt agcctgtgga aagcccattc    1620
ggaacaatgt ttttcacttg gaggatggtg aaccctactg tgagactgat tattatgccc    1680
tctttggtac tatatgccat ggatgtgaat ttcccataga agctggtgac atgttcctgg    1740
aagctctggg ctacacctgg catgacactt gctttgtatg ctcagtgtgt tgtgaaagtt    1800
tggaaggtca gaccttttc tccaagaagg acaagcccct gtgtaagaaa catgctcatt    1860
ctgtgaattt tgaaagtca acagttcagg agaagagaag gaatttgaag agaaaaagga    1920
aaattaaaat tactaattaa ttttttagatt caatatttat atggagtttt gaaaaataat    1980
agtggccctg aaggaataaa ttccagcttt aaaaaccaag tctgaggaaa tatttggctt    2040
cataaagtaa agagacggtt tggcatttat tattacttttt tcctgtattt tatgcccata    2100
aaataagctt tataaaaacc aatttcctga tggactatta aattcatctt agaataaatt    2160
agtgaagaat ttaattttag aataaataat ccaatctgaa ataattatac cttctttcct    2220
tgttaggtag ttatgagtaa atctgcaaaa ggcaatgaaa atgccttaaa ttttatcaat    2280
aacagaatta ttgtatttaa aaaaaaacta atacttatct ttaaaatagt aaataggatt    2340
ttaaacagag aattttatca gtaataggtg tcagtttta aaaaattgct tgtaggctga    2400
gcgcggtggc tcacgcctgt aatcccagca ctttgggagg ccaaggtggg tggaccacat    2460
gaggtcagga gtttgagatc agcctggcca acatggtgaa accccatctc tactaaaaat    2520
acaaaaatta gccggacgca gtggcacgcg cctgtaatcc cagctactca agaggctgag    2580
gcacgagaat cacttgaacc cgggagggag aggttgcagt gagccaagat cgtaccactg    2640
cactccagcc tgggtgacag agtgagactc cgtctccaaa aaaaaacttt gcttgtatat    2700
tatttttgcc ttacagtgga tcattctagt aggaaaggac aataagattt tttatcaaaa    2760
tgtgtcatgc cagtaagaga tgttatattc ttttcttatt tcttcccac ccaaaaataa    2820 gctaccatat agcttataag tctcaaattt ttgccttttta ctaaaatgtg attgtttctg    2880
ttcattgtgt atgcttcatc acctatatta ggcaaattcc attttttccc ttgcgctaag    2940
gtaaagattt aattaaataa ttttggcctc tcatagtttt ctctctcttt aaagagaata    3000
aatagagggc caggtgtggt ggctcacgcc tgtgatccca gcactttggg aggccaagac    3060
gggcggatca tgaggtcaag agatcaagat catcctggcc aacatggtga aaccctgtct    3120
ctactaaaaa tacaaaaatg agctgggcat ggtggggcgt gcctgtagtc ccatgtactt    3180
gggaggctga ggcaggaaaa ttcttgaacc caggagacgg aagttgcagt gagctgagat    3240
cacaccactg cactccagcc tggtgacaga gcaagactcc ggctctt            3287
```

<210> SEQ ID NO 38
<211> LENGTH: 1254
<212> TYPE: DNA
<213> ORGANISM: human

```
<400> SEQUENCE: 38
atggcagtgg agaccacggt ccacactcac ctctctgcgt ctccaccgca gggctctccc      60
tacgaccaca cacccggcat ggcgggctcc ttggggtacc atccttacgc ggcgcccctg     120
ggatcgtacc cttacgggga cccagcgtac cggaagaacg ccacaaggga cgccacggct     180
accctcaagg cctggctcaa cgagcaccgc aagaacccct accccaccaa gggcgagaag     240
atcatgctgg ccatcatcac caagatgacc ctcacccagt gtccacctg gttcgccaac      300 gcgcgccggc gcctcaagaa agagaataaa atgacgtgga cgccgcggaa ccgcagcgag     360
gacgaggaag aggaggagaa cattgacctg gagaagaacg acgaggacga gccccagaag     420
cccgaggaca agggcgaccc cgagggcccc gaagcaggag gagctgagca gaaggcggct     480
tcgggctgcg aacggcttca gggaccaccc acccctgcag gcaaggagac ggagggcagc     540
ctcagcgact cggattttaa ggagccgccc tcggagggcc gcctcgacgc gctgcagggc     600
ccccccgcca ccggcgggcc ctcccggct gggccagcgg cggcgcggct ggcggaggac      660
ccggcccctc actaccccgc cggagcgccg gcgcccggcc cgcatccagc gcgggcgag     720 gtgcctccgg gtcccggcgg gccctcggtt atccattcgc cgcctccgcc gccgcctcct     780
gcggtgctcg ccaagcccaa actgtggtct ttggcagaga tcgccacatt gtcggacaag     840
gtcaaggacg gggcggcgg gaacgagggc tctccatgcc caccgtgtcc cgggcccata     900
gccgggcaag ccctaggagg cagccgggcg tcgccggccc cggcgccgtc acgctcgccc     960
tcggcgcagt gtccttttcc aggcgggacg gtgctgtccc ggcctctcta ctacaccgcg    1020
cccttctatc ccggctacac gaactatggc tccttcggac accttcatgg ccacccgggg    1080
cccgggccag gccccacaac cggtccgggg tctcatttca atggattaaa ccagaccgtg    1140
ttgaaccgag cggacgcttt ggctaaagac ccgaaaatgt tgcggagcca gtctcagcta    1200
gacctgtgca aagactctcc ctatgaattg aagaaaggta tgtccgacat ttaa           1254

<210> SEQ ID NO 39
<211> LENGTH: 2560
<212> TYPE: DNA
<213> ORGANISM: human

<400> SEQUENCE: 39
gaattccggc cagaagaaat ctggcctcgg aacacgccat tctccgcgcc gcttccaata      60
accactaaca tccctaacga gcatccgagc cgagggctct gctcggaaat cgtcctggcc     120
caactcggcc cttcgagctc tcgaagatta ccgcatctat ttttttttc ttttttttct      180 tttcctagcg cagataaagt gagcccggaa agggaaggag ggggcgggga caccattgcc     240
ctgaaagaat aaataagtaa ataaacaaac tggctcctcg ccgcagctgg acgcggtcgg     300
ttgagtccag gttgggtcgg acctgaaccc ctaaaagcgg aaccgcctcc cgccctcgcc     360
atcccggagc tgagtcgccg gcggcggtgg ctgctgccag accggagtt tcctctttca      420 ctggatggag ctgaactttg ggcggccaga gcagcacagc tgtccgggga tcgctgcacg     480
ctgagctccc tcggcaagac ccagcggcgg ctcgggattt ttttggggggg gcggggacca    540 gccccgcgcc ggcaccatgt tcctggcgac cctgtacttc gcgctgccgc tcttggactt     600
gctcctgtcg gccgaagtga gcggcggaga ccgcctggat tgcgtgaaag ccagtgatca     660
gtgcctgaag gagcagagct gcagcaccaa gtaccgcacg ctaaggcagt gcgtggcggg     720
caaggagacc aacttcagcc tggcatccgg cctggaggcc aaggatgagt gccgcagcgc     780
catggaggcc ctgaagcaga agtcgctcta caactgccgc tgcaagcggg gtatgaagaa     840
```

```
ggagaagaac tgcctgcgca tttactggag catgtaccag agcctgcagg gaaatgatct      900
gctggaggat tccccatatg aaccagttaa cagcagattg tcagatatat tccgggtggt      960
cccattcata tcagatgttt ttcagcaagt ggagcacatt cccaaaggga caaactgcct     1020
ggatgcagcg aaggcctgca acctcgacga catttgcaag aagtacaggt cggcgtacat     1080
caccccgtgc accaccagcg tgtccaacga tgtctgcaac cgccgcaagt gccacaaggc     1140
cctccggcag ttctttgaca aggtcccggc caagcacagc tacggaatgc tcttctgctc     1200
ctgccgggac atcgcctgca cagagcgagg gcgacagacc atcgtgcctg tgtgctccta     1260
tgaagagagg gagaagccca actgtttgaa tttgcaggac tcctgcaaga cgaattacat     1320
ctgcagatct cgccttgcgg attttttttac caactgccag ccagagtcaa ggtctgtcag     1380
cagctgtcta aggaaaaact acgctgactg cctcctcgcc tactcggggc ttattggcac     1440
agtcatgacc cccaactaca tagactccag tagcctcagt gtggcccccat ggtgtgactg     1500 cagcaacagt gggaacgacc tagaagagtg cttgaaattt ttgaatttct tcaaggacaa     1560
tacatgtctt aaaaatgcaa ttcaagcctt tggcaatggc tccgatgtga ccgtgtggca     1620
gccagccttc ccagtacaga ccaccactgc cactaccacc actgccctcc gggttaagaa     1680
caagcccctg gggccagcag ggtctgagaa tgaaattccc actcatgttt tgccaccgtg     1740
tgcaaattta caggcacaga agctgaaatc caatgtgtcg ggcaatacac acctctgtat     1800
ttccaatggt aattatgaaa agaaggtct cggtgcttcc agccacataa ccacaaaatc     1860
aatggctgct cctccaagct gtggtctgag cccactgctg gtcctggtgg taaccgctct     1920
gtccacccta ttatctttaa cagaaacatc atagctgcat taaaaaaata caatatggac     1980
atgtaaaaag acaaaaacca agttatctgt ttcctgttct cttgtatagc tgaaattcca     2040
gtttaggagc tcagttgaga aacagttcca ttcaactgga acatttttt tttcctttt      2100 aagaaagctt cttgtgatcc ttcggggctt ctgtgaaaaa cctgatgcag tgctccatcc     2160
aaactcagaa ggctttggga tatgctgtat tttaaaggga cagtttgtaa cttgggctgt     2220
aaagcaaact ggggctgtgt tttcgatgat gatgatcatc atgatcatga tgattttaac     2280
agttttactt ctggcctttc ctagctagag aaggagttaa tatttctaag gtaactccca     2340
tatctccttt aatgacattg atttctaatg atataaattt cagcctacat tgatgccaag     2400
cttttttgcc acaaagaaga ttcttaccaa gagtgggctt tgtggaaaca gctggtactg     2460
atgttcacct ttatatatgt actagcattt tccacgctga tgtttatgta ctgtaaacag     2520
ttctgcactc ttgtacaaaa gaaaaaacca cccggaattc                           2560

<210> SEQ ID NO 40
<211> LENGTH: 2560
<212> TYPE: DNA
<213> ORGANISM: human

<400> SEQUENCE: 40
gaattccggc cagaagaaat ctggcctcgg aacacgccat tctccgcgcc gcttccaata       60
accactaaca tccctaacga gcatccgagc cgagggctct gctcggaaat cgtcctggcc      120
caactcggcc cttcgagctc tcgaagatta ccgcatctat tttttttttc tttttttct      180 tttcctagcg cagataaagt gagcccggaa agggaaggag ggggcgggga caccattgcc      240
ctgaaagaat aaataagtaa ataaacaaac tggctcctcg ccgcagctgg acgcggtcgg      300
ttgagtccag gttgggtcgg acctgaaccc ctaaaagcgg aaccgcctcc cgccctcgcc      360
```

-continued

```
atcccggagc tgagtcgccg gcggcggtgg ctgctgccag acccggagtt tcctctttca      420
ctggatggag ctgaactttg gcggccaga gcagcacagc tgtccgggga tcgctgcacg      480
ctgagctccc tcggcaagac ccagcggcgg ctcgggattt ttttgggggg gcggggacca      540
gccccgcgcc ggcaccatgt tcctggcgac cctgtacttc gcgctgccgc tcttggactt      600
gctcctgtcg gccgaagtga gcggcggaga ccgcctggat tgcgtgaaag ccagtgatca      660
gtgcctgaag gagcagagct gcagcaccaa gtaccgcacg ctaaggcagt gcgtggcggg      720
caaggagacc aacttcagcc tggcatccgg cctggaggcc aaggatgagt gccgcagcgc      780
catggaggcc ctgaagcaga agtcgctcta caactgccgc tgcaagcggg gtatgaagaa      840
ggagaagaac tgcctgcgca tttactggag catgtaccag agcctgcagg gaaatgatct      900
gctggaggat tccccatatg aaccagttaa cagcagattg tcagatatat tccgggtggt      960
cccattcata tcagatgttt ttcagcaagt ggagcacatt cccaaaggga caactgcct     1020
ggatgcagcg aaggcctgca acctcgacga catttgcaag aagtacaggt cggcgtacat     1080
caccccgtgc accaccagcg tgtccaacga tgtctgcaac cgccgcaagt gccacaaggc     1140
cctccggcag ttcttttgaca aggtcccggc caagcacagc tacggaatgc tcttctgctc     1200
ctgccgggac atcgcctgca cagagcggag gcgacagacc atcgtgcctg tgtgctccta     1260
tgaagagagg gagaagccca actgtttgaa tttgcaggac tcctgcaaga cgaattacat     1320
ctgcagatct cgccttgcgg atttttttac caactgccag ccagagtcaa ggtctgtcag     1380
cagctgtcta aaggaaaact acgctgactg cctcctcgcc tactcggggc ttattggcac     1440
agtcatgacc cccaactaca tagactccag tagcctcagt gtggcccat ggtgtgactg      1500
cagcaacagt gggaacgacc tagaagagtg cttgaaattt ttgaatttct tcaaggacaa     1560
tacatgtctt aaaaatgcaa ttcaagcctt tggcaatggc tccgatgtga ccgtgtggca     1620
gccagccttc ccagtacaga ccaccactgc cactaccacc actgccctcc gggttaagaa     1680
caagcccctg gggccagcag ggtctgagaa tgaaattccc actcatgttt tgccaccgtg     1740
tgcaaattta caggcacaga agctgaaatc caatgtgtcg ggcaatacac acctctgtat     1800
ttccaatggt aattatgaaa agaaggtct cggtgcttcc agccacataa ccacaaaatc      1860
aatggctgct cctccaagct gtggtctgag cccactgctg gtcctggtgg taaccgctct     1920
gtccacccta ttatctttaa cagaaacatc atagctgcat aaaaaaata caatatggac     1980
atgtaaaaag acaaaaacca agttatctgt ttcctgttct cttgtatagc tgaaattcca     2040
gtttaggagc tcagttgaga aacagttcca ttcaactgga acatttttt ttttcctttt      2100
aagaaagctt cttgtgatcc ttcggggctt ctgtgaaaaa cctgatgcag tgctccatcc     2160
aaactcagaa ggctttggga tatgctgtat tttaaaggga cagtttgtaa cttgggctgt     2220
aaagcaaact ggggctgtgt tttcgatgat gatgatcatc atgatcatga tgatttttaac    2280
agttttactt ctggccttc ctagctagag aaggagttaa tatttctaag gtaactccca     2340
tatctccttt aatgacattg atttctaatg atataaattt cagcctacat tgatgccaag     2400
ctttttttgcc acaagaaga ttcttaccaa gagtgggctt tgtggaaaca gctggtactg      2460
atgttcacct ttatatatgt actagcattt tccacgctga tgtttatgta ctgtaaacag     2520
ttctgcactc ttgtacaaaa gaaaaaacca cccggaattc                           2560
```

<210> SEQ ID NO 41
<211> LENGTH: 2439
<212> TYPE: DNA
<213> ORGANISM: human

<400> SEQUENCE: 41

```
cagcacccag ctccccgcca ccgccatggt ccccgacacc gcctgcgttc ttctgctcac      60
cctggctgcc ctcggcgcgt ccggacaggg ccagagcccg ttgggctcag acctgggccc     120
gcagatgctt cgggaactgc aggaaaccaa cgcggcgctg caggacgtgc gggactggct     180
gcggcagcag gtcagggaga tcacgttcct gaaaaacacg gtgatggagt gtgacgcgtg     240
cgggatgcag cagtcagtac gcaccggcct acccagcgtg cggcccctgc tccactgcgc     300
gcccggcttc tgcttccccg gcgtggcctg catccagacg gagagcggcg gccgctgcgg     360
ccctgcccc gcgggcttca cgggcaacgg ctcgcactgc accgacgtca acgagtgcaa     420
cgcccacccc tgcttccccc gagtccgctg tatcaacacc agcccggggt ccgctgcga     480
ggcttgcccg ccggggtaca gcggccccac ccaccagggc gtggggctgg ctttcgccaa     540
ggccaacaag caggtttgca cggacatcaa cgagtgtgag accgggcaac ataactgcgt     600
ccccaactcc gtgtgcatca cacccgggg ctccttccag tgcggcccgt gccagcccgg     660
cttcgtgggc gaccaggcgt ccggctgcca gcgcggcgca cagcgcttct gccccgacgg     720
ctcgcccagc gagtgccacg agcatgcaga ctgcgtccta gagcgcgatg gctcgcggtc     780
gtgcgtgtgt cgcgttggct gggccggcaa cgggatcctc tgtggtcgcg acactgacct     840
agacggcttc ccggacgaga agctgcgctg cccggagccg cagtgccgta aggacaactg     900
cgtgactgtg cccaactcag gcaggagga tgtggaccgc gatggcatcg gagacgcctg     960
cgatccggat gccgacgggg acgggtcccc caatgaaaag acaactgccc gctggtgcg    1020
gaacccagac cagcgcaaca cggacgagga caagtggggc gatgcgtgcg acaactgccg    1080
gtcccagaag aacgacgacc aaaaggacac agaccaggag ggccggggcg atgcgtgcga    1140
cgacgacatc gacggcgacc ggatccgcaa ccaggccgac aactgcccta gggtacccaa    1200
ctcagaccag aaggacagtg atggcgatgg tatagggga tgcctgtgaca actgtcccca    1260
gaagagcaac ccggatcagg cggatgtgga ccacgacttt gtgggagatg cttgtgacag    1320
cgatcaagac caggatggag acggacatca ggactctcgg gacaactgtc ccacggtgcc    1380
taacagtgcc caggaggact cagaccacga tggccagggt gatgcctgcg acgacgacga    1440
cgacaatgac ggagtccctg acagtcggga caactgccgc tggtgcctta ccccggcca    1500
ggaggacgcg gacagggacg gcgtgggcga cgtgtgccag gacgactttg atgcagacaa    1560
ggtggtagac aagatcgacg tgtgtccgga gaacgctgaa gtcacgctca ccgacttcag    1620
ggccttccag acagtcgtgc tggacccgga gggtgacgcg cagattgacc ccaactgggt    1680
ggtgctcaac cagggaaggg agatcgtgca gacaatgaac agcgacccag gcctggctgt    1740
gggttacact gccttcaatg gcgtggactt cgagggcacg ttccatgtga acacggtcac    1800
ggatgacgac tatgcgggct tcatctttgg ctaccaggac agctccagct tctacgtggt    1860
catgtggaag cagatggagc aaacgtattg gcaggcgaac cccttccgtg ctgtggccga    1920
gcctggcatc caactcaagg ctgtgaagtc ttccacaggc cccggggaac agctgcggaa    1980
cgctctgtgg catacaggag acacagagtc ccaggtgcgg ctgctgtgga aggacccgcg    2040
aaacgtgggt tggaaggaca agaagtccta tcgttggttc ctgcagcacc ggccccaagt    2100
gggctacatc agggtgcgat tctatgaggg ccctgagctg gtggccgaca gcaacgtggt    2160
cttggacaca accatgcggg gtggccgcct gggggtcttc tgcttctccc aggagaacat    2220
catctgggcc aacctgcgtt accgctgcaa tgacaccatc ccagaggact atgagaccca    2280
```

```
tcagctgcgg caagcctagg gaccagggtg aggacccgcc ggatgacagc caccctcacc    2340
gcggctggat gggggctctg cacccagccc aagggtggc  cgtcctgagg gggaagtgag    2400
aagggctcag agaggacaaa ataaagtgtg tgtgcaggg                           2439
```

<210> SEQ ID NO 42
<211> LENGTH: 2439
<212> TYPE: DNA
<213> ORGANISM: human

<400> SEQUENCE: 42

```
cagcacccag ctccccgcca ccgccatggt ccccgacacc gcctgcgttc ttctgctcac      60
cctggctgcc ctcggcgcgt ccggacaggg ccagagcccg ttgggctcag acctgggccc     120
gcagatgctt cggaactgc  aggaaaccaa cgcggcgctg caggacgtgc gggactggct     180
gcggcagcag gtcagggaga tcacgttcct gaaaaacacg gtgatggagt gtgacgcgtg     240
cgggatgcag cagtcagtac gcaccggcct acccagcgtg cggcccctgc tccactgcgc     300
gcccggcttc tgcttccccg gcgtggcctg catccagacg gagagcggcg gccgctgcgg     360
cccctgcccc gcgggcttca cgggcaacgg ctcgcactgc accgacgtca acgagtgcaa     420
cgcccacccc tgcttccccc gagtccgctg tatcaacacc agcccggggt tccgctgcga     480
ggcttgcccg ccggggtaca gcggccccac ccaccagggc gtggggctgg ctttcgccaa     540
ggccaacaag caggtttgca cggacatcaa cgagtgtgag accggcaac  ataactgcgt     600
ccccaactcc gtgtgcatca acacccgggg ctccttccag tgcggccgt  gccagcccgg    660
cttcgtgggc gaccaggcgt ccggctgcca gcgcggcgca cagcgcttct gccccgacgg     720
ctcgcccagc gagtgccacg agcatgcaga ctgcgtccta gagcgcgatg gctcgcggtc     780
gtgcgtgtgt cgcgttggct gggccggcaa cgggatcctc tgtggtcgcg acactgacct     840
agacggcttc ccggacgaga agctgcgctg cccggagccg cagtgccgta aggacaactg     900
cgtgactgtg cccaactcag ggcaggagga tgtggaccgc gatggcatcg agacgcctg      960
cgatccggat gccgacgggg acgggtcccc caatgaaaag gacaactgcc cgctggtgcg    1020
gaacccagac cagcgcaaca cggacgagga caagtggggc gatgcgtgcg caactgccg    1080
gtcccagaag aacgacgacc aaaaggacac agaccaggac ggccgggcg  atgcgtgcga   1140
cgacgacatc gacggcgacc ggatccgcaa ccaggccgac aactgcccta gggtacccaa    1200
ctcagaccag aaggacagtg atggcgatgg tataggggat gcctgtgaca actgtccca     1260
gaagagcaac ccggatcagg cggatgtgga ccacgacttt gtgggagatg cttgtgacag    1320
cgatcaagac caggatggag acggacatca ggactctcgg gacaactgtc ccacggtgcc    1380
taacagtgcc caggaggact cagaccacga tggccagggt gatgcctgcg acgacgacga    1440
cgacaatgac ggagtccctg acagtcggga caactgccgc ctggtgccta ccccggcca    1500
ggaggacgcg gacagggacg gcgtgggcga cgtgtgccag gacgactttg atgcagacaa    1560
ggtggtagac aagatcgacg tgtgtccgga gaacgctgaa gtcacgctca ccgacttcag    1620
ggccttccag acagtcgtgc tggacccgga gggtgacgcg cagattgacc caactgggt    1680
ggtgctcaac cagggaaggg agatcgtgca gacaatgaac agcgacccag gctggctgt    1740
gggttacact gccttcaatg gcgtggactt cgagggcacg ttccatgtga acacggtcac    1800
ggatgacgac tatgcgggct tcatctttgg ctaccaggac agctccagct tctacgtggt    1860
catgtggaag cagatggagc aaacgtattg gcagcgaac  cccttccgtg ctgtggccga    1920
gcctggcatc caactcaagg ctgtgaagtc ttccacaggc cccgggggaac agctgcggaa    1980
```

```
cgctctgtgg catacaggag acacagagtc ccaggtgcgg ctgctgtgga aggacccgcg    2040
aaacgtgggt tggaaggaca agaagtccta tcgttggttc ctgcagcacc ggccccaagt    2100
gggctacatc agggtgcgat tctatgaggg ccctgagctg gtggccgaca gcaacgtggt    2160
cttggacaca accatgcggg gtggccgcct gggggtcttc tgcttctccc aggagaacat    2220
catctgggcc aacctgcgtt accgctgcaa tgacaccatc ccagaggact atgagaccca    2280
tcagctgcgg caagcctagg gaccagggtg aggacccgcc ggatgacagc caccctcacc    2340
gcggctggat gggggctctg cacccagccc aaggggtggc cgtcctgagg gggaagtgag    2400
aagggctcag agaggacaaa ataaagtgtg tgtgcaggg                           2439

<210> SEQ ID NO 43
<211> LENGTH: 1385
<212> TYPE: DNA
<213> ORGANISM: human

<400> SEQUENCE: 43
ctccagccat tggtgtctgt gtcattacta atagagtctt gtaaacactc gttaatcacg      60
gaagccgccg gcctggggct ccgcacgcca gcctgtgcgg gtcttccccg cctctgcagc     120
ctagtgggaa ggaggtggga ggaaagaagg aagaaaggga gggagggagg aggcaggcca     180
gagggaggga ccgcctcgga ggcagaagag ccgcgaggag ccagcggagc accgcgggct     240
ggggcgcagc cacccgccgc tcctcgagtc ccctcgcccc tttcccttcg tgccccccgg     300
cagcctccag cgtcggtccc caggcagcat ggtgaggtct gctcccggtc cctcgccacc     360
atgtacgtga gctacctcct ggacaaggac gtgagcatgt accctagctc cgtgcgccac     420
tctggcggcc tcaacctggc gccgcagaac ttcgtcagcc ccccgcagta cccggactac     480
ggcggttacc acgtggcggc cgcagctgca gcggcagcga acttggacag cgcgcagtcc     540 ccgggggccat cctggccggc agcgtatggc gccccactcc gggaggactg gaatggctac     600
gcgcccggag gcgccgcggc cgccgccaac gccgtggctc acggcctcaa cggtggctcc     660
ccggccgcag ccatgggcta cagcagcccc gcagactacc atccgcacca ccaccccgcat     720 caccacccgc accacccggc cgcggcgcct tcctgcgctt ctgggctgct gcaaacgctc     780
aaccccggcc ctcctgggcc cgccgccacc gctgccgccg agcagctgtc tccggcggc      840 cagcggcgga acctgtgcga gtggatgcgg aagccggcgc agcagtccct cggcagccaa     900
gtgaaaacca ggacgaaaga caaatatcga gtggtgtaca cggaccacca gcggctggag     960
ctggagaagg agtttcacta cagtcgctac atcaccatcc ggaggaaagc cgagctagcc    1020
gccacgctgg ggctctctga gaggcaggtt aaaatctggt ttcagaaccg cagagcaaag    1080
gagaggaaaa tcaacaagaa gaagttgcag cagcaacagc agcagcagcc accacagccg    1140
cctccgccgc caccacagcc tccccagcct cagccaggtc ctctgagaag tgtcccagag    1200
cccttgagtc cggtgtcttc cctgcaagcc tcagtgtctg gctctgtccc tggggttctg    1260
gggccaactg gggggtgct aaaccccacc gtcacccagt gacccaccgg ggttctgcag     1320
cggcagagca attccaggct gagccatgag gagcgtggac tctgctagac tcctcaggag    1380
agacc                                                                1385

<210> SEQ ID NO 44
<211> LENGTH: 4098
<212> TYPE: DNA
<213> ORGANISM: human
```

```
<400> SEQUENCE: 44
ggtggcctct gtggccgtcc aggctagcgg cggcccgcag gcggcgggga gaaagactct      60
ctcacctggt cttgcggctg tggccaccgc cggccagggg tgtggagggc gtgctgccgg     120
agacgtccgc cgggctctgc agttccgccg ggggtcgggc agctatggag ccgcggccca     180
cggcgccctc ctccggcgcc ccgggactgg ccggggtcgg ggagacgccg tcagccgctg     240
cgctggccga agccagggtg gaactgcccg gcacggctgt gccctcggtg ccggaggatg     300
ctgcgcccgc gagccgggac ggcggcgggg tccgcgatga gggccccgcg gcggccgggg     360
acgggctggg cagaccccttg gggcccaccc cgagccagac ccgtttccag gtggacctgg     420
tttccgagaa cgccgggcgg gccgctgctg cggcggcggc ggcggcggcg gcagcggcgg     480
cggctggtgc tggggcgggg gccaagcaga ccccgcgga cggggaagcc agcggcgaga     540
gcgagccagc taaaggcagc gaggaagcca agggccgctt ccgcgtgaac ttcgtggacc     600
cagctgcctc ctcgtcggct gaagacagcc tgtcagatgc tgccggggtc ggagtcgacg     660
ggcccaacgt gagcttccag aacggcgggg acacggtgct gagcgagggc agcagcctgc     720
actccggcgg cggcggcggc agtgggcacc accagcacta ctattatgat acccacacca     780
acacctacta cctgcgcacc ttcggccaca acaccatgga cgctgtgccc aggatcgatc     840
actaccggca cacagccgcg cagctgggcg agaagctgct ccggcctagc ctggcggagc     900
tccacgacga gctggaaaag gaaccttttg aggatggctt tgcaaatggg gaagaaagta     960
ctccaaccag agatgctgtg gtcacgtata ctgcagaaag taaggagtc gtgaagtttg    1020
gctggatcaa gggtgtatta gtacgttgta tgttaaacat ttggggtgtg atgcttttca    1080
ttagattgtc atggattgtg ggtcaagctg gaataggtct atcagtcctt gtaataatga    1140
tggccactgt tgtgacaact atcacaggat tgtctacttc agcaatagca actaatggat    1200
ttgtaagagg aggaggagca tattatttaa tatctagaag tctagggcca gaatttggtg    1260
gtgcaattgg tctaatcttc gcctttgcca acgctgttgc agttgctatg tatgtggttg    1320
gatttgcaga aaccgtggtg gagttgctta aggaacattc catacttatg atagatgaaa    1380
tcaatgatat ccgaattatt ggagccatta cagtcgtgat tcttttaggt atctcagtag    1440
ctggaatgga gtgggaagca aaagctcaga ttgttctttt ggtgatccta cttcttgcta    1500
ttggtgattt cgtcatagga acatttatcc cactggagag caagaagcca aagggtttt    1560
ttggttataa atctgaaata tttaatgaga actttgggcc cgattttcga gaggaagaga    1620
ctttctttc tgtatttgcc atctttttc ctgctgcaac tggtattctg gctggagcaa    1680
atatctcagg tgatcttgca gatcctcagt cagccatacc caaaggaaca ctcctagcca    1740
ttttaattac tacattggtt tacgtaggaa ttgcagtatc tgtaggttct tgtgttgttc    1800
gagatgccac tggaaacgtt aatgacacta tcgtaacaga gctaacaaac tgtacttctg    1860
cagcctgcaa attaaacttt gattttttcat cttgtgaaag cagtccttgt tcctatggcc    1920
taatgaacaa cttccaggta atgagtatgg tgtcaggatt tacaccacta atttctgcag    1980
gtatattttc agccactctt tcttcagcat tagcatccct agtgagtgct cccaaaatat    2040
ttcaggctct atgtaaggac aacatctacc cagctttcca gatgtttgct aaaggttatg    2100
ggaaaaataa tgaacctctt cgtggctaca tcttaacatt cttaattgca cttggattca    2160
tcttaattgc tgaactgaat gttattgcac caattatctc aaacttcttc cttgcatcat    2220
atgcattgat caattttca gtattccatg catcacttgc aaaatctcca ggatggcgtc    2280
ctgcattcaa atactacaac atgtggatat cacttcttgg agcaattctt tgttgcatag    2340
```

```
taatgttcgt cattaactgg tgggctgcat tgctaacata tgtgatagtc cttgggctgt      2400
atatttatgt tacctacaaa aaaccagatg tgaattgggg atcctctaca caagccctga      2460
cttacctgaa tgcactgcag cattcaattc gtctttctgg agtggaagac cacgtgaaaa      2520
actttaggcc acagtgtctt gttatgacag gtgctccaaa ctcacgtcca gctttacttc      2580
atcttgttca tgatttcaca aaaaatgttg gtttgatgat ctgtggccat gtacatatgg      2640
gtcctcgaag acaagccatg aaagagatgt ccatcgatca agccaaatat cagcgatggc      2700
ttattaagaa caaatgaag gcattttatg ctccagtaca tgcagatgac ttgagagaag       2760
gtgcacagta tttgatgcag gctgctggtc ttggtcgtat gaagccaaac acacttgtcc      2820
ttggatttaa gaaagattgg ttgcaagcag atatgaggga tgtggatatg tatataaact      2880
tatttcatga tgcttttgac atacaatatg gagtagtggt tattcgccta aaagaaggtc      2940
tggatatatc tcatcttcaa ggacaagaag aattattgtc atcacaagag aaatctcctg      3000
gcaccaagga tgtggtagta agtgtggaat atagtaaaaa gtccgattta gatacttcca      3060
aaccactcag tgaaaaacca attacacaca aagttgagga agaggatggc aagactgcaa      3120
ctcaaccact gttgaaaaaa gaatccaaag gccctattgt gcctttaaat gtagctgacc      3180
aaaagcttct tgaagctagt acacagtttc agaaaaaaca aggaaagaat actattgatg      3240
tctggtggct ttttgatgat ggaggtttga ccttattgat accttacctt ctgacgacca      3300
agaaaaaatg gaaagactgt aagatcagag tattccattgg tggaaagata aacagaatag      3360
accatgaccg gagagcgatg gctactttgc ttagcaagtt ccggatagac ttttctgata      3420
tcatggttct aggagatatc aataccaaac caaagaaaga aaatattata gcttttgagg      3480
aaatcattga gccatacaga cttcatgaag atgataaaga gcaagatatt gcagataaaa      3540
tgaaagaaga tgaaccatgg cgaataacag ataatgagct tgaactttat aagaccaaga      3600
cataccggca gatcaggtta aatgagttat taaggaaca ttcaagcaca gctaatatta      3660
ttgtcatgag tctcccagtt gcacgaaaag gtgctgtgtc tagtgctctc tacatggcat      3720
ggttagaagc tctatctaag gacctaccac caatcctcct agttcgtggg aatcatcaga      3780
gtgtccttac cttctattca taaatgttct atacagtgga cagccctcca gaatggtact      3840
tcagtgccta gtgtagtaac ctgaaatctt caatgacaca ttaacatcac aatggcgaat      3900
ggtgactttt ctttcacgat ttcattaatt tgaaagcaca caggaaagct tgctccattg      3960
ataacgtgta tggagacttc ggttttagtc aattccatat ctcaatctta atggtgattc      4020
ttctctgttg aactgaagtt tgtgagagta gttttccttt gctacttgaa tagcaataaa      4080
agcgtgttaa cttttttgg                                                   4098

<210> SEQ ID NO 45
<211> LENGTH: 4098
<212> TYPE: DNA
<213> ORGANISM: human

<400> SEQUENCE: 45
ggtggcctct gtggccgtcc aggctagcgg cggcccgcag gcggcgggga gaaagactct        60
ctcacctggt cttgcggctg tggccaccgc cggccagggg tgtggagggc gtgctgccgg       120
agacgtccgc cgggctctgc agttccgccg ggggtcgggc agctatggag ccgcggccca       180
cggcgccctc ctccggcgcc ccgggactgg ccggggtcgg ggagacgccg tcagccgctg       240
cgctggccgc agccagggtg gaactgcccg gcacggctgt gccctcggtg ccggaggatg       300
```

```
ctgcgcccgc gagccgggac ggcggcgggg tccgcgatga gggcccccgcg gcggccgggg      360 acgggctggg cagacccttg ggcccaccc cgagccagag ccgttccag gtggacctgg         420 tttccgagaa cgccgggcgg gccgctgctg cggcggcgcc ggcggcgcg cagcggcgg         480 cggctggtgc tggggcgggg gccaagcaga ccccgcgga cggggaagcc agcggcgaga        540
gcgagccagc taaaggcagc gaggaagcca agggccgctt ccgcgtgaac ttcgtggacc       600
cagctgcctc ctcgtcggct gaagacagcc tgtcagatgc tgccggggtc ggagtcgacg      660
ggcccaacgt gagcttccag aacggcgggg acacggtgct gagcgagggc agcagcctgc      720
actccggcgg cggcggcggc agtgggcacc accagcacta ctattatgat acccacacca      780
acacctacta cctgcgcacc ttcggccaca acaccatgga cgctgtgccc aggatcgatc     840
actaccggca cacagccgcg cagctgggcg agaagctgct ccggcctagc ctggcggagc     900
tccacgacga gctggaaaag gaaccttttg aggatggctt tgcaaatggg gaagaaagta    960
ctccaaccag agatgctgtg gtcacgtata ctgcagaaag taaaggagtc gtgaagtttg    1020
gctggatcaa gggtgtatta gtacgttgta tgttaaacat ttggggtgtg atgcttttca    1080
ttagattgtc atggattgtg ggtcaagctg aataggtct atcagtcctt gtaataatga     1140
tggccactgt tgtgacaact atcacaggat tgtctacttc agcaatagca actaatggat    1200
ttgtaagagg aggaggagca tattatttaa tatctagaag tctagggcca gaatttggtg     1260
gtgcaattgg tctaatcttc gcctttgcca acgctgttgc agttgctatg tatgtggttg    1320
gatttgcaga accgtggtg gagttgctta aggaacattc catacttatg atagatgaaa     1380
tcaatgatat ccgaattatt ggagccatta cagtcgtgat tctttttaggt atctcagtag    1440 ctggaatgga gtgggaagca aaagctcaga ttgttctttt ggtgatccta cttcttgcta    1500
ttggtgattt cgtcatagga acatttatcc cactggagag caagaagcca aagggttttt   1560
ttggttataa atctgaaata tttaatgaga actttgggcc cgattttcga gaggaagaga    1620
ctttcttttc tgtatttgcc atctttttc ctgctgcaac tggtattctg gctggagcaa     1680
atatctcagg tgatcttgca gatcctcagt cagccatacc caaaggaaca ctcctagcca    1740
ttttaattac tacattggtt tacgtaggaa ttgcagtatc tgtaggttct tgtgttgttc    1800
gagatgccac tggaaacgtt aatgacacta tcgtaacaga gctaacaaac tgtacttctg   1860
cagcctgcaa attaaacttt gatttttcat cttgtgaaag cagtccttgt tcctatggcc     1920
taatgaacaa cttccaggta atgagtatgg tgtcaggatt tacaccacta atttctgcag     1980
gtatattttc agccactctt tcttcagcat tagcatccct agtgagtgct cccaaaatat     2040
ttcaggctct atgtaaggac aacatctacc cagctttcca gatgttttgct aaaggttatg    2100 ggaaaaataa tgaacctctt cgtggctaca tcttaacatt cttaattgca cttggattca    2160
tcttaattgc tgaactgaat gttattgcac caattatctc aaacttcttc cttgcatcat    2220
atgcattgat caattttcca gtattccatg catcacttgc aaaatctcca ggatggcgtc    2280
ctgcattcaa atactacaac atgtggatat cacttcttgg agcaattctt tgttgcatag    2340
taatgttcgt cattaactgg tgggctgcat tgctaacata tgtgatagtc cttgggctgt     2400
atatttatgt tacctacaaa aaaccagatg tgaattgggg atcctctaca caagccctga    2460
cttacctgaa tgcactgcag cattcaattc gtctttctgg agtggaagac cacgtgaaaa    2520
actttaggcc acagtgtctt gttatgacag gtgctccaaa ctcacgtcca gctttacttc    2580
atcttgttca tgatttcaca aaaaatgttg gtttgatgat ctgtggccat gtacatatgg    2640
gtcctcgaag acaagccatg aaagagatgt ccatcgatca agccaaatat cagcgatggc    2700
```

```
ttattaagaa caaaatgaag gcattttatg ctccagtaca tgcagatgac ttgagagaag    2760
gtgcacagta tttgatgcag gctgctggtc ttggtcgtat gaagccaaac acacttgtcc    2820
ttggatttaa gaaagattgg ttgcaagcag atatgaggga tgtggatatg tatataaact    2880
tatttcatga tgcttttgac atacaatatg gagtagtggt tattcgccta aaagaaggtc    2940
tggatatatc tcatcttcaa ggacaagaag aattattgtc atcacaagag aaatctcctg    3000
gcaccaagga tgtggtagta agtgtggaat atagtaaaaa gtccgattta gatacttcca    3060
aaccactcag tgaaaaacca attacacaca aagttgagga agaggatggc aagactgcaa    3120
ctcaaccact gttgaaaaaa gaatccaaag gccctattgt gcctttaaat gtagctgacc    3180
aaaagcttct tgaagctagt acacagtttc agaaaaaaca aggaaagaat actattgatg    3240
tctggtggct ttttgatgat ggaggtttga ccttattgat accttacctt ctgacgacca    3300
agaaaaaatg aaagactgt aagatcagag tattcattgg tggaaagata aacagaatag    3360
accatgaccg gagagcgatg gctactttgc ttagcaagtt ccggatagac ttttctgata    3420
tcatggttct aggagatatc aataccaaac caagagaaga aaatattata gcttttgagg    3480
aaatcattga gccatacaga cttcatgaag atgataaaga gcaagatatt gcagataaaa    3540
tgaaagaaga tgaaccatgg cgaataacag ataatgagct tgaactttat aagaccaaga    3600
cataccggca gatcaggtta aatgagttat taaaggaaca ttcaagcaca gctaatatta    3660
ttgtcatgag tctcccagtt gcacgaaaag gtgctgtgtc tagtgctctc tacatggcat    3720
ggttagaagc tctatctaag gacctaccac caatcctcct agttcgtggg aatcatcaga    3780
gtgtccttac cttctattca taaatgttct atacagtgga cagccctcca gaatggtact    3840
tcagtgccta gtgtagtaac ctgaaatctt caatgacaca ttaacatcac aatggcgaat    3900
ggtgactttt ctttcacgat ttcattaatt tgaaagcaca caggaaagct tgctccattg    3960
ataacgtgta tggagacttc ggttttagtc aattccatat ctcaatctta atggtgattc    4020
ttctctgttg aactgaagtt tgtgagagta gttttccttt gctacttgaa tagcaataaa    4080
agcgtgttaa cttttttgg                                                 4098

<210> SEQ ID NO 46
<211> LENGTH: 3311
<212> TYPE: DNA
<213> ORGANISM: human

<400> SEQUENCE: 46
tgctaatgct tttggtacaa atggatgtgg aatataattg aatattttct tgtttaaggg      60
gagcatgaag aggtgttgag gttatgtcaa gcatctggca cagctgaagg cagatggaaa     120
tatttacaag tacgcaattt gagactaaga tattgttatc attctcctat tgaagacaag     180
agcaatagta aaacacatca ggtcagggg ttaaagacct gtgataaacc acttccgata      240
agttggaaac gtgtgtctat attttcatat ctgtatatat ataatggtaa agaaagacac     300
cttcgtaacc cgcattttcc aaagagagga atcacaggga gatgtacagc aatgggccca     360
tttaagagtt ctgtgttcat cttgattctt caccttctag aaggggccct gagtaattca     420
ctcattcagc tgaacaacaa tggctatgaa ggcattgtcg ttgcaatcga ccccaatgtg     480
ccagaagatg aaacactcat tcaacaaata aaggacatgt tgacccaggc atctctgtat     540
ctgtttgaag ctacaggaaa gcgattttat ttcaaaaatg ttgccatttt gattcctgaa     600
acatggaaga caaaggctga ctatgtgaga ccaaaacttg agacctacaa aaatgctgat     660
```

```
gttctggttg ctgagtctac tcctccaggt aatgatgaac cctacactga gcagatgggc      720
aactgtggag agaagggtga aaggatccac ctcactcctg atttcattgc aggaaaaaag      780
ttagctgaat atggaccaca aggtaaggca tttgtccatg agtgggctca tctacgatgg      840
ggagtatttg acgagtacaa taatgatgag aaattctact tatccaatgg aagaatacaa      900
gcagtaagat gttcagcagg tattactggt acaaatgtag taaagaagtg tcagggaggc      960
agctgttaca ccaaaagatg cacattcaat aaagttacag gactctatga aaaaggatgt     1020
gagtttgttc tccaatcccg ccagacggag aaggcttcta taatgtttgc acaacatgtt     1080
gattctatag ttgaattctg tacagaacaa accacaaca aagaagctcc aaacaagcaa      1140
aatcaaaaat gcaatctccg aagcacatgg gaagtgatcc gtgattctga ggactttaag     1200
aaaaccactc ctatgacaac acagccacca atcccacct tctcattgct gcagattgga      1260
caaagaattg tgtgtttagt ccttgacaaa tctggaagca tggcgactgg taaccgcctc     1320
aatcgactga atcaagcagg ccagcttttc ctgctgcaga cagttgagct ggggtcctgg     1380
gttgggatgg tgacatttga cagtgctgcc catgtacaaa gtgaactcat acagataaac     1440
agtggcagtg acagggacac actcgccaaa agattacctg cagcagcttc aggagggacg     1500
tccatctgca gcgggcttcg atcggcattt actgtgatta ggaagaaata tccaactgat     1560
ggatctgaaa ttgtgctgct gacggatggg gaagacaaca ctataagtgg gtgctttaac     1620
gaggtcaaac aaagtggtgc catcatccac acagtcgctt gggggccctc tgcagctcaa     1680
gaactagagg agctgtccaa aatgacagga ggtttacaga catatgcttc agatcaagtt     1740
cagaacaatg gcctcattga tgcttttggg gccctttcat caggaaatgg agctgtctct     1800
cagcgctcca tccagcttga gagtaaggga ttaaccctcc agaacagcca gtggatgaat     1860
ggcacagtga tcgtggacag caccgtggga aaggacactt tgtttcttat cacctggaca     1920
acgcagcctc cccaaatcct tctctgggat cccagtggac agaagcaagg tggctttgta     1980
gtggacaaaa acaccaaaat ggcctacctc caaatcccag gcattgctaa ggttggcact     2040
tggaaataca gtctgcaagc aagctcacaa accttgaccc tgactgtcac gtcccgtgcg     2100
tccaatgcta ccctgcctcc aattacagtg acttccaaaa cgaacaagga caccagcaaa     2160
ttccccagcc ctctggtagt ttatgcaaat attcgccaag gagcctcccc aattctcagg     2220
gccagtgtca cagccctgat tgaatcagtg aatggaaaaa cagttacctt ggaactactg     2280
gataatggag caggtgctga tgctactaag gatgacggtg tctactcaag gtatttcaca     2340
acttatgaca cgaatggtag atacagtgta aaagtgcggg ctctgggagg agttaacgca     2400
gccagacgga gagtgataec ccagcagagt ggagcactgt acatacctgg ctggattgag     2460
aatgatgaaa tacaatggaa tccaccaaga cctgaaatta taaggatga tgttcaacac     2520 aagcaagtgt gtttcagcag aacatcctcg ggaggctcat tgtggcttc tgatgtccca     2580 aatgctccca tacctgatct cttcccacct ggccaaatca ccgacctgaa ggcggaaatt     2640 cacggggggca gtctcattaa tctgacttgg acagctcctg ggatgatta tgaccatgga     2700 acagctcaca gtatatcat tcgaataagt acaagtattc ttgatctcag agacaagttc     2760
aatgaatctc ttcaagtgaa tactactgct ctcatcccaa aggaagccaa ctctgaggaa     2820 gtcttttttgt ttaaaccaga aaacattact tttgaaaatg gcacagatct tttcattgct     2880
attcaggctg ttgataaggt cgatctgaaa tcagaaatat ccaacattgc acgagtatct     2940
ttgtttattc ctccacagac tccgccagag acacctagtc ctgatgaaac gtctgctcct     3000
tgtcctaata ttcatatcaa cagcaccatt cctggcattc acatttttaaa aattatgtgg     3060
```

-continued

| | |
|---|---|
| aagtggatag gagaactgca gctgtcaata gcctagggct gaattttgt cagataaata | 3120 |
| aaataaatca ttcatccttt ttttgattat aaaattttct aaaatgtatt ttagacttcc | 3180 |
| tgtagggggc gatatactaa atgtatatag tacatttata ctaaatgtat tcctgtaggg | 3240 |
| ggcgatatac taaatgtatt ttagacttcc tgtagggggc gataaaataa aatgctaaac | 3300 |
| aactgggtaa a | 3311 |

<210> SEQ ID NO 47
<211> LENGTH: 3311
<212> TYPE: DNA
<213> ORGANISM: human

<400> SEQUENCE: 47

| | |
|---|---|
| tgctaatgct tttggtacaa atggatgtgg aatataattg aatattttct tgtttaaggg | 60 |
| gagcatgaag aggtgttgag gttatgtcaa gcatctggca cagctgaagg cagatggaaa | 120 |
| tatttacaag tacgcaattt gagactaaga tattgttatc attctcctat tgaagacaag | 180 |
| agcaatagta aaacacatca ggtcaggggg ttaaagacct gtgataaacc acttccgata | 240 |
| agttggaaac gtgtgtctat attttcatat ctgtatatat ataatggtaa agaaagacac | 300 |
| cttcgtaacc cgcatttttcc aaagagagga atcacaggga gatgtacagc aatgggcca | 360 |
| tttaagagtt ctgtgttcat cttgattctt caccttctag aaggggccct gagtaattca | 420 |
| ctcattcagc tgaacaacaa tggctatgaa ggcattgtcg ttgcaatcga ccccaatgtg | 480 |
| ccagaagatg aaacactcat tcaacaaata aaggacatgg tgacccaggc atctctgtat | 540 |
| ctgtttgaag ctacaggaaa gcgatttttat ttcaaaaatg ttgccatttt gattcctgaa | 600 |
| acatggaaga caaaggctga ctatgtgaga ccaaaacttg agacctacaa aaatgctgat | 660 |
| gttctggttg ctgagtctac tcctccaggt aatgatgaac cctacactga gcagatgggc | 720 |
| aactgtggag agaagggtga aaggatccac ctcactcctg atttcattgc aggaaaaaag | 780 |
| ttagctgaat atggaccaca aggtaaggca tttgtccatg agtgggctca tctacgatgg | 840 |
| ggagtatttg acgagtacaa taatgatgag aaattctact tatccaatgg aagaatacaa | 900 |
| gcagtaagat gttcagcagg tattactggt acaaatgtag taaagaagtg tcagggaggc | 960 |
| agctgttaca ccaaaagatg cacattcaat aaagttacag gactctatga aaaggatgt | 1020 |
| gagtttgttc tccaatcccg ccagacggag aaggcttcta taatgtttgc acaacatgtt | 1080 |
| gattctatag ttgaattctg tacagaacaa accacaacaa aagaagctcc aaacaagcaa | 1140 |
| aatcaaaaat gcaatctccg aagcacatgg gaagtgatcc gtgattctga ggactttaag | 1200 |
| aaaccactc ctatgacaac acagccacca aatcccacct tctcattgct gcagattgga | 1260 |
| caaagaattg tgtgtttagt ccttgacaaa tctggaagca tggcgactgg taaccgcctc | 1320 |
| aatcgactga atcaagcagg ccagcttttc ctgctgcaga cagttgagct ggggtcctgg | 1380 |
| gttgggatgg tgacatttga cagtgctgcc catgtacaaa gtgaactcat acagataaac | 1440 |
| agtggcagtg acagggacac actcgccaaa agattacctg cagcagcttc aggagggacg | 1500 |
| tccatctgca gcgggcttcg atcggcattt actgtgatta ggaagaaata tccaactgat | 1560 |
| ggatctgaaa ttgtgctgct gacggatggg gaagacaaca ctataagtgg gtgctttaac | 1620 |
| gaggtcaaac aaagtggtgc catcatccac acagtcgctt tggggccctc tgcagctcaa | 1680 |
| gaactagagg agctgccaa aatgacagga ggtttacaga catatgcttc agatcaagtt | 1740 |
| cagaacaatg gcctcattga tgctttttggg gccctttcat caggaaatgg agctgtctct | 1800 |

```
cagcgctcca tccagcttga gagtaaggga ttaaccctcc agaacagcca gtggatgaat   1860
ggcacagtga tcgtggacag caccgtggga aaggacactt tgtttcttat cacctggaca   1920
acgcagcctc cccaaatcct tctctgggat cccagtggac agaagcaagg tggctttgta   1980
gtggacaaaa acaccaaaat ggcctacctc caaatcccag gcattgctaa ggttggcact   2040
tggaaataca gtctgcaagc aagctcacaa accttgaccc tgactgtcac gtcccgtgcg   2100
tccaatgcta ccctgcctcc aattacagtg acttccaaaa cgaacaagga caccagcaaa   2160
ttccccagcc ctctggtagt ttatgcaaat attcgccaag gagcctcccc aattctcagg   2220
gccagtgtca cagccctgat tgaatcagtg aatggaaaaa cagttacctt ggaactactg   2280
gataatggag caggtgctga tgctactaag gatgacggtg tctactcaag gtatttcaca   2340
acttatgaca cgaatggtag atacagtgta aaagtgcggg ctctgggagg agttaacgca   2400
gccagacgga gagtgatacc ccagcagagt ggagcactgt acatacctgg ctggattgag   2460
aatgatgaaa tacaatggaa tccaccaaga cctgaaatta ataaggatga tgttcaacac   2520
aagcaagtgt gtttcagcag aacatcctcg ggaggctcat tgtggcttc  tgatgtccca   2580
aatgctccca tacctgatct cttcccacct ggccaaatca ccgacctgaa ggcggaaatt   2640
cacgggggca gtctcattaa tctgacttgg acagctcctg gggatgatta tgaccatgga   2700
acagctcaca gtatatcat  tcgaataagt acaagtattc ttgatctcag agacaagttc   2760
aatgaatctc ttcaagtgaa tactactgct ctcatcccaa aggaagccaa ctctgaggaa   2820
gtcttttttgt ttaaaccaga aaacattact tttgaaaatg cacagatct  tttcattgct   2880
attcaggctg ttgataaggt cgatctgaaa tcagaaatat ccaacattgc acgagtatct   2940
ttgtttattc ctccacagac tccgccagag cacctagtc  ctgatgaaac gtctgctcct   3000
tgtcctaata ttcatatcaa cagcaccatt cctggcattc acattttaaa aattatgtgg   3060
aagtggatag gagaactgca gctgtcaata gcctagggct gaattttgt  cagataaata   3120
aaataaatca ttcatccttt ttttgattat aaaattttct aaaatgtatt ttagacttcc   3180
tgtaggggc  gatatactaa atgtatatag tacatttata ctaaatgtat tcctgtaggg   3240
ggcgatatac taaatgtatt ttagacttcc tgtaggggc  gataaaataa aatgctaaac   3300
aactgggtaa a                                                         3311
```

<210> SEQ ID NO 48
<211> LENGTH: 3697
<212> TYPE: DNA
<213> ORGANISM: human

<400> SEQUENCE: 48

```
agggagtgtt cccgggggag atactccagt cgtagcaaga gtctcgacca ctgaatggaa    60
gaaaaggact tttaaccacc attttgtgac ttacagaaag gaatttgaat aaagaaaact   120
atgatacttc aggcccatct tcactccctg tgtcttctta tgctttattt ggcaactgga   180
tatggccaag aggggaagtt tagtggaccc ctgaacccca tgacattttc tatttatgaa   240
ggccaagaac cgagtcaaat tatattccag tttaaggcca atcctcctgc tgtgactttt   300
gaactaactg gggagacaga caacatattt gtgatagaac gggagggact tctgtattac   360
aacagagcct ggacaggga  acaagatct  actcacaatc tccaggttgc agccctggac   420
gctaatggaa ttatagtgga gggtccagtc cctatcacca tagaagtgaa ggacatcaac   480
gacaatcgac ccacgtttct ccagtcaaag tacgaaggct cagtaaggca gaactctcgc   540
ccaggaaagc ccttcttgta tgtcaatgcc acagacctgg atgatccggc cactcccaat   600
```

-continued

```
ggccagcttt attaccagat tgtcatccag cttcccatga tcaacaatgt catgtacttt     660
cagatcaaca acaaaacggg agccatctct cttacccgag agggatctca ggaattgaat     720
cctgctaaga atccttccta taatctggtg atctcagtga aggacatggg aggccagagt     780
gagaattcct tcagtgatac cacatctgtg gatatcatag tgacagagaa tatttggaaa     840
gcaccaaaac ctgtggagat ggtggaaaac tcaactgatc ctcaccccat caaaatcact     900
caggtgcggt ggaatgatcc cggtgcacaa tattccttag ttgacaaaga gaagctgcca     960
agattcccat tttcaattga ccaggaagga gatatttacg tgactcagcc cttggaccga    1020
gaagaaaagg atgcatatgt tttttatgca gttgcaaagg atgagtacgg aaaaccactt    1080
tcatatccgc tggaaattca tgtaaaagtt aaagatatta atgataatcc acctacatgt    1140
ccgtcaccag taaccgtatt tgaggtccag gagaatgaac gactgggtaa cagtatcggg    1200
acccttactg cacatgacag ggatgaagaa aatactgcca acagttttct aaactacagg    1260
attgtggagc aaactcccaa acttcccatg gatggactct tcctaatcca aacctatgct    1320
ggaatgttac agttagctaa acagtccttg aagaagcaag atactcctca gtacaactta    1380
acgatagagg tgtctgacaa agatttcaag acccttttgtt ttgtgcaaat caacgttatt    1440
gatatcaatg atcagatccc catctttgaa aaatcagatt atggaaacct gactcttgct    1500
gaagacacaa acattgggtc caccatctta accatccagg ccactgatgc tgatgagcca    1560
tttactggga gttctaaaat tctgtatcat atcataaagg gagacagtga gggacgcctg    1620
ggggttgaca cagatcccca taccaacacc ggatatgtca taattaaaaa gcctcttgat    1680
tttgaaacag cagctgtttc caacattgtg ttcaaagcag aaaatcctga gcctctagtg    1740
tttggtgtga agtacaatgc aagttctttt gccaagttca cgcttattgt gacagatgtg    1800
aatgaagcac ctcaattttc ccaacacgta ttccaagcga aagtcagtga ggatgtagct    1860
ataggcacta aagtgggcaa tgtgactgcc aaggatccag aaggtctgga cataagctat    1920
tcactgaggg gagacacaag aggttggctt aaaattgacc acgtgactgg tgagatcttt    1980
agtgtggctc cattggacag agaagccgga agtccatatc gggtacaagt ggtggccaca    2040
gaagtagggg ggtcttcctt gagctctgtg tcagagttcc acctgatcct tatggatgtg    2100
aatgacaacc ctcccaggct agccaaggac tacacgggct gttcttctg ccatcccctc     2160
agtgcacctg gaagtctcat tttcgaggct actgatgatg atcagcactt atttcggggt    2220
ccccatttta catttttccct cggcagtgga agcttacaaa acgactggga agtttccaaa   2280
atcaatggta ctcatgcccg actgtctacc aggcacacag agtttgagga gagggagtat    2340
gtcgtcttga tccgcatcaa tgatgggggt cggccaccct tggaaggcat tgtttctta    2400
ccagttacat tctgcagttg tgtggaagga agttgtttcc ggccagcagg tcaccagact    2460
gggataccca ctgtgggcat ggcagttggt tatactgctga ccaccttct ggtgattggt    2520
ataattttag cagttgtgtt tatccgcata aagaaggata aaggcaaaga taatgttgaa    2580
agtgctcaag catctgaagt caaacctctg agaagctgaa tttgaaaagg aatgtttgaa    2640
tttatatagc aagtgctatt tcagcaacaa ccatctcatc ctattacttt tcatctaacg    2700
tgcattataa tttttaaac agatattccc tcttgtcctt taatatttgc taaatatttc     2760
ttttttgagg tggagtcttg ctctgtcgcc caggctggag tacagtggtg tgatcccagc    2820
tcactgcaac ctccgcctcc tgggttcaca tgattctcct gcctcagctt cctaagtagc    2880
tgggtttaca ggcaccccacc accatgccca gctaattttt gtattttaa tagagacggg    2940
```

-continued

| | |
|---|---:|
| gtttcgccat tggccaggc tggtcttgaa ctcctgacgt caagtgatct gcctgccttg | 3000 |
| gtctcccaat acaggcatga accactgcac ccacctactt agatatttca tgtgctatag | 3060 |
| acattagaga gattttcat tttccatga cattttcct ctctgcaaat ggcttagcta | 3120 |
| cttgtgtttt tccctttgg ggcaagacag actcattaaa tattctgtac atttttcct | 3180 |
| tatcaaggag atatatcagt gttgtctcat agaactgcct ggattccatt tatgttttt | 3240 |
| ctgattccat cctgtgtccc cttcatcctt gactcctttg gtatttcact gaatttcaaa | 3300 |
| catttgtcag agaagaaaaa cgtgaggact caggaaaaat aaataaataa agaacagcc | 3360 |
| ttttcccta gtattaacag aaatgtttct gtgtcattaa ccatctttaa tcaatgtgac | 3420 |
| atgttgctct ttggctgaaa ttcttcaact tggaaatgac acagaccac agaaggtgtt | 3480 |
| caaacacaac ctactctgca aaccttggta aaggaaccag tcagctggcc agatttcctc | 3540 |
| actacctgcc atgcatacat gctgcgcatg ttttcttcat tcgtatgtta gtaaagtttt | 3600 |
| ggttattata tatttaacat gtggaagaaa acaagacatg aaaagagtgg tgacaaatca | 3660 |
| agaataaaca ctggttgtag tcagtttgt ttgttaa | 3697 |

<210> SEQ ID NO 49
<211> LENGTH: 3697
<212> TYPE: DNA
<213> ORGANISM: human

<400> SEQUENCE: 49

| | |
|---|---:|
| agggagtgtt cccgggggag atactccagt cgtagcaaga gtctcgacca ctgaatggaa | 60 |
| gaaaaggact tttaaccacc attttgtgac ttacagaaag gaatttgaat aaagaaaact | 120 |
| atgatacttc aggcccatct tcactccctg tgtcttctta tgctttattt ggcaactgga | 180 |
| tatggccaag aggggaagtt tagtggaccc ctgaaaccca tgacattttc tatttatgaa | 240 |
| ggccaagaac cgagtcaaat tatattccag tttaaggcca atcctcctgc tgtgactttt | 300 |
| gaactaactg gggagacaga caacatattt gtgatagaac gggagggact tctgtattac | 360 |
| aacagagcct tggacaggga aacaagatct actcacaatc tccaggttgc agccctggac | 420 |
| gctaatggaa ttatagtgga gggtccagtc cctatcacca tagaagtgaa ggacatcaac | 480 |
| gacaatcgac ccacgtttct ccagtcaaag tacgaaggct cagtaaggca gaactctcgc | 540 |
| ccaggaaagc ccttcttgta tgtcaatgcc acagacctgg atgatccggc cactcccaat | 600 |
| ggccagcttt attaccagat tgtcatccag cttcccatga tcaacaatgt catgtacttt | 660 |
| cagatcaaca acaaaacggg agccatctct cttacccgag agggatctca ggaattgaat | 720 |
| cctgctaaga atccttccta taatctggtg atctcagtga aggacatggg aggccagagt | 780 |
| gagaattcct tcagtgatac cacatctgtg gatatccatg tgacagagaa tatttggaaa | 840 |
| gcaccaaaac ctgtggagat ggtggaaaac tcaactgatc ctcacccat caaaatcact | 900 |
| caggtgcggt ggaatgatcc cggtgcacaa tattccttag ttgacaaaga gaagctgcca | 960 |
| agattcccat tttcaattga ccaggaagga gatatttacg tgactcagcc cttggaccga | 1020 |
| gaagaaaagg atgcatatgt tttttatgca gttgcaaagg atgagtacgg aaaaccactt | 1080 |
| tcatatccgc tggaaattca tgtaaaagtt aaagatatta tgataatcc acctacatgt | 1140 |
| ccgtcaccag taaccgtatt tgaggtccag gagaatgaac gactgggtaa cagtatcggg | 1200 |
| acccttactg cacatgacag ggatgaagaa aatactgcca acagtttct aaactacagg | 1260 |
| attgtggagc aaaactccca acttcccatg gatggactct tcctaatcca aacctatgct | 1320 |
| ggaatgttac agttagctaa acagtccttg aagaagcaag atactcctca gtacaactta | 1380 |

-continued

```
acgatagagg tgtctgacaa agatttcaag acccttgtt ttgtgcaaat caacgttatt    1440
gatatcaatg atcagatccc catctttgaa aaatcagatt atggaaacct gactcttgct   1500
gaagacacaa acattgggtc caccatctta accatccagg ccactgatgc tgatgagcca   1560
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaattttc ccaacacgta ttccaagcga aagtcagtga ggatgtagct   1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccattttta cattttccct cggcagtgga agcttacaaa acgactggga agtttccaaa   2280
atcaatggta ctcatgcccg actgtctacc aggcacacag agtttgagga gagggagtat   2340
gtcgtcttga tccgcatcaa tgatgggggt cggccaccct tggaaggcat tgtttcttta   2400
ccagttacat tctgcagttg tgtggaagga agttgtttcc ggccagcagg tcaccagact   2460
gggatacccca ctgtgggcat ggcagttggt atactgctga ccaccctttct ggtgattggt   2520
ataatttttag cagttgtgtt tatccgcata aagaaggata aaggcaaaga taatgttgaa   2580
agtgctcaag catctgaagt caaacctctg agaagctgaa tttgaaaagg aatgtttgaa   2640
tttatatagc aagtgctatt tcagcaacaa ccatctcatc ctattacttt tcatctaacg   2700
tgcattataa tttttaaac agatattccc tcttgtcctt taatatttgc taaatatttc   2760
tttttttgagg tggagtcttg ctctgtcgcc caggctggag tacagtggtg tgatcccagc   2820
tcactgcaac ctccgcctcc tgggttcaca tgattctcct gcctcagctt cctaagtagc   2880
tgggtttaca ggcacccacc accatgccca gctaattttt gtattttaa tagagacggg   2940
gtttcgccat ttggccaggc tggtcttgaa ctcctgacgt caagtgatct gcctgccttg   3000
gtctcccaat acaggcatga accactgcac ccacctactt agatatttca tgtgctatag   3060
acattagaga gatttttcat ttttccatga catttttcct ctctgcaaat ggcttagcta   3120
cttgtgttt tccctttttgg ggcaagacag actcattaaa tattctgtac atttttttctt   3180
tatcaaggag atatatcagt gttgtctcat agaactgcct ggattccatt tatgtttttt   3240
ctgattccat cctgtgtccc cttcatcctt gactcctttg gtatttcact gaatttcaaa   3300
catttgtcag agaagaaaaa cgtgaggact caggaaaaat aaataaataa aagaacagcc   3360
ttttcccctta gtattaacag aaatgttttct gtgtcattaa ccatctttaa tcaatgtgac   3420
atgttgctct ttggctgaaa ttcttcaact tggaaatgac acagacccac agaaggtgtt   3480
caaacacaac ctactctgca aaccttggta aaggaaccag tcagctggcc agatttcctc   3540
actacctgcc atgcatacat gctgcgcatg ttttcttcat tcgtatgtta gtaaagtttt   3600
ggttattata tatttaacat gtggaagaaa acaagacatg aaaagagtgg tgacaaatca   3660
agaataaaca ctggttgtag tcagttttgt ttgttaa                           3697
```

-continued

<210> SEQ ID NO 50
<211> LENGTH: 3803
<212> TYPE: DNA
<213> ORGANISM: human

<400> SEQUENCE: 50

```
ccatggtagg agcgctcgcc tcgctgcggt gcccgctgag gccatgccgg ggccccggcg      60
ccccgctggc tcccgcctgc gcctgctcct gctcctgctg ctgccgccgc tgctgctgct     120
gctccggggc agccacgcgg gcaacctgac ggtagccgtg gtactgccgc tggccaatac     180
ctcgtaccccc tggtcgtggg cgcgcgtggg acccgccgtg gagctggccc tggcccaggt     240
gaaggcgcgc cccgacttgc tgccgggctg gacggtccgc acggtgctgg gcagcagcga     300
aaacgcgctg ggcgtctgct ccgacaccgc agcgccctg gccgcggtgg acctcaagtg     360
ggagcacaac cccgctgtgt tcctgggccc cggctgcgtg tacgccgccg ccccagtggg     420
gcgcttcacc gcgcactggc gggtcccgct gctgaccgcc ggcgcccgg cgctgggctt     480
cggtgtcaag gacgagtatg cgctgaccac ccgcgcgggg cccagctacg ccaagctggg     540
ggacttcgtg gcgcgcgctgc accgacggct gggctgggag cgccaagcgc tcatgctcta     600
cgcctaccgg ccgggtgacg aagagcactg cttcttcctc gtggaggggc tgttcatgcg     660
ggtccgcgac cgcctcaata ttacggtgga ccacctggga ttcgccgagg acgacctcag     720
ccactacacc aggctgctgc ggaccatgcc gcgcaaaggc cgagttatct acatctgcag     780
ctccctgat gccttcagaa ccctcatgct cctggccctg gaagctggct tgtgtgggga     840
ggactacgtt ttcttccacc tggatatctt tgggcaaagc ctgcaaggtg acagggccc     900
tgctccccgc aggccctggg agagaggga tgggcaggat gtcagtgccc gccaggcctt     960
tcaggctgcc aaaatcatta catataaaga cccagataat cccgagtact ggaattcct    1020
gaagcagtta aaacacctgg cctatgagca gttcaacttc accatggagg atggcctggt    1080
gaacaccatc ccagcatcct tccacgacgg gctcctgctc tatatccagg cagtgacgga    1140
gactctggca catgggggaa ctgttactga tggggagaac atcactcagc ggatgtggaa    1200
ccgaagcttt caaggtgtga caggatacct gaaaattgat agcagtggcg atcgggaaac    1260
agacttctcc ctctgggata tggatcccga gaatggtgcc ttcagggttg tactgaacta    1320
caatgggact tcccaagagc tggtggctgt gtcggggcgc aaactgaact ggcccctggg    1380
gtaccctcct cctgacatcc ccaaatgtgg ctttgacaac gaagaccag catgcaacca    1440
agatcacctt tccaccctgg aggtgctggc ttttggtggc agcctctcct tgctcggcat    1500
tctgattgtc tccttcttca tatacaggaa gatgcagctg gagaaggaac tggcctcgga    1560
gctgtggcgg gtgcgctggg aggacgttga gcccagtagc cttgagaggc acctgcggag    1620
tgcaggcagc cggctgaccc tgagcgggag aggctccaat tacggctccc tgctaaccac    1680
agagggccag ttccaagtct tgccaagac agcatatat aagggcaacc tcgtggctgt    1740
gaaacgtgtg aaccgtaaac gcattgagct gacacgaaaa gtcctgtttg aactgaagca    1800
tatgcgggat gtgcagaatg aacacctgac caggtttgtg ggagcctgca cgaccccccc    1860
caatatctgc atcctcacag agtactgtcc ccgtgggagc ctgcaggaca ttctggagaa    1920
tgagagcatc accctggact ggatgttccg gtactcactc accaatgaca tcgtcaaggg    1980
catgctgttt ctacacaatg gggctatctg ttcccatggg aacctcaagt catccaactg    2040
cgtggtagat gggcgctttg tgctcaagat caccgactat gggctggaga gcttcaggga    2100
cctggaccccca gagcaaggac acaccgttta tgccaaaaag ctgtggacgg ccccctgagct    2160
```

-continued

```
cctgcgaatg gcttcacccc ctgtgcgggg ctcccaggct ggtgacgtat acagctttgg      2220
gatcatcctt caggagattg ccctgaggag tggggtcttc cacgtggaag gtttggacct      2280
gagccccaaa gagatcatcg agcgggtgac tcggggtgag cagccccccT tccggccctc      2340
cctggccctg cagagtcacc tggaggagtt ggggctgctc atgcagcggt gctgggctga      2400
ggacccacag gagaggccac cattccagca gatccgcctg acgttgcgca aatttaacag      2460
ggagaacagc agcaacatcc tggacaacct gctgtcccgc atggagcagt acgcgaacaa      2520
tctggaggaa ctggtggagg agcggaccca ggcatacctg gaggagaagc gcaaggctga      2580
ggccctgctc taccagatcc tgcctcactc agtggctgag cagctgaagc gtggggagac      2640
ggtgcaggcc gaagcctttg acagtgttac catctacttc agtgacattg tgggtttcac      2700
agcgctgtcg gcggagagca cacccatgca ggtggtgacc ctgctcaatg acctgtacac      2760
ttgctttgat gctgtcatag acaactttga tgtgtacaag gtggagacaa ttggcgatgc      2820
ctacatggtg gtgtcagggc tccctgtgcg gaacgggcgg ctacacgcct gcgaggtagc      2880
ccgcatggcc ctggcactgc tggatgctgt gcgctccttc cgaatccgcc accggcccca      2940
ggagcagctg cgcttgcgca ttggcatcca cacaggacct gtgtgtgctg gagtggtggg      3000
actgaagatg ccccgttact gtctctttgg ggatacagtc aacacagcct caagaatgga      3060
gtctaatggg gaagccctga agatccactt gtcttctgag accaaggctg tcctggagga      3120
gtttggtggt ttcgagctgg agcttcgagg ggatgtagaa atgaagggca aaggcaaggt      3180
tcggacctac tggctccttg gggagagggg gagtagcacc cgaggctgac ctgcctcctc      3240
tcctatccct ccacacctcc cctaccctgt gccagaagca acagaggtgc caggcctcag      3300
cctcacccac agcagcccca tcgccaaagg atggaagtaa tttgaatagc tcaggtgtgc      3360
tgacccccagt gaagacacca gataggacct ctgagagggg actggcatgg ggggatctca      3420
gagcttacag gctgagccaa gcccacggcc atgcacaggg acactcacac aggcacacgc      3480
acctgctctc cacctggact caggccgggc tgggctgtgg atccttgatc ccctcccctc      3540
cccatgctct cctccctcag ccttgctacc ctgtgactta ctgggaggag agtcacctga      3600
aggggaacat gaaaagagac taggtgaaga gagggcaggg gagcccacat ctggggctgg      3660
cccacaatac ctgctccccc gacccctcc acccagcagt agacacagtg cacagggag      3720
aagagggtg gcgcagaagg gttggggcc tgtatgcctt gcttctacca tgagcagaga      3780
caattaaaat ctttattcca gtg                                              3803
```

<210> SEQ ID NO 51
<211> LENGTH: 3803
<212> TYPE: DNA
<213> ORGANISM: human

<400> SEQUENCE: 51

```
ccatggtagg agcgctcgcc tcgctgcggt gcccgctgag gccatgccgg ggccccggcg        60
ccccgctggc tcccgcctgc gcctgctcct gctcctgctg ctgccgccgc tgctgctgct       120
gctccggggc agccacgcgg gcaacctgac ggtagccgtg gtactgccgc tggccaatac       180
ctcgtacccc tggtcgtggg cgcgcgtggg accgccgtg gagctggccc tggcccaggt       240
gaaggcgcgc cccgacttgc tgccgggctg gacggtccgc acggtgctgg gcagcagcga       300
aaacgcgctg ggcgtctgct ccgacaccgc agcgccctg gccgcggtgg acctcaagtg       360
ggagcacaac cccgctgtgt tcctgggccc cggctgcgtg tacgccgccg ccccagtggg       420
```

```
gcgcttcacc gcgcactggc gggtcccgct gctgaccgcc ggcgcccgg cgctgggctt    480 cggtgtcaag gacgagtatg cgctgaccac ccgcgcgggg cccagctacg ccaagctggg    540
ggacttcgtg gcggcgctgc accgacggct gggctgggag cgccaagcgc tcatgctcta    600
cgcctaccgg ccgggtgacg aagagcactg cttcttcctc gtggagggc tgttcatgcg    660 ggtccgcgac cgcctcaata ttacggtgga ccacctggag ttcgccgagg acgacctcag    720
ccactacacc aggctgctgc ggaccatgcc gcgcaaaggc cgagttatct acatctgcag    780
ctcccctgat gccttcagaa ccctcatgct cctggccctg aagctggct tgtgtgggga    840 ggactacgtt ttcttccacc tggatatctt tgggcaaagc ctgcaaggtg gacagggccc    900
tgctccccgc aggccctggg agagagggga tgggcaggat gtcagtgccc gccaggcctt    960
tcaggctgcc aaaatcatta catataaaga cccagataat cccgagtact tggaattcct   1020
gaagcagtta aaacacctgg cctatgagca gttcaacttc accatggagg atggcctggt   1080
gaacaccatc ccagcatcct tccacgacgg gctcctgctc tatatccagg cagtgacgga   1140
gactctggca catgggggaa ctgttactga tggggagaac atcactcagc ggatgtggaa   1200
ccgaagcttt caaggtgtga caggatacct gaaaattgat agcagtggcg atcgggaaac   1260
agacttctcc ctctgggata tggatcccga gaatggtgcc ttcagggttg tactgaacta   1320
caatgggact tcccaagagc tggtggctgt gtcggggcgc aaactgaact ggcccctggg   1380
gtaccctcct cctgacatcc ccaaatgtgg ctttgacaac gaagacccag catgcaacca   1440
agatcacctt tccaccctgg aggtgctggc tttggtgggc agcctctcct tgctcggcat   1500
tctgattgtc tccttcttca tatacaggaa gatgcagctg gagaaggaac tggcctcgga   1560
gctgtggcgg gtgcgctggg aggacgttga gcccagtagc cttgagaggc acctgcggag   1620
tgcaggcagc cggctgaccc tgagcgggag aggctccaat tacggctccc tgctaaccac   1680
agagggccag ttccaagtct tgccaagac agcatattat aagggcaacc tcgtggctgt   1740
gaaacgtgtg aaccgtaaac gcattgagct gacacgaaaa gtcctgtttg aactgaagca   1800
tatgcgggat gtgcagaatg aacacctgac caggtttgtg ggagcctgca ccgaccccc   1860 caatatctgc atcctcacag agtactgtcc ccgtgggagc ctgcaggaca ttctggagaa   1920
tgagagcatc accctggact ggatgttccg gtactcactc accaatgaca tcgtcaaggg   1980
catgctgttt ctacacaatg gggctatctg ttcccatggg aacctcaagt catccaactg   2040
cgtggtagat gggcgctttg tgctcaagat caccgactat gggctggaga gcttcaggga   2100 cctggacccca gagcaaggac acaccgttta tgccaaaaag ctgtggacgg cccctgagct   2160
cctgcgaatg gcttcacccc ctgtgcgggg ctcccaggct ggtgacgtat acagctttgg   2220
gatcatcctt caggagattg ccctgaggag tgggtcttc cacgtggaag gtttggacct   2280
gagccccaaa gagatcatcg agcgggtgac tcggggtgag cagccccct tccggccctc   2340 cctgccctg cagagtcacc tggaggagtt ggggctgctc atgcagcggt gctgggctga   2400
ggacccacag gagaggccac cattccagca gatccgcctg acgttgcgca aatttaacag   2460
ggagaacagc agcaacatcc tggacaacct gctgtcccgc atggagcagt acgcgaacaa   2520
tctggaggaa ctggtggagg agcggaccca ggcatacctg aggagaagc gcaaggctga   2580 ggccctgctc taccagatcc tgcctcactc agtggctgag cagctgaagc gtggggagac   2640
ggtgcaggcc gaagcctttg acagtgttac catctacttc agtgacattg tgggtttcac   2700
agcgctgtcg gcggagagca cacccatgca ggtggtgacc ctgctcaatg acctgtacac   2760
ttgctttgat gctgtcatag acaactttga tgtgtacaag gtggagacaa ttggcgatgc   2820
```

```
ctacatggtg gtgtcagggc tccctgtgcg gaacgggcgg ctacacgcct gcgaggtagc    2880
ccgcatggcc ctggcactgc tggatgctgt gcgctccttc cgaatccgcc accggcccca    2940
ggagcagctg cgcttgcgca ttggcatcca cacaggacct gtgtgtgctg gagtggtggg    3000
actgaagatg ccccgttact gtctctttgg ggatacagtc aacacagcct caagaatgga    3060
gtctaatggg gaagccctga agatccactt gtcttctgag accaaggctg tcctggagga    3120
gtttggtggt ttcgagctgg agcttcgagg ggatgtagaa atgaagggca aaggcaaggt    3180
tcggacctac tggctccttg gggagagggg gagtagcacc cgaggctgac ctgcctcctc    3240
tcctatccct ccacacctcc cctaccctgt gccagaagca acagaggtgc caggcctcag    3300
cctcacccac agcagcccca tcgccaaagg atggaagtaa tttgaatagc tcaggtgtgc    3360 tgacccccagt gaagacacca gataggacct ctgagagggg actggcatgg ggggatctca    3420
gagcttacag gctgagccaa gcccacggcc atgcacaggg acactcacac aggcacacgc    3480
acctgctctc cacctggact caggccgggc tgggctgtgg atccttgatc ccctcccctc    3540
cccatgctct cctccctcag ccttgctacc ctgtgactta ctgggaggag agtcacctga    3600
aggggaacat gaaaagagac taggtgaaga gagggcaggg gagcccacat ctggggctgg    3660
cccacaatac ctgctccccc gacccccctcc acccagcagt agacacagtg cacaggggag    3720 aagagggtg gcgcagaagg gttgggggcc tgtatgcctt gcttctacca tgagcagaga    3780
caattaaaat ctttattcca gtg                                            3803

<210> SEQ ID NO 52
<211> LENGTH: 1155
<212> TYPE: DNA
<213> ORGANISM: human

<400> SEQUENCE: 52
atggattgca gtaacggatc ggcagagtgt accggagaag gaggatcaaa agaggtggtg      60
gggactttta aggctaaaga cctaatagtc acaccagcta ccatttttaaa ggaaaaacca     120 gaccccaata atctggtttt tggaactgtg ttcacggatc atatgctgac ggtggagtgg     180
tcctcagagt ttggatggga gaaacctcat atcaagcctc ttcagaacct gtcattgcac     240
cctggctcat cagcttttgca ctatgcagtg gaattatttg aaggattgaa ggcatttcga     300
ggagtagata taaaaattcg actgtttcag ccaaaacctca acatggatag aatgtatcgc     360
tctgctgtga gggcaactct gccggtattt gacaaagaag agctcttaga gtgtattcaa     420
cagcttgtga aattggatca agaatgggtc ccatattcaa catctgctag tctgtatatt     480
cgtcctgcat tcattggaac tgagccttct cttggagtca agaagcctac caaagccctg     540
ctctttgtac tcttgagccc agtgggacct tatttttcaa gtggaacctt taatccagtg     600
tccctgtggg ccaatcccaa gtatgtaaga gcctggaaag gtggaactgg ggactgcaag     660
atgggaggga ttacggctc atctcttttt gcccaatgtg aagacgtaga taatgggtgt     720
cagcaggtcc tgtggctcta tggcagagac catcagatca ctgaagtggg aactatgaat     780
ctttttcttt actggataaa tgaagatgga gaagaagaac tggcaactcc tccactagat     840
ggcatcattc ttccaggagt gacaaggcgg tgcattctgg acctggcaca tcagtggggt     900
gaatttaagg tgtcagagag atacctcacc atggatgact tgcaacagc cctggagggg     960 aacagagtga gagagatgtt tagctctggt acagcctgtg ttgtttgccc agtttctgat    1020
atactgtaca aaggcgagac aatacacatt ccaactatgg agaatggtcc taagctggca    1080
```

| | |
|---|---|
| agccgcatct tgagcaaatt aactgatatc cagtatggaa gagaagagag cgactggaca | 1140 |
| attgtgctat cctga | 1155 |

<210> SEQ ID NO 53
<211> LENGTH: 2511
<212> TYPE: DNA
<213> ORGANISM: human

<400> SEQUENCE: 53

| | |
|---|---|
| cttttcacac tggccttaaa gaggatatat tagaagttga agtaggaagg gagccagaga | 60 |
| ggccgatggc gcaaaggtac gacgatctac cccattacgg gggcatggat ggagtaggca | 120 |
| tccccctccac gatgtatggg gacccgcatg cagccaggtc catgcagccg gtccaccacc | 180 |
| tgaaccacgg gcctcctctg cactcgcatc agtacccgca cacagctcat accaacgcca | 240 |
| tggcccccag catgggctcc tctgtcaatg acgctttaaa gagagataaa gatgccattt | 300 |
| atggacaccc cctcttccct ctcttagcac tgattttga gaaatgtgaa ttagctactt | 360 |
| gtaccccccg cgagccgggg gtggcgggcg gggacgtctg ctcgtcagag tcattcaatg | 420 |
| aagatatagc cgtgttcgcc aaacagattc gcgcagaaaa acctctattt tcttctaatc | 480 |
| cagaactgga taacttgatg attcaagcca tacaagtatt aaggtttcat ctattggaat | 540 |
| tagagaaggt acacgaatta tgtgacaatt tctgccaccg gtatattagc tgtttgaaag | 600 |
| ggaaaatgcc tatcgatttg gtgatagacg atagagaagg aggatcaaaa tcagacagtg | 660 |
| aagatataac aagatcagca aatctaactg accagccctc ttggaacaga gatcatgatg | 720 |
| acacggcatc tactcgttca ggaggaaccc caggcccttc cagcggtggc cacacgtcac | 780 |
| acagtgggga caacagcagt gagcaaggtg atggcttgga caacagtgta gcttccccca | 840 |
| gcacaggtga cgatgatgac cctgataagg acaaaaagcg tcacaaaaag cgtggcatct | 900 |
| ttcccaaagt agccacaaat atcatgagggg cgtggctgtt ccagcatcta acacacccttt | 960 |
| acccttctga agaacagaaa aagcagttgg cacaagacac gggactcacc atccttcaag | 1020 |
| tgaacaattg gtttattaat gcccggagaa gaatagtgca gcccatgata gaccagtcca | 1080 |
| accgagcagt aagtcaagga acaccttata atcctgatgg acagcccatg ggaggtttcg | 1140 |
| taatggacgg tcagcaacat atgggaatta gagcaccagg acctatgagt ggaatgggca | 1200 |
| tgaatatggg catggagggg cagtggcact acatgtaacc ttcatctagt taaccaatcg | 1260 |
| caaagcaagg gggaaggctg caaagtatgc caggggagta tgtagcccgg ggtggtccaa | 1320 |
| tgggtgtgag tatgggacag ccaagttata cccaaccccca gatgcccccc catcctgctc | 1380 |
| agctgcgtca tgggcccccc atgcatacgt acattcctgg acaccctcac cacccaacag | 1440 |
| tgatgatgca tggaggaccg ccccaccctg gaatgccaat gtcagcatca agccccacag | 1500 |
| ttcttaatac aggagaccca acaatgagtg acaagtcat ggacattcat gctcagtagc | 1560 |
| ttaagggaat atgcattgtc tgcaatggtg actgatttca aatcatgttt ttctgcaat | 1620 |
| gactgtggag ttccattctt ggcatctact ctggaccaag gagcatccct aattcttcat | 1680 |
| agggaccttt aaaaagcagg aaataccaac tgaagtcaat ttgggggaca tgctaaataa | 1740 |
| ctatataaga cattaagaga acaaagagtg aaatattgta aatgctatta tactgttatc | 1800 |
| catattacgt tgtttcttat agattttta aaaaaatgt gaaattttc cacactatgt | 1860 |
| gtgttgtttc catagctctt cacttcctcc agaagcctcc ttacattaaa aagccttaca | 1920 |
| gttatcctgc aagggacagg aaggtctgat ttgcaggatt tttagagcat taaaataact | 1980 |
| atcaggcaga agaatctttc ttctcgccta ggatttcagc catgcgcgcg ctctctctct | 2040 |

-continued

```
ttctctctct tttcctctct ctccctcttt ctagcctggg gcttgaattt gcatgtctaa    2100
ttcatttact caccatattt gaattggcct gaacagatgt aaatcgggaa ggatgggaaa    2160
aactgcagtc atcaacaatg attaatcagc tgttgcaggc agtgtcttaa ggagactggt    2220
aggaggaggc atggaaacca aaaggccgtg tgtttagaag cctaattgtc acatcaagca    2280
tcattgtccc catgcaacaa ccaccacctt atacatcact tcctgtttta agcagctcta    2340
aaacatagac tgaagattta tttttaatat gttgacttta tttctgagca aagcatcggt    2400
catgtgtgta ttttttcata gtcccacctt ggagcattta tgtagacatt gtaaataaat    2460
tttgtgcaaa aaggactgga aaaatgaact gtattattgc aattttttt t              2511

<210> SEQ ID NO 54
<211> LENGTH: 1887
<212> TYPE: DNA
<213> ORGANISM: human

<400> SEQUENCE: 54
tcgcccaatt ccgggctcag acactgggct cccagctggg gactgctcca tggccatgga      60
gatagacagc aggcctgggg ggctcccccgg cagtagctgc aacctaggtg cagcccgaga     120
acacatgcag gcggtcaccc gaaactacat cacccacccc cgtgtcacct acaggactgt     180
gtgcagcgtg aacgggcccc tggtggtgct ggaccgggtc aagtttgccc agtatgcgga     240
gatcgtccac ttcaccctcc cagatggggac tcagaggagc gggcaggtgc ttgaggtggc    300
tggcaccaag gcgattgttc aggtgtttga agggacatca gggatcgatg ccaggaagac    360
cacttgcgaa tttacagggg acatcctacg aactccggtg tcagaggaca tgctgggtcg    420
ggttttcaat ggctccggca agcccattga caaggggcca gtggtcatgg cggaggactt    480
tctggatatc aatggccagc ccatcaaccc gcactccgc atctaccccg aggagatgat    540
tcagacgggc atttctccta ttgacgtcat gaacagcatt gcccgcggcc agaagatccc    600
catcttctca gcagccgggc tcccccacaa tgagattgcc gctcagatct gccgccaggc    660
ggggctggtg aagaagtcca aggctgtgct ggattaccat gacgcaaact tcgccatcgt    720
ctttgcagcc atgggggtga acatggagac agccagattc ttcaagtctg acttttgagca    780 gaatggaacc atggggaacg tctgcctctt cctgaacttg gccaatgacc ccacgatcga    840
gcggatcatc accccgcgcc tggcgctgac cactgctgaa ttccttgcct accagtgtga    900
gaagcatgtg ctggtcatac tgacggacat gagttcctat gcagaggcct tgcgggaggt    960
ctctgctgct agagaggagg tgcctgggcg ccgagggttt cctggatata tgtacacaga   1020
cctggccacc atctacgagc gggcggggcg tgtggagggt cggggaggat ccatcacaca   1080
gatccccatc ctcaccatgc caacgacga tatcacccac cctatcccag acttgacggg   1140
cttcatcaca gagggacaga tctacgtgga cagacagctt cacaacagac agatctaccc   1200
ccccatcaac gtgctcccctt ccctgtcgcg gctgatgaag tcagccattg gggaaggcat   1260
gacaagaaag gaccatggag atgtctccaa ccagctgtac gcctgctatg ccatcgggaa   1320
ggacgtgcag gccatgaagg cagtagttgg ggaggaggcg ctcacctctg aggacctgct   1380
ctacctggaa ttcctgcaga gtttgagaa gaacttcatc aatcagggcc ctacgagaa    1440 ccgctcgatg ttcgagtcgc tggaccttag ctggaagctg ctgcgcatct tccccaagga   1500
gatgctgaag cgcattccgc aggccgtgat cgacagttc tattcccgcg aggggcggct    1560
gcaggacctc gcgcctgaca ctgcgctcta gccccgcgcg ccgtgcacc ccaacaccgg    1620
```

| caggaaccta | ccctcggctc | ccgggtctcc | ccgtccctcg | ccacccctaa | ccagcggctt | 1680 |
| tcgcgccgcc | ctccgccctc | cgtggctccg | aggtggtggg | gggcgccgca | gtcatccctt | 1740 |
| tcctcgctcg | attccttttc | ccgcgctcca | tgcctccccc | tcagctcccg | gtgctgcgga | 1800 |
| agaactgaag | gttcatgcct | actctgacgg | gagcatctgt | attttttatg | ttaaaagccc | 1860 |
| acaaaataaa | aataaaaatg | aactgag | | | | 1887 |

<210> SEQ ID NO 55
<211> LENGTH: 1506
<212> TYPE: DNA
<213> ORGANISM: human

<400> SEQUENCE: 55

| aggcggacaa | agcccgattg | ttcctgggcc | ctttccccat | cgcgcctggg | cctgctcccc | 60 |
| agcccggggc | aggggcgggg | gccagtgtgg | tgacacacgc | tgtagctgtc | tccccggctg | 120 |
| gctggctcgc | tctctcctgg | ggacacagag | gtcggcaggc | agcacacaga | gggacctacg | 180 |
| ggcagctgtt | ccttcccccg | actcaagaat | ccccggaggc | ccggaggcct | gcagcaggag | 240 |
| cggccatgaa | gaagctgatg | gtggtgctga | gtctgattgc | tgcagcctgg | gcagaggagc | 300 |
| agaataagtt | ggtgcatggc | ggaccctgcg | acaagacatc | tcacccctac | caagctgccc | 360 |
| tctacacctc | gggccacttg | ctctgtggtg | gggtccttat | ccatccactg | tgggtcctca | 420 |
| cagctgccca | ctgcaaaaaa | ccgaatcttc | aggtcttcct | ggggaagcat | aaccttcggc | 480 |
| aaagggagag | ttcccaggag | cagagttctg | ttgtccgggc | tgtgatccac | cctgactatg | 540 |
| atgccgccag | ccatgaccag | gacatcatgc | tgttgcgcct | ggcacgccca | gccaaactct | 600 |
| ctgaactcat | ccagcccctt | cccctggaga | gggactgctc | agccaacacc | accagctgcc | 660 |
| acatcctggg | ctggggcaag | acagcagatg | gtgatttccc | tgacaccatc | cagtgtgcat | 720 |
| acatccacct | ggtgtcccgt | gaggagtgtg | agcatgccta | ccctggccag | atcacccaga | 780 |
| acatgttgtg | tgctggggat | gagaagtacg | gaaggattc | ctgccagggt | gattctgggg | 840 |
| gtccgctggt | atgtgagac | cacctccgag | gccttgtgtc | atggggtaac | atccctgtg | 900 |
| gatcaaagga | gaagccagga | gtctacacca | acgtctgcag | atacacgaac | tggatccaaa | 960 |
| aaaccattca | ggccaagtga | ccctgacatg | tgacatctac | ctcccgacct | accaccccac | 1020 |
| tggctggttc | cagaacgtct | ctcacctaga | ccttgcctcc | cctcctctcc | tgcccagctc | 1080 |
| tgaccctgat | gcttaataaa | cgcagcgacg | tgagggtcct | gattctccct | ggttttaccc | 1140 |
| cagctccatc | cttgcatcac | tggggaggac | gtgatgagtg | aggacttggg | tcctcggtct | 1200 |
| tacccccacc | actaagagaa | tacaggaaaa | tcccttctag | gcatctcctc | tccccaaccc | 1260 |
| ttccacacgt | ttgatttctt | cctgcagagg | cccagccacg | tgtctggaat | cccagctccg | 1320 |
| ctgcttactg | tcggtgtccc | cttgggatgt | acctttcttc | actgcagatt | tctcacctgt | 1380 |
| aagatgaaga | taaggatgat | acagtctcca | tcaggcagtg | gctgttggaa | agatttaaga | 1440 |
| tttcacacct | atgacataca | tgggatagca | cctgggccgc | catgcactca | ataaagaatg | 1500 |
| tatttt | | | | | | 1506 |

<210> SEQ ID NO 56
<211> LENGTH: 2907
<212> TYPE: DNA
<213> ORGANISM: human

<400> SEQUENCE: 56

| gccatctggg | cccaggcccc | atgccccgag | gaggggtggt | ctgaagccca | ccagagcccc | 60 |

```
ctgccagact gtctgcctcc cttctgactg tggccgcttg gcatggccag caacagcagc    120
tcctgcccga cacctggggg cgggcacctc aatgggtacc cggtgcctcc ctacgccttc    180
ttcttccccc ctatgctggg tggactctcc ccgccaggcg ctctgaccac tctccagcac    240
cagcttccag ttagtggata tagcacacca tccccagcca ccattgagac ccagagcagc    300
agttctgaag agatagtgcc cagccctccc tcgccacccc ctctacccccg catctacaag   360 ccttgctttg tctgtcagga caagtcctca ggctaccact atggggtcag cgcctgtgag    420
ggctgcaagg gcttcttccg ccgcagcatc cagaagaaca tggtgtacac gtgtcaccgg    480
gacaagaact gcatcatcaa caaggtgacc cggaaccgct gccagtactg ccgactgcag    540
aagtgctttg aagtgggcat gtccaaggag tctgtgagaa cgaccgaaa caagaagaag     600 aaggaggtgc ccaagcccga gtgctctgag agctacacgc tgacgccgga ggtgggggag    660
ctcattgaga aggtgcgcaa agcgcaccag gaaaccttcc ctgccctctg ccagctgggc    720
aaatacacta cgaacaacag ctcagaacaa cgtgtctctc tggacattga cctctgggac    780
aagttcagtg aactctccac caagtgcatc attaagactg tggagttcgc caagcagctg    840
cccggcttca ccaccctcac catcgccgac cagatcaccc tcctcaaggc tgcctgcctg    900
gacatcctga tcctgcggat ctgcacgcgc tacacgcccg agcaggacac catgaccttc    960
tcggacgggc tgaccctgaa ccggacccag atgcacaacg ctggcttcgg ccccctcacc    1020
gacctggtct ttgccttcgc caaccagctg ctgccctgg agatggatga tgcggagacg      1080
gggctgctca gcgccatctg cctcatctgc ggagaccgcc aggacctgga gcagccggac    1140
cgggtgagca tgctgcagga gccgctgctg gaggcgctaa aggtctacgt gcggaagcgg    1200
aggcccagcc gccccacat gttccccaag atgctaatga agattactga cctgcgaagc     1260
atcagcgcca agggggctga gcgggtgatc acgctgaaga tggagatccc gggctccatg    1320
ccgcctctca tccaggaaat gttggagaac tcagagggcc tggacactct gagcggacag    1380
ccggggggtg ggggggcggga cggggtggc ctggcccccc cgccaggcag ctgtagcccc      1440
agcctcagcc ccagctccaa cagaagcagc ccggccaccc actccccgtg accgccacg     1500 ccacatggac acagccctcg ccctccgccc cggcttttct ctgccttct accgaccatg     1560 tgacccccgca ccagccctgc ccccacctgc cctcccgggc agtactgggg accttccctg    1620
ggggacgggg agggaggagg cagcgactcc ttggacagag gcctgggccc tcagtggact    1680
gcctgctccc acagcctggg ctgacgtcag aggccgaggc caggaactga gtgaggcccc    1740
tggtcctggg tctcaggatg ggtcctgggg gcctcgtgtt catcaagaca cccctctgcc    1800
cagctcacca catcttcatc accagcaaac gccaggactt ggctccccca tcctcagaac    1860
tcacaagcca ttgctcccca gctggggaac ctcaacctcc ccctgcctc ggttggtgac     1920 agaggggtg ggacagggc ggggggttcc ccctgtacat accctgccat accaaccca        1980 ggtattaatt ctcgctggtt ttgttttttat tttaattttt ttgttttgat tttttttaata  2040 agaatttcca ttttaagcac atttatactg aaggaatttg tgctgtgtat tgggggggagc   2100 tggatccaga gctggagggg gtgggtccgg gggagggagt ggctcggaag gggcccccac    2160
tctcctttca tgtccctgtg ccccccagtt ctcctcctca gccttttcct cctcagtttt    2220
ctctttaaaa ctgtgaagta ctaactttcc aaggcctgcc ttcccctccc tcccactgga   2280
gaagccgcca gccccttct ccctctgcct gaccactggg tgtggacggt gtggggcagc     2340
cctgaaagga caggctcctg gccttggcac ttgcctgcac ccaccatgag gcatggagca    2400
```

| | |
|---|---:|
| gggcagagca agggccccgg gacagagttt tcccagacct ggctcctcgg cagagctgcc | 2460 |
| tcccgtcagg gcccacatca tctaggctcc ccagccccca ctgtgaaggg gctggccagg | 2520 |
| ggcccgagct gcccccaccc ccggcctcag ccaccagcac ccccataggg cccccagaca | 2580 |
| ccacacacat gcgcgtgcgc acacacacaa acacacacac actggacagt agatgggccg | 2640 |
| acacacactt ggcccgagtt cctccatttc cctggcctgc cccccacccc caacctgtcc | 2700 |
| cacccccgtg cccctccttt accccgcagg acgggcctac aggggggtct cccctcaccc | 2760 |
| ctgcaccccc agctggggga gctggctctg ccccgacctc cttcaccagg ggttggggcc | 2820 |
| ccttcccctg gagcccgtgg gtgcacctgt tactgttggg cttccactg agatctactg | 2880 |
| gataaagaat aaagttctat ttattct | 2907 |

<210> SEQ ID NO 57
<211> LENGTH: 2907
<212> TYPE: DNA
<213> ORGANISM: human

<400> SEQUENCE: 57

| | |
|---|---:|
| gccatctggg cccaggcccc atgccccgag gaggggtggt ctgaagccca ccagagcccc | 60 |
| ctgccagact gtctgcctcc cttctgactg tggccgcttg gcatggccag caacagcagc | 120 |
| tcctgcccga cacctggggg cgggcacctc aatgggtacc cggtgcctcc ctacgccttc | 180 |
| ttcttccccc ctatgctggg tggactctcc ccgccaggcg ctctgaccac tctccagcac | 240 |
| cagcttccag ttagtggata tagcacacca tccccagcca ccattgagac ccagagcagc | 300 |
| agttctgaag agatagtgcc cagccctccc tcgccacccc ctctaccccg catctacaag | 360 |
| ccttgctttg tctgtcagga caagtcctca ggctaccact atggggtcag cgcctgtgag | 420 |
| ggctgcaagg gcttcttccg ccgcagcatc cagaagaaca tggtgtacac gtgtcaccgg | 480 |
| gacaagaact gcatcatcaa caaggtgacc cggaaccgct gccagtactg ccgactgcag | 540 |
| aagtgctttg aagtgggcat gtccaaggag tctgtgagaa cgaccgaaa caagaagaag | 600 |
| aaggaggtgc ccaagcccga gtgctctgag agctacacgc tgacgccgga ggtgggggag | 660 |
| ctcattgaga aggtgcgcaa agcgcaccag gaaaccttcc ctgccctctg ccagctgggc | 720 |
| aaatacacta cgaacaacag ctcagaacaa cgtgtctctc tggacattga cctctgggac | 780 |
| aagttcagtg aactctccac caagtgcatc attaagactg tggagttcgc caagcagctg | 840 |
| cccggcttca ccaccctcac catcgccgac cagatcaccc tcctcaaggc tgcctgcctg | 900 |
| gacatcctga tcctgcggat ctgcacgcgg tacacgcccg agcaggacac catgaccttc | 960 |
| tcggacgggc tgaccctgaa ccggacccag atgcacaacg ctggcttcgg cccccctcacc | 1020 |
| gacctggtct ttgccttcgc caaccagctg ctgcccctgg agatggatga tgcggagacg | 1080 |
| gggctgctca gcgccatctg cctcatctgc ggagaccgcc aggacctgga gcagccggac | 1140 |
| cgggtggaca tgctgcagga gccgctgctg gaggcgctaa aggtctacgt gcggaagcgg | 1200 |
| aggcccagcc gccccacat gttccccaag atgctaatga agattactga cctgcgaagc | 1260 |
| atcagcgcca aggggctga gcgggtgatc acgctgaaga tggagatccc gggctccatg | 1320 |
| ccgcctctca tccaggaaat gttggagaac tcagagggcc tggacactct gagcggacag | 1380 |
| ccgggggggtg gggggcggga cggggtggc ctggcccccc cgccaggcag ctgtagcccc | 1440 |
| agcctcagcc ccagctccaa cagaagcagc ccggccaccc actcccgtg accgcccacg | 1500 |
| ccacatggac acagccctcg ccctccgccc cggcttttct ctgcctttct accgaccatg | 1560 |
| tgaccccgca ccagccctgc ccccaccctgc cctcccgggc agtactgggg accttccctg | 1620 |

-continued

```
ggggacgggg agggaggagg cagcgactcc ttggacagag gcctgggccc tcagtggact      1680
gcctgctccc acagcctggg ctgacgtcag aggccgaggc caggaactga gtgaggcccc      1740
tggtcctggg tctcaggatg ggtcctgggg gcctcgtgtt catcaagaca cccctctgcc      1800
cagctcacca catcttcatc accagcaaac gccaggactt ggctccccca tcctcagaac      1860
tcacaagcca ttgctcccca gctggggaac ctcaacctcc ccctgcctc ggttggtgac       1920 agaggggtg ggacaggggc gggggttcc ccctgtacat accctgccat accaaccccca       1980 ggtattaatt ctcgctggtt ttgtttttat tttaattttt ttgttttgat ttttttaata      2040
agaattttca ttttaagcac atttatactg aaggaatttg tgctgtgtat tgggggggagc    2100 tggatccaga gctggagggg gtgggtccgg gggagggagt ggctcggaag gggcccccac      2160
tctcctttca tgtccctgtg cccccagtt ctcctcctca gccttttcct cctcagtttt      2220
ctctttaaaa ctgtgaagta ctaactttcc aaggcctgcc ttcccctccc tcccactgga     2280
gaagccgcca gccccttct ccctctgcct gaccactggg tgtggacggt gtggggcagc      2340
cctgaaagga caggctcctg gccttggcac ttgcctgcac ccaccatgag gcatggagca     2400
gggcagagca agggccccgg gacagagttt tcccagacct ggctcctcgg cagagctgcc    2460
tcccgtcagg gcccacatca tctaggctcc ccagccccca ctgtgaaggg gctggccagg    2520
ggcccgagct gccccccaccc ccggcctcag ccaccagcac cccataggg ccccagaca      2580 ccacacacat gcgcgtgcgc acacacacaa acacacacac actggacagt agatgggccg     2640
acacacactt ggcccgagtt cctccatttc cctggcctgc cccccacccc caacctgtcc     2700 caccccgtg cccctcctt accccgcagg acgggcctac aggggggtct cccctcaccc       2760
ctgcaccccc agctggggga gctggctctg ccccgacctc cttcaccagg ggttggggcc     2820
ccttcccctg gagcccgtgg gtgcacctgt tactgttggg cttccactg agatctactg      2880 gataaagaat aaagttctat ttattct                                          2907
```

<210> SEQ ID NO 58
<211> LENGTH: 5026
<212> TYPE: DNA
<213> ORGANISM: human

<400> SEQUENCE: 58

```
agaggaggaa attgttcctc gtctgataag acaacagtgg agaaaggacg catgctgttt       60
cttagggaca cggctgactt ccagatatga ccatgtattt gtggcttaaa ctcttggcat      120
ttggctttgc ctttctggac acagaagtat ttgtgacagg gcaaagccca acaccttccc      180
ccactggatt gactacagca aagatgccca gtgttccact ttcaagtgac cccttaccta     240
ctcacaccac tgcattctca cccgcaagca cctttgaaag agaaaatgac ttctcagaga     300
ccacaacttc tcttagtcca gacaatactt ccacccaagt atccccggac tctttggata     360
atgctagtgc tttaatacc acaggtgttt catcagtaca gacgcctcac cttcccacgc      420
acgcagactc gcagacgccc tctgctggaa ctgacgcga gacattcagc ggctccgccg      480
ccaatgcaaa actcaaccct accccaggca gcaatgctat ctcagatgtc ccaggagaga      540
ggagtacagc cagcaccttt cctacagacc cagtttcccc attgacaacc accctcagcc      600
ttgcacacca cagctctgct gccttacctg cacgcacctc caacaccacc atcacagcga     660
acacctcaga tgcctacctt aatgcctctg aaacaaccac tctgagccct tctggaagcg      720
ctgtcatttc aaccacaaca atagctacta ctccatctaa gccaacatgt gatgaaaaat      780
```

```
atgcaaacat cactgtggat tacttatata acaaggaaac taaattattt acagcaaagc    840
taaatgttaa tgagaatgtg gaatgtggaa acaatacttg cacaaacaat gaggtgcata    900
accttacaga atgtaaaaat gcgtctgttt ccatatctca taattcatgt actgctcctg    960
ataagacatt aatattagat gtgccaccag gggttgaaaa gtttcagtta catgattgta   1020
cacaagttga aaaagcagat actactattt gtttaaaatg gaaaaatatt gaaacccttta  1080
cttgtgatac acagaatatt acctacagat ttcagtgtgg taatatgata tttgataata   1140
aagaaattaa attagaaaac cttgaacccg aacatgagta taagtgtgac tcagaaatac   1200
tctataataa ccacaagttt actaacgcaa gtaaaattat taaaacagat tttgggagtc   1260
caggagagcc tcagattatt ttttgtagaa gtgaagctgc acatcaagga gtaattacct   1320
ggaatccccc tcaaagatca tttcataatt ttaccctctg ttatataaaa gagacagaaa   1380
aagattgcct caatctggat aaaaacctga tcaaatatga tttgcaaaat ttaaaacctt   1440
atacgaaata tgttttatca ttacatgcct acatcattgc aaaagtgcaa cgtaatggaa   1500
gtgctgcaat gtgtcatttc acaactaaaa gtgctcctcc aagccaggtc tggaacatga   1560
ctgtctccat gacatcagat aatagtatgc atgtcaagtg taggcctccc agggaccgta   1620
atggccccca tgaacgttac catttggaag ttgaagctgg aaatactctg gttagaaatg   1680
agtcgcataa gaattgcgat ttccgtgtaa aagatcttca atattcaaca gactacactt   1740
ttaaggccta ttttcacaat ggagactatc ctggagaacc ctttatttta catcattcaa   1800
catcttataa ttctaaggca ctgatagcat ttctggcatt tctgattatt gtgacatcaa   1860
tagccctgct tgttgttctc tacaaaatct atgatctaca taagaaaaga tcctgcaatt   1920
tagatgaaca gcaggagctt gttgaaaggg atgatgaaaa acaactgatg aatgtggagc   1980
caatccatgc agatattttg ttggaaactt ataagaggaa gattgctgat gaaggaagac   2040
tttttctggc tgaatttcag agcatcccgc gggtgttcag caagtttcct ataaaggaag   2100
ctcgaaagcc ctttaaccag aataaaaacc gttatgttga cattcttcct tatgattata   2160
accgtgttga actctctgag ataaacggag atgcagggtc aaactacata aatgccagct   2220
atattgatgg tttcaaagaa cccaggaaat acattgctgc acaaggtccc agggatgaaa   2280
ctgttgatga tttctggagg atgatttggg aacagaaagc cacagttatt gtcatggtca   2340
ctcgatgtga agaaggaaac aggaacaagt gtgcagaata ctggccgtca atggaagagg   2400
gcactcgggc ttttggagat gttgttgtaa agatcaacca gcacaaaaga tgtccagatt   2460
acatcattca gaaattgaac attgtaaata aaaagaaaa agcaactgga agagaggtga   2520
ctcacattca gttcaccagc tggccagacc acggggtgcc tgaggatcct cacttgctcc   2580
tcaaactgag aaggagagtg aatgccttca gcaatttctt cagtggtccc attgtggtgc   2640
actgcagtgc tggtgttggg cgcacaggaa cctatatcgg aattgatgcc atgctagaag   2700
gcctggaagc cgagaacaaa gtggatgttt atggttatgt tgtcaagcta aggcgacaga   2760
gatgcctgat ggttcaagta gaggcccagt acatcttgat ccatcaggct ttggtggaat   2820
acaatcagtt tggagaaaca gaagtgaatt tgtctgaatt acatccatat ctacataaca   2880
tgaagaaaag ggatccaccc agtgagccgt ctccactaga ggctgaattc cagagacttc   2940
cttcatatag gagctggagg acacagcaca ttggaaatca agaagaaat aaaagtaaaa    3000
acaggaattc taatgtcatc ccatatgact ataacagagt gccacttaaa catgagctgg   3060
aaatgagtaa agagagtgag catgattcag atgaatcctc tgatgatgac agtgattcag   3120
aggaaccaag caaatacatc aatgcatctt ttataatgag ctactggaaa cctgaagtga   3180
```

```
tgattgctgc tcagggacca ctgaaggaga ccattggtga cttttggcag atgatcttcc    3240
aaagaaaagt caaagttatt gttatgctga cagaactgaa acatggagac caggaaatct    3300
gtgctcagta ctgggagaa ggaaagcaaa catatggaga tattgaagtt gacctgaaag     3360
acacagacaa atcttcaact tatacccttc gtgtctttga actgagacat tccaagagga    3420
aagactctcg aactgtgtac cagtaccaat atacaaactg gagtgtggag cagcttcctg    3480
cagaacccaa ggaattaatc tctatgattc aggtcgtcaa acaaaaactt ccccagaaga    3540
attcctctga agggaacaag catcacaaga gtacacctct actcattcac tgcagggatg    3600
gatctcagca acgggaata ttttgtgctt tgttaaatct cttagaaagt gcggaaacag      3660
aagaggtagt ggatattttt caagtggtaa aagctctacg caaagctagg ccaggcatgg    3720
tttccacatt cgagcaatat caattcctat atgacgtcat tgccagcacc taccctgctc    3780
agaatggaca agtaaagaaa acaaccatc aagaagataa aattgaattt gataatgaag      3840
tggacaaagt aaagcaggat gctaattgtg ttaatccact tggtgcccca gaaaagctcc    3900
ctgaagcaaa ggaacaggct gaaggttctg aacccacgag tggcactgag gggccagaac    3960
attctgtcaa tggtcctgca agtccagctt taaatcaagg ttcataggaa aagacataaa    4020
tgaggaaact ccaaacctcc tgttagctgt tatttctatt tttgtagaag taggaagtga    4080
aaataggtat acagtggatt aattaaatgc agcgaaccaa tatttgtaga agggttatat    4140
tttactactg tggaaaaata tttaagatag ttttgccaga acagtttgta cagacgtatg    4200
cttattttaa aattttatct cttattcagt aaaaaacaac ttctttgtaa tcgttatgtg    4260
tgtatatgta tgtgtgtatg ggtgtgtgtt tgtgtgagag acagagaaag agagagaatt    4320 cttttcaagtg aatctaaaag cttttgcttt tcctttgttt ttatgaagaa aaaatacatt   4380
ttatattaga agtgttaact tagcttgaag gatctgttt taaaaatcat aaactgtgtg     4440
cagactcaat aaaatcatgt acatttctga aatgacctca agatgtcctc cttgttctac    4500
tcatatatat ctatcttata tacttactat tttacttcta gagatagtac ataaaggtgg    4560
tatgtgtgtg tatgctacta caaaaaagtt gttaactaaa ttaacattgg gaaatcttat    4620
attccatata ttagcattta gtccaatgtc ttttaagct tatttaatta aaaaatttcc     4680
agtgagctta tcatgctgtc tttacatggg gttttcaatt ttgcatgctc gattattccc    4740
tgtacaatat ttaaaattta ttgcttgata cttttgacaa caaattaggt tttgtacaat    4800
tgaacttaaa taaatgtcat taaaataaat aaatgcaata tgtattaata ttcattgtat    4860
aaaaatagaa gaatacaaac atatttgtta aatatttaca tatgaaatt aatatagcta     4920 tttttatgga atttttcatt gatatgaaaa atatgatatt gcatatgcat agttcccatg    4980
ttaaatccca ttcataactt tcattaaagc atttactttg aatttc                   5026

<210> SEQ ID NO 59
<211> LENGTH: 625
<212> TYPE: DNA
<213> ORGANISM: human

<400> SEQUENCE: 59
aggcgggccg ctcccacttc ggcacgaggg gcacgaggta aatctttct gcttactgaa       60 aaggaagagt ctgatgatta gttactgatc ctctttgcat ttgtaaagct ttggagatat     120
tgaatcatgt taccatttct gttttttcc accctgtttt cttccatatt tactgaagct     180
cagaagcagt attgggtctg caactcatcc gatgcaagta tttcatacac ctactgtgat    240
```

```
aaaatgcaat acccaatttc aattaatgtt aaccoctgta tagaattgaa aggatccaaa    300
ggattattgc acattttcta cattccaagg agagatttaa agcaattata tttcaatctc    360
tatataactg tcaacaccat gaatcttcca aagcgcaaag aagttatttg ccgaggatct    420
gatgacgatt actcttttg cagagctctg aagggagaga ctgtgaatac aacaatatca     480
ttctccttca agggaataaa attttctaag ggaaaataca aatgtgttgt tgaagctatt    540
tctgggagcc cagaagaaat gctcttttgc ttggagtttg tcatcctaca ccaacctaat    600
tcaaattaga ataaattgag tattt                                          625
```

<210> SEQ ID NO 60
<211> LENGTH: 2088
<212> TYPE: DNA
<213> ORGANISM: human

<400> SEQUENCE: 60

```
gaattcggca cgagcgcgcg gcgaatctca acgctgcgcc gtctgcgggc gcttccgggc     60
caccagtttc tctgctttcc accctggcgc cccccagccc tggctcccca gctgcgctgc    120
cccgggcgtc cacgccctgc gggcttagcg ggttcagtgg gctcaatctg cgcagcgcca    180
cctccatgtt gaccaagcct ctacaggggc ctcccgcgcc cccggggacc cccacgccgc    240
cgccaggagg caaggatcgg gaagcgttcg aggccgagta tcgactcggc cccctcctgg    300 gtaaggggg cttggcacc gtcttcgcag acaccgcct cacagatcga ctccaggtgg       360
ccatcaaagt gattccccgg aatcgtgtgc tgggctggtc ccccttgtca gactcagtca    420
catgcccact cgaagtcgca ctgctatgga aagtgggtgc aggtggtggg caccctggcg    480
tgatccgcct gcttgactgg tttgagacac aggaaggctt catgctggtc ctcgagcggc    540 cttttgcccgc ccaggatctc tttgactata tcacagagaa gggcccactg ggtgaaggcc    600
caagccgctg cttctttggc caagtagtgg cagccatcca gcactgccat tcccgtggag    660
ttgtccatcg tgacatcaag gatgagaaca tcctgataga cctacgccgt ggctgtgcca    720
aactcattga ttttggttct ggtgccctgc ttcatgatga ccctacact gactttgatg     780 ggacaagggt gtacagcccc ccagagtgga tctctcgaca ccagtaccat gcactcccgg    840
ccactgtctg gtcactgggc atcctcctct atgacatggt gtgtgggac attccctttg    900 agagggacca ggagattctg gaagctgagc tccacttccc agcccatgtc tccccagact    960
gctgtgccct aatccgccgg tgcctggccc ccaaaccttc ttcccgaccc tcactggaag   1020
agatcctgct ggaccctgg atgcaaacac cagccgagga tgttaccct caaccctcc     1080 aaaggaggcc ctgcccttt ggcctggtcc ttgctaccct aagcctggcc tggcctggcc   1140
tggcccccaa tggtcagaag agccatccca tggccatgtc acagggatag atggacttt    1200 gttgacttgg ttttacaggt cattaccagt cattaaagtc cagtattact aaggtaaggg   1260
attgaggatc aggggttaga agacataaac caagtttgcc cagttccctt cccaatccta   1320
caaaggagcc ttcctcccag aacctgtggt ccctgatttt ggaggggaa cttcttgctt    1380 ctcattttgc taaggaagtt tattttggtg aagttgttcc cattttgagc ccgggactc    1440 ttattttgat gatgtgtcac cccacattgg cacctcctac taccaccaca caaacttagt   1500
tcatatgctt ttacttgggc aagggtgctt tccttccaat accccagtag cttttatttt    1560
agtaaaggga ccctttcccc tagcctaggg tcccatattg ggtcaagctg cttacctgcc   1620
tcagcccagg attttttatt ttgggggagg taatgcctg ttgttacccc aaggcttctt    1680
tttttttttt tttttttttg ggtgaggga ccctactttg ttatcccaag tgctcttatt    1740
```

| | | | | |
|---|---|---|---|---|
| ctggtgagaa | gaaccttaat | tccataattt | gggaaggaat | ggaagatgga caccaccgga | 1800 |
| caccaccaga | caataggatg | ggatggatgg | ttttttgggg | gatgggctag gggaaataag | 1860 |
| gcttgctgtt | tgttttcctg | gggcgctccc | tccaattttg | cagattttg caacctcctc | 1920 |
| ctgagccggg | attgtccaat | tactaaaatg | taaataatca | cgtattgtgg ggaggggagt | 1980 |
| tccaagtgtg | ccctcctttt | ttttcctgcc | tggattattt | aaaaagccat gtgtggaaac | 2040 |
| ccactattta | ataaaagtaa | tagaatcaga | aaaaaaaaaa | aaaaaaa | 2088 |

<210> SEQ ID NO 61
<211> LENGTH: 2270
<212> TYPE: DNA
<213> ORGANISM: human

<400> SEQUENCE: 61

| | | | | | |
|---|---|---|---|---|---|
| ctcctccagc | ctctcacact | ctcctcagct | ctctcatctc | ctggaaccat ggccagcaca | 60 |
| tccaccacca | tcaggagcca | cagcagcagc | cgccggggtt | tcagtgccaa ctcagccagg | 120 |
| ctccctgggg | tcagccgctc | tggcttcagc | agcgtctccg | tgtcccgctc caggggcagt | 180 |
| ggtggcctgg | gtggtgcatg | tggaggagct | ggctttggca | gccgcagtct gtatggcctg | 240 |
| gggggctcca | agaggatctc | cattggaggg | ggcagctgtg | ccatcagtgg cggctatggc | 300 |
| agcagagccg | gaggcagcta | tggctttggt | ggcgccggga | gtggatttgg tttcggtggt | 360 |
| ggagccggca | ttggctttgg | tctgggtggt | ggagccggcc | ttgctggtgg ctttggggc | 420 |
| cctggcttcc | ctgtgtgccc | ccctggaggc | atccaagagg | tcaccgtcaa ccagagtctc | 480 |
| ctgactcccc | tcaacctgca | aatcgatccc | accatccagc | gggtgcgggc tgaggagcgt | 540 |
| gaacagatca | agaccctcaa | caacaagttt | gcctccttca | tcgacaaggt gcggttcctg | 600 |
| gagcagcaga | acaaggttct | ggaaacaaag | tggaccctgc | tgcaggagca gggcaccaag | 660 |
| actgtgaggc | agaacctgga | gccgttgttc | gagcagtaca | tcaacaacct caggaggcag | 720 |
| ctggacagca | ttgtcgggga | acggggccgc | ctggactcag | agctcagagg catgcaggac | 780 |
| ctggtggagg | acttcaagaa | caaatatgag | gatgaaatca | caagcgcac agcagcagag | 840 |
| aatgaatttg | tgactctgaa | gaaggatgtg | gatgctgcct | acatgaacaa ggttgaactg | 900 |
| caagccaagg | cagacactct | cacagacgag | atcaacttcc | tgagagcctt gtatgatgca | 960 |
| gagctgtccc | agatgcagac | ccacatctca | gacacatctg | tggtgctgtc catggacaac | 1020 |
| aaccgcaacc | tggacctgga | cagcatcatc | gctgaggtca | aggcccaata tgaggagatt | 1080 |
| gctcagagaa | gccggctga | ggctgagtcc | tggtaccaga | ccaagtacga ggagctgcag | 1140 |
| gtcacagcag | gcagacatgg | ggacgacctg | cgcaacacca | gcaggagat tgctgagatc | 1200 |
| aaccgcatga | tccagaggct | gagatctgag | atcgaccacg | tcaagaagca gtgcgccaac | 1260 |
| ctgcaggccg | ccattgctga | tgctgagcag | cgtggggaga | tggccctcaa ggatgccaag | 1320 |
| aacaagctgg | aagggctgga | ggatgccctg | cagaaggcca | gcaggacct ggcccggctg | 1380 |
| ctgaaggagt | accaggagct | gatgaatgtc | aagctggccc | tggacgtgga gatcgccacc | 1440 |
| taccgcaagc | tgctggaggg | tgaggagtgc | aggctgaatg | gcgaaggcgt tggacaagtc | 1500 |
| aacatctctg | tggtgcagtc | caccgtctcc | agtggctatg | cggtgccag tggtgtcggc | 1560 |
| agtggcttag | gctgggtgg | aggaagcagc | tactccatg | gcagtggtct ggcgttgga | 1620 |
| ggtggcttca | gttccagcag | tggcagagc | attgggggtg | gcctcagctc tgttggaggc | 1680 |
| ggcagttcca | ccatcaagta | caccaccacc | tcctcctcca | gcaggaagag ctataagcac | 1740 |

-continued

| | |
|---|---|
| taaagtgcgt ctgctagctc tcggtcccac agtcctcagg cccctctctg gctgcagagc | 1800 |
| cctctcctca ggttgcctgt cctctcctgg cctccagtct cccctgctgt cccaggtaga | 1860 |
| gctggggatg aatgcttagt gccctcactt cttctctctc tctctatacc atctgagcac | 1920 |
| ccattgctca ccatcagatc aacctctgat tttacatcat gatgtaatca ccactggagc | 1980 |
| ttcactgtta ctaaattatt aatttcttgc ctccagtgtt ctatctctga ggctgagcat | 2040 |
| tataagaaaa tgacctctgc tccttttcat tgcagaaaat tgccaggggc ttatttcaga | 2100 |
| acaacttcca cttactttcc actggctctc aaactctcta acttataagt gttgtgaacc | 2160 |
| cccacccagg cagtatccat gaaagcacaa gtgactagtc ctatgatgta caaagcctgt | 2220 |
| atctctgtga tgatttctgt gctcttcact gtttgcaatt gctaaataaa | 2270 |

<210> SEQ ID NO 62
<211> LENGTH: 2048
<212> TYPE: DNA
<213> ORGANISM: human

<400> SEQUENCE: 62

| | |
|---|---|
| atgtgaaggc acaagctgct gttatataca acagagtgaa ctgagcatca gtcagaaaaa | 60 |
| gtctatgttt gcagaaatac agatccaaga caaagacagg atgggcactg ctggaaaagt | 120 |
| tattaaatgc aaagcagctg tgctttggga gcagaagcaa cccttctcca ttgaggaaat | 180 |
| agaagttgcc ccaccaaaga ctaaagaagt tcgcattaag attttggcca caggaatctg | 240 |
| tcgcacagat gaccatgtga taaaaggaac aatggtgtcc aagtttccag tgattgtggg | 300 |
| acatgaggca actgggattg tagagagcat tggagaagga gtgactacag tgaaaccagg | 360 |
| tgacaaagtc atccctctct ttctgccaca atgtagagaa tgcaatgctt gtcgcaaccc | 420 |
| agatggcaac ctttgcatta ggagcgatat tactggtcgt ggagtactgg ctgatggcac | 480 |
| caccagattt acatgcaagg gcaaaccagt acaccacttc atgaacacca gtacatttac | 540 |
| cgagtacaca gtggtggatg aatcttctgt tgctaagatt gatgatgcag ctcctcctga | 600 |
| gaaagtctgt ttaattggct gtgggttttc cactggatat ggcgctgctg ttaaaactgg | 660 |
| caaggtcaaa cctggttcca cttgcgtcgt cttttggcctg ggaggagttg gcctgtcagt | 720 |
| catcatgggc tgtaagtcag ctggtgcatc taggatcatt gggattgacc tcaacaaaga | 780 |
| caaatttgag aaggccatgg ctgtaggtgc cactgagtgt atcagtccca aggactctac | 840 |
| caaacccatc agtgaggtgc tgtcagaaat gacaggcaac aacgtgggat acaccttga | 900 |
| agttattggg catcttgaaa ccatgattga tgccctggca tcctgccaca tgaactatgg | 960 |
| gaccagcgtg gttgtaggag ttcctccatc agccaagatg ctcacctatg acccgatgtt | 1020 |
| gctcttcact ggacgcacat ggaagggatg tgtctttgga ggtttgaaaa gcagagatga | 1080 |
| tgtcccaaaa ctagtgactg agttcctggc aaagaaattt gacctggacc agttgataac | 1140 |
| tcatgttta ccatttaaaa aaatcagtga aggatttgag ctgctcaatt caggacaaag | 1200 |
| cattcgaacg gtcctgacgt tttgagatcc aaagtggcag gaggtctgtg ttgtcatggt | 1260 |
| gaactggagt ttctcttgtg agagttccct catctgaaat catgtatctg tctcacaaat | 1320 |
| acaagcataa gtagaagatt tgttgaagac atagaaccct tataaagaat tattaacctt | 1380 |
| tataaacatt taaagtcttg tgagcacctg ggaattagta taataacaat gttaatattt | 1440 |
| ttgatttaca ttttgtaagg ctataattgt atcttttaag aaaacataca cttggatttc | 1500 |
| tatgttgaaa tggagatttt taagagtttt aaccagctgc tgcagatata taactcaaaa | 1560 |
| cagatatagc gtataaagat atagtaaatg catctcccag agtaatattc acttaacaca | 1620 |

```
ttgaaactat tattttttag atttgaatat aaatgtattt tttaaacact tgttatgagt    1680
taacttggat tacattttga aatcagttca ttccatgatg catattactg gattagatta    1740
agaaagacag aaaagattaa gggacgggca cattttccaa cgattaagaa tcatcattac    1800
ataacttggt gaaactgaaa agtatatca tatgggtaca caaggctatt tgccagcata    1860
tattaatatt ttagaaaata ttccttttgt aatactgaat ataaacatag agctagagtc    1920
atattatcat acttatcata atgttcaatt tgatacagta gaattgcaag tccctaagtc    1980
cctattcact gtgcttagta gtgactccat ttaataaaaa gtgttttag tttttaacaa     2040 ctaaaccg                                                             2048

<210> SEQ ID NO 63
<211> LENGTH: 2048
<212> TYPE: DNA
<213> ORGANISM: human

<400> SEQUENCE: 63
atgtgaaggc acaagctgct gttatataca acagagtgaa ctgagcatca gtcagaaaaa    60
gtctatgttt gcagaaatac agatccaaga caaagacagg atgggcactg ctggaaaagt    120
tattaaatgc aaagcagctg tgctttggga gcagaagcaa cccttctcca ttgaggaaat    180
agaagttgcc ccaccaaaga ctaaagaagt tcgcattaag attttggcca caggaatctg    240
tcgcacagat gaccatgtga taaaaggaac aatggtgtcc aagtttccag tgattgtggg    300
acatgaggca actgggattg tagagagcat tggagaagga gtgactacag tgaaaccagg    360
tgacaaagtc atccctctct ttctgccaca atgtagagaa tgcaatgctt gtcgcaaccc    420
agatggcaac ctttgcatta ggagcgatat tactggtcgt ggagtactgg ctgatggcac    480
caccagattt acatgcaagg gcaaaccagt acaccacttc atgaacacca gtacatttac    540
cgagtacaca gtggtggatg aatcttctgt tgctaagatt gatgatgcag ctcctcctga    600
gaaagtctgt ttaattggct gtgggttttc cactggatat ggcgctgctg ttaaaactgg    660
caaggtcaaa cctggttcca cttgcgtcgt ctttggcctg ggaggagttg gcctgtcagt    720
catcatgggc tgtaagtcag ctggtgcatc taggatcatt gggattgacc tcaacaaaga    780
caaatttgag aaggccatgg ctgtaggtgc cactgagtgt atcagtccca aggactctac    840
caaacccatc agtgaggtgc tgtcagaaat gacaggcaac aacgtgggat cacctttga    900 agttattggg catcttgaaa ccatgattga tgccctggca tcctgccaca tgaactatgg    960
gaccagcgtg gttgtaggag ttcctccatc agccaagatg ctcacctatg cccgatgtt    1020 gctcttcact ggacgcacat ggaagggatg tgtctttgga ggtttgaaaa gcagagatga    1080
tgtcccaaaa ctagtgactg agttcctggc aaagaaattt gacctggacc agttgataac    1140
tcatgtttta ccatttaaaa aaatcagtga aggatttgag ctgctcaatt caggacaaag    1200
cattcgaacg gtcctgacgt tttgagatcc aaagtggcag gaggtctgtg ttgtcatggt    1260
gaactggagt ttctcttgtg agagttccct catctgaaat catgtatctg tctcacaaat    1320
acaagcataa gtagaagatt tgttgaagac atagaaccct tataaagaat tattaacctt    1380
tataaacatt taagtcttg tgagcacctg ggaattagta taataacaat gttaatattt     1440
ttgatttaca ttttgtaagg ctataattgt atctttaag aaaacataca cttggatttc     1500
tatgttgaaa tggagatttt taagagttt aaccagctgc tgcagatata taactcaaaa     1560
cagatatagc gtataaagat atagtaaatg catctcccag agtaatattc acttaacaca    1620
```

-continued

| | |
|---|---|
| ttgaaactat tatttttag atttgaatat aaatgtattt tttaaacact tgttatgagt | 1680 |
| taacttggat tacattttga aatcagttca ttccatgatg catattactg gattagatta | 1740 |
| agaaagacag aaaagattaa gggacgggca catttttcaa cgattaagaa tcatcattac | 1800 |
| ataacttggt gaaactgaaa aagtatatca tatgggtaca caaggctatt tgccagcata | 1860 |
| tattaatatt ttagaaaata ttccttttgt aatactgaat ataaacatag agctagagtc | 1920 |
| atattatcat acttatcata atgttcaatt tgatacagta gaattgcaag tccctaagtc | 1980 |
| cctattcact gtgcttagta gtgactccat ttaataaaaa gtgtttttag ttttttaacaa | 2040 |
| ctaaaccg | 2048 |

<210> SEQ ID NO 64
<211> LENGTH: 2816
<212> TYPE: DNA
<213> ORGANISM: human

<400> SEQUENCE: 64

| | |
|---|---|
| tcgttgatat caaagacagt tgaaggaaat gaattttgaa acttcacggt gtgccaccct | 60 |
| acagtactgc cctgacccct acatccagcg tttcgtagaa acccagctca tttctcttgg | 120 |
| aaagaaagtt attaccgatc caccatgtcc cagagcacac agacaaatga attcctcagt | 180 |
| ccagaggttt tccagcatat ctgggatttt ctggaacagc ctatatgttc agttcagccc | 240 |
| attgacttga actttgtgga tgaaccatca gaagatggtg cgacaaacaa gattgagatt | 300 |
| agcatggact gtatccgcat gcaggactcg gacctgagtg accccatgtg gccacagtac | 360 |
| acgaacctgg ggctcctgaa cagcatggac cagcagattc agaacggctc ctcgtccacc | 420 |
| agtccctata acacagacca cgcgcagaac agcgtcacgg cgccctcgcc ctacgcacag | 480 |
| cccagctcca ccttcgatgc tctctctcca tcacccgcca tccctccaa caccgactac | 540 |
| ccaggcccgc acagtttcga cgtgtccttc cagcagtcga gcaccgccaa gtcggccacc | 600 |
| tggacgtatt ccactgaact gaagaaactc tactgccaaa ttgcaaagac atgccccatc | 660 |
| cagatcaagg tgatgacccc acctcctcag ggagctgtta ccgcgccat gcctgtctac | 720 |
| aaaaaagctg agcacgtcac ggaggtggtg aagcggtgcc ccaaccatga gctgagccgt | 780 |
| gaattcaacg agggacagat tgcccctcct agtcatttga ttcgagtaga ggggaacagc | 840 |
| catgcccagt atgtagaaga tcccatcaca ggaagacaga gtgtgctggt accttatgag | 900 |
| ccaccccagg ttggcactga attcacgaca gtcttgtaca atttcatgtg taacagcagt | 960 |
| tgtgttggag ggatgaaccg ccgtccaatt ttaatcattg ttactctgga aaccagagat | 1020 |
| gggcaagtcc tgggccgacg ctgctttgag gcccggatct gtgcttgccc aggaagagac | 1080 |
| aggaaggcgg atgaagatag catcagaaag cagcaagttt cggacagtac aaagaacggt | 1140 |
| gatggtacga agcgcccgtt tcgtcagaac acacatggta tccagatgac atccatcaag | 1200 |
| aaacgaagat cccagatgat gaactgttta tacttaccag tgaggggccg tgagacttat | 1260 |
| gaaatgctgt tgaagatcaa agagtccctg gaactcatgc agtaccttcc tcagcacaca | 1320 |
| attgaaacgt acaggcaaca gcaacagcag cagcaccagc acttacttca gaaacatctc | 1380 |
| ctttcagcct gcttcaggaa tgagcttgtg gagccccgga gagaaactcc aaaacaatct | 1440 |
| gacgtcttct ttagacattc caagccccca aaccgatcag tgtacccata gagccctatc | 1500 |
| tctatatttt aagtgtgtgt gttgtatttc catgtgtata tgtgagtgtg tgtgtgtgta | 1560 |
| tgtgtgtgcg tgtgtatcta gccctcataa acaggacttg aagacacttt ggctcagaga | 1620 |
| cccaactgct caaaggcaca aagccactag tgagagaatc ttttgaaggg actcaaacct | 1680 |

| | |
|---|---|
| ttacaagaaa ggatgttttc tgcagatttt gtatccttag accggccatt ggtgggtgag | 1740 |
| gaaccactgt gtttgtctgt gagctttctg ttgtttcctg ggagggaggg gtcaggtggg | 1800 |
| gaaaggggca ttaagatgtt tattggaacc cttttctgtc ttcttctgtt gtttttctaa | 1860 |
| aattcacagg gaagcttttg agcaggtctc aaacttaaga tgtcttttta agaaaaggag | 1920 |
| aaaaaagttg ttattgtctg tgcataagta agttgtaggt gactgagaga ctcagtcaga | 1980 |
| ccctttaat gctggtcatg taataatatt gcaagtagta agaaacgaag gtgtcaagtg | 2040 |
| tactgctggg cagcgaggtg atcattacca aaagtaatca actttgtggg tggagagttc | 2100 |
| tttgtgagaa cttgcattat ttgtgtcctc ccctcatgtg taggtagaac atttcttaat | 2160 |
| gctgtgtacc tgcctctgcc actgtatgtt ggcatctgtt atgctaaagt ttttcttgta | 2220 |
| catgaaaccc tggaagacct actacaaaaa aactgttgtt tggcccccat agcaggtgaa | 2280 |
| ctcattttgt gcttttaata gaaagacaaa tccaccccag taatattgcc cttacgtagt | 2340 |
| tgtttaccat tattcaaagc tcaaaataga atttgaagcc ctctcacaaa atctgtgatt | 2400 |
| aatttgctta attagagctt ctatccctca agcctaccta ccataaaacc agccatatta | 2460 |
| ctgatactgt tcagtgcatt tagccaggag acttacgttt tgagtaagtg agatccaagc | 2520 |
| agacgtgtta aaatcagcac tcctggactg gaaattaaag attgaaaggg tagactactt | 2580 |
| ttctttttt tactcaaaag tttagagaat ctctgtttct ttccatttta aaaacatatt | 2640 |
| ttaagataat agcataaaga ctttaaaaat gttcctcccc tccatcttcc cacacccagt | 2700 |
| caccagcact gtatttctg tcaccaagac aatgatttct tgttattgag gctgttgctt | 2760 |
| ttgtggatgt gtgattttaa ttttcaataa acttttgcat cttggtttaa aagaaa | 2816 |

<210> SEQ ID NO 65
<211> LENGTH: 2816
<212> TYPE: DNA
<213> ORGANISM: human

<400> SEQUENCE: 65

| | |
|---|---|
| tcgttgatat caaagacagt tgaaggaaat gaatttgaa acttcacggt gtgccaccct | 60 |
| acagtactgc cctgacccctt acatccagcg tttcgtagaa acccagctca tttctcttgg | 120 |
| aaagaaagtt attaccgatc caccatgtcc cagagcacac agacaaatga attcctcagt | 180 |
| ccagaggttt tccagcatat ctgggatttt ctggaacagc ctatatgttc agttcagccc | 240 |
| attgacttga actttgtgga tgaaccatca gaagatggtg cgacaaacaa gattgagatt | 300 |
| agcatggact gtatccgcat gcaggactcg gacctgagtg accccatgtg ccacagtac | 360 |
| acgaacctgg ggctcctgaa cagcatggac cagcagattc agaacggctc ctcgtccacc | 420 |
| agtccctata cacagaccca cgcgcagaac agcgtcacgg cgccctcgcc ctacgcacag | 480 |
| cccagctcca ccttcgatgc tctctctcca tcacccgcca tccctccaa caccgactac | 540 |
| ccaggcccgc acagtttcga cgtgtccttc cagcagtcga gcaccgccaa gtcggccacc | 600 |
| tggacgtatt ccactgaact gaagaaactc tactgccaaa ttgcaaagac atgcccatc | 660 |
| cagatcaagg tgatgacccc acctcctcag ggagctgtta tccgcgccat gctgtctac | 720 |
| aaaaaagctg agcacgtcac ggaggtggtg aagcggtgcc caaccatga gctgagccgt | 780 |
| gaattcaacg agggacagat tgcccctcct agtcatttga ttcgagtaga ggggaacagc | 840 |
| catgcccagt atgtagaaga tcccatcaca ggaagacaga gtgtgctggt accttatgag | 900 |
| ccaccccagg ttggcactga attcacgaca gtcttgtaca atttcatgtg taacagcagt | 960 |

```
tgtgttggag ggatgaaccg ccgtccaatt ttaatcattg ttactctgga aaccagagat    1020
gggcaagtcc tgggccgacg ctgctttgag gcccggatct gtgcttgccc aggaagagac    1080
aggaaggcgg atgaagatag catcagaaag cagcaagttt cggacagtac aaagaacggt    1140
gatggtacga agcgcccgtt tcgtcagaac acacatggta tccagatgac atccatcaag    1200
aaacgaagat ccccagatga tgaactgtta tacttaccag tgaggggccg tgagacttat    1260
gaaatgctgt tgaagatcaa agagtccctg gaactcatgc agtaccttcc tcagcacaca    1320
attgaaacgt acaggcaaca gcaacagcag cagcaccagc acttacttca gaaacatctc    1380
ctttcagcct gcttcaggaa tgagcttgtg gagccccgga gagaaactcc aaaacaatct    1440
gacgtcttct ttagacattc caagccccca aaccgatcag tgtacccata gagccctatc    1500
tctatatttt aagtgtgtgt gttgtatttc catgtgtata tgtgagtgtg tgtgtgtgta    1560
tgtgtgtgcg tgtgtatcta gccctcataa acaggacttg aagacacttt ggctcagaga    1620
cccaactgct caaggcaca aagccactag tgagagaatc ttttgaaggg actcaaacct    1680
```

-continued

| | |
|---|---|
| tctctcttga tgcctccatg cattctcagc tcagaatcct ggatgaggag catcccaagg | 360 |
| gaaagtacca tcatggcttg agtgctctga agcccatccg gactacttcc aaacaccagc | 420 |
| acccagtgga caatgctggg cttttttcct gtatgacttt ttcgtggctt tcttctctgg | 480 |
| cccgtgtggc ccacaagaag ggggagctct caatggaaga cgtgtggtct ctgtccaagc | 540 |
| acgagtcttc tgacgtgaac tgcagaagac tagagagact gtggcaagaa gagctgaatg | 600 |
| aagttgggcc agacgctgct tccctgcgaa gggttgtgtg gatcttctgc cgcaccaggc | 660 |
| tcatcctgtc catcgtgtgc ctgatgatca cgcagctggc tggcttcagt ggaccagcct | 720 |
| tcatggtgaa acacctcttg gagtataccc aggcaacaga gtctaacctg cagtacagct | 780 |
| tgttgttagt gctgggcctc ctcctgacgg aaatcgtgcg gtcttggtcg cttgcactga | 840 |
| cttgggcatt gaattaccga accggtgtcc gcttgcgggg ggccatccta accatggcat | 900 |
| ttaagaagat ccttaagtta aagaacatta aagagaaatc cctgggtgag ctcatcaaca | 960 |
| tttgctccaa cgatgggcag agaatgtttg aggcagcagc cgttggcagc ctgctggctg | 1020 |
| gaggacccgt tgttgccatc ttaggcatga tttataatgt aattattctg ggaccaacag | 1080 |
| gcttcctggg atcagctgtt tttatcctct tttacccagc aatgatgttt gcatcacggc | 1140 |
| tcacagcata tttcaggaga aaatgcgtgg ccgccacgga tgaacgtgtc cagaagatga | 1200 |
| atgaagttct tacttacatt aaatttatca aaatgtatgc ctgggtcaaa gcattttctc | 1260 |
| agagtgttca aaaaatccgc gaggaggagc gtcggatatt ggaaaaagcc gggtacttcc | 1320 |
| agggtatcac tgtgggtgtg gctcccattg tggtggtgat tgccagcgtg gtgaccttct | 1380 |
| ctgttcatat gaccctgggc ttcgatctga cagcagcaca ggctttcaca gtggtgacag | 1440 |
| tcttcaattc catgactttt gctttgaaag taacaccgtt ttcagtaaag tccctctcag | 1500 |
| aagcctcagt ggctgttgac agatttaaga gtttgtttct aatggaagag gttcacatga | 1560 |
| taaagaacaa accagccagt cctcacatca agatagagat gaaaaatgcc accttggcat | 1620 |
| gggactcctc ccactccagt atccagaact cgcccaagct gaccccccaaa atgaaaaaag | 1680 |
| acaagagggc ttccagggc aagaaagaga aggtgaggca gctgcagcgc actgagcatc | 1740 |
| aggcggtgct ggcagagcag aaaggccacc tcctcctgga cagtgacgag cggcccagtc | 1800 |
| ccgaagagga agaaggcaag cacatccacc tgggccacct cgcgcttacag aggacactgc | 1860 |
| acagcatcga tctggagatc aagagggta aactggttgg aatctgcggc agtgtgggaa | 1920 |
| gtggaaaaac ctctctcatt tcagccattt taggccagat gacgcttcta gagggcagca | 1980 |
| ttgcaatcag tggaaccttc gcttatgtgg cccagcaggc ctggatcctc aatgctactc | 2040 |
| tgagagacaa catcctgttt gggaaggaat atgatgaaga agatacaac tctgtgctga | 2100 |
| acagctgctg cctgaggcct gacctggcca ttcttcccag cagcgacctg acggagattg | 2160 |
| gagagcgagg agccaacctg agcggtgggc agcgccagag gatcagcctt gcccgggcct | 2220 |
| tgtatagtga caggagcatc tacatcctgg acgaccccct cagtgccttta gatgcccatg | 2280 |
| tgggcaacca catcttcaat agtgctatcc ggaaacatct caagtccaag acagttctgt | 2340 |
| ttgttaccca ccagttacag tacctggttg actgtgatga agtgatcttc atgaaagagg | 2400 |
| gctgtattac ggaaagaggc acccatgagg aactgatgaa tttaaatggt gactatgcta | 2460 |
| ccatttttaa taacctgttg ctgggagaga caccgccagt tgagatcaat tcaaaaaagg | 2520 |
| aaaccagtgg ttcacagaag aagtcacaag caagggtcc taaaacagga tcagtaaaga | 2580 |
| aggaaaaagc agtaaagcca gaggaagggc agcttgtgca gctggaagag aaagggcagg | 2640 |

| | |
|---|---|
| gttcagtgcc ctggtcagta tatggtgtct acatccaggc tgctgggggc cccttggcat | 2700 |
| tcctggttat tatggccctt ttcatgctga atgtaggcag caccgccttc agcacctggt | 2760 |
| ggttgagtta ctggatcaag caaggaagcg ggaacaccac tgtgactcga gggaacgaga | 2820 |
| cctcggtgag tgacagcatg aaggacaatc ctcatatgca gtactatgcc agcatctacg | 2880 |
| ccctctccat ggcagtcatg ctgatcctga aagccattcg aggagttgtc tttgtcaagg | 2940 |
| gcacgctgcg agcttcctcc cggctgcatg acgagctttt ccgaaggatc cttcgaagcc | 3000 |
| ctatgaagtt ttttgacacg acccccacag ggaggattct caacaggttt tccaaagaca | 3060 |
| tggatgaagt tgacgtgcgg ctgccgttcc aggccgagat gttcatccag aacgttatcc | 3120 |
| tggtgttctt ctgtgtggga atgatcgcag gagtcttccc gtggttcctt gtggcagtgg | 3180 |
| ggccccttgt catcctcttt tcagtcctgc acattgtctc cagggtcctg attcgggagc | 3240 |
| tgaagcgtct ggacaatatc acgcagtcac ctttcctctc ccacatcacg tccagcatac | 3300 |
| agggccttgc caccatccac gcctacaata aagggcagga gtttctgcac agataccagg | 3360 |
| agctgctgga tgacaaccaa gctccttttt ttttgtttac gtgtgcgatg cggtggctgg | 3420 |
| ctgtgcggct ggacctcatc agcatcgccc tcatcaccac cacggggctg atgatcgttc | 3480 |
| ttatgcacgg gcagattccc ccagcctatg cgggtctcgc catctcttat gctgtccagt | 3540 |
| taacggggct gttccagttt acggtcagac tggcatctga cagaagct cgattcacct | 3600 |
| cggtggagag gatcaatcac tacattaaga ctctgtcctt ggaagcacct gccagaatta | 3660 |
| agaacaaggc tccctcccct gactggcccc aggagggaga ggtgaccttt gagaacgcag | 3720 |
| agatgaggta ccgagaaaac ctccctcttg tcctaaagaa agtatccttc acgatcaaac | 3780 |
| ctaaagagaa gattggcatt gtggggcgga caggatcagg gaagtcctcg ctggggatgg | 3840 |
| ccctcttccg tctggtggag ttatctggag gctgcatcaa gattgatgga gtgagaatca | 3900 |
| gtgatattgg ccttgccgac ctccgaagca aactctctat cattcctcaa gagccggtgc | 3960 |
| tgttcagtgg cactgtcaga tcaaatttgg accccttcaa ccagtacact gaagaccaga | 4020 |
| tttgggatgc cctggagagg acacacatga aagaatgtat tgctcagcta cctctgaaac | 4080 |
| ttgaatctga agtgatggag aatggggata acttctcagt gggggaacgg cagctcttgt | 4140 |
| gcatagctag agccctgctc cgccactgta agattctgat tttagatgaa gccacagctg | 4200 |
| ccatggacac agagacagac ttattgattc aagagaccat ccgagaagca tttgcagact | 4260 |
| gtaccatgct gaccattgcc catcgcctgc acacggttct aggctccgat aggattatgg | 4320 |
| tgctggccca gggacaggtg gtggagtttg acaccccatc ggtccttctg tccaacgaca | 4380 |
| gttcccgatt ctatgccatg tttgctgctg cagagaacaa ggtcgctgtc aagggctgac | 4440 |
| tcctccctgt tgacgaagtc ttttttcttt agagcattgc cattccctgc ctggggcggg | 4500 |
| cccctcatcg cgtcctccta ccgaaacctt gcctttctcg attttatctt tcgcacagca | 4560 |
| gttccggatt ggcttgtgtg tttcactttt agggagagtc atatttgat tattgtattt | 4620 |
| attccatatt catgtaaaca aaatttagtt tttgttctta attgcactct aaaaggttca | 4680 |
| gggaaccgtt attataattg tatcagaggc ctataatgaa gctttatacg tgtagccтaтa | 4740 |
| tctatatata attctgtaca tagcctatat ttacagtgaa aatgtaagct gtttatttta | 4800 |
| tattaaaata agcactgtgc taataacagt gcatattcct ttctatcatt tttgtacagt | 4860 |
| tgctgtact agagatctgg ttttgctatt agactgtagg aagagtagca тттcaтттcтт | 4920 |
| ctctagctgg tggtttcacg gtgccaggtt ttctgggtgt ccaaaggaag acgtgtggca | 4980 |
| atagtgggcc ctccgacagc cccctctgcc gcctccccac agccgctcca ggggtggctg | 5040 |

```
gagacgggtg ggcggctgga gaccatgcag agcgccgtga gttctcaggg ctcctgcctt      5100
ctgtcctggt gtcacttact gtttctgtca ggagagcagc ggggcgaagc ccaggcccct      5160
tttcactccc tccatcaaga atggggatca cagagacatt cctccgagcc ggggagtttc      5220
tttcctgcct tcttcttttt gctgttgttt ctaaacaaga atcagtctat ccacagagag      5280
tcccactgcc tcaggttcct atggctggcc actgcacaga gctctccagc tccaagacct      5340
gttggttcca agccctggag ccaactgctg cttttgagg tggcactttt tcatttgcct       5400
attcccacac ctccacagtt cagtggcagg gctcaggatt cgtgggtct gttttccttt       5460 ctcaccgcag tcgtcgcaca gtctctctct ctctctcccc tcaaagtctg caactttaag      5520
cagctcttgc taatcagtgt ctcacactgg cgtagaagtt tttgtactgt aaagagacct      5580
acctcaggtt gctggttgct gtgtggtttg gtgtgttccc gcaaacccc tttgtgctgt       5640 ggggctggta gctcaggtgg gcgtggtcac tgctgtcatc agttgaatgg tcagcgttgc      5700
atgtcgtgac caactagaca ttctgtcgcc ttagcatgtt tgctgaacac cttgtggaag      5760
caaaaatctg aaaatgtgaa taaaattatt ttggattttg taaaaaaaaa aaaaaaaaa      5820 aaaaaaaaaa aaaaaaaa                                                    5838

<210> SEQ ID NO 67
<211> LENGTH: 1181
<212> TYPE: DNA
<213> ORGANISM: human

<400> SEQUENCE: 67
ggcacgaggc ccgggccccc caaagtcccg gccgggccga gggtcggcgg ccgccggcgg        60
gccgggcccg cgcacagcgc cgcatgtac aacatgatgg agacggagct gaagccgccg       120
ggcccgcagc aaacttcggg gggcggcggc ggcaactcca ccgcggcggc ggccggcggc       180
aaccagaaaa acagcccgga ccgcgtcaag cggcccatga atgccttcat ggtgtggtcc       240
cgcgggcagc ggcgcaagat ggcccaggag aaccccaaga tgcacaactc ggagatcagc       300
aagcgcctgg gcgccgagtg gaaacttttg tcggagacgg agaagcggcc gttcatcgac       360
gaggctaagc ggctgcgagc gctgcacatg aaggagcacc cggattataa ataccggccc       420
cggcggaaaa ccaagacgct catgaagaag gataagtaca cgctgcccgg cgggctgctg       480
gcccccggcg gcaatagcat ggcgagcggg gtcggggtgg gcgccggcct gggcgcgggc       540
gtgaaccagc gcatggacag ttacgcgcac atgaacggct ggagcaacgg cagctacagc       600
atgatgcagg accagctggg ctacccgcag cacccgggcc tcaatgcgca cggcgcagcg       660
cagatgcagc ccatgcaccg ctacgacgtg agcgccctgc agtacaactc catgaccagc       720
tcgcagacct acatgaacgg ctcgcccacc tacagcatgt cctactcgca gcagggcacc       780
cctggcatgg ctcttggctc catgggttcg gtggtcaagt ccgaggccag ctccagcccc       840
cctgtggtta cctcttcctc ccactccagg gcgccctgcc aggccgggga cctccgggac       900
atgatcagca tgtatctccc cggcgccgag gtgccggaac ccgccgcccc cagcagactt       960
cacatgtccc agcactacca gagcggcccg gtgcccggca cggccattaa cggcacactg      1020
cccctctcac acatgtgagg gccggacagc gaactggagg ggggagaaat tttcaaagaa      1080
aaacgaggga atgggaggg gtgcaaaaga ggagagtaag aaacagcatg gagaaaaccc       1140
ggtacgctca aaaaaaaaa aaaaaaaaa aaaaaaaaa a                             1181

<210> SEQ ID NO 68
```

<211> LENGTH: 4755
<212> TYPE: DNA
<213> ORGANISM: human

<400> SEQUENCE: 68

```
gctgctctcg ttcgcttggc tcagctcagc tcagctcagc gcagctccgc ggccgccaag      60
ccgaggcggg cacggtctcc gagtcgcgga cgccagctcc gagctccctc tctccgccgc     120
gcctccgcca ggtcgcgcct tcgtcgggac cacttcgggc aggagtcgcg tggcgaaggc     180
ctgcggccgc ggcacaaagt tggggccgc gaagatgagg ctgtccccgg cgccctgaa      240
gctgagccga actccggcac tgctggccct ggcgctgccc ctggccgcgg cgctggcctt     300
ctccgacgag accctggaca aagtgcccaa gtcagagggc tactgcagcc gtatcctgcg     360
cgcccagggc acgcggcgcg agggctacac cgagttcagc ctccgcgtgg agggcgaccc     420
cgacttctac aagccgggaa ccagctaccg cgtaacactt tcagctgctc ctccctccta     480
cttcagagga ttcacattaa ttgccctcag agaacagga gaggtgata aggaagaaga      540
ccatgctggg accttccaga tcatagacga agaagaaact cagtttatga gcaattgccc     600
tgttgcagtc actgaaagca ctccacgagg aggacccgg atccaggtgt tttggatagc     660
accaccagcg ggaacaggct gcgtgattct gaaggccagc atcgtacaaa aacgcattat     720
ttatttttcaa gatgagggct ctctgaccaa gaaactttgt gaacaagatt ccacatttga     780
tggggtgact gacaaaccca tcttagactg ctgtgcctgc ggaactgcca agtacagact     840
cacattttat gggaattggt ccgagaagac cacccaaag gattaccctc gtcgggccaa     900
ccactggtct gcgatcatcg gaggatccca ctccaagaat tatgtactgt gggaatatgg     960
aggatatgcc agcgaaggcg tcaaacaagt tgcagaattg gctcacccg tgaaaatgga    1020
ggaagaaatt cgacaacaga gtgatgaggt cctcaccgtc atcaaagcca agcccagtg    1080
gccagcctgg cagcctctca cgtgagagc agcaccttca gctgaatttt ccgtggacag    1140
aacgcgccat ttaatgtcct tcctgaccat gatgggccct agtccgact ggaacgtagg    1200
cttatctgca gaagatctgt gcaccaagga atgtggctgg gtccagaagg tggtgcaaga    1260
cctgattccc tgggacgctg gcaccgacag cggggtgacc tatgagtcac ccaacaaacc    1320
caccattccc caggagaaaa tccggccccct gaccagcctg gaccatcctc agagtccttt    1380
ctatgaccca gagggtgggt ccatcactca gtagccaga gttgtcatcg agagaatcgc    1440
acggaagggt gaacaatgca atattgtacc tgacaatgtc gatgatattg tagctgacct    1500
ggctccagaa gagaaagatg aagatgacac ccctgaaacc tgcatctact ccaactggtc    1560
cccatggtcc gcctgcagct cctccacctg tgacaaggc aagaggatgc gacagcgcat    1620
gctgaaagca cagctggacc tcagcgtccc ctgccctgac acccaggact ccagccctg    1680
catgggccct ggctgcagtg acgaagacgg ccccacctgc accatgtccg agtggatcac    1740
ctggtcgccc tgcagcatct cctgcggcat gggcatgagg tcccgggaga gtatgtgaa    1800
gcagttcccg gaggacggct ccgtgtgcac gctgcccact gaggaaacgg agaagtgcac    1860
ggtcaacgag gagtgctctc ccagcagctg cctgatgacc gagtggggcg agtgggacga    1920
gtacagcgcc acctgcggca tgggcatgaa gaagcggcac cgcatgatca agatgaaccc    1980
cgcagatggc tccatgtgca aagccgagac atcacaggca gagaagcgca tgatgccaga    2040
gtgccacacc atcccatgct tgctgtcccc atggtccgag tggagtgact gcagcgtgac    2100
ctgcgggaag gcatgcgaa cccgacagcg gatgctcaag tctctggcag aacttggaga    2160
ctgcaatgag gatctggagc aggtggagaa gtgcatgctc cctgaatgcc ccattgactg    2220
```

-continued

```
tgagctcacc gagtggtccc agtggtcgga atgtaacaag tcatgtggga aaggccacgt    2280
gattcgaacc cggatgatcc aaatggagcc tcagtttgga ggtgcaccct gcccagagac    2340
tgtgcagcga aaaaagtgcc gcatccgaaa atgccttcga aatccatcca tccaaaagct    2400
acgctggagg gaggcccgag agagccggcg gagtgagcag ctgaaggaag agtctgaagg    2460
ggagcagttc ccaggttgta ggatgcgccc atggacggcc tggtcagaat gcaccaaact    2520
gtgcggaggt ggaattcagg aacgttacat gactgtaaag aagagattca aaagctccca    2580
gtttaccagc tgcaaagaca agaaggagat cagagcatgc aatgttcatc cttgttagca    2640
agggtacgag ttccccaggg ctgcactcta gattccagag tcaccaatgg ctggattatt    2700
tgcttgttta agacaattta aattgtgtac gctagttttc attttgcag tgtggttcgc     2760 ccagtagtct tgtggatgcc agagacatcc tttctgaata cttcttgatg ggtacaggct    2820
gagtggggcg ccctcacctc cagccagcct cttcctgcag aggagtagtg tcagccacct    2880
tgtactaagc tgaaacatgt ccctctggag cttccacctg gccagggagg acggagactt    2940
tgacctactc cacatggaga ggcaaccatg tctggaagtg actatgcctg agtcccaggg    3000
tgcggcaggt aggaaacatt cacagatgaa gacagcagat tcccccacatt ctcatctttg    3060 gcctgttcaa tgaaaccatt gtttgcccat ctcttcttag tggaacttta ggtctctttt    3120
caagtctcct cagtcatcaa tagttcctgg ggaaaaacag agctggtaga cttgaagagg    3180
agcattgatg ttgggtggct tttgttcttt cactgagaaa ttcggaatac atttgtctca    3240
cccctgatat tggttcctga tgccccccca acaaaaataa ataaataaat tatggctgct    3300
ttatttaaat ataaggtagc tagttttttac acctgagata ataataaagc ttagagtgta    3360
ttttctcctt gcttttgggg gttcagagga gtatgtacaa ttcttctggg aagccagcct    3420
tctgaacttt ttggtactaa atccttattg gaaccaagac aaaggaagca aaattggtct    3480
ctttagagac caatttgcct aaattttaaa atcttcctac acacatctag acgttcaagt    3540
ttgcaaatca gttttagca agaaaacatt tttgctatac aaacatttgg ctaagtctgc     3600
ccaaagcccc cccaatgcat tccttcaaca aaatacaatc tctgtacttt aaagttattt    3660
tagtcatgaa attttatatg cagagagaaa aagttaccga gacagaaaac aaatctaagg    3720
gaaaggaata ttatgggatt aagctgagca agcaattctg gtggaaagtc aaacctgtca    3780
gtgctccaca ccagggctgt ggtcctccca gacatgcata ggaatggcca caggtttaca    3840
ctgccttccc agcaattata agcacaccag attcagggag actgaccacc aagggatagt    3900
gtaaaaggac attttctcag ttgggtccat cagcagtttt tcttcctgca tttattgttg    3960
aaaactattg tttcatttct tcttttatag gccttattac tgcttaatcc aaatgtgtac    4020
cattggtgag acacatacaa tgctctgaat acactacgaa tttgtattaa acacatcaga    4080
atatttccaa atacaacata gtatagtcct gaatatgtac ttttaacaca agagagacta    4140
ttcaataaaa actcactggg tctttcatgt ctttaagcta agtaagtgtt cagaaggttc    4200 tttttttatat tgtcctccac ctccatcatt ttcaataaaa gatagggctt ttgctcccctt   4260 gttcttggag ggaccattat tacatctctg aactaccttt gtatccaaca tgttttaaat    4320
ccttaaatga attgctttct cccaaaaaaa gcacagtata aagaaacaca agatttaatt    4380 attttctac ttgggggaa aaaagtcctc atgtagaagc acccactttt gcaatgttgt      4440
tctaagctat ctatctaact ctcagcccat gataaagttc cttaagctgg tgattcctaa    4500
tcaaggacaa gccaccctag tgtctcatgt ttgtatttgg tcccagttgg gtacatttta    4560
```

```
aaatcctgat tttggagact taaaaccagg ttaatggcta agaatgggta acatgactct    4620
tgttggattg ttatttttttg tttgcaatgg ggaatttata agaagcatca agtctctttc    4680
ttaccaaagt cttgttaggt ggtttatagt tcttttggct aacaaatcat tttggaaata    4740
aagatttttt actac                                                     4755
```

<210> SEQ ID NO 69
<211> LENGTH: 6841
<212> TYPE: DNA
<213> ORGANISM: human

<400> SEQUENCE: 69

```
gccggagggc gcccgagggg ccccgggccg cggcgctcag ggcccgggcg gccggcggcg      60
gccccggggc tgggggagt ccagcccgga tattgagtgc agccattgag aaaagccaaa     120
ctcttgtgtg tgcgcgtctc gatagccccc aagatggccg ccaatgtggg atcgatgttt     180
caatattgga agcgatttga tctacggcga ctccagaagg agcttaattc cgtcgcttct     240
gagctgtctg cacggcagga ggagagtgaa cattctcata acatttaat tgaactccgc      300 cgggaattta agaaaaatgt acctgaggaa atcagagaga tggtggctcc tgtattaaaa    360
agcttccaag ccgaggtggt ggcccttagt aagagaagtc aggaggcgga ggctgctttt     420
ctgagtgttt acaagcaatt aattgaagca ccagaccccg tgcctgtgtt tgaggcggca    480
cgcagcctag acgacagact gcagccccccc agctttgacc ccagtgggca gccccggcga    540
gacctccaca cttcgtggaa gaggaacccc gagctcctca gccccaaaga gcagagagag    600
gggacgtcgc ctgccgggcc cacgctgacc gagggaagcc gcctcccagg cattcccggg    660
aaagccctcc tgacagaaac cttgctgcag agaaatgagg cggaaaaaca aaagggcctt    720
caagaagtac agatcacttt ggcggccaga ctgggggagg cagaggagaa aatcaaagtc    780
ctacattcag cgctaaaggc tacgcaggca gagctgctag agctgcggcg gaagtacgac    840
gaggaggcag catccaaggc agatgaagtc ggcctgatca tgaccaacct ggagaaagct    900
aatcagcgag ctgaggctgc ccagcgggag gtggaaagtc tccgggaaca gctggcctct    960
gtcaacagct ccatccgcct ggcttgctgc tctccccagg ggcccagtgg ggataaggtg   1020
aacttcactc tgtgctcggg ccctcggctg gaggccgcgc tggcctccaa ggacagggag   1080
atcctgcggc tgctgaagga cgtgcagcac ctccagagct cactgcagga gctggaggag   1140
gcatccgcca accagatcgc cgacctggag cggcagctca cggccaagtc cgaggccata   1200
gaaaagctgg aagagaagct ccaggcccag tctgactatg aggaaattaa aacggagctg   1260
agcatcctga aagccatgaa gctggcctcc agcacctgca gcctccccca gggcatggcc   1320
aagcctgaag actcactgct tattgcaaag gaggccttct tccccacgca gaaattcctt   1380
ctggagaagc ccagcctcct ggccagccct gaggaagacc catcagagga cgattccatc   1440
aaggattcac tgggcacgga gcagtcctac ccctcccctc agcagctccc acctccacca   1500
gggccagaag accccctgtc tccagccccc gggcagcccc tgctgggccc cagcttgggg   1560
cctgacggca ctcggacttt ctcgctgtcc cccttcccca gctggcatc aggggagaga   1620 ctgatgatgc cccagccgc cttcaaggga gaggcgggcg gcctgctggt gttcccccca    1680
gccttctatg gcgccaagcc ccccacagcc cctgccaccc cggcccctgg ccctgagcca   1740
ctgggcggtc ctgagcccgc ggatggtggt gggggcggag cggcggggcc cggggcagag   1800
gaggagcagc tggacacggc agagatcgcc ttccaggtga aggagcagct gctgaaacac   1860
aacatcgggc agcgggtgtt tgggcattac gtgctggggc tgtcgcaggg ctcggtcagc   1920
```

```
gagatcctag cccggcccaa gccctggcgc aagctcacgg tgaagggcaa ggagcccttc    1980
atcaagatga agcagttcct gtcggatgag cagaatgtac tggcgctcag gaccatccaa    2040
gtgcggcagc gaggcagcat cacccccgaga atccgcacgc ctgagacagg ctcagacgac    2100
gccatcaaga gcattctaga gcaggccaag aaggagatcg agtcgcagaa gggcggcgag    2160
cccaagacct cggtggcccc gctgagcatc gccaacggca cgaccccgc cagcacctcg    2220 gaggacgcca tcaagagcat cctggagcag gcacgccgtg agatgcaggc gcaacagcag    2280
gcgctgctgg agatggaggt ggcgcccagg ggccgctcgg tgcccccctc gccccccggag    2340 cggccatcac tggccaccgc gagccagaac ggggcccccgg ccttggtgaa gcaggaggag    2400
ggcagcgggg ccccgcgca ggcgccgctc ccggtcctgt cccccgccgc cttcgtgcag    2460
agcatcatcc gcaaggtcaa gtccgagatc ggcgacgccg gctacttcga ccaccactgg    2520
gcctccgacc gcggcctgct cagccgcccc tacgcctccg tgtcgccctc gctgtcctcc    2580
tcctcctcct ctggctactc tggccagccc aacggccgcg cctggccccg cggggacgag    2640
gcccctgtgc cccccgagga cgaggcggcg gcagggcgg aggacgaacc ccccaggacg    2700
ggcgagctca aggctgaggg gcgcgacgcc gaggcgggcg cgcggctgcc ctactacccg    2760
gcctacgtgc cgcgcaccct gaagcccacc gtgccgccgc tgaccccccga gcagtacgag    2820 ctgtacatgt accgtgaggt agacacgctg gagctcaccc gccaggtcaa ggagaagctg    2880
gccaagaacg gcatctgcca gaggatcttc ggggagaagg tgctgggcct gtcacagggc    2940
agcgtgagcg acatgctgtc ccggccgaag ccatggagca agctgacgca gaaggggcgg    3000
gagcccttca tccgcatgca gctgtggctc tctgaccagc tcggccaggc agtgggccag    3060
cagcctggtg cctcccaggc cagtcccaca gaaccaaggt cctcaccatc ccacccccc    3120 agccccacag agcctgagaa gagctcccag gagccgttga gcctgtccct ggagagcagc    3180
aaggagaacc agcagccaga gggccgctcc agctcctcgt tgagcgggaa gatgtactca    3240
ggcagccagg ccccaggggg catccaggag atcgtggcca tgtcccccga gctggacacg    3300
tactccatca ccaagagggt gaaggaggtc ctcacagaca caatctaggg gcagcggctg    3360
tttggggaaa gcatcctggg tctgacacag gctccgtgt ctgacctgct gtcccggccc    3420
aaaccctggc acaagctgag cctgaagggg cgggagcctt ttgtccgcat gcagctgtgg    3480
ctcaatgacc cccataacgt ggagaagctg agggatatga agaagctgga gaagaaagcc    3540
tacctgaaac gtcgctatgg cctcatcagc accggctcag acagtgagtc cccggccacc    3600
cgctcagagt gccccagccc ctgcctgcag ccccaggacc tgagcctcct gcagatcaag    3660
aagcccggga tggtgctggc acccgaggag aaggaggcac tgcggaaggc ctatcagctg    3720
gaaccctacc cctcgcagca gaccatcgag ctcctctcct tccagctcaa cctcaagacc    3780
aacaccgtca tcaactggtt ccacaactac aggtcccgga tgcgccggga gatgttggtg    3840
gaggggaccc aggatgagcc agaccttgat ccaagcgggg tcctggaat cctaccgcca    3900 ggccactccc acccagaccc cacccccgcag agccctgact ctgagactga ggaccagaag    3960
ccaaccgtga aggaactgga gcttcaggag ggccctgagg agaacagcac acccctgacc    4020
acccaggaca aggcccaagt gaggatcaag caggaacaga tggaggagga tgctgaggaa    4080
gaggcaggca gccagcccca ggactcaggg gagctggaca aaggccaagg tcccccaaa    4140 gaggagcatc ccgaccctcc gggtaatgat ggactcccaa aagtggctcc cgggcccctc    4200
cttccaggtg gatccacccc agactgtccc tcacttcatc cccaacagga gagtgaggcc    4260
```

-continued

```
ggggagcgac ttcacccgga ccctttaagt tttaagtcag cctcagagtc ctcacgctgc   4320
agcctggagg tgtcactgaa ctcgcccctcg gccgcctcct caccaggcct catgatgtct   4380
gtgtcacctg tcccctcctc ctcagctccc atctccccat ccccacctgg cgccccccct   4440
gccaaagtgc cgagtgccag ccccactgct gacatggctg gagccttgca ccccagtgcc   4500
aaggtgaacc ccaacttgca gcggcggcat gagaagatgg ccaatctgaa caacatcatt   4560
taccgactag agcgggctgc caatcgggag gaggccctgg agtgggagtt ctgaaggcag   4620
ggtgaggggg caagggacat accctggtaa ctaccttcct tctcgcactt actctcctca   4680
acaggatggg gtaagggagg gaggaactca accatcaaaa tgtggacagc aatgttatgc   4740
cgtttacgtt ttttgttgta atcctagttc tatgaagctg tgtgagcagg tgggtcaaat   4800
gccattgcct ccacttttct gcaccccct gctcctcttc accctgaccc ctctgcagga   4860
ggcagaagca aaatggcacc acatattcac ctgaaaactc caaactcttt tagaaaaata   4920
aataaatatt tatagacctc ttttagatat tttaataaag gatcctttgg aatttatccc   4980
agctgatgct gttttgatat tacagagagt tataaaatca ggatgctgtc acaactgttg   5040
cgaagtatac actgaagttg tgtcgttttt gccactagat gagattaaaa gaagacaatt   5100
attcaaagcc atcacaaaac actataagac tgaccaaaat ttagataacc tttgaaccac   5160
gattttttc cacatctgtc tgtgagacac agcgcaatgc tactgcccctt ccagaaactg   5220
tgctaaaaag agaaagtcca aaagactcta acaaaaacc tcgacgccgt tgaggatgtg   5280
tttcattctg gtggtctgtt ttgcaagctt gataacagaa tgtccgtgcc attgtaaatg   5340
ttgtagagat gtgggccgtg gcccaaccgt cctatatgag atgtagcatg gtacagaaca   5400
aactgcttac acaggtctca ctagttagaa acctgtgggc catggaggtc agacatccat   5460
cttgtccatc tataggcaag aagtgtttcc agatcctttg gaaaggtggg catggggcag   5520
gtgcttggag agtggcgttt gagccagagc gaccccattt cccgtgtgaa ccataggcac   5580
aacccaggaa gtttccccac ttgtaggagt gtgggtattc cagagcaaga ctgtggccac   5640
catcttcccc tcttggtgtt ttccgaaagt gacagtgttg gtcatcccat gaccactgaa   5700
gcttagtaac cagcgccaaa aagtagattc atcaaactag agaccccagc tccccttctc   5760
gccatcttct ttctcaagtt gaccgtggtg ctgtttctgg aaggcatctg caactccaag   5820
tccatgcaga actctggaag gccaagttca tcgcagcatg ttcaccatat cccagcctcc   5880
aaatctatcc tcctaccttc caacgcatga cctgttgggg agcagagact taaccccccaa   5940
ctcagaggaa cccttcctcc agcgtctttg gcatggtttc tagggtgaga gttcccaatt   6000
tggatagaac ggccaccata ttggttactg aatctctctc ccttgttttt attacgtttc   6060
cttttcaaa ctgtccatgg gaaggctgaa ttgagtgact cccagaatg aagatgagaa   6120
ggtgaatata atcaatgcca atgtaatgcc agcgggtgag atggccgatg gaggtttcaa   6180
agatgtagct agcattttga aaccatatgg gcaaaacccg gcaaccagaa ggggacagat   6240
aaggaccgtt ccagaaatcc caactctcac acccagccca ggctgcagtc tccacaccaa   6300
acagtcaaca aaacacaaac cctgaaggaa aaccttttcc atacacccag gctatgcatt   6360
gaagagtttt ccactgtata cattttttatc cagatgaagg tatttttata ttttgacaat   6420
aggaaacagt gaccatttc agagtaatca aatctgaac aaatgaaaca tcttttagcc   6480
accaccaccc tgttgcaatt aagacaaccg tggggaaca caccactttt tactgttgaa   6540
accaacacaa cgttgaaatc caggcttata cgcagactcc gattcctaga gaactaaatt   6600
tggctttagt gtgacgggat ttgattaagc acttagtata gtcttttgaa cacggaaatc   6660
```

```
ctgttgtact taaagctagc ggacccgtga acaactttgt caggttcacg tcctataacg    6720
gttaaaaaac acacacacac atacacaaac cgtttctatg agagattgat gaactttgtt    6780
taaaatttta aaaaaggaa cacgttctgt aaacgagtcg ctaaatacag aattgtataa     6840
t                                                                    6841

<210> SEQ ID NO 70
<211> LENGTH: 443
<212> TYPE: DNA
<213> ORGANISM: human

<400> SEQUENCE: 70 ttttttttttt tttttccatt aacccaacac aagtttatttt actaagtcaa gtcaaactga    60
ggagtatttg tttctttggt agttggtaga caaagaatac atatacatat tctatttccc    120
attaagcatt cgatcatgtt acaaaacaat ggcctagaga actatcattg aagatttacc    180
aaatctgcct gaagcaaaat gtgataaact gcagaaatgg tggagaatga cactggaagt    240
cataaagttg attctcaaac acgggtttga actgcatagg accgcttata tgcatatttt    300
gataaatata ttgaaaattt ttttggaaat ttgcaacaat ttaaaaaact tgcagatgca    360
ccatgtagct tagaaatact gaaaaactaa gaaaaaggtg tgtcatgaat tcatataata    420
tatgtagaca ctagtctatt tta                                            443

<210> SEQ ID NO 71
<211> LENGTH: 2432
<212> TYPE: DNA
<213> ORGANISM: human

<400> SEQUENCE: 71
ggcgagtggc gagtggcgag tgtcagggg gcggccggcg ggggcggggc ggccggagga      60
ggcgttggca gcgggctcgg acccacgcgg cgccgcggcc cgcctggcct gcagcgctcc    120
cacccccggc ggcggcacga tgcccttga cttcaggagg tttgacatct acaggaaggt    180
gcccaaggac cttacgcagc caacgtacac cggggccatt atctccatct gctgctgcct    240
cttcatcctc ttcctcttcc tctcggagct caccggattt ataacgacag aagttgtgaa    300
cgagctctat gtcgatgacc cagacaagga cagcggtggc aagatcgacg tcagtctgaa    360
catcagttta cccaatctgc actgcgagtt ggttgggctt gacattcagg atgagatggg    420
caggcacgaa gtgggccaca tcgacaactc catgaagatc ccgctgaaca tgggggcagg    480
ctgccgcttc gagggcagt tcagcatcaa caaggtcccc ggcaacttcc acgtgtccac    540
acacagtgcc acagcccagc cacagaaccc agacatgacg catgtcatcc acaagctctc    600
ctttggggac acgctacagg tccagaacat ccacggagct ttcaatgctc tcgggggagc    660
agacagactc acctccaacc ccctggcctc ccacgactac atcctgaaga ttgtgcccac    720
ggtttatgag acaagagtg gcaagcagcg gtactcctac cagtacacgg tggccaacaa    780
ggaatacgtc gcctacagcc acacggggcg catcatccct gcaatctggt tccgctacga    840
cctcagcccc atcacggtca agtacacaga gagacggcag ccgctgtaca gattcatcac    900
cacgatctgt gccatcattg gcgggacctt caccgtcgcc ggcatcctgg actcatgcat    960
cttcacagcc tctgaggcct ggaagaagat ccagctgggc aagatgcatt gacgccacac   1020
ccagcctaat ggccgaggac cctgggcatc gccagccttg cctccagtgc cctgtctcct   1080
ttggccctca atctggtccc aaatctggct gtgtcccaaa gggtgtgtgg gaagtggggg   1140
```

```
gaaagtagag gatggctcga tgttttgcag ctacctcttt tccccgtgtt tcttttttaga   1200 caaattacac tgcctgaagt tgcagttccc ctttccctgg ggagcccaa gaacagagtc    1260 aggcaagggg tggggagtcc agggatcttg ggaccctc ctaggagagc tgcagtctct     1320
tccctcaggg gaacatccca gaatgcatat cgatcagctc tcagccaggc ttcgacaatc   1380
tcgcagcccc cactaggtgg acacattaat gatttggttt ctcccctggg cagccaacct   1440
gccccagagg caccagacct gggctttcag ctttgggacc aggctgccca aaggtactcc   1500
tttatacacc cggcaccttc cacgaaagat ggtacttccc aagcaagccc ctatgatttg   1560
tcactataga tggaaccctg acttctgccc catcccttcc tgcccaacct agaacccagg   1620
cctcaagtct ttaccccacc cctttcttgt tcttccaaga agcagatgcc cagttgctca   1680
gcagcagcgg tagagacttg aatctgccca ccagtcacaa ggcgggtcac agattcctct   1740
tcctctcttc tcctcgttcc tctgaaccct ccaccaatgt gcctcagcct gtgtgctgtg   1800
tggcaacagc attctggttc ccactgccaa gatctcccac cactctgctg ggatctgcag   1860
tggcagggag tgggggttgt gtaaagggga agtcatcttt tgagatccag atagacatgg   1920
tttgtgcact tacgtccaga tgggaagcat ccttcctgca accctaaaat aatcatgcag   1980
cctctcagac ggacgccatc ggtcccaagg ccttaggtgg aggaagcaaa gcaggccagg   2040
cctgtcctgt ccgtggacct ctaccttctg gactccctac gggtgcagag cacttgggtt   2100
tctctacagc catcgtggcc cacttgacac tgtgctcctc catcagctgg tcacatgcca   2160
acacgttccc agcccctgag gcagctccag ggtgccccac ctgctcctga ggtgggtccc   2220
taccctgctg ctcctcttca tcctttccct tttgtcctga aagggaggag caatggtcca   2280
ggcattaatt ccacccaggg aattttagct atgccctcat gtcccaggga gagagccaca   2340
cgcctgtttt ccatttatag caagattgtt tgcatacttt tgtaatgaag gggagtgtcc   2400
agtggaagga tttttaaaat tatcttatgg at                                 2432
```

<210> SEQ ID NO 72
<211> LENGTH: 2782
<212> TYPE: DNA
<213> ORGANISM: human

<400> SEQUENCE: 72

```
gcggccgcgg cggggcggcg cgggaaccgg gccccggggg gagtcggccg ggctgctgct    60
gctgctgctc caggtgctgc cgcccggggc tacggcaggg ccgggacgcc ggggcacgcg   120
gggcgctggc ggcggcggcg tctgctggcc cggcgcggcc ccagcctttc cccgggacgc   180
gcggctgctg ctgctcctgc cgccgctgcc gccactgtcg ccgccgccgc cgagctccgc   240 gccccgcagcc tccgcctccc ggatggacgc tctgccccgc agcgggctga acctgaagga   300
ggagccgctg ctgcccgccg gcctgggctc agtgcgctcc tggatgcagg gcgcgggcat   360 cctgacgcc agcaccgcgg cgcagagtgg cgtgggtctg gcacgagcac attttgagaa   420
gcagcctccc tccaacctca ggaaatccaa cttcttccac ttcgtgctgg ccatgtacga   480
ccggcagggg cagcccgtgg aggtggagcg cacagccttc atcgacttcg tggaaaagga   540
ccgagagccc ggggcggaaa agactaacaa tgggatccat taccgcctcc ggctggtgta   600
taacaatgga ctgcggacag agcaagacct ctacgtgcgt ctcatcgact ccatgtccaa   660
acaggccatc atctatgagg ggcaggacaa gaaccccgaa atgtgccgag tgctgctcac   720
ccatgagatc atgtgcagcc ggtgctgtga ccggaagagc tgtggcaacc ggaatgagac   780
gccctcagac cccgtcatca ttgacaggtt cttcctcaag ttcttcctca aatgcaacca   840
```

```
gaactgcctg aagaatgcgg ggaatcccag agacatgcgc cgcttccagg tggtggtgtc    900
cacgacggtg agcgtggacg gacacgtgct ggccgtgtcc gacaacatgt tgtgcacaa     960
caactccaag catggccgca gggcgcgccc cctggacccc tccgaagctg ccaccccctg   1020
catcaaggcc atcagccccg ggagggctg gaccacgggc ggcgccaccg tcattgtcat    1080
cggcgacaac ttcttcgacg ggttgcaggt cgtgttcgga aacgtgctcg tgtgcagcga   1140
gctcatcacg ccccacgcca tccgggtgca gacgcccccg cggcacatcc ccggggtggt   1200
ggaggtgacc ctctcctaca agtccaagca gttttgcaag ggatgccccg gccgctttgt   1260
ctacacagct ctgaacgagc ccaccattga ctacggattc cagaggctac agaaagtcat   1320
tcccagacac cccggagacc ccgagaggct gcccaaggaa gtgctgctga agcgggcggc   1380
cgacttggca gaagccctgt acggagtgcc cggcagtaac caggagctgc tcctgaagcg   1440
cgcggcggac gtggccgagg ctctgtacag caccccccgc gcaccgggcc gctcgcacc    1500
cctggccccg agccacccac actccgccgt cgtgggcatc aacgccttca gcagcccgct   1560
ggccatcgcc gtcggggacg ccaccccggg gcccgagccg gctacgcgc gcagctgcag    1620
cagcgcgtcc ccccgcgggt tcgcgcccag ccccggctcg cagcagagcg gctacggcgg   1680
cggcctcgga gctggcctgg gcggctacgc cgcgccgggc gtggccggcc tcggcgtgcc   1740
tgggtccccc agcttcctca atggctccac cgccacctcg cccttcgcca aggagcgcct   1800
tcgcccccgt gctgcgcccc ccaagctccc caccccaggc ctgccccaga gccacggag    1860
aggggcttcc agaccagtct tttgaggatt ctgacaagtt ccactctcca gcccgggggc   1920
ttcagggcct ggcatactcc taattacggt ctgcagctgt tcccatggag cccggactgg   1980
aggtccctct gggattcaca gccacacccc ggatggtggc acagacagat gcagggccag   2040
ggccatgggc ggacctcaac ccgtgagctg aacggggaga ggccttcacc ccatgctcaa   2100
gcctccccgc tagcagcccc acaggcttct ctcgcctccc tgtcttgggg tagtcagaag   2160
ccccagcact gtgcagatgc tcttggcagg acagcatcgc agggaggtgc tgggattctg   2220
ggcctcactg tctgggtctt ggttcctctg aaagagatgg atcttgtgca gaccagggtt   2280
gttgagtgag gggagcgtgg gatggggacc gtgggaaaga ggacagctca gggagaagtg   2340
acctggaaag gtcctgtttg catctgaccc atctcaactg gcccagcatc ccaacttctc   2400
tgcagcgaaa gggtggcgcc ccgcagcctc gggaggcctg cccaggctcc cgtggagctt   2460
ccaacagctg cttggccccg cagctgcccc cacttccttt gagacctgca ctctcatgct   2520
tgccgcatca tgcctccctg tgggggcttt gggcatggag gaggcagaag aggggtgcc    2580
aggcctcctg tatttggggt cttccccag tggatgtctc atggactctg ccccacaca    2640
ctcacaatga ctctggctgg ccccacgcag cgggcccagc cgcccccag gtggcctcac    2700
attctgctct gctaagtttg gagaaaacag aacaataaac cagatgcagg tggtgcccgc   2760
ccggcctctc acctgcctcc tt                                            2782

<210> SEQ ID NO 73
<211> LENGTH: 1722
<212> TYPE: DNA
<213> ORGANISM: human

<400> SEQUENCE: 73
ggggaaaaga gctaggaaag agctgcaaag cagtgtgggc ttttccctt tttttgctcc      60
ttttcattac ccctcctccg ttttcaccct tctccggact tcgcgtagaa cctgcgaatt    120
```

| | |
|---|---|
| tcgaagagga ggtggcaaag tgggagaaaa gaggtgttag ggtttgggt tttttgttt | 180 |
| ttgttttgt tttttaattt cttgatttca acattttctc ccaccctctc ggctgcagcc | 240 |
| aacgcctctt acctgttctg cggcgccgcg caccgctggc agctgagggt tagaaagcgg | 300 |
| ggtgtatttt agattttaag caaaaatttt aaagataaat ccattttct ctcccacccc | 360 |
| caacgccatc tccactgcat ccgatctcat tatttcggtg gttgcttggg ggtgaacaat | 420 |
| tttgtggctt tttttcccct ataattctga cccgctcagg cttgagggtt tctccggcct | 480 |
| ccgctcactg cgtgcacctg gcgctgccct gcttccccca acctgttgca aggctttaat | 540 |
| tcttgcaact gggacctgct cgcaggcacc ccagccctcc acctctctct acattttgc | 600 |
| aagtgtctgg gggagggcac ctgctctacc tgccagaaat tttaaaacaa aacaaaaac | 660 |
| aaaaaaatct ccgggggccc tcttggcccc tttatccctg cactctcgct ctcctgcccc | 720 |
| accccgaggt aaaggggcg actaagagaa gatggtgttg ctcaccgcgg tcctcctgct | 780 |
| gctgccgcc tatgcgggc cggcccgag cctgggctcc ttcgtgcact gcgagccctg | 840 |
| cgacgagaaa gccctctcca tgtgcccccc cagccccctg ggctgcgagc tggtcaagga | 900 |
| gccgggctgc ggctgctgca tgacctgcgc cctggccgag gggcagtcgt gcggcgtcta | 960 |
| caccgagcgc tgcgcccagg ggctgcgctg cctcccccgg caggacgagg agaagccgct | 1020 |
| gcacgccctg ctgcacggcc gcggggtttg cctcaacgaa aagagctacc gcgagcaagt | 1080 |
| caagatcgag agagactccc gtgagcacga ggagcccacc acctctgaga tggccgagga | 1140 |
| gacctactcc cccaagatct tccggcccaa acacacccgc atctccgagc tgaaggctga | 1200 |
| agcagtgaag aaggaccgca gaaagaagct gacccagtcc aagtttgtcg ggggagccga | 1260 |
| gaacactgcc caccccggga tcatctctgc acctgagatg agacaggagt ctgagcaggg | 1320 |
| cccctgccgc agacacatgg aggcttccct gcaggagctc aaagccagcc cacgcatggt | 1380 |
| gccccgtgct gtgtacctgc ccaattgtga ccgcaaagga ttctacaaga gaaagcagtg | 1440 |
| caaaccttcc cgtggccgca agcgtggcat ctgctggtgc gtggacaagt acgggatgaa | 1500 |
| gctgccaggc atggagtacg ttgacggga ctttcagtgc acaccttcg acagcagcaa | 1560 |
| cgttgagtga tgcgtccccc cccaacccttt ccctcacccc ctcccacccc cagccccgac | 1620 |
| tccagccagc gcctcctcc accccaggac gccactcatt tcatctcatt taagggaaaa | 1680 |
| atatatatct atctatttga ggaaaaaaaa aaaaaaaaa aa | 1722 |

<210> SEQ ID NO 74
<211> LENGTH: 2626
<212> TYPE: DNA
<213> ORGANISM: human

<400> SEQUENCE: 74

| | |
|---|---|
| gggtacggct gcgagaagac gacagaaggg gatgtcacct gctttatttc tggctttggc | 60 |
| ctgtggtctg tgatacccat cctgcttgat gttctgcaga atggcacttg actgctgggc | 120 |
| atgcatgaag ttaagggcaa gaaacagtat gccatgtgtt ctgtaccatc atgtgtctct | 180 |
| tcttgcttct gggcccttct actggtgaac tttcatcaag atctgcgcca tgccgtgtca | 240 |
| ctatcaagcc attaagtttt gtctgggttg ctgtcagccc cagttggctt cctggtcaac | 300 |
| aaggacctca gaactgcct gtggaccgag gcccctacc agtgcatgag acacacacct | 360 |
| accctcccca gctttccagg aaccctactg gctgccagac tgatgggcgg gctggtatgt | 420 |
| gtggacatgt gttcactgtc attatgctgt ggctccaggt gagggtgagg actgggccta | 480 |
| tatagaatcc agataccatt gtcaacttcc cttattcccg tctaagatgt gagcagagtg | 540 |

-continued

```
ccatagtagg ggttctggga agaggtattt ctgatttgtg ggcctctgct tgcttgactt      600
caggtcactt atacttctta ttttgcttgc ctgccttcat ccctcatttc ctccctctca      660
ttcttctttc ctccctccct ttcctggtag cctccttttcc tccccttctg ccttcccctt     720
ccttctttcc ttattctttt ttattttgtt taaatagtac cacagagaaa acaactgaaa      780
aaccacattt ttctacatac agctggggag gtagctgaga acttggcact gcgcacacat      840
actaggttga aagagagttg aggaaaccag aaggccaagt ggatctgctg gcaaaccctg      900
aacctgtctc ctgcgcttgc tctacagttc tgaagttgaa aatcgttttc atgcctagca      960
tctgcttgag ttataaaccc caaggcagcc atgtcataga ctagtgttta ctcttgtttt     1020
gactttgttt taatgcttcc taagacccaa gtgcctcctg ctgtttcctc ctttgtggta     1080
gcctctggcc atctggacct caatccccag ctttcccact ttcagcagtc ctttgctctc     1140
tttgcttcta cctcaaatag ccccaggagt gggctttagt ctccaatatg gagcatctca     1200
agcttctcct gggggatggg gattgggatg ggcggaatct gttttggatc tccgggttat     1260
ttccagtggg tgtaaaagca gagctgggcc tttccctctc ttatccctga gggtgggtaa     1320
gaaggactgt atctacacct gttcttccct accttctctt ttgttaggga ggcctcattc     1380
taagttcctc aagagagtcc ttggcttaaa gctgtagcaa gggtgtgcta ggtgggggat     1440
ttggagcaaa accgtcgagt aggcatgata ctggtatgga gtgggcctgc aaaatcagac     1500
agaaatggct tgagaagccg caggggagc atgcctgtct ctcagtgata gagtatggga     1560
gggacctccc tagcttggaa aatgagaatt gaaggggtta tgaacaaata ggatgcctag     1620
ttgaggatgt tcccaaagtt ttgtccaatc ttatcattag tagatttat aagccacaga     1680 gacaaaccag aaacggaata atgttacttt ggatgctttt ttttttttgt ctaggtgtgg     1740
ctttgtacat gcagaagaat gctatatgct gcacattttg cctttaaagt cttacgactt     1800
tccccatttt agtctaatgg gaagatacag atgtgcaagt ctgcttttt gttttttgtt     1860 attatttttt tttttgctct gtgttatgga cattttcaga catgcacaga agtggagagg     1920
atggtccttg gaccccatgt gtccatcacc tagctgcatc acttatcagc tatggtcaac     1980
ctggtttcat ctgtatctct ctcttttcac ctgtattgtt tattgaaaat ccaagacact     2040
atgccaatgc aaccgtgact actttgggag attggtagtc tcttttgatg gtgatagtga     2100
tggggtgcac tatcataatc acatcaggtc tgcttttgc ttttaatgtt aactaatgaa     2160
gttccagaga tgggccttag aaatgtgttt taagaattaa caaggagtct caaaaagaaa     2220
tgagagggat gcttcctttc ccttgcatct acaaaacaag agagagactg ttctgttgta     2280
aaactctttc aaaaattctg atatggtaag gtacttgaga cccttcacca gaatgtcaat     2340 cttttttct gtgtaacatg gaaacttgtg tgaccattag cattgttatc agcttgtact     2400
ggtctcataa ctctggtttt ggaagaataa tttggaaatt gttgctgtgt tctgtgaaaa     2460
taacctcccc aaaataatta gtaactggtt gttctacttg gtaatttgac accctgttaa     2520
taacgcaatt atttctgtgt tcttaaacag tataaatagt tgtaagtttg catgcatgat     2580
ggaaaaataa aaacctgtat ctctgtcaaa aaaaaaaaaa aaaaaa                    2626
```

<210> SEQ ID NO 75
<211> LENGTH: 3337
<212> TYPE: DNA
<213> ORGANISM: human

<400> SEQUENCE: 75

-continued

```
gtcgagcctc tagcccgccc gggtttcctt cgcagtcgcg caccgacgct caaacgcgcg      60
ctccaacccg cagcctcctc ctgcctcacc gcccgaagat ggcggctctc aaactcctct     120
cctccgggct tcggctctgc gcctctgccc gcggatctgg ggcaacctgg tacaagggat     180
gtgtttgttc cttttccacc agtgctcatc gccataccaa gttttataca gatccagtag     240
aagctgtaaa agacatccct gatggtgcca cggttttggt tggtggtttt gggctatgtg     300
gaattccaga gaatcttata gatgctttac tgaaaactgg agtaaaagga ctaactgcag     360
tcagcaacaa tgcaggggtt gacaattttg gtttggggct tttgcttcgg tcgaagcaga     420
taaaacgcat ggtctcttca tatgtgggag aaaatgcaga atttgaacga cagtacttat     480
ctggtgaatt agaagtggag ctgacaccac agggcacact gcagagagg atccgtgcag      540
gcggggctgg agttcctgca ttttacaccc aacagggta tgggaccctg gtacaagaag      600
gaggatcgcc catcaaatac aacaaagatg gcagtgttgc cattgccagt aagccaagag     660
aggtgaggga gttcaatggt cagcacttta ttttggagga agcaattaca ggggattttg     720
cttttggtgaa agcctggaag gcggaccgag caggaaacgt gattttcagg aaaagtgcaa     780
ggaatttcaa cttgccaatg tgcaaagctg cagaaaccac agtggtagag gttgaagaaa     840
ttgtggatat tggagcattt gctccagaag acatccatat tcctcagatt tatgtacatc     900
gccttataaa gggagaaaaa tatgagaaaa gaattgagcg tttatcaatc cggaaagagg     960
gagatgggga agccaaatct gctaaacctg gagatgacgt aagggaacga atcatcaaga    1020
gggccgctct tgagtttgag gatggcatgt atgctaattt gggcatagga atccctctcc    1080
tggccagcaa ttttatcagc ccaaatataa ctgttcatct tcaaagtgaa aatggagttc    1140
tgggtttggg tccatatcca cgacaacatg aagctgatgc agatctcatc aatgcaggca    1200
aggaaacagt tactattctt ccaggagcct cttttttctc cagcgatgaa tcatttgcaa    1260
tgattagagg tggacacgtc gatctgacaa tgctaggagc gatgcaggtt tccaaatatg    1320
gtgacctggc taactggatg atacctggga agatggtgaa aggaatggga ggtgctatgg    1380
atttagtgtc cagtgcgaaa accaaagtgg tggtcaccat ggagcattct gcaagggaa    1440
atgcacataa aatcatggag aaatgtacat taccattgac tggaaagcaa tgtgtcaacc    1500
gcattattac tgaaaaggct gtgtttgatg tggacaagaa gaaagggttg actctgattg    1560
agctctggga aggcctgaca gtggatgacg tacaaaagag tactgggtgt gattttgcag    1620
tttcaccaaa actcatgcca atgcagcaga tcgcaaattg aaatatggat atttgtacca    1680
ggctgcgtgt ttttcatttt aaacacacaa gatttaattg aaaggacatc aataatcata    1740
attgtgtatt taacaggtgg ttttttatta gttttcttgt gtttcagact ttatgcagcc    1800
atataaactg ttctctaggc atgctgtgac attttaataa aaagcaaaag gagcatttat    1860
aattatctca tttgttaagg ctgagaaggt tgttttata ataggtaatt atattgaatg     1920
catttttcact gaatatggta tgtatgctaa attatatgaa cctttcccca agaagggccc    1980
tagaaattga tgtggctttc ctcttaaata ttaattatta gtcctgaaag aaagataaca    2040
tatgtgattt ttgtgttag gagagttgct gtcatgattg ttttttcttc agcctcctct     2100
gacttttctt ttggggcttc agattttatg attacatctt gtcccctag aacatccccc     2160
ttcctcccat actgctttta aacagatgcc caagaaggca agcaggaatg cctcttgtgg    2220
gggagggcag ggagaaataa ctagttcaaa ccaactatct atctatgctt tgcaaagact    2280
aaggcgtatt ataggaagag ggctagaaac ctaactgatt cttctcagtt ttctcatttt    2340
aaaacagccc agtattcctt tgtatcctca agggtccttg agaatacttc tgttattgaa    2400
```

```
accctgtggg ctacttgtac tgtacctcct ctcaagccaa gaagggctgt gggataattt    2460
accatgaatc cttagtagca atgacagcag agttaaaaaa taaaaggtgt tttactttca    2520
ggctcttgtt ttggttcaga ggagatttta aatattgaat gacacttcta cagaacaacg    2580
gttttctttc tgccaaggct acttcctttta acgaagtgcc tttaattcag ccttatccaa    2640
ctagggaaaa taatgttgga caagtctagg atttgaagag tcagtgaact tttagtgtca    2700
gggaataaac atggtgggta gattaggttt gaaaaaaact tccttagagg tatttattct    2760
caatacctga caggggccca tgggaatgac ttcagaagca tcccggataa tagatgggta    2820
aaaagtctag gcaccctgaa aacaggtga gacagctggc ctctggacag aggtaggcat    2880
agtacagtac gatatatcat tcctctggtc ctaaatatac aaacttattc atgtttttag    2940
gtgatgatgg tcattgaaac tcacttcttt tcaggtgtag ctacaattgt gtaatgtaca    3000
atattagaga aaggacaggc ttttttatgag taacacacac catatataaa acagcctttc    3060
tggctgacca catggttaaa tgcataccct cccagtactg gggggaaaat gacccttctt    3120
agaatgtgca agttccatag agtaatatat tgatatgatt ttgaaaagaa ttgttgatag    3180
ttacatcttc aaacttatca ttccagtatg catctttaag ataatgtgat tctaagtaga    3240
tgactttata ttcttgatta aagagtgcta tacatgttaa gaaatgcatt aaggaataca    3300
ataaatattc taaactgatg aaaaaaaaaa aaaaaaa                             3337

<210> SEQ ID NO 76
<211> LENGTH: 2460
<212> TYPE: DNA
<213> ORGANISM: human

<400> SEQUENCE: 76
aaagtcaaac cccgacaccg cggcgggccg gtgagctcac tagctgaccc ggcaggtcag      60
gatctggctt agcggcgccg cgagctccag tgcgcgcacc cgtggccgcc tcccagccct     120
ctttgccgga cgagctctgg gccgccacaa gactaaggaa tggccacccc gcccaagaga     180
agctgcccgt ctttctcagc cagctctgag gggacccgca tcaagaaaat ctccatcgaa     240
gggaacatcg ctgcagggaa gtcaacattt gtgaatatcc ttaaacaatt gtgtgaagat     300
tgggaagtgg ttcctgaacc tgttgccaga tggtgcaatg ttcaaagtac tcaagatgaa     360
tttgaggaac ttacaatgtc tcagaaaaat ggtgggaatg ttcttcagat gatgtatgag     420
aaacctgaac gatggtcttt taccttccaa acatatgcct gtctcagtcg aataagagct     480
cagcttgcct ctctgaatgg caagctcaaa gatgcagaga aacctgtatt attttttgaa     540
cgatctgtgt atagtgacag gtatattttt gcatctaatt tgtatgaatc tgaatgcatg     600
aatgagacag agtggacaat ttatcaagac tggcatgact ggatgaataa ccaatttggc     660
caaagccttg aattggatgg aatcatttat cttcaagcca ctccagagac atgcttacat     720
agaatatatt tacggggaag aaatgaagag caaggcattc ctcttgaata tttagagaag     780
cttcattata aacatgaaag ctggctcctg cataggacac tgaaaaccaa cttcgattat     840
cttcaagagg tgcctatctt aacactggat gttaatgaag actttaaaga caaatatgaa     900
agtctggttg aaaaggtcaa agagtttttg agtactttgt gatcttgctg aagactacag     960
gcagccaaat ggttccagat acttcagctt tgtgtatctt cgtaacttca tattaatata    1020
agtttcttta gaaacccaag ttttttaatc gttttttgttt taaggaaaaa agattttttaa    1080
aatgaatctt atgcaaaact ttttgatcag tttcttttct tttgtttttt ttttaaaaaa    1140
```

-continued

```
gacatttaaa gacaaagaca ttatttctca tagcaggaaa tgtagaggta gatggttcca    1200
gtatcagcat agtgactaaa ctacattata aaagatccag cttccttctg tcattcccct    1260
cttttgtctt cctcagcagg ttggcttttt tccctggtgc ctctcacttc gttggtgacc    1320
agtttcttaa actgaaagct ttaatgttac atagtaaatg gtagtgtgtc ctgtgtaaat    1380
tagtgtacct attaaaagtt gcaaagtgga attaaaggaa tccctagaat aaggattctg    1440
aagtttattt ttaaattatt atcttcttaa cagtttagtc ccacctctta cttcctgcct    1500
cagtctgctt tctctactgt ctggattaat taggcagcct gctataaagt taaagtcaca    1560
catttctatt ttgcaaacac tgtgattact cttttgctttg tagtttgctt tgctttgtag   1620
ggttctgctt ttaagttttt ctcttttttca gacaaattac tgataaaaat gatattgctc   1680
tatatgtaat atatcctgaa agcattattt tttgttgaat aggaaataaa attaatgaag    1740
acagaggcta gaaagcatcc attaattaat gagacacact taactactta tctctaaacc    1800
atctatgtga atatttgtaa aaataatgaa tggactcatc ttagttctgt atataaatat    1860
attttctttc tagtttgttt agttaaggtg tgcagtgttt ttcctgtgta ttaaaccttt    1920
ccattttacg ttttagaaaa ttttatgtat tttaaaataa ggggaagagt cattttcacc    1980
tttaaactac tatttttctt tccaagtcat ttttgttttt ggtttcttat tcaaagatga    2040
taatttagtg gattaaccag tccagacgca ctgatctttg caaggagac ttaatttcaa     2100 atctgtaatt accatacata aactgtctca ttatacgtat gcattttttt agtttgtttt    2160
tgtttggtat aaattaattt gttaattaaa tatttcttaa gtataaacct tatgaactac    2220
agtggagcta cactcattga aatgtaattt cagttctaaa aagatgtaat aatcatttta    2280
gaattaaaat ttattctact tttaaataaa ttatgaatat taaaggtgaa aattgtataa    2340
attactttga ttccatttta agtggagaca tatttcagtg attttagta acctttaaaa     2400 atgtataatg acttttaaaa tttgtagaat tgaaaagacg ctaataaaaa tttattattt    2460
```

<210> SEQ ID NO 77
<211> LENGTH: 7680
<212> TYPE: DNA
<213> ORGANISM: human

<400> SEQUENCE: 77

```
gcggacactc ctctcggctc ctccccggca gcggcggcgg ctcggagcgg gctccggggc     60
tcgggtgcag cggccagcgg gcctggcggc gaggattacc cggggaagtg gttgtctcct    120
ggctggagcc gcgagacggg cgctcagggc gcggggccgg cggcggcgaa cgagaggacg    180
gactctggcg gccgggtcgt tggccggggg agcgcgggca ccgggcgagc aggccgcgtc    240
gcgctcacca tggtcagcta ctgggacacc ggggtcctgc tgtgcgcgct gctcagctgt    300
ctgcttctca caggatctag ttcaggttca aaattaaaag atcctgaact gagtttaaaa    360
ggcacccagc acatcatgca agcaggccag acactgcatc tccaatgcag gggggaagca    420
gcccataaat ggtctttgcc tgaaatggtg agtaaggaaa gcgaaaggct gagcataact    480
aaatctgcct gtgaagaaa tggcaaacaa ttctgcagta cttaaccctt gaacacagct     540
caagcaaacc acactggctt ctacagctgc aaatatctag ctgtacctac ttcaaagaag    600
aaggaaacag aatctgcaat ctatatattt attagtgata caggtagacc tttcgtagag    660
atgtacagtg aaatccccga aattatacac atgactgaag gaagggagct cgtcattccc    720
tgccgggtta cgtcacctaa catcactgtt acttttaaaaa agtttccact tgacactttg    780
atccctgatg gaaaacgcat aatctgggac agtagaaagg gcttcatcat atcaaatgca    840
```

| | |
|---|---|
| acgtacaaag aaatagggct tctgacctgt gaagcaacag tcaatgggca tttgtataag | 900 |
| acaaactatc tcacacatcg acaaaccaat acaatcatag atgtccaaat aagcacacca | 960 |
| cgcccagtca aattacttag aggccatact cttgtcctca attgtactgc taccactccc | 1020 |
| ttgaacacga gagttcaaat gacctggagt taccctgatg aaaaaaataa gagagcttcc | 1080 |
| gtaaggcgac gaattgacca aagcaattcc catgccaaca tattctacag tgttcttact | 1140 |
| attgacaaaa tgcagaacaa agacaaagga ctttatactt gtcgtgtaag gagtggacca | 1200 |
| tcattcaaat ctgttaacac ctcagtgcat atatatgata aagcattcat cactgtgaaa | 1260 |
| catcgaaaac agcaggtgct tgaaaccgta gctggcaagc ggtcttaccg gctctctatg | 1320 |
| aaagtgaagg catttccctc gccggaagtt gtatggttaa aagatgggtt acctgcgact | 1380 |
| gagaaatctg ctcgctattt gactcgtggc tactcgttaa ttatcaagga cgtaactgaa | 1440 |
| gaggatgcag ggaattatac aatcttgctg agcataaaac agtcaaatgt gtttaaaaac | 1500 |
| ctcactgcca ctctaattgt caatgtgaaa ccccagattt acgaaaaggc cgtgtcatcg | 1560 |
| tttccagacc cggctctcta cccactgggc agcagacaaa tcctgacttg taccgcatat | 1620 |
| ggtatccctc aacctacaat caagtggttc tggcaccccct gtaaccataa tcattccgaa | 1680 |
| gcaaggtgtg acttttgttc caataatgaa gagtccttta tcctggatgc tgacagcaac | 1740 |
| atgggaaaca gaattgagag catcactcag cgcatggcaa taatagaagg aaagaataag | 1800 |
| atggctagca ccttggttgt ggctgactct agaatttctg gaatctacat ttgcatagct | 1860 |
| tccaataaag ttgggactgt gggaagaaac ataagctttt atatcacaga tgtgccaaat | 1920 |
| gggtttcatg ttaacttgga aaaaatgccg acggaaggag aggacctgaa actgtcttgc | 1980 |
| acagttaaca agttcttata cagagacgtt acttggattt tactgcggac agttaataac | 2040 |
| agaacaatgc actacagtat tagcaagcaa aaaatggcca tcactaagga gcactccatc | 2100 |
| actcttaatc ttaccatcat gaatgtttcc ctgcaagatt caggcaccta tgcctgcaga | 2160 |
| gccaggaatg tatacacagg ggaagaaatc ctccagaaga agaaattac aatcagagat | 2220 |
| caggaagcac catacctcct gcgaaacctc agtgatcaca cagtggccat cagcagttcc | 2280 |
| accactttag actgtcatgc taatggtgtc cccgagcctc agatcacttg gtttaaaaac | 2340 |
| aaccacaaaa tacaacaaga gcctggaatt attttaggac caggaagcag cacgctgttt | 2400 |
| attgaaagag tcacagaaga ggatgaaggt gtctatcact gcaaagccac caaccagaag | 2460 |
| ggctctgtgg aaagttcagc atacctcact gttcaaggaa cctcggacaa gtctaatctg | 2520 |
| gagctgatca ctctaacatg cacctgtgtg gctgcgactc tcttctggct cctattaacc | 2580 |
| ctccttatcc gaaaaatgaa aaggtcttct tctgaaataa agactgacta cctatcaatt | 2640 |
| ataatggacc cagatgaagt tcctttggat gagcagtgtg agcggctccc ttatgatgcc | 2700 |
| agcaagtggg agtttgcccg ggagagactt aaactgggca aatcacttgg aagagggct | 2760 |
| tttggaaaag tggttcaagc atcagcattt ggcattaaga atcacctac gtgccggact | 2820 |
| gtggctgtga aaatgctgaa agaggggcc acggccagcg agtacaaagc tctgatgact | 2880 |
| gagctaaaaa tcttgaccca cattggccac catctgaacg tggttaacct gctgggagcc | 2940 |
| tgcaccaagc aaggagggcc tctgatggtg attgttgaat actgcaaata tggaaatctc | 3000 |
| tccaactacc tcaagagcaa acgtgactta tttttctca caaggatgc agcactacac | 3060 |
| atggagccta agaagaaaa aatggagcca ggcctggaac aaggcaagaa accaagacta | 3120 |
| gatagcgtca ccagcagcga aagctttgcg agctccggct ttcaggaaga taaagtctg | 3180 |

```
agtgatgttg aggaagagga ggattctgac ggtttctaca aggagcccat cactatggaa    3240
gatctgattt cttacagttt tcaagtggcc agaggcatgg agttcctgtc ttccagaaag    3300
tgcattcatc gggacctggc agcgagaaac attcttttat ctgagaacaa cgtggtgaag    3360
atttgtgatt ttggccttgc ccgggatatt tataagaacc ccgattatgt gagaaaagga    3420
gatactcgac ttcctctgaa atggatggct cccgaatcta tctttgacaa aatctacagc    3480
accaagagcg acgtgtggtc ttacggagta ttgctgtggg aaatcttctc cttaggtggg    3540
tctccatacc caggagtaca aatggatgag acttttgca gtcgcctgag ggaaggcatg    3600
aggatgagag ctcctgagta ctctactcct gaaatctatc agatcatgct ggactgctgg    3660
cacagagacc caaaagaaag gccaagattt gcagaacttg tggaaaaact aggtgatttg    3720
cttcaagcaa atgtacaaca ggatggtaaa gactacatcc caatcaatgc catactgaca    3780
ggaaatagtg ggtttacata ctcaactcct gccttctctg aggacttctt caaggaaagt    3840
atttcagctc cgaagtttaa ttcaggaagc tctgatgatg tcagatatgt aaatgctttc    3900
aagttcatga gcctggaaag aatcaaaacc tttgaagaac ttttaccgaa tgccacctcc    3960
atgtttgatg actaccaggg cgacagcagc actctgttgg cctctcccat gctgaagcgc    4020
ttcacctgga ctgacagcaa acccaaggcc tcgctcaaga ttgacttgag agtaaccagt    4080
aaaagtaagg agtcggggct gtctgatgtc agcaggccca gtttctgcca ttccagctgt    4140
gggcacgtca gcgaaggcaa gcgcaggttc acctacgacc acgctgagct ggaaaggaaa    4200
atcgcgtgct gctccccgcc cccagactac aactcggtgg tcctgtactc caccccaccc    4260
atctagagtt tgacacgaag ccttatttct agaagcacat gtgtatttat accccagga    4320 aactagcttt tgccagtatt atgcatatat aagtttacac ctttatcttt ccatgggagc    4380
cagctgcttt ttgtgatttt tttaatagtg ctttttttt ttgactaaca agaatgtaac    4440
tccagataga gaaatagtga caagtgaaga acactactgc taaatcctca tgttactcag    4500
tgttagagaa atccttccta aacccaatga cttccctgct ccaaccccg ccacctcagg    4560 gcacgcagga ccagtttgat tgaggagctg cactgatcac ccaatgcatc acgtaccccca   4620 ctgggccagc cctgcagccc aaaacccagg gcaacaagcc cgttagcccc aggggatcac    4680
tggctggcct gagcaacatc tcgggagtcc tctagcaggc ctaagacatg tgaggaggaa    4740
aaggaaaaaa agcaaaaagc aagggagaaa agagaaaccg ggagaaggca tgagaaagaa    4800
tttgagacgc accatgtggg cacggagggg gacgggctc agcaatgcca tttcagtggc    4860
ttcccagctc tgacccttct acatttgagg gcccagccag gagcagatgg acagcgatga    4920
ggggacattt tctggattct gggaggcaag aaaaggacaa atatcttttt tggaactaaa    4980
gcaaatttta gacctttacc tatggaagtg gttctatgtc cattctcatt cgtggcatgt    5040
tttgatttgt agcactgagg gtggcactca actctgagcc catacttttg gctcctctag    5100
taagatgcac tgaaaactta gccagagtta ggttgtctcc aggccatgat ggccttacac    5160
tgaaaatgtc acattctatt ttgggtatta atatatagtc cagacactta actcaatttc    5220
ttggtattat tctgttttgc acagttagtt gtgaaagaaa gctgagaaga atgaaaatgc    5280
agtcctgagg agagttttct ccatatcaaa acgagggctg atggaggaaa aaggtcaata    5340
aggtcaaggg aagaccccgt ctctatacca accaaaccaa ttcaccaaca cagttgggac    5400
ccaaaacaca ggaagtcagt cacgtttcct tttcatttaa tggggattcc actatctcac    5460
actaatctga aaggatgtgg aagagcatta gctggcgcat attaagcact ttaagctcct    5520
tgagtaaaaa ggtggtatgt aatttatgca aggtatttct ccagttggga ctcaggatat    5580
```

```
tagttaatga gccatcacta gaagaaaagc ccattttcaa ctgctttgaa acttgcctgg    5640
ggtctgagca tgatgggaat agggagacag gtaggaaag ggcgcctact cttcagggtc    5700
taaagatcaa gtgggccttg gatcgctaag ctggctctgt ttgatgctat ttatgcaagt    5760
tagggtctat gtatttagga tgcgcctact cttcagggtc taaagatcaa gtgggccttg    5820
gatcgctaag ctggctctgt ttgatgctat ttatgcaagt tagggtctat gtatttagga    5880
tgtctgcacc ttctgcagcc agtcagaagc tggagaggca acagtggatt gctgcttctt    5940
ggggagaaga gtatgcttcc ttttatccat gtaatttaac tgtagaacct gagctctaag    6000
taaccgaaga atgtatgcct ctgttcttat gtgccacatc cttgtttaaa ggctctctgt    6060
atgaagagat gggaccgtca tcagcacatt ccctagtgag cctactggct cctggcagcg    6120
gcttttgtgg aagactcact agccagaaga gaggagtggg acagtcctct ccaccaagat    6180
ctaaatccaa acaaaagcag gctagagcca gaagagagga caaatctttg ttgttcctct    6240
tctttacaca tacgcaaacc acctgtgaca gctggcaatt ttataaatca ggtaactgga    6300
aggaggttaa actcagaaaa agaagacct cagtcaattc tctactttt tttttttttt     6360 tccaaatcag ataatagccc agcaaatagt gataacaaat aaaaccttag ctgttcatgt    6420
cttgatttca ataattaatt cttaatcatt aagagaccat aataaatact ccttttcaag    6480
agaaaagcaa accattaga attgttactc agctccttca aactcaggtt tgtagcatac    6540
atgagtccat ccatcagtca aagaatggtt ccatctggag tcttaatgta gaaagaaaaa    6600
tggagacttg taataatgag ctagttacaa agtgcttgtt cattaaaata gcactgaaaa    6660
ttgaaacatg aattaactga taatattcca atcatttgcc atttatgaca aaaatggttg    6720
gcactaacaa agaacgagca cttcctttca gagtttctga gataatgtac gtggaacagt    6780
ctgggtggaa tggggctgaa accatgtgca agtctgtgtc ttgtcagtcc aagaagtgac    6840
accgagatgt taattttagg gacccgtgcc ttgtttccta gcccacaaga atgcaaacat    6900
caaacagata ctcgctagcc tcatttaaat tgattaaagg aggagtgcat ctttggccga    6960
cagtggtgta actgtgtgtg tgtgtgtgtg tgtgtgtgtg tgtgtgtgtg tgtgggtgtg    7020
ggtgtatgtg tgttttgtgc ataactattt aaggaaactg gaattttaaa gttacttta    7080 tacaaaccaa gaatatatgc tacagatata agacagacat ggtttggtcc tatatttcta    7140
gtcatgatga atgtattttg tataccatct tcatataata tacttaaaaa tatttcttaa    7200
ttgggatttg taatcgtacc aacttaattg ataaacttgg caactgcttt tatgttctgt    7260
ctccttccat aaattttca aaatactaat tcaacaaga aaagctctt tttttcta       7320 aaataaactc aaatttatcc ttgtttagag cagagaaaaa ttaagaaaaa ctttgaaatg    7380
gtctcaaaaa attgctaaat attttcaatg gaaaactaaa tgttagttta gctgattgta    7440
tggggttttc gaacctttca cttttgtttt gttttaccta tttcacaact gtgtaaattg    7500
ccaataattc ctgtccatga aaatgcaaat tatccagtgt agatatattt gaccatcacc    7560
ctatggatat tggctagttt tgcctttatt aagcaaattc atttcagcct gaatgtctgc    7620
ctatatattc tctgctcttt gtattctcct ttgaacccgt taaaacatcc tgtggcactc    7680

<210> SEQ ID NO 78
<211> LENGTH: 3160
<212> TYPE: DNA
<213> ORGANISM: human

<400> SEQUENCE: 78
```

```
attctcgccg cgcccgggcg gacgatccag cgaacagccc cgcttctaac ccgagatgct    60
gctgccggcg ccccgcgctcc gccgcgccct gctgtcccgc ccctggaccg gggccggcct   120
gcggtggaag cacacctcct ccctgaaggt ggccaacgag cccgtcttag ccttcacgca   180
gggcagccct gagcgagatg ccctgcaaaa ggccttgaag gacctgaagg gccggatgga   240
agccatccca tgcgtggtgg gggatgagga ggtgtggacg tcggacgtgc agtaccaagt   300
gtcgccttt aaccatggac ataaggtggc caagttctgt tatgcagaca agagcctgct   360
caacaaagcc attgaggctg ccctggctgc ccggaaagag tgggacctga agcctattgc   420
agaccgggcc cagatcttcc tgaaggcggc agacatgctg agtgggccgc gcagggctga   480
gatcctcgcc aagaccatgg tgggacaggg taagaccgtg atccaagcgg agattgacgc   540
tgcagcggaa ctcatcgact tcttccggtt caatgccaag tatgcggtgg agctggaggg   600
gcagcagccc atcagcgtgc ccccgagcac caacagcacg gtgtaccggg gtctggaggg   660
cttcgtggcg gccatctcgc cctttaactt cactgcaatc ggcggcaacc tggcgggggc   720
accggccctg atgggcaacg tggtcctatg gaagcccagt gacactgcca tgctggccag   780
ctatgctgtc taccgcatcc ttcgggaggc tggcctgccc ccaacatca tccagtttgt   840
gccagctgat gggcccctat ttggggacac tgtcaccagc tcagagcacc tctgtggcat   900
caacttcaca ggcagtgtgc ccaccttcaa acacctgtgg aagcaggtgg cccagaacct   960
ggaccggttc cacaccttcc cacgcctggc tggagagtgc ggcggaaaga acttccactt  1020
cgtgcaccgc tcggccgacg tggagagcgt ggtgagcggg accctccgct cagccttcga  1080
gtacggtggc cagaagtgtt ccgcctgctc gcgtctctac gtgccgcact cgctgtggcc  1140
gcagatcaaa gggcggctgc tggaggagca cagtcggatc aaagtgggcg accctgcaga  1200
ggattttggg accttcttct ctgcagtgat tgatgccaag tcctttgccc gtatcaagaa  1260
gtggctggag cacgcgcgct cctcgcccag cctcaccatc ctggctgggg gcaagtgtga  1320
tgactccgtg ggctactttg tggagccctg catcgtggag agcaaggacc ctcaggagcc  1380
catcatgaag gaggagatct tcgggcctgt actgtctgtg tacgtctacc cggacgacaa  1440
gtacaaggag acgctgcagc tggttgacag caccaccagc tatggcctca cggggggcagt  1500
gttctcccag gataaggacg tcgtgcagga ggccacaaag gtgctgagga atgctgccgg  1560
caacttctac atcaacgaca gtccactgg ctcgatagtg ggccagcagc cctttggggg  1620
ggcccgagcc tctggaacca atgacaagcc aggggcccca cactcatcc tgcgctggac  1680
gtcgccgcag gtcatcaagg agacacataa gcccctgggg gactggagct acgcgtacat  1740
gcagtgagcc cctctcgggc tccaccgtcc agctgtctgt ccgtccaggt ggccgacctc  1800
actgcacaga ccccactcca gcccctccac cccttcttca tgcacagctg cctttctata  1860
atccgggctt gactcccttc ttaccactgt attctggcct ctcccatgcc tcaggctctg  1920
gtttgagatc gtgctgggga ggaacatggc cactacccct tatcccatcg ccatgtgggg  1980
aggtatgacc ctggtgcctg caggttctc cctctgccct ccactgggcc cagtggctca  2040
gggacctggg gaaaggagat ggagcagctc ttgggatcct ttggggaaaa ggaggccatt  2100
ctgggcccct tggcaaacct caccactcac agaggctcct ggccttgatc cctgcccctc  2160
caggtgtcca gggtaaagtg taactcagac tgacctgtgg ggcacagggg gcaccagctg  2220
gccttgccct ctctggtctg ggctgtctac cttcctcact gtatctttgc ccagacccac  2280
ctgggccagt aggcccctgt ccccagccac acacctaga tgctggcatg ccttactcca  2340
ggtgcctgtg tttggccgag gcctgtgtga ttcccggtct gcaccacatg gcggggttgg  2400
```

| | | | | |
|---|---|---|---|---|
| ggggccgctg | gaggccacct | gccaaggcgt | gggatgggat | ggtcctgccg gtttaggccg | 2460 |
| tgattctgga | aaaccttgga | tgggccttcg | tcctatgtca | gccttcccctt tgatcctcag | 2520 |
| gccctacctg | tagagacctc | cactcctaga | gccagtctca | gggtctggga tttccctgca | 2580 |
| ggagctcagc | caccactgtg | ccatggtgac | acaggccaag | gcagacattg ccctcccctt | 2640 |
| ctcccagccc | ccagaggcct | ggccttgggt | tcgtcagcat | gggccgagga cgttgcctgt | 2700 |
| agaatcctcc | tctgcctggg | agtggctctg | tgtggaccag | tccctcactg gcccattctt | 2760 |
| tttttgacgc | agccaatctg | tgaccacgat | tcctcccaca | gatgcctcct gcttggattc | 2820 |
| tgagtggtca | gagatctgta | aagcatgact | ttcaaggatg | gttcttaggg gactgtgaaa | 2880 |
| gtgttgggtc | ttcctccagg | atgcctgcat | gggaccccac | ccggagctgg tgtgccatt | 2940 |
| ccccaagtgc | cactggccca | tggatgggggt | tgggtgctgg | tgccagctgg gctgggtgtg | 3000 |
| ggttctgtgt | ccttccagga | tatgtgtcat | ttcccatgag | gggccggggc aggtggctgg | 3060 |
| gtggggggcac | aggctggagt | attcttagtt | ctactggttc | tacactgtga ggtggcaatg | 3120 |
| ggatttgctc | agatgccacc | caataaaatg | cctgttactt | | 3160 |

<210> SEQ ID NO 79
<211> LENGTH: 1546
<212> TYPE: DNA
<213> ORGANISM: human

<400> SEQUENCE: 79

| | | | | | |
|---|---|---|---|---|---|
| cacggccgga | gagacgcgga | ggaggagaca | tgagccggcg | ggcgcccaga cggagcggcc | 60 |
| gtgacgcttt | cgcgctgcag | ccgcgcgccc | cgaccccgga | gcgctgaccc ctggccccac | 120 |
| gcagctccgc | gccggggccg | gagagcgcaa | ctcggcttcc | agacccgccg cgcatgctgt | 180 |
| ccccggactg | agccgggcag | ccagcctccc | acggacgccc | ggacggccgg ccggccagca | 240 |
| gtgagcgagc | ttccccgcac | cggccaggcg | cctcctgcac | agcggctgcc gccccgcagc | 300 |
| ccctgcgcca | gcccggaggg | cgcagcgctc | gggaggagcc | gcgcggggcg ctgatgccgc | 360 |
| agggcgcgcc | gcggagcgcc | ccggagcagc | agagtctgca | gcagcagcag ccggcgagga | 420 |
| gggagcagca | gcagcggcgg | cggcggcggc | ggcggcggcg | gaggcgcccg gtcccggccg | 480 |
| cgcggagcgg | acatgtgcag | gctgggctag | gagccgccgc | ctcccctcccg cccagcgatg | 540 |
| tattcagcgc | cctccgcctg | cacttgcctg | tgtttacact | tcctgctgct gtgcttccag | 600 |
| gtacaggtgc | tggttgccga | ggagaacgtg | gacttccgca | tccacgtgga gaaccagacg | 660 |
| cgggctcggg | acgatgtgag | ccgtaagcag | ctgcggctgt | accagctcta cagccggacc | 720 |
| agtgggaaac | acatccaggt | cctgggccgc | aggatcagtg | cccgcggcga ggatggggac | 780 |
| aagtatgccc | agctcctagt | ggagacagac | accttcggta | gtcaagtccg gatcaagggc | 840 |
| aaggagacga | aattctacct | gtgcatgaac | cgcaaaggca | agctcgtggg gaagcccgat | 900 |
| ggcaccagca | aggagtgtgt | gttcatcgag | aaggttctgg | agaacaacta cacggccctg | 960 |
| atgtcggcta | agtactccgg | ctggtacgtg | gccttcacca | gaagggggcg gccgcggaag | 1020 |
| ggccccaaga | cccgggagaa | ccagcaggac | gtgcatttca | tgaagcgcta ccccaagggg | 1080 |
| cagccggagc | ttcagaagcc | cttcaagtac | acgacggtga | ccaagaggtc ccgtcggatc | 1140 |
| cggcccacac | accctgccta | ggccaccccg | ccgcggcccc | tcaggtcgcc ctggcccacac | 1200 |
| tcacactccc | agaaaactgc | atcagaggaa | tattttttaca | tgaaaaataa ggaagaagct | 1260 |
| ctattttgt | acattgtgtt | taaagaagaa | caaaaactga | accaaaactc ttgggggag | 1320 |

```
gggtgataag gattttattg ttgacttgaa accccccgatg acaaaagact cacgcaaagg    1380
gactgtagtc aacccacagg tgcttgtctc tctctaggaa cagacaactc taaactcgtc    1440
cccagaggag gacttgaatg aggaaaccaa cactttgaga aaccaaagtc cttttttccca   1500 aaggttctga aaggaaaaaa aaaaaaaaac aaaaaaaaaa aaaaaa                   1546
```

<210> SEQ ID NO 80
<211> LENGTH: 2819
<212> TYPE: DNA
<213> ORGANISM: human

<400> SEQUENCE: 80

```
ctgggcccag ctcccccgag aggtggtcgg atcctctggg ctgctcggtc gatgcctgtg      60
ccactgacgt ccaggcatga ggtggttcct gccctgacg ctggcagcag tgacagcagc     120
agccgccagc accgtcctgg ccacggccct ctctccagcc cctacgacca tggactttac    180
cccagctcca ctggaggaca cctcctcacg ccccccaattc tgcaagtggc catgtgagtg   240
cccgccatcc ccaccccgct gcccgctggg ggtcagcctc atcacagatg ctgtgagtg    300 ctgtaagatg tgcgctcagc agcttgggga caactcacg gaggctgcca tctgtgaccc    360
ccaccggggc ctctactgtg actacagcgg ggaccgcccg aggtacgcaa taggagtgtg    420
tgcacaggtg gtcggtgtgg gctgcgtcct ggatggggtg cgctacaaca acggccagtc   480
cttccagcct aactgcaagt acaactgcac gtgcatcgac ggcgcggtgg gctgcacacc   540
actgtgcctc cgagtgcgcc cccgcgtctct ctggtgcccc cacccgcggc gcgtgagcat  600
acctggccac tgctgtgagc agtgggtatg tgaggacgac gccaagaggc cacgcaagac   660 cgcacccccgt gacacaggag ccttcgatgc tgtgggtgag gtggaggcat ggcacaggaa  720
ctgcatagcc tacacaagcc cctggagccc ttgctccacc agctgcggcc tggggtctc   780 cactcggatc tccaatgtta acgcccagtg ctggcctgag caagagagcc gcctctgcaa    840
cttgcggcca tgcgatgtgg acatccatac actcattaag gcagggaaga agtgtctggc   900
tgtgtaccag ccagaggcat ccatgaactt cacacttgcg ggctgcatca gcacacgctc   960
ctatcaaccc aagtactgtg gagtttgcat ggacaatagg tgctgcatcc cctacaagtc  1020
taagactatc gacgtgtcct tccagtgtcc tgatgggctt ggcttctccc gccaggtcct  1080
atggattaat gcctgcttct gtaacctgag ctgtaggaat cccaatgaca tctttgctga  1140 cttgaatcc taccctgact tctcagaaat tgccaactag gcaggcacaa atcttgggtc   1200
ttggggacta acccaatgcc tgtgaagcag tcagccctta tggccaataa cttttcacca  1260
atgagcctta gttaccctga tctggaccct tggcctccat ttctgtctct aaccattcaa   1320
atgacgcctg atggtgctgc tcaggcccat gctatgagtt ttctccttga tatcattcag   1380
catctactct aaagaaaaat gcctgtctct agctgttctg gactacaccc aagcctgatc   1440 cagccttttcc aagtcactag aagtcctgct ggatcttgcc taaatcccaa gaatggaat    1500 caggtagact tttaatatca ctaatttctt ctttagatgc caaaccacaa gactctttgg    1560
gtccattcag atgaatagat ggaatttgga acaatagaat aatctattat ttggagcctg    1620
ccaagaggta ctgtaatggg taattctgac gtcagcgcac caaaactatc ctgattccaa    1680
atatgtatgc acctcaaggt catcaaacat ttgccaagtg agttaatag ttgcttaatt    1740 ttgattttta atgaaagtt gtatccatta acctgggcat tgttgaggtt aagtttctct     1800
tcacccctac actgtgaagg gtacagatta ggtttgtccc agtcagaaat aaaatttgat   1860
aaacattcct gttgatggga aaagccccca gttaatactc cagagacagg gaaaggtcag    1920
```

```
cccgtttcag aaggaccaat tgactctcac actgaatcag ctgctgactg gcagggcttt   1980
gggcagttgg ccaggctctt ccttgaatct tctcccttgt cctgcttggg gttcatagga   2040
attggtaagg cctctggact ggcctgtctg gccctgaga gtggtgccct ggaacactcc    2100
tctactctta cagagccttg agagacccag ctgcagacca tgccagaccc actgaaatga   2160
ccaagacagg ttcaggtagg ggtgtgggtc aaaccaagaa gtgggtgccc ttggtagcag   2220
cctggggtga cctctagagc tggaggctgt gggactccag ggcccccgt gttcaggaca    2280
catctattgc agagactcat ttcacagcct ttcgttctgc tgaccaaatg ccagttttc    2340
tggtaggaag atggaggttt accggttgtt tagaaacaga aatagactta ataaaggttt   2400
aaagctgaag aggttgaagc taaaaggaaa aggttgttgt taatgaatat caggctatta   2460
tttattgtat taggaaaata taatatttac tgttagaatt cttttattta gggccttttc   2520
tgtgccagac attgctctca gtgctttgca tgtattagct cactgaatct tcacgacaat   2580
gttgagaagt tcccattatt atttctgttc ttacaaatgt gaaacggaag ctcatagagg   2640
tgagaaaact caaccagagt cacccagttg gtgactggga agttaggat tcagatcgaa    2700
attggactgt ctttataacc catatttcc ccctgttttt agagcttcca aatgtgtcag    2760
aataggaaaa cattgcaata aatggcttga ttttttaaaa aaaaaaaaa aaaaaaaa     2819

<210> SEQ ID NO 81
<211> LENGTH: 2584
<212> TYPE: DNA
<213> ORGANISM: human

<400> SEQUENCE: 81
tggcggcggc ggcggcggtt gtcccggctg tgccggttgg tgtggcccgt cagcccgcgt     60
accacagcgc ccgggccgcg tcgagcccag tacagccaag ccgctgcggc cgggtccggc    120
gcgggcggcg cgcgcagacg gagggcggcg gccgcggcca gggcggcccg tgggaccgcg    180
ggcccccggc gcagcgctgc ccggctcccg gccctgccgg cctcctccct tggcgccgcg    240
gccatggcgg ccagcgcgaa gcggaagcag gaggagaagc acctgaagat gctgcgggac    300
atgaccggcc tcccgcgcaa ccgaaagtgc ttcgactgcg accagcgcgg ccccacctac    360
gttaacatga cggtcggctc cttcgtgtgt acctcctgct ccggcagcct gcgaggatta    420
aatccaccac acagggtgaa atctatctcc atgacaacat tcacacaaca ggaaattgaa    480
ttcttacaaa acatggaaa tgaagtctgt aaacagattt ggctaggatt atttgatgat    540
agatcttcag caattccaga cttcagggat ccacaaaaag tgaaagagtt tctacaagaa   600
aagtatgaaa agaaaagatg gtatgtcccg ccagaacaag ccaaagtcgt ggcatcagtt    660
catgcatcta tttcagggtc ctctgccagt agcacaagca gcacacctga ggtcaaacca   720
ctgaaatctc ttttagggga ttctgcacca acactgcact taaataaggg cacacctagt   780
cagtccccag ttgtaggtcg ttctcaaggg cagcagcagg agaagaagca atttgacctt   840
ttaagtgatc tcggctcaga catctttgct gctccagctc ctcagtcaac agctacagcc   900
aattttgcta actttgcaca tttcaacagt catgcagctc agaattctgc aaatgcagat   960
tttgcaaact tgatgcatt tggacagtct agtggttcga gtaattttgg aggttttcccc  1020
acagcaagtc actctccttt tcagccccaa actacaggtg gaagtgctgc atcagtaaat  1080
gctaattttg ctcattttga taacttcccc aaatcctcca gtgctgattt tggaaccttc  1140
aatacttccc agagtcatca aacagcatca gctgttagta aagtttcaac gaacaaagct  1200
```

```
ggtttacaga ctgcagacaa atatgcagca cttgctaatt tagacaatat cttcagtgcc      1260
gggcaaggtg gtgatcaggg aagtggcttt gggaccacag gtaaagctcc tgttggttct      1320
gtggtttcag ttcccagtca gtcaagtgca tcttcagaca agtatgcagc tctggcagaa      1380
ctagacagcg ttttcagttc tgcagccacc tccagtaatg cgtatacttc cacaagtaat      1440
gctagcagca atgttttttgg aacagtgcca gtggttgctt ctgcacagac acagcctgct      1500
tcatcaagtg tgcctgctcc atttggacgt acgccttcca caaatccatt tgttgctgct      1560
gctggtcctt ctgtggcatc ttctacaaac ccatttcaga ccaatgccag aggagcaaca      1620
gcggcaacct ttggcactgc atccatgagc atgcccacgg gattcggcac tcctgctccc      1680
tacagtcttc ccaccagctt tagtggcagc tttcagcagc ctgcctttcc agcccaagca      1740
gctttccctc aacagacagc tttttctcaa cagcccaatg tgcaggttt  tgcagcattt      1800 ggacaaacaa agccagtagt aacccctttt ggtcaagttg cagctgctgg agtatctagt      1860
aatcctttta tgactggtgc accaacagga caatttccaa caggaagctc atcaaccaat      1920
cctttcttat agccttatat agacaattta ctggaacgaa cttttatgtg gtcacattac      1980
atctctccac ctcttgcact gttgtcttgt ttcactgatc ttagctttaa acacaagaga      2040
agtctttaaa aagcctgcat tgtgtattaa acaccaggta atatgtgcaa aaccgagggc      2100
tccagtaaca ccttctaacc tgtgaattgg cagaaaaggg tagcggtatc atgtatatta      2160
aaattggcta atattaagtt attgcagata ccacattcat tatgctgcag tactgtacat      2220 attttttctta gaaattagct atttgtgcat atcagtattt gtaactttaa cacattgtta      2280
tgtgagaaat gttactgggg aaatagatca gccactttta aggtgctgtc atatatcttg      2340
gaatgaatga cctaaaatca ttttaaccat tgctactgga aagtaacaga gtcaaaattg      2400
gaaggtttta ttcattcttg aattttttcct ttctaaagag ctcttctatt tatacatgcc      2460
taaattcttt taaaatgtag agggataacct gtctgcataa taaagctgat catgttttgc      2520
tacagtttgc aggtgaaaaa aataaaatat tataaaataa aaaaaaaaaa aagaaaaaa      2580 aaaa                                                                   2584
```

<210> SEQ ID NO 82
<211> LENGTH: 2115
<212> TYPE: DNA
<213> ORGANISM: human

<400> SEQUENCE: 82

```
gaaatgaacc tctcttattg attttttattg gcctagagcc aggagtactg cattcagttg        60
actttcaggg taaaaagaaa acagtcctgg ttgttgtcat cataaacata tggaccagtg       120
tgatggtgaa atgagatgag gctccgcaat ggaactgtag ccactgctt  agcatttatc       180 acttccttcc ttactttgtc ttggtatact acatggcaaa atgggaaaga aaaactgatt       240
gcttatcaac gagaattcct tgcttttgaaa gaacgtcttc gaatagctga acacagaatc       300
tcacagcgct cttctgaatt aaatacgatt gtgcaacagt tcaagcgtgt aggagcagaa       360
acaaatggaa gtaaggatgc gttgaataag ttttcagata ataccctaaa gctgttaaag       420
gagttaacaa gcaaaaaatc tcttcaagtg ccaagtattt attatcattt gcctcattta       480
ttgaaaaatg aaggaagtct tcaacctgct gtacagattg gcaacggaag aacaggagtt       540
tcaatagtca tggcattcc  cacagtgaag agagaagtta aatcttacct catagaaact       600
cttcattccc ttattgataa cctgtatcct gaagagaagt tggactgtgt tatagtagtc       660
ttcataggag agacagatat tgattatgta catggtgttg tagccaacct ggagaaagaa       720
```

```
ttttctaaag aaatcagttc tggcttggtg gaagtcatat caccccctga aagctattat    780
cctgacttga caaacctaaa ggagacattt ggagactcca agaaagagt aagatggaga    840 acaaagcaaa acctagatta ctgttttcta atgatgtatg ctcaagaaaa gggcatatat    900
tacattcagc ttgaagatga tattattgtc aaacaaaatt attttaatac cataaaaaat    960
tttgcacttc aactttcttc tgaggaatgg atgattctag agttttccca gctgggcttc   1020
attggtaaaa tgtttcaagc gccggatctt actctgattg tagaattcat attcatgttt   1080
tacaaggaga aacccattga ttggctcctg gaccatattc tctgggtgaa agtctgcaac   1140
cctgaaaaag atgcaaaaca ttgtgataga cagaaagcaa atctgcgaat tcgcttcaga   1200
ccttcccttt tccaacatgt tggtctgcac tcatcactat caggaaaaat ccaaaaactc   1260
acggataaag attatatgaa accattactt cttaaaatcc atgtaaaccc acctgcggag   1320
gtatctactt ccttgaaggt ctaccaaggg catacgctgg agaaaactta catgggagag   1380
gatttcttct gggctatcac accgatagct ggagactaca tcttgtttaa atttgataaa   1440
ccagtcaatg tagaaagtta tttgttccat agcggcaacc aagaacatcc tggagatatt   1500
ctgctaaaca caactgtgga agttttgcct tttaagagtg aaggtttgga aataagcaaa   1560
gaaaccaaag acaaacgatt agaagatggc tatttcagaa taggaaaatt tgagaatggt   1620
gttgcagaag aatggtgga tccaagtctc aatcccattt cagcctttcg actttcagtt   1680
attcagaatt ctgctgtttg gccattctt aatgagattc atattaaaaa agccaccaac   1740
tgatcatctg agaaaccaac acattttttc ctgtgaattt gttaattaaa gatagttaag   1800
catgtatctt ttttttattt ctacttgaac actacctctt gtgaagtcta ctgtagataa   1860
gacgattgtc atttccactt ggaaagtgaa tctcccataa taattgtatt tgtttgaaac   1920
taagctgtcc tcagatttta acttgactca acattttttc aattatgaca gcctgttaat   1980
atgacttgta ctattttggt attatactaa tacataagag ttgtacatat tgttacattc   2040
tttaaatttg agaaaaacta atgttacata catttatga agggggtact tttgaggttc   2100
acttatttta ctatt                                                    2115

<210> SEQ ID NO 83
<211> LENGTH: 1635
<212> TYPE: DNA
<213> ORGANISM: human

<400> SEQUENCE: 83
gggggtggcg gggacgcgag tggcggccgc ggggccccgg acaagggtcc gcagagctgc     60
agccttcgag ggccagccct ctccgagtcc ggggctgggt cccaccagtg acaaggcggc    120
agccccgcgc acaccaaaga gaaagcggct gtggcggcag cggcagcccc agccatgctg    180
tgttatgtga cgaggccgga cgcggtgctg atggaggtgg agtggggagc gaaagccaac    240
ggcgaggact gcctcaacca ggtgtgcagg cgactgggaa tcatagaagt tgactatttt    300
ggactgcaat ttacgggtag caaaggtgaa agtttatggc taaacctgag aaaccggatc    360
tcccagcaga tggatgggct agccccttac aggcttaaac ttagagtcaa gttcttcgtg    420
gagcctcatc tcatcttaca ggagcagact aggcatatct ttttcttgca catcaaggag    480
gccctcttgg caggccacct cttgtgttcc ccagagcagg cagtggaact cagtgccctc    540
ctggcccaga ccaagtttgg agactacaac cagaacactg ccaagtataa ctatgaggag    600
ctctgtgcca aggagctctc ctctgccacc ttgaacagca ttgttgcaaa acataaggag    660
```

```
ttggagggga ccagccaggc ttcagctgaa taccaagttt tgcagattgt gtcggcaatg      720
gaaaactatg gcatagaatg gcattctgtg cgggatagcg aagggcagag actgctcatt      780
ggggttggac ctgaaggaat ctcaatttgt aaagatgact ttagcccaat taataggata      840
gcttatcctg tggtgcagat ggccacccag tcaggaaaga atgtatattt gacggtcacc      900
aaggaatctg gaacagcat cgtgctcttg tttaaaatga tcagcaccag gcggccagc       960 gggctctacc gagcgataac agagacgcac gcattctaca ggtgtgacac agtgaccagc     1020
gccgtgatga tgcagtatag ccgtgacttg aagggccact tggcatctct gtttctgaat     1080
gaaaacatta accttggcaa gaaatatgtc tttgatatta aagaacatc aaaggaggtg      1140 tatgaccatg ccaggagggc tctgtacaat gctggcgttg tggacctcgt ttcaagaagc     1200
aaccagagcc cttcacactc gcctctgaag tcctcagaaa gcagcatgaa ctgcagcagc     1260
tgcgagggcc tcagctgcca gcagacccgg gtgctgcagg agaagctacg caagctgaag     1320
gaagccatgc tgtgcatggt gtgctgcgag gaggagatca actccacctt ctgtccctgt     1380
ggccacactg tgtgctgtga gctgcgcc gcccagctac agtcatgtcc cgtctgcagg       1440
tcgcgtgtgg agcatgtcca gcacgtctat ctgccaacgc acaccagtct tctcaatctg     1500
actgtaatct aatctgttgt gcttttgttg gacttggcat gtttccatga actgcactat     1560
tataaactat taaatgata gatgttggag aaagtaatta ttccaacacc catctgccca      1620
tgcgatgtta aaaaa                                                      1635

<210> SEQ ID NO 84
<211> LENGTH: 2118
<212> TYPE: DNA
<213> ORGANISM: human

<400> SEQUENCE: 84
ctgtgaagat ggcgctctcc agggtgtgct gggctcggtc ggctgtgtgg ggctcggcag       60 tcaccctgg acattttgtc acccggaggc tgcaacttgg tcgctctggc ctggcttggg      120
gggcccctcg gtcttcaaag cttcacctttt ctccaaaggc agatgtgaag aacttgatgt     180
cttatgtggt aaccaagaca aaagcgatta atgggaaata ccatcgtttc ttgggtcgtc     240
atttcccccg cttctatatc ctgtacacaa tcttcatgaa aggattgcag atgttatggg     300
ctgatgccaa aaaggctaga agaataaaga caaatatgtg gaagcacaat ataaagtttc     360
atcaacttcc ataccgggag atggagcatt tgagacagtt ccgccaagac gtcaccaagt     420
gtctttcctt aggtattatt tccattccac cttttgccaa ctacctggtc ttcttgctaa     480
tgtacctgtt tcccaggcaa ctactgatca ggcatttctg gaccccaaaa caacaaactg     540
atttcttaga tatctatcat gctttccgga agcagtccca cccagaaatt attagttatt     600
tagaaaaggt catccctctc atttctgatg caggactccg gtggcgtctg acagatctgt     660
gcaccaagat acagcgtggt acccacccag caatacatga tatcttggct ctgagagagt     720
gtttctctaa ccatcctctg ggcatgaacc aactccaggc tttgcacgtg aaagccttga     780
gccgggccat gcttctcaca tcttacctgc ctcctccctt gttgagacat cgtttgaaga     840
ctcatacaac tgtgattcac caactggaca aggctttggc aaagctgggg attggccagc     900
tgactgctca ggaagtaaaa tcggcttgtt atctccgtgg cctgaattct acgcatattg     960
gtgaagatag gtgtcgaact tggctgggag aatggctgca gatttcctgc agcctgaaag    1020
aagctgagct gtctctcttg ctgcacaacg tggtcctgct ctccaccaac taccttggga    1080
caaggcgctg aatgaaccat ggagcggatg gcattgtcct gcagtcgtat agtatagcag    1140
```

```
tgcaggaaca aacagcactt gccagcaaag tctgtgtgta ctgttaagtg tgtgggaggc   1200
agagagagga gcaggggcca tgggcttcac agcatggcac acctgtggga actgcagaca   1260
ttcctctcac agctagaact gaaacaaacc ctcttgctag gggtggtccg tgtgaggtgt   1320
catcctgtcc ccctcataat tactaatagc tggaactggc agcagcctct actgggcttt   1380
tactgtgatg tgttcagttc atgtcctagg aagtcagctt ttgccccagg tgggaatcct   1440
tatttggctt aggactgatc cacttccatg ttacttacat ctgtgggttt ttgttgttgc   1500
tgttagaaaa ttttttggctg gtgaaaacag cactcctttg gctggagcac ttgtgtccat   1560
gcatgtactt gggtgtttcc ctccatcctt tctgatatga ccaaaaatca agttgttttg   1620
ttttttgtca ccttcactgg catgggctaa ccacttcttt ttcaaaccct ctgaacacct   1680
ttttctgatg ggtaacttgc aggaatattc tattggaaaa gataacagga agtacaagtg   1740
cttcttgacc ccttcctcaa tgtttctagc cttcactctc cattgtcttt tctgggctgt   1800
attacagccc tctgtggatc ttcaactctg ctgcctccac tgtgatgcag cagtccaact   1860
gtaactgaca gtggctgcct tctctgggcc atggatcaca cctgtaaggt actaattact   1920
gcccagcctg gggagatcag gagaggtctg catagttagt aagttgggtt tagcttttgt   1980
gtgtgcatca gtgacttaga gttctgtaat aacttattgt aaatgcatga agcactgttt   2040
ttaaacccaa gtaaagactg cttgaaacct gttgatggaa aaaaaaaaaa aaaaaaaaa    2100 aaaaaaaaaa aaaaaaaa                                                2118

<210> SEQ ID NO 85
<211> LENGTH: 4221
<212> TYPE: DNA
<213> ORGANISM: human

<400> SEQUENCE: 85
cgataacgat ttgtgttgtg agaggcgcaa gctgcgattt ctgctgaact tggaggcatt     60
tctacgactt ttctctcagc tgaggctttt cctccgaccc tgatgctctt caattcggtg    120
ctccgccagc cccagcttgg cgtcctgaga aatggatggt cttcacaata ccctcttcaa    180
tcccttctga ctggttatca gtgcagtggt aatgatgaac acacttctta tggagaaaca    240
ggagtcccag ttcctccttt tggatgtacc ttctcttctg ctcccaatat ggaacatgta    300
ctagcagttg ccaatgaaga aggctttgtt cgattgtata cacagaatc acaaagtttc     360 agaaagaagt gcttcaaaga atggatggct cactggaatg ccgtctttga cctggcctgg    420
gttcctggtg aacttaaaact tgttacagca gcaggtgatc aaacagccaa attttgggac    480
gtaaaagctg gtgagctgat tggaacatgc aaaggtcatc aatgcagcct caagtcagtt    540
gccttttcta agtttgagaa agctgtattc tgtacgggtg aagagatgg caacattatg     600 gtctgggata ccaggtgcaa caaaaaagat gggttttata gcaagtgaa tcaaatcagt    660 ggagctcaca atacctcaga caagcaaacc ccttcaaaac ccaagaagaa acagaattca    720
aaaggacttg ctccttctgt ggatttccag caaagtgtta ctgtggtcct ctttcaagac    780 gagaataccct tagtctcagc aggagctgtg gatgggataa tcaaagtatg ggatttacgt    840
aagaattata ctgcttatcg acaagaaccc atagcatcca agtctttcct gtacccaggt    900
agcagcactc gaaaacttgg atattcaagt ctgatttggg attccactgg ctctacttta    960
tttgctaatt gcacagacga taacatctac atgtttaata tgactgggtt gaagacttct   1020
ccagtggcta ttttcaatgg acaccagaac tctaccttt atgtaaaatc cagccttagt   1080
```

```
ccagatgacc agtttttagt cagtggctca agtgatgaag ctgcctacat atggaaggtc    1140
tccacaccct ggcaacctcc tactgtgctc ctgggtcatt ctcaagaggt cacgtctgtg    1200
tgctggtgtc catctgactt cacaaagatt gctacctgtt ctgatgacaa tacactaaaa    1260
atctggcgct tgaatagagg cttagaggag aaaccaggag gtgataaact ttccacggtg    1320
ggttgggcct ctcagaagaa aaaagagtca agacctggcc tagtaacagt aacgagtagc    1380
cagagtactc ctgccaaagc ccccagggta aagtgcaatc catccaattc ttccccgtca    1440
tccgcagctt gtgccccaag ctgtgctgga gacctccctc ttccttcaaa tactcctacg    1500
ttctctatta aaacctctcc tgccaaggcc cggtctccca tcaacagaag aggctctgtc    1560
tcctccgtct ctcccaagcc accttcatct ttcaagatgt cgattagaaa ctgggtgacc    1620
cgaacacctt cctcatcacc acccatcact ccacctgctt cggagaccaa gatcatgtct    1680
ccgagaaaag cccttattcc tgtgagccag aagtcatccc aagcagaggc ttgctctgag    1740
tctagaaata gagtaaagag gaggctagac tcaagctgtc tggagagtgt gaaacaaaag    1800
tgtgtgaaga gttgtaactg tgtgactgag cttgatggcc aagttgaaaa tcttcatttg    1860
gatctgtgct gccttgctgg taaccaggaa gaccttagta aggactctct aggtcctacc    1920
aaatcaagca aaattgaagg agctggtacc agtatctcag agcctccgtc tcctatcagt    1980
ccgtatgctt cagaaagctg tggaacgcta cctcttcctt tgagaccttg tggagaaggg    2040
tctgaaatgg taggcaaaga gaatagttcc ccagagaata aaaactggtt gttggccatg    2100
gcagccaaac ggaaggctga gaatccatct ccacgaagtc cgtcatccca gacacccaat    2160
tccaggagac agagcggaaa gacattgcca agcccggtca ccatcacgcc cagctccatg    2220
aggaaaatct gcacatactt ccatagaaag tcccaggagg acttctgtgg tcctgaacac    2280
tcaacagaat tatagattct aatctgagtg agttactgag ctttggtcca ctaaaacaag    2340
ctgagctttg gtccactaaa acaagatgaa aaatacaaga gtgactctat aactctggtc    2400
tttaagaaag ctgccttttc attttagac aaaatctttt caacgctgaa atgtacctaa    2460
tctggttcta ctaccataat gtatatgcag cttcccgagg atgaatgctg tgtttaaatt    2520
tcataaagta aatttgtcac tctagcattt tgaatgaata gtcttcactt tttaaattat    2580
tcatcttctc tataataatg acatcccagt tcatggaggc aaaaaacaag tttcttgtta    2640
tcctgaaact ttctatgctc agtggaaagt atctgccagc cacagcatga ggcctgtgaa    2700
ggctgactga gaaatcctct gctgaagacc cctggttctg ttctgcctcc aacatgtata    2760
attttatttg aaatacataa tcttttcact atgcttttgt ggggtttttt ttaagtatgt    2820
gtaaaaatgt gatgctcaga taagtacatt tatatcagtt cagtgttaaa atgcagtctc    2880
ttgagttaaa gtcatcttta ttttaaatgc agtgataaat gtcaactctt cggagaaact    2940
aggagaacaa caacagaaag ctgtgtttgt cttttttctc tcaaatatat ctcccgtatg    3000
agatttcagg tccccatgtt ttcaccaagc aatctgctat gtcagccaac ccaacatcac    3060
tttctacagg aggttatgat ttttgccatt tactagagga agatgtttta tgaaatcaat    3120
ttggggtttg aattcaggtg cagtcatcag ttctttaggg gctgcaatgt tttaaaaaaa    3180
ataagtcatc agattttaag aaaaagtga tgatttctta ttgatatttt tgtaacagaa    3240
tatagctctt aactgaaaat ccagaaccag aaacataaat cttgagtttc ttttcatgta    3300
cataaaaagc aatagccttt tagtatagat agccctgagc caaaaagtaa tagaatttc     3360 tctagatatt taatacagag agtgtataga ctgactctaa gttaataatg tgcaaaatat    3420
cttaaacatc cctccccctta ttcaacaatt atgtatcagt gatcttgaac cattgtttta    3480
```

```
tatttttcac ctttgtaacc tcatggaaag aggctttaca tactttctat gtactattta    3540
cttagaaggg agcccccttc cagtcatgaa acttcatttg ttttatccat atccctgagg    3600
actgtgtaga cttatgtca gttctgtgta gactttatgt cagttttgt cattatttga     3660 aaatctattc tgacaacttt ttaattcctt tgatcttata agttaaagct gtaacaactg    3720
aaattgcatg gatcaagtaa gcatagtttt atccagggag aaaaataaaa ggaagccata   3780
gaattgctct ggtcaaaacc aagcacacca tagccttaac tgaatatta ggaaatctgc    3840 ctaatctgct tatatttggt gtttgttttt tgactgttgg gctttgggaa gatgttattt    3900
atgaccaata tctgccagta acgctgttta tctcacttgc tttgaaagcc aatgggggaa    3960
aaaaatccat gaaaaaaaaa agattgataa agtagatgat tttgtttgta tccctaccca    4020
tctcctggca gccctactga gtgaaattgg gatacatttg gctgtcagaa attataccga    4080
gtctactggg tataacatgt ctcacttgga aagctagtac tttaaatgg gtgccaaagg    4140 tcaactgtaa tgagataatt atccctgcct gtgtccatgt cagactttga gctgatcctg    4200
aataataaag ccttttacct t                                             4221

<210> SEQ ID NO 86
<211> LENGTH: 867
<212> TYPE: DNA
<213> ORGANISM: human

<400> SEQUENCE: 86
cgtttcagcg tggcggcgct ggtgctggcg ttggccctgg aggacggccc cgagtgatgg     60
ctggcgcctg cctcccgggt gtctcccggg tacagatgga gtcgtcccgc ggccgccggc    120
ggcaaggtcg gcagctgcga ggccaagaga gaccccagga cacacacagc tgcctcccgg    180
tgcgagaaga agaccccggc ttgagagtga gatggcgttt aatgattgct tcagtttgaa    240
ctaccctggc aaccccctgcc caggggactt gatcgaagtg ttccgtcctg gctatcagca    300
ctgggccctg tacttgggtg atggttacgt tatcaacata gcacctgtag atggcattcc    360
tgcgtccttt acaagcgcca agtctgtatt cagcagtaag gccctggtga aaatgcagct    420
cttgaaggat gttgtgggaa atgacacata cagaataaac aataaatacg atgaaacgta    480 ccccctctc cctgtggaag aaatcataaa gcggtcagag tttgtaattg gacaggaggt    540
ggcctataac ttacttgtca acaactgtga acattttgtg acattgcttc gctatggaga    600
aggagtttca gagcaggcca accgagcgat aagtaccgtt gagtttgtga cagctgctgt    660
tggtgtcttc tcattcctgg gcttgtttcc aaaaggacaa agagcaaaat actattaaca    720
atttaccaaa gagatattga tattgaagga atttgggagg aggaaaagaa acctggggtg    780
aatacttatt ttcagtgcat cattactgtt ccagattcct atgatggatg gcagactctt    840
taataaattg cttactgata ttatctt                                       867

<210> SEQ ID NO 87
<211> LENGTH: 561
<212> TYPE: DNA
<213> ORGANISM: human
<220> FEATURE:
<221> NAME/KEY: misc_feature
<222> LOCATION: (534)..(534)
<223> OTHER INFORMATION: any kind of base

<400> SEQUENCE: 87
tttttttttc aaatttatt ttttgtactt ttattgaaaa ggtacattta aaaaaataca     60
```

```
cagacatttt accatttaca ggttgcagat atagatgctc taaaagagtc cactctattt      120
tgttgttcta tgataactct tgcccctgat atcacaaaca ttccagtctt gttgatatcg      180
gcttaaaaag gggggcatgg gagcatgacc tgcaatatat tcagcgaaca gaaagacaaa      240
ttgttcaatt ataaattttt ttatcttctg tacattattg cattagggag ccacaaaatt      300
atgtagcatc attacaaatg aaaacaggtt aaaaatgaag aagatactta tatagaaata      360
catggattca ttgtcttctt gcagaatgca caagaggtgc aaaaatgtgc aatttaggaa      420 gctcttttc tgtttgtata cgtttgctta gcaacacaaa ccagtgagga agctacaaaa       480
taagttaaac aaaaatagca aacaggtagt aattatagct atgttatatg gctntctatt      540
tcatttaaat atctccaaat a                                                561

<210> SEQ ID NO 88
<211> LENGTH: 471
<212> TYPE: DNA
<213> ORGANISM: human

<400> SEQUENCE: 88
tttcatgaat aattttatt ttattttggt catgactttt taaaattaat ggaaagtctc        60
agtctgctca aatgataaac caaaaaatgg ggtcatgaag caaattcagt ctttgcattt      120
cttcaacaac caactcacat ttctctgctc cttgactcag aggctggaca tgtgctaaca      180 gctttttgc ttctgtatat ccttaatagg atggcagaat cccggtgtta aaagaatctt       240
aaagtcagcc gtgtcaccat gggacctcga ttagcaaaca gatgtagaca ttccttccaa      300
attcagtcaa agaaaaaact ctaataccag cagccatgtt cagggtgtgc acgacatgct      360
gagcgcttgg gatacatccc cttgtttaat tctcacagaa actttgtgag acaagtacta      420
taatccctgt ttaacagatg ggcaaactga ggtttggaaa acactcatt t                471

<210> SEQ ID NO 89
<211> LENGTH: 727
<212> TYPE: DNA
<213> ORGANISM: human

<400> SEQUENCE: 89
taaaatatta cctttatt tctcaggcac acaagtgatt tggataccaa ttatcaagac         60
attttactga tttcccttta gaatgatcta ttttaaatct tcagccacct tagaaaaagt      120
ttgcagcaat cactttgcaa ttcataagta tcaggttaga atttagttgt ggaataagtt      180
aacagtttat gttcaatatg tgaggttatt tgaactcctg agttttaaat atcctgtgga      240
acagtgattc ctctcccttc taatggcttt tcagattaaa gcaatgactt taaaaagatt      300
acatcctaaa tacttgatta caacagaaat cgaccaatct aaaaatcaga tagtgttata      360
ctgaacatca ttctgatata atgagtagcc tctggctgaa acaaaattcc accaccaagg      420
ccatcaacca ggttagtact gttttttcctg gggtctatgt aaactctcct tttctctgca     480
aatgctgctt ggctgtgaac agcatggatt tacctgcacc aatgtggcac acacctagca     540
actttctcaa gcattctaaa gatatcccca gagctacaat attgacatat gcacagcact     600
ttctctagac agtccaatca gcgtgcacat cacacacaca gaatgctggg atatgctata     660
ctgcacactt agtacacagg tggaatagag tacaatgact aaagctcaca gaaaatgttt     720
tagtctt                                                                727

<210> SEQ ID NO 90
<211> LENGTH: 460
```

```
<212> TYPE: DNA
<213> ORGANISM: human

<400> SEQUENCE: 90 ttttttgatat aaagggcttt tatttctttt acagttttct gtattttcca aatttctaca     60
taaacataca cataaaagtc ataaaaatgt ccctcaaaat gacactccct ccaatgcagg    120
gagtgaggag gtgtgtgctg ggacgccaca gggtggctgc tgcagctaat ccctgtgcag    180
gtgcagccac tgctacactc cagcgtctga ggcccctctg cactggcagt gttagaatgg    240
ctgtctgaga gccaaggctg ttcacccgag cagagagtca tggagctggt acaggcagga    300
gccaaggtaa gcactaggct ggtgtgtgcc ctccaggggg caccctcctt gaagcaggcc    360
ctccaaggta ctcgcccccT gaggcagccg ataacagccg gaagccttcc cctgggggga    420
cctggccatt tgtggagcag ggaaaggctc cactgccagt                          460

<210> SEQ ID NO 91
<211> LENGTH: 392
<212> TYPE: DNA
<213> ORGANISM: human

<400> SEQUENCE: 91
tttttttttt tttttttgag ttgctgaaaa gtttactttt gagttttaaa ctgtactttg     60
aaaactatat tgtgaactgt gttgacatga ggaaaggctg ggctccctga aaacatccag    120
ttccacagca gggcgggccc aagcccagcc aatccccagg caatgcaggg cagggatccc    180
acctggtata agtacgggca gagggcagag ccaggctgta tcgaggggcg cgctgggac     240
cctcctcgcc cagaattcct actcatcccc agcacagaag tgctctgtag ggccagctga    300
ggacaccccg gttcactgag ggtggcccac agtaagtcgc cgtctggcag taagttagct    360
ctgcaggtgt ggaccccaag accacacacg gc                                  392

<210> SEQ ID NO 92
<211> LENGTH: 496
<212> TYPE: DNA
<213> ORGANISM: human

<400> SEQUENCE: 92 tttttttgtat ttttctcaat ataatgttgc aagatgtcat tatattctca ttacccataa    60
cttcccatcc aaatcttaat ggcacatttg atattttttc aaatggcttt gagatataat    120
tcacatacca cacaattcat gtatctaaag tatacagttc tgtagttctg tggttgttgg    180
ttacatccac cagactgagg gctccctgag ggttggtgcc tcagctttcc cttcacttac    240
tcattcacca aacattcagc gcctactgag tactgggggtt atgatggcca acaggagaga    300
cagtctctgc ctactgtttg gtgggggtgg agtacttagt aaccgtcgtc attattgagt    360
gcttacctgt gctgggcaca gtgctgctac tgggtgactg tgtccccagg gctgtcccag    420
gctgggggtc tggaggagta gttatcagtt gaactgagtt aatccacagt ggaaggtaac    480
ccactccctg ccctag                                                    496

<210> SEQ ID NO 93
<211> LENGTH: 472
<212> TYPE: DNA
<213> ORGANISM: human

<400> SEQUENCE: 93
ttaacacaaa agcttttact tggaaactgg caaatactgg actagaatac tgacatgctc     60
```

```
acgctctggc gggagctcgg atgcagaagc tattgcacaa agcccctctg attgccttgc    120
tcctctttgg catgtatcag cagagcccca agggccaatt gcccacaggt ggggactgtt    180
ctccatcaag gtatgggac ccctacttcc ttgttttgtt aaaaagtgca ggtaggcgaa    240
gaaagcccag gcagttgacc cagtctttga aacagctgac tccccagagc tggggccagg    300
ggagcctggt cttgaggggt aagggctgca gggccaggct gatggcctgt gtcatggcat    360
tggccatctc ctctccagct tctcctcagc catcgcccgt ccgtcatggt ggtgtcggct    420
gcacctggac cttcctgcct ctccgctcag gcagcagca gtgagtgcag ca             472
```

<210> SEQ ID NO 94
<211> LENGTH: 585
<212> TYPE: DNA
<213> ORGANISM: human

<400> SEQUENCE: 94

```
tttttatatt atagtaaatt tatttggtat aattacatat taacattatt tacaatgcta     60
atttttttat ttataaagta tctttatatg gacaaaaaga tacaaactgt tatcattta    120 agtacaaagt atttctagaa atacattata agccattaaa aaaaaaaacg atatttcaag    180
attggttctt acatgctatg accaactcat atgaaagagc aagttgctcc cccttcattc    240
cttcccccaa ctccaagggg aaggaatttg atatttaggg cttaaaaaaa tttcctacta    300
cctttatctt ttaaaaaacc ctactcaaaa caactatctc ttataaggga aaatatcata    360
gataagattt tcctttagaa aatgacatta aaagtggcat gagccctaga atgatatgtg    420
tattagaggc acttaaaaaa aatcagaagg gatccatagg aaggaattta attcagcaaa    480
tactgagtgt ccactgcatg caaggtaccc tgccagaaat ctcaaatgag taagttgtcc    540
ttagggatag aaggtgctaa gcatcatgca aagatatga actga                     585
```

<210> SEQ ID NO 95
<211> LENGTH: 400
<212> TYPE: DNA
<213> ORGANISM: human

<400> SEQUENCE: 95

```
ttattgtttt ttaaaaatac aattttgaaa tttattgttg aaaatggaca catggaacaa     60
accaaacctt gttttatcat gtaattttca gaaaatatgt gatccataaa gattaaaaga    120
aagttgtatt aagtctggca gctttagtat taacttgaaa taaaatatgg caagcttttcc    180 acgtcctcct ttatttccac aatccatatg tacgagctag attccagtca gaacttccac    240
aaatacttca ctctttggta gcagcggtta taaattacgc ctttgctaat ttgcgttgtt    300
cccaaccagg agaaacatta ccacaaaaaa agtcagtttc atcctgcagt gttcccgcag    360
caaccatatt aaagctgaag aataaagctc ctttgtagta                          400
```

<210> SEQ ID NO 96
<211> LENGTH: 461
<212> TYPE: DNA
<213> ORGANISM: human

<400> SEQUENCE: 96

```
ttatgccatg aattccttt tactgaaata ccgtaggact cactaccaca ataagtactt     60
aagctgaaag agtttctaat gggagccaag taaattcagc tctccactgt gcaaagcatc    120
ttgtcatttc tataataaaa gtcttttcat gttcagtcca ctttggctct ggaacctgga    180
tgagtcatgc ttggggccca gggtgcctgt gaggatgctg catgagaatt tcagctgtgg    240
```

```
tggcagtggc tgggagtccc actgactcag ggggaggcca ggcgagatga gctggaactt    300
ttaggggaga gctggcactt agggacatca ttgattgtgc ttttcttagc ctagttctgt    360
cctgcaattt attttcttta tcatgtgact gtcggctgaa gtctgggg tt atttggtttc    420 tttttcttct tccttgctgg acagtctcca tggggtcacg g                        461

<210> SEQ ID NO 97
<211> LENGTH: 542
<212> TYPE: DNA
<213> ORGANISM: human

<400> SEQUENCE: 97
taaatccagt aaagcatagt actagattca tcatacttgt acaatacaac gggcgacatg     60
aaaatggcaa aggctctcct ttttgtgaac aatttaatac aactggtggt ccataactc    120 tacaatcagc cttgtagagg tcattaaaga cagaatcctg aaagtccgtg actacaaata    180
cattttcaaa ttccggagaa tccaaacctt caaattcttc cactgactcc atctttacaa    240
agcccacttt aatgtccttt aaggctttta taagttcttc ttgttttcca gcttcttgaa    300
ccaatatcac tcttgtttca atctgaggca tctcttcttc tacatatgaa gtagatccaa    360
taagtaagtt ttccttggaa atctcagtaa ctttagaatc aaaaatggaa gagtctgcca    420
agctagtcct cccagtagtg gatgttaata cactatttc agccatgatt tgtattcttc     480
taaatcagca ctctcaaaaa agccctagga gttccacctc ttcaaacgcc gactcctctc    540
ac                                                                   542

<210> SEQ ID NO 98
<211> LENGTH: 1017
<212> TYPE: DNA
<213> ORGANISM: human

<400> SEQUENCE: 98
atgggcacct ggcttctggc ctgcacctgc gtctgcacct gtgtctgctc gggagtctct     60
gtctcagggg atgacgagg ccaagggct ggaacctcca cctgcctcac caacaacatt    120
ctcaggattg attgccactg gtctgcccca gagctgggtc agggctccag ccccgggctc    180
cccttcatca gccccgtggt gctgacacat gccttttca gcaaccaggc tgctggtggc    240
acacagaagt gcatctggca gggcagtgag tgcactgtag tgttgccgcc caaggcagca    300
ctcctgccat ctgacaattt catcatcact ttctaccact gcatgtccgg gagggatcag    360
agcacgtcag ctcgccactg catcctgacc tggagcctca gtcctgcctt ggagtcaatg    420
accacacttc tcagctatga gctggacttc aagaggcagg aagaggcctg ggagcgggcc    480
cagcacaggg atcacattgt cggggtgacc tggctcatac ttgaagcctt tgagctggac    540
cctggcttta tccttgaggc caggctgcgt gtccagacgg ccatgctggg ggatgacggg    600
gcacaggagg agcgagggga gccagcccat gggaagagtg aggcccagga gtgtggttca    660
cacaaggtcc ttcagcaggt gacacaaacc tccaaggccc atcacaaggt ccttcagcag    720
atgacacaaa cctccaaggc tcatcacaaa ccttccactt tggcccaggg cactaaaggg    780 cgcactttg ccagccctgg gcccttcctg cccacggacc ctctgatccc accctgggg    840 tggccaggca cacctttgt tgctgtgtcc atctttctcc tgctgactgg cccgacctac    900
ctcctgttca gctgtcgcc cagactcctc actttgggca aaggacaaga agcaactcgg    960 atggggggccc acagggctgg tgtgctgctg agccaggact gtgctggcac ccgatga     1017
```

<210> SEQ ID NO 99
<211> LENGTH: 1099
<212> TYPE: DNA
<213> ORGANISM: human

<400> SEQUENCE: 99

| | | | | | |
|---|---|---|---|---|---|
| agccccaagc | ttaccacctg | cacccggaga | gctgtgtcac | catgtgggtc | ccggttgtct | 60 |
| tcctcaccct | gtccgtgacg | tggattggtg | agaggggcca | tggttggggg | gatgcaggag | 120 |
| agggagccag | ccctgactgt | caagctgagg | ctctttcccc | cccaacccag | caccccagcc | 180 |
| cagacaggga | gctgggctct | tttctgtctc | tcccagcccc | actccaagcc | catacccccca | 240 |
| gcccctccat | attgcaacag | tcctcactcc | cacaccaggt | cccgctccc | tcccacttac | 300 |
| cccagaactt | tctccccatt | gcccagccag | ctccctgctc | cagctgctt | tactaaaggg | 360 |
| gaagttcctg | ggcatctccg | tgtttctctt | tgtgggctc | aaaacctcca | aggacctctc | 420 |
| tcaatgccat | tggttccttg | gaccgtatca | ctggtccacc | tcctgagccc | tcaatccta | 480 |
| tcacagtcta | ctgactttc | ccattcagct | gtgagtgccc | aaccctatcc | cagagacctt | 540 |
| gatgcttggc | ctcccaatct | tgccctagga | tacccagatg | ccaaccagac | acctccttct | 600 |
| tcctagccag | gctatctggc | ctgagacaac | aaatgggtcc | ctcagtctgg | caatgggact | 660 |
| ctgagaactc | ctcattccct | gactcttagc | cccagactct | tcattcagtg | cccacatt | 720 |
| tccttaggaa | aaacatgagc | atcccagcc | acaactgcca | gctctctgat | tccccaaatc | 780 |
| tgcatccttt | tcaaaaccta | aaaacaaaaa | gaaaacaaa | taaaacaaaa | ccaactcaga | 840 |
| ccagaactgt | tttctcaacc | tgggacttcc | taaactttcc | aaaaccttcc | tcttccagca | 900 |
| actgaacctc | gccataaggc | acttatccct | ggttcctagc | accccttatc | ccctcagaat | 960 |
| ccacaacttg | taccaagttt | cccttctccc | agtccaagac | cccaaatcac | cacaaaggac | 1020 |
| ccaatcccca | gactcaagat | atggtctggg | cgctgtcttg | tgtctcctac | cctgatccct | 1080 |
| gggttcaact | ctgctccca | | | | 1099 |

<210> SEQ ID NO 100
<211> LENGTH: 1095
<212> TYPE: DNA
<213> ORGANISM: human

<400> SEQUENCE: 100

| | | | | | |
|---|---|---|---|---|---|
| ccaagcttac | cacctgcacc | cggagagctg | tgtcaccatg | tgggtcccgg | ttgtcttcct | 60 |
| caccctgtcc | gtgacgtgga | ttggtgagag | gggccatggt | tgggggatg | caggagaggg | 120 |
| agccagccct | gactgtcaag | ctgaggctct | ttcccccca | acccagcacc | ccagcccaga | 180 |
| cagggagctg | ggctcttttc | tgtctctccc | agccccactt | caagcccata | cccccagccc | 240 |
| ctccatattg | caacagtcct | cactcccaca | ccaggtcccc | gctccctccc | acttacccca | 300 |
| gaactttctc | cccattgccc | agccagctcc | ctgctcccag | ctgctttact | aaaggggaag | 360 |
| ttcctgggca | tctccgtgtt | tctctttgtg | ggctcaaaa | cctccaagga | cctctctcaa | 420 |
| tgccattggt | tccttggacc | gtatcactgg | tccatctcct | gagcccctca | atcctatcac | 480 |
| agtctactga | cttttcccat | tcagctgtga | gtgtccaacc | ctatcccaga | gaccttgatg | 540 |
| cttggcctcc | caatcttgcc | ctaggatacc | cagatgccaa | ccagcacct | ccttcttcct | 600 |
| agccaggcta | tctggcctga | cacaacaaat | gggtccctca | gtctggcaat | gggactctga | 660 |
| gaactcctca | ttccctgact | cttagcccca | gactcttcat | tcagtggccc | acattttcct | 720 |
| taggaaaaac | atgagcatcc | ccagccacaa | ctgccagctc | tctgagtccc | caaatctgca | 780 |

```
tccttttcaa aacctaaaaa caaaaagaaa aacaaataaa acaaaaccaa ctcagaccag      840
aactgttttc tcaacctggg acttcctaaa ctttccaaaa ccttcctctt ccagcaactg      900
aacctcgcca taaggcactt atccctggtt cctagcaccc cttatcccct cagaatccac      960
aacttgtacc aagtttccct tctcccagtc caagacccca aatcaccaca aaggacccaa     1020
tccccagact caagatatgg tctgggcgct gtcttgtgtc tcctaccctg atccctgggt     1080
tcaactctgc tccca                                                     1095
```